United States Patent
Jadhav et al.

(10) Patent No.: US 12,109,303 B2
(45) Date of Patent: Oct. 8, 2024

(54) ORALLY DISSOLVING ANTIMICROBIAL FILM COMPOSITIONS AND METHODS OF THEIR USE

(71) Applicant: ISHA Therapeutics LLC, Hillsborough, NJ (US)

(72) Inventors: Manoj P. Jadhav, Hillsborough, NJ (US); Mangal Shailesh Nagarsenkar, Maharashtra (IN); Supriya Shrihari Shidhaye, Maharashtra (IN); Shivali Hargovind Tank, Maharashtra (IN)

(73) Assignee: ISHA THERAPEUTICS LLC, Hillsborough, NJ (US)

( * ) Notice: Subject to any disclaimer, the term of this patent is extended or adjusted under 35 U.S.C. 154(b) by 0 days.

(21) Appl. No.: 18/302,720

(22) Filed: Apr. 18, 2023

(65) Prior Publication Data

US 2023/0330012 A1    Oct. 19, 2023

Related U.S. Application Data

(63) Continuation of application No. PCT/US2023/065861, filed on Apr. 17, 2023.

(60) Provisional application No. 63/331,956, filed on Apr. 18, 2022.

(51) Int. Cl.
| | |
|---|---|
| *A61K 9/00* | (2006.01) |
| *A61K 31/7048* | (2006.01) |
| *A61K 47/18* | (2017.01) |
| *A61K 47/22* | (2006.01) |
| *A61P 31/10* | (2006.01) |

(52) U.S. Cl.
CPC .......... *A61K 9/006* (2013.01); *A61K 31/7048* (2013.01); *A61K 47/18* (2013.01); *A61K 47/186* (2013.01); *A61K 47/22* (2013.01); *A61P 31/10* (2018.01)

(58) Field of Classification Search
None
See application file for complete search history.

(56) References Cited

U.S. PATENT DOCUMENTS

| | | | | |
|---|---|---|---|---|
| 4,049,898 | A | * | 9/1977 | Metzger ................ C07H 17/08 536/6.5 |
| 4,642,316 | A | | 2/1987 | Fawzi |
| 5,965,156 | A | | 10/1999 | Proffitt |
| 2004/0063617 | A1 | | 4/2004 | Huang |
| 2015/0038594 | A1 | | 2/2015 | Borges |
| 2017/0304287 | A1 | | 10/2017 | Karpati |
| 2018/0155305 | A1 | * | 6/2018 | Qian ................... C13K 13/002 |
| 2019/0388545 | A1 | | 12/2019 | Zakrewsky |
| 2021/0085622 | A1 | | 3/2021 | Vasisht |
| 2021/0353565 | A1 | | 11/2021 | Mitragotri |
| 2021/0361573 | A1 | | 11/2021 | Mecozzi |

FOREIGN PATENT DOCUMENTS

| | | |
|---|---|---|
| CN | 100490898 C | 5/2009 |
| CN | 112175029 | 1/2021 |

OTHER PUBLICATIONS

Beggs, "Enhancement of Amphotericin B Activity With Vitamin C and Sulfhydryl-Containing Compounds," General Medical Research and Medicine Services, Veterans Administration Medical Center, Minneapolis, MN 55417, U.S.A., received Aug. 3, 1979.
Machine translation of CN100490898C, 7 pp. First invention Liu. Published May 27, 2009.
Egorova, "Biological Activity of Ionic Liquids and Their Application in Pharmaceutics and Medicine." Chem Rev. May 24, 2017;117(10):7132-7189. doi: 10.1021/acs.chemrev.6b00562. Epub Jan. 26, 2017. PMID: 28125212.
Garcia-Cuesta, "Current treatment of oral candidiasis: A literature review," Journal section: Oral Medicine and Pathology, doi: 10.4317/jced.51798, http://dx.doi.org/10.4317/jced.51798.
Hartmann, "Tailoring amphotericin B as an ionic liquid: an upfront strategy to potentiate the biological activity of antifungal drugs." RSC Adv. Apr. 16, 2021;11(24):14441-14452. doi: 10.1039/d1ra00234a. PMID: 35423994; PMCID: PMC8697833.
McCrary, "Drug specific, tuning of an ionic liquid's hydrophilic-lipophilic balance to improve water solubility of poorly soluble active pharmaceutical ingredients," Article in New Journal of Chemistry, Apr. 2013.
Özakar, "Current Overview of Oral Thin Films," Atatürk University Faculty of Pharmacy, Department of Pharmaceutical Technology, Erzurum, Turkey, Turk J Pharm Sci 2021;18(1):111-121, DOI: 10.4274/tjps.galenos.2020.76390.
Serrano, "Designing Fast-Dissolving Orodispersible Films of Amphotericin B for Oropharyngeal Candidiasis," Received: Jun. 7, 2019; Accepted: Jul. 22, 2019; Published: Aug. 1, 2019, Pharmaceutics 2019, 11, 369; doi:10.3390/pharmaceutics11080369 www.mdpi.com/journal/pharmaceutics.

(Continued)

*Primary Examiner* — Dale R Miller
(74) *Attorney, Agent, or Firm* — Transformative Legal LLC; Len S. Smith; Denise M. Brown

(57) ABSTRACT

Disclosed herein are ionic liquid composition(s) of amphotericin B comprising amphotericin B; a complexing agent component; a solvent component comprising acidified solvent(s); and a solubilizing component. Disclosed composition(s) comprise at least two complexing agents and two or more constituents of the composition provide two or more functional activities. Ionic liquid composition(s) disclosed are in aspects provided as oral dissolve film(s) useful in the treatment of oral microbial infection(s), e.g., oral candidiasis. Disclosed ionic liquid composition(s) of amphotericin B and ODF(s) thereof have a solubility of amphotericin B in water of at least 3 mg/mL. ODF film(s) provided deliver a localized concentration of amphotericin B to the oral cavity of a recipient wherein the concentration of amphotericin B available for treating a source of a local infection is detectably or significantly greater than that provided by an orally delivered, intravenously delivered, or either orally or intravenously delivered treatment comprising amphotericin B.

20 Claims, 4 Drawing Sheets

(56) References Cited

OTHER PUBLICATIONS

Figure 1:
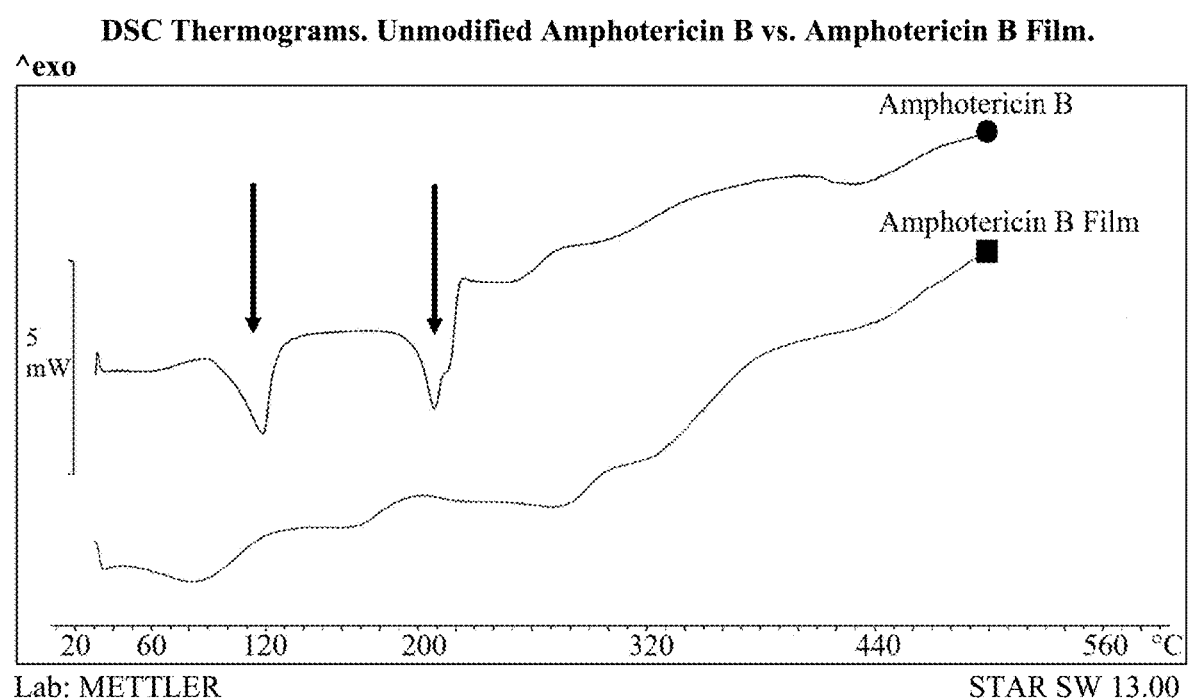

Shamshina, "Are Myths and Preconceptions Preventing US from Applying Ionic Liquid Forms of Antiviral Medicines to the Current Health Crisis?," International Journal of Molecular Sciences, Received: Jul. 28, 2020; Accepted: Aug. 18, 2020; Published: Aug. 20, 2020, Int. J. Mol. Sci. 2020, 21, 6002; doi:10.3390/ijms21176002 www.mdpi.com/journal/jms.

Fungilin® Lozenges Amphotericin B, 10 mg/Lozenge leaflet, New Zealand Consumer Medicine Information. Mar. 5, 2012.

Public Summary for Fungilin amphotericin B (amphotericin) 10 mg lozenge bottle, Australian Government, Department of Health and Aged Care. Effective date Jan. 8, 2022.

Lim et al. Preparation, Characterization, and In Vivo Pharmacokinetic Study of the Supercritical Fluid-Processed Liposomal Amphotericin B, Pharmaceutics, vol. 11, Nov. 8, 2019, Nov. 8, 2019, Lim, Chang-Baek.

International Search Report on Sep. 1, 2023 for PCT/US2023/065861, Sep. 1, 2023, WO, Search Report.

\* cited by examiner

FIGURES 2A – 2C
In Vitro Antifungal Assays – *Candida albicans*:
Unmodified Amphotericin B (A) vs. Amphotericin B Film (B).
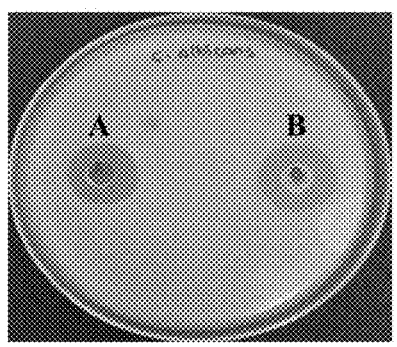
Fig. 2A
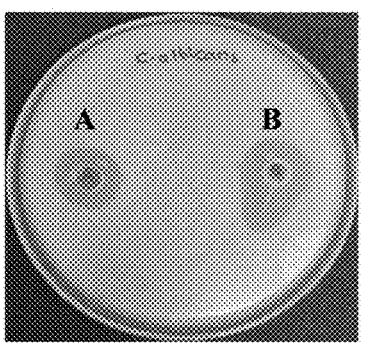
Fig. 2B
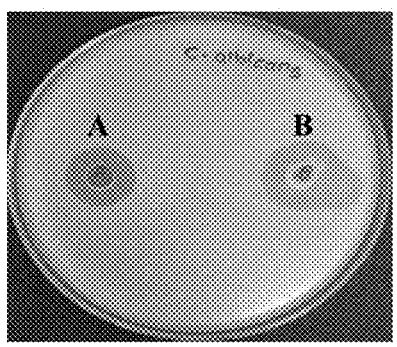
Fig. 2C
FIGURES 3A – 3C
In Vitro Antifungal Assays – *Candida tropicalis*:
Unmodified Amphotericin B (A) vs. Amphotericin B Film (B).
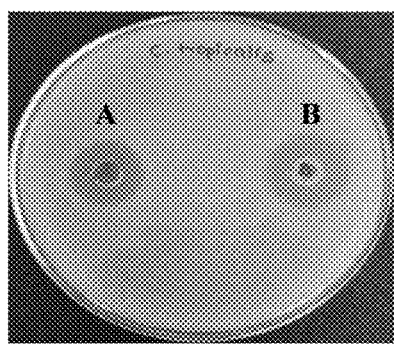
Fig. 3A
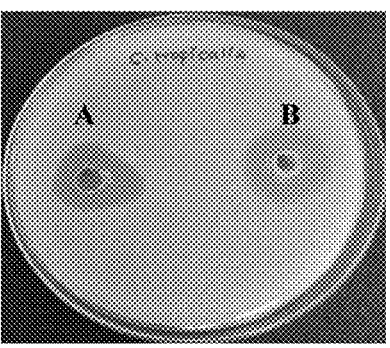
Fig. 3B
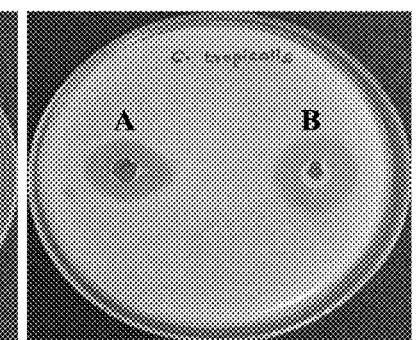
Fig. 3C

*Candida tropicalis*

*Candida albicans*

ORALLY DISSOLVING ANTIMICROBIAL FILM COMPOSITIONS AND METHODS OF THEIR USE

RELATED APPLICATIONS/PRIORITY

This patent Application is a bypass continuation of PCT application number PCT/US2023/065861 filed Apr. 17, 2023, entitled, "Orally Dissolving Antimicrobial Film Compositions & Methods of Their Use," which claims priority to U.S. Provisional Patent Application No. 63/331,956 filed Apr. 18, 2022, entitled, "Orally dissolving film compositions comprising Amphotericin B." This Application claims the benefit of priority to, and incorporates by reference the entirety of, these above-referenced priority applications.

FIELD OF THE INVENTION

The invention primarily relates to orally dissolving film compositions comprising amphotericin B in ionic liquid form for use in the treatment of oral infections such as oral candidiasis, mucocutaneous candidiasis, and refractory mucocutaneous candidiasis.

BACKGROUND OF THE INVENTION

Amphotericin B is an antifungal medication used for serious fungal infections and the parasitic disease leishmaniasis. It is used for the treatment of various fungal and potentially fatal infections such as opportunistic mycoses, e.g., aspergillosis, candidiasis, cryptococcosis, fusariosis, mucormycosis, hyalohyphomycosis, and phaohyphomycosis, as well as severe and widespread forms of endemic mycoses, e.g., histoplasmosis, paracoccidioidomycosis, blastomycosis, coccidioidomycosis, sporotrichosis, talaromycosis (*Talaromyces marneffei*, formally *Penicillium marneffei*), and emergomycosis.

Amphotericin B is known to act by binding to ergosterol, the major sterol found in fungal cytoplasmic membranes, and creating transmembrane channels. The fungicidal activity of amphotericin B is due to the damage caused to the cell barrier and subsequent cell death through leakage of essential nutrients from the fungal cell.

Chemically, amphotericin B is $C_{47}H_{73}NO_{17}$, (1R,3S,5R,6R,9R,11R,15S,16R,17R,18S,19E,21E, 23E, 25E, 27E,29E,31E,33R,35S,36R,37S)-33-[(2R,3S,4S,5S,6R)-4-amino-3,5-di hydroxy-6-methyloxan-2-yl] oxy-1,3,5,6,9,11,17,37-octahydroxy-15,16,18-trimethyl-13-oxo-14,39-dioxabicyclo[33.3.1]nonatriaconta-19,21,23, 25, 27,29,31-heptaene-36-carboxylic acid), has a molecular weight of 924 Da, and has the following structure:

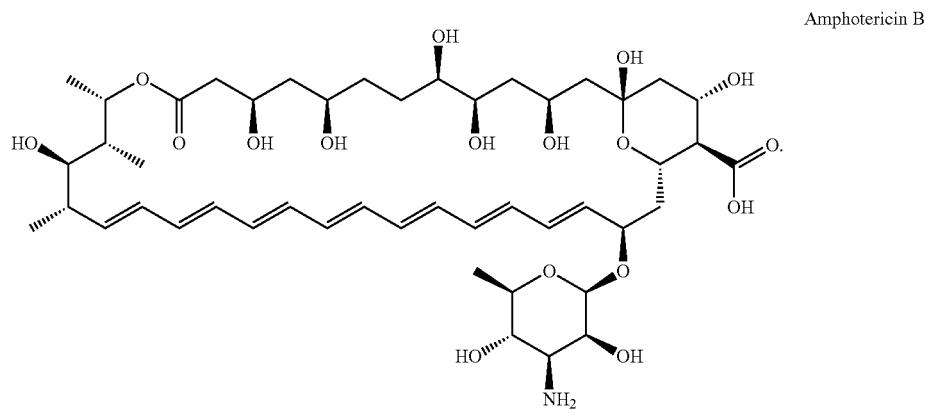 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2C(=O)O]

Amphotericin B

The compound gets its name from the fact that it is amphoteric, forming soluble salts in both acidic and basic environments.

Amphotericin B is recognized as a beneficial therapeutic treatment for microbial infection(s), and, e.g., often more specifically or especially fungal infections. Amphotericin B maintains a position as the gold standard for fungal infections and has done so for over 60 years. Unfortunately, however, amphotericin B is classified in the Biopharmaceutics Classification System ("BCS"; a system characterizing two of the most significant factors influencing oral drug absorption, solubility and intestinal permeability) as a class IV drug, having limited solubility and permeability properties; e.g., it is considered poorly absorbed from the gastrointestinal (GI) tract. Its limited solubility and permeability properties lead to low oral bioavailability of the active pharmaceutical ingredient (API). A solubility of 0.2% to about 0.9% (as reported by Serrano in, e.g., "Oral amphotericin B: The journey from bench to market," Journal of Drug Delivery Science and Technology 42 (2017) 75-83) severely limits the clinical utility of Amphotericin B despite its attractive chemotherapeutic properties.

Further adding to the challenges of successfully administering amphotericin B in therapeutically effective amounts is its notorious instability in acidic environments, such as, e.g., the low pH environments of the stomach and the relatively lower pH of the small intestine (e.g., compared to the large intestine). As a result, amphotericin B is typically administered by intravenous (IV) administration. "Designing Fast-Dissolving Orodispersible Films of Amphotericin B for Oropharyngeal Candidiasis," by Dolores R. Serrano et al. (published in Pharmaceutics 2019, 11(8), 369) ("Serrano") discloses some of the challenges presented by the API, such as amphotericin B's poor water solubility and high molecular weight compared to other antifungal drugs such as miconazole and clotrimazole which hamper its efficacy under physiological conditions of, specifically, the oropharyngeal cavity (saliva pH; limited volume for dissolution). These challenges limit the clinical utility of amphotericin B in treating oropharyngeal candidiasis. Further complicating utility of the API is its amphipathic nature-even when administered by IV. Amphotericin B itself is insoluble in saline at a physiological pH, and therefore the API is typically prescribed in a combination wherein amphotericin B is present with the detergent sodium deoxycholate. Unfortunately, amphotericin B deoxycholate has a narrow therapeutic index, demonstrating a high toxicity manifested as acute infusion-related reactions and dose-related nephrotoxicity.

In an effort to improve upon the solubility of amphotericin B and other similarly insoluble APIs, formulators have attempted to manipulate the structure of the compound and/or the environment within which the drug is delivered. The formation of salts, solid dispersions, use of prodrug(s), or, e.g., use of crystal engineering, surfactants to generate micelles establishing nano-scale delivery systems have all been explored (see, e.g., M. Vallet-Regi, et. al., Chem., Int. Ed., 2007, 46, 7548-7558; A. Sharma and U. S. Sharma, Int. J. Pharm., 1997, 154, 123-140; A. T. M. Serajuddin, Adv. Drug Delivery Rev., 2007, 59, 603-616; R. Banerjee, et. al., Cryst. Growth Des., 2005, 5, 2299-2309; S. K. Patil, et. al., Int. J. Pharm. Sci. Rev. Res., 2011, 8, 74-80; C. Leuner and J. Dressman, Eur. J. Pharm. Biopharm., 2000, 50, 47-60; M. C. Singh, et. al., J. Pharm. Res., 2010, 3, 2494-2501; P. Ettmayer, et. al., J. Med.Chem., 2004, 47, 2393-2404; V. J. Stella, J. Pharm. Sci., 2010, 99, 4755-4765; O. A. Cojocaru, et. al., Med. Chem. Commun., 2013, 4, 559-563; J. F. Remenar, et. al., J. Am. Chem. Soc., 2003, 125, 8456-8457; S. L. Childs, et. al., J. Am. Chem. Soc., 2004, 126, 13335-13342; A. V. Trask, et. al., Cryst. Growth Des., 2005, 5, 1013-1021; A. Alhalaweh, et. al., CrystEngComm, 2012, 14, 5078-5088; and, e.g., A. Choucair and A. Eisenburg, J. Am. Chem. Soc., 2003, 125, 11993-12000.) In recent years, other solutions to overcoming the challenges of amphotericin B limited solubility and high toxicity have emerged, such as use of, e.g., poly(D,L-lactide-co-glycolide) nanoparticles with amphotericin B.

Since its first clinical use in 1959, lipid formulations of amphotericin B have been commercialized, such as, for example, a colloidal dispersion formulation, a formulation utilizing a lipid complex, and a liposomal composition of amphotericin B. Such formulations are designed to promote slow release of amphotericin B and to limit (decrease) toxicity-related side effect(s). These formulations, however, are considerably expensive, and some reports indicate adverse health effects of their prolonged use.

An alternative approach to problematic API solubility which has gained attention in recent years is the use of ionic liquids. Use of ionic liquids has provided formulators with an additional tool for use in drug development, as is described in, e.g., Egorova, et. al., "Biological Activity of Ionic Liquids and Their Application in Pharmaceutics and Medicine," Chem. Rev. 2017,117,7132-7189.

United States patent publication number US2021/0361573 ("Mecozzi") discloses emulsion compositions (emulsions being a type of colloid) utilizing ionic liquid(s). The disclosure of Mecozzi is directed to, per the abstract therein, a nanoemulsion formulation comprising an ionic liquid composition, at least one polymer, a hydrophobic liquid, an aqueous liquid, and a hydrophobic or hydrophilic therapeutic agent, wherein the ionic liquid composition comprises an at least partially hydrophobic ionic liquid, wherein the at least partially hydrophobic ionic liquid comprises a di cation comprising two monocationic groups linked by a bridging group and wherein the bridging group provides an at least partially hydrophobic character, the ionic liquid composition optionally further including a hydrophilic ionic liquid which may include a quaternary ammonium group.

US2019/0388545 discloses compositions and methods described herein are topically applied to the skin with negligible or no skin irritation and can direct or prevent transport through the skin. The compositions contain neat ionic liquids, optionally in combination with a drug to be delivered. In a preferred embodiment, the compositions increase transdermal transport of the drug to be delivered. In some embodiments, the compositions disrupt bacterial biofilms. This is particularly beneficial in the treatment of antibiotic resistant skin infections. In other embodiments, the compositions direct delivery within the skin. In still other embodiments, the compositions prevent transfer of substances through the stratum corneum. The disclosed compositions and methods can be tuned and modified such that they can be used to treat or prevent a variety of different diseases and disorders.

Unfortunately, ionic liquids, too, present formulators with significant challenges. See, e.g., Shamshina, et. al., "Are Myths and Preconceptions Preventing Us from Applying Ionic Liquid Forms of Antiviral Medicines to the Current Health Crisis?" Int. J. Mol. Sci. 2020, 21, 6002. API-ionic liquids are often viscous and can cause problems in manufacturing, handling, and dosing. As ionic liquids are thought to be hygroscopic, impact on stability during manufacture, handling, and storage is a concern (see, e.g., Balk, A.; Holzgrabe, U.; Meinel, L. 'Pro et contra' ionic liquid drugs-Challenges and opportunities for pharmaceutical translation. Eur. J. Pharm. Biopharm. 2015, 94, 291-304.). Toxicity of ionic liquids is often considered a risk, or, at a minimum, an unknown. Further, ionic liquids are presumed less stable than solid crystalline state (see, e.g., FDA Guidance Document "Oral Solutions and Suspensions (8/94)," available at fda.gov/inspections-compliance-enforcement-and-criminal-investigations/inspection-guides/oral-solutions-and-suspensions-894).

Candidiasis, introduced above, is a fungal infection due to any type of *Candida* spp. (a type of yeast). Various Species of oral *Candida* include *C. albicans, C. glabrata, C. krusei, C. parapsilosis, C. pseudotropicalis, C. stellatoidea*, and *C. tropicalis*. Signs and symptoms include white patches on the tongue or other areas of the mouth and throat. Other symptoms may include soreness and problems swallowing. As such infections are often localized in the oral cavity, oral compositions are the preferred for candidiasis treatment. One proposed mechanism for oral delivery of a therapeutically effective amount of amphotericin B is via an oral film.

Serrano (supra) describes fast-dissolving orodispersible films with high API loading (1% w/w) made via a solvent casting method. The proposed approach allegedly enables amphotericin B to remain solubilized in saliva in equilibrium between the monomeric and dimeric states, and produces a local, antifungal effect. Disclosed amphotericin B-loaded orodispersible films combine dextran and/or maltodextrin as dextrose-derived-polymer film formers with cellulose-derived film formers (hydroxypropylmethyl/hydroxypropyl cellulose in a 1:4 weight ratio). Compositions further comprise sorbitol for taste masking, microcrystalline cellulose (Avicel 200) or microcrystalline cellulose-carboxymethylcellulose sodium (Avicel CL-611) for enhancing the mechanical strength of the film, and polyethylene glycol 400 and glycerol (present in a 1:1 w/w ratio) as plasticizers. Optimized amphotericin B orodispersible films therein, containing 1% amphotericin B, 25% dextran, 25% maltodextrin, 5% sorbitol, 10% Avicel 200, 10% polyethylene glycol 400, 10% glycerol, 3% hydroxypropylmethyl cellulose acetate succinate, and 12% hydroxypropyl cellulose), are described as possessing a fast disintegration time (60±3 seconds), quick release in artificial saliva (>80% in 10 minutes), high burst strength (2190 mN mm), and high efficacy against several Candida spp. (C. albicans, C. parapsilosis and C. krusei) (>15 mm inhibition halo). Disclosed films are stable for two weeks at room temperature (25° C.) and up to 1 year under refrigerated conditions. Aspects of orodispersible films are disclosed in Serrano which readers may find useful in putting certain aspects of the invention into practice, and accordingly this reference is specifically incorporated herein with respect to such film(s) and the production, use, or both, thereof.

US2021085622 discloses a pharmaceutical active-containing transmucosal polymer film delivery device. The polymer film comprises a polymer matrix and the film has a pH in the range of about 4 to about 9. A pharmaceutical active composition is disposed on a surface of the polymer film. The composition comprises at least one API in the form of particles having an average particle size of about 100 nm to about 5 microns, an anti-crystallization agent, and a pH adjusting agent. The concentration of the API is at least 20% w/w relative to the total weight of the API composition. The delivery device (film) exhibits a residence time in the mouth of a subject ranging from about 5 minutes to about 30 minutes and is substantially mucoadhesive to a mucosal surface when placed sublingually under the tongue or placed buccally at the inner lining of the cheek.

Finally, US2015/038594 discloses orodispersible films comprising a film-forming hydrophobic polymer, a disintegrant, a plasticizer and a stabilizer. The list of possible APIs deliverable by such films includes Amphotericin B.

Unfortunately, none of the above literature directed to orally dissolvable film preparations comprising amphotericin B have led to a successfully marketed product for the treatment of oral candidiasis, mucocutaneous candidiasis, and refractory mucocutaneous candidiasis. In fact, while the state of the art demonstrates that various attempts have been made to increase the solubility of amphotericin B and to provide new forms of amphotericin B to broaden its clinical utility, options for orally delivered amphotericin B, and, e.g., specifically film(s) of amphotericin B, remain painfully limited. Thus IV delivery, despite its negative side effects, remains the standard of care. Over the course of decades, no successful and commercially viable solution has been identified. Overcoming these challenges will take significant creativity and inventive ingenuity.

CONSTRUCTION, TERMS, AND ACRONYMS

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," or "embodiments"). The invention encompasses all aspects as described individually and as can be arrived at by any combination of such individual aspects. The breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower example(s) or description(s) provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" & "herein" mean "in this disclosure." The term "i.a." means "inter alia" or "among other things." "Also known as" is abbreviated "aka" or "AKA." "Elsewhere" means "elsewhere herein."

For conciseness, symbols are used where appropriate. E.g., "&" is used for "and," & "-" for "about." Symbols such as <and > are given their ordinary meaning (e.g., "5" means "less than or equal to" & "?" means "greater than or equal to"). A slash "/" can represent "or" ("AB" means "A or B") or identify synonyms of an element, as will be clear from context.

The inclusion of "(s)" after an element or a step indicates that 21 of such an element is present, step performed, and the like. E.g., "element(s)" means both 1 element or 2 elements, with the understanding that each thereof is an independent aspect of the invention. Uncontradicted, where an element is only provided in standard plural form (e.g., "compositions" as opposed to composition(s)), the reader should interpret such disclosure as encompassing a single composition as if presented as "composition(s)". Uncontradicted, any aspect disclosed herein in with an element or step expressed in the singular provides implicit support for a corresponding embodiment in which the element(s)/step(s) are present in the plural (two or more), and vice versa.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means any or all possible/suitable combinations of such elements/steps.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all of an intended function, without causing or imparting significant negative/detrimental impact.

Uncontradicted, heading(s) (e.g., "Construction, Terms . . . ") and subheadings are included for convenience and do not limit the scope of any aspect(s). Uncontradicted, aspect(s), step(s), or element(s) described under one heading can apply to other aspect(s) or step(s)/element(s) here.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "~," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing, e.g., ±5%, ±2%, ±1%, and ±0.5%.

This disclosure includes aspects associated with particular characteristics, such as amounts of components (or ranges thereof), In cases, several such characteristics of varying scope may be provided. Readers will understand that each such characteristic can be associated with particular properties that distinguish such aspects from other aspects, and, accordingly, each such range can be viewed as critical to a particular aspect of the invention, even if the associated results, properties, functions, etc., associated with such aspects are not directly communicated in association with such characteristics.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)."

Uncontradicted, any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both. Explicit listing of percentages of elements/steps in connection with aspects does not limit or contradict such implicit disclosure.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

The term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most," or "mostly," means detectably >50% (e.g., mostly comprises, predominately includes, etc., mean >50%) (e.g., a system that mostly includes element X is composed of >50% of element X). The term "generally" means 75% (e.g., generally consists of, generally associated with, generally comprises, etc., means 75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" an element mean comprising ≤~25% of an element and terms such as "substantially free" of an element mean comprising ≤~5% of an element.

In certain embodiments describing API(s), excipient(s), or both present in amounts of "at least" or "greater than" a given amount or, e.g., present in amounts of "no more than" or "no greater than" or "less than" a given amount, the reader should interpret such disclosure as disclosing, e.g., encompassing and explicitly including, such undefined low or high amount(s) ranging to the opposite amount (high or low) that is maximally/minimally therapeutically effective, typically suitable, or both. For example, use of the phrase "at least" (and similar descriptors) in connection with an amount of a component of a formulation or of an entire formulation/composition can be interpreted as at least the amount described but that is no more than a maximally suitable or therapeutically effective amount (in the individual or in a population, such as determined in a clinical study). Similarly, phrases such as "less than" (and similar descriptors) an indicated amount can be interpreted referring to an amount that is still suitable (including, where appropriate, no amount, e.g., 0 units of the indicated component) or therapeutically effective (e.g., an amount that results in a DOS result in a significant number of individuals in a well-controlled and adequate study) but is less than the indicated amount.

Constituents herein are typically present in "effective amounts," and uncontradicted, any described class/type of, e.g., excipient (often referred to as a "component" herein—e.g., a "solvent component" may include one or more solvent(s)) or specific excipient, or, e.g., in certain aspects active pharmaceutical ingredient(s) (API(s)) is understood to be present in the associated composition/formulation in an effective amount, which generally means, in this context, an amount that is effective for the described function(s) associated with the excipient/API (it being understood that some excipient or API compound(s)/ingredient(s) exhibit more than one effect). E.g., a solubilizing agent will be understood to be present in a composition/formulation in an amount that is effective to impart an indicated solubilizing effect, a solubilizing effect that is required for suitability of the composition, or an effect that imparts a detectable or significant solubilizing effect on a composition or constituent thereof (with respect to a comparator composition lacking the compound(s)/ingredient(s)).

The phrase "substantially identical" may be used in certain contexts to reflect that tests that would be considered substantially identical by those of skill in the art (not differing meaningfully in terms of outcome) or that component(s) or step(s) can achieve the same result in a similar way as a referenced set of component(s)/step(s) so as to not meaningfully differ in intended result and manner of achieving such a result. It will be appreciated that the phrase "substantially identical" in such contexts comprises the use of identical amounts, identical formulations, and identical conditions, or, e.g., in other respects, composition(s) demonstrate an identical performance as a comparator.

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition can be assembled in any suitable manner by any suitable method. In general, any methods and materials similar or equivalent to those described here can be used in the practice of embodiments. Uncontradicted, the use of ordinal numbers such as "first," "second," "third," etc. is to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

All original claims contained in this disclosure when filed are incorporated into this specification as if they were a part of the description.

Additional Terms, Concepts, and Acronyms

The following description of certain terms and acronyms is provided to assist readers in understanding the invention. Additional acronyms may be only provided in other parts of this disclosure and acronyms that are well known in the art may not be provided here.

Uncontradicted, reference to a "compound", e.g., an active pharmaceutical ingredient (API) compound, refers to any known or identifiable stereoisomer(s), enantiomer(s), diastereomer(s), tautomer(s), isotope(s), metabolite(s), prodrug(s), derivative(s) of such compounds, or pharmaceutically acceptable salt(s), hydrate(s), solvate(s) thereof, including compound(s) demonstrating sufficient chemical or physical similarity thereto, including analogues of any or all thereof, and e.g., compounds sharing at least 70% or greater similarity as defined by the Tanimoto rule of similarity (chemical, physical, or both) to any or all such compounds. In aspects, compound(s) herein can comprise one or more deuterium atoms, e.g., a sufficient number of deuterium atoms so as to detectably or significantly differentiate the compound(s) from that which would otherwise occur naturally relative to the presence of deuterium atom(s), such that the compound(s) is/are characterizable as deuterized compound(s). In aspects, compound(s) described herein are pharmaceutically acceptable compound(s). In aspects, compound(s) described herein are suitable for oral administration or for administration to the oral cavity of a mammalian recipient, such as, e.g., via an oral dissolve (orally dissolvable or orodispersible) film (ODF).

Uncontradicted, any description of weight is weight/ volume percent ("% w/v".) In certain aspects, values presented herein represent values in % w/v or percent by weight ("wt. %.")

Except where explicitly indicated or clearly indicated by context, "improved" herein means "increased." In aspects, "improved" means "reduced," such as with respect to the toxicity of a composition. Uncontradicted, terms such as "enhanced," "improved," and the like are used synonymously.

"Pharmaceutical suitability," "pharmaceutically suitable,", or similar phrases are phrases typically used to refer to compositions that are safe and effective for pharmaceutical administration and application, having sufficient potency, purity, strength, quality, and safety for pharmaceutical application, in cases specifically to oral delivery (or, e.g., delivery to the oral cavity of a mammalian recipient), as may be judged by regulatory authority review,
    and as established by, e.g., one or more well controlled and adequate clinical studies performed in compliance with generally prevailing regulatory authority standards. Composition(s) described as "pharmacologically/pharmaceutically suitable" should be interpreted to mean suitable for delivery, e.g. oral delivery, e.g., delivery to an oral cavity of a mammalian recipient, when provided in a potency, purity, strength, or quality making it safe for oral use. Component(s) described as "pharmacologically/pharmaceutically suitable" should be interpreted in a similar manner. Uncontradicted, a description of "suitability" implicitly means that the referenced element, step, etc., is pharmacologically/ pharmaceutically suitable or otherwise medically suitable (e.g., safe and effective as determined by proper nonclinical/clinical testing).

Excipients herein are typically present in "effective amounts," and, uncontradicted, any described class of excipient or specific excipient is understood to be present in the associated composition/formulation in an effective amount, which generally means, in this context, an amount that is effective for the described function(s) associated with the excipient (it being understood that some excipient compound(s)/ingredient(s) exhibit more than one effect). E.g., a tonicity agent will be understood to be present in a composition/formulation in an amount that is effective to impart an indicated tonicity effect, a tonicity effect that is required for suitability of the composition, or an effect that imparts a significant tonicity effect on a composition (with respect to a comparator composition lacking the compound(s)/ingredient(s)).

A "subject," "individual," or "patient," is used interchangeably herein, which refers to a vertebrate, preferably a mammal, more preferably a human. Where applicable, methods provided herein can be substituted by administration/application or effects in (or at the level of) tissues, cells or their progeny, e.g., of a biological entity, e.g., obtained in vitro or cultured in vitro and readers will understand that such aspects are implicitly disclosed where uncontradicted.

As used herein, in aspects, the phrase "in need thereof" means that the animal or mammal has been identified as having a need for, or potentially benefiting from the receipt of, the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent. In aspects, "in need thereof" means diagnosed by a qualified medical doctor or other authorized medical professional.

In aspects, methods of the invention are limited to treatment of those in need thereof. In aspects, methods also or alternatively encompass prevention of disease, prevention of disease progression, reduction of symptoms, and the like, delay of onset, and other aspects of prevention/prophylaxis. Readers will understand that both such characterizations are implicitly provided in any disclosure herein relating to treatment or prevention of any disease or condition.

As used herein, the terms "prevention" or "preventing" means, e.g., a reduction of the risk of acquiring a particular disease, condition, or disorder. As noted elsewhere, prevention can also or alternatively mean also delay in onset, delay in spread after onset, delay in severity upon onset, complete prevention, reduction of likelihood of incurrence of disease, reduction in likelihood of severity of disease impact, and the like.

As used herein, the terms "treat," "treated," or "treating" means therapeutic measures wherein the object is to slow down (lessen) or eliminate an undesired physiological condition, disorder, or disease, or obtain beneficial or desired clinical results.

For purposes of this invention, beneficial or desired clinical results include, but are not limited to, alleviation of one or more symptom(s); diminishment of extent of condition(s), disorder(s), or disease(s); stabilization (i.e., not worsening) of a state of condition(s), disorder(s), or disease(s); delaying the onset or slowing the progression of condition(s), disorder(s), or disease(s); amelioration of the condition, disorder, or disease state(s) or remission thereof (whether partial or total), whether detectable or undetectable; amelioration of at least one measurable physical parameter, not necessarily discernible by the patient; enhancement or improvement of condition(s), disorder(s) or disease(s); or any combination of any or all thereof.

In some cases, descriptions of terms and/or acronyms are repeated one or more times in the following portions of the disclosure to aid readability.

SUMMARY OF THE INVENTION

The embodiment(s) of the invention described and claimed herein have many attributes and aspects including, but not limited to, those set forth in, e.g., described or referenced in, this Summary. This Summary of the Invention ("Summary") is not intended to be all-inclusive, and the scope of the invention is not limited to or by the aspects, features, elements, or embodiments provided in this Summary, which is included for illustrative purposes only and not restriction. Any of the aspects described under this section can be combined with any other aspect described in this section or with any other aspect of this disclosure.

In certain aspects, the invention provides ionic liquid-surfactant-solubilizer-complexing system(s). In aspects, the ionic liquid-surfactant-solubilizer-complexing system improves the solubility of one or more active pharmaceutical ingredient(s) (API(s)), such as, e.g., amphotericin B.

According to certain aspects, the invention provides ionic liquid-surfactant-solubilizer complexing system(s) wherein the system(s) comprise an API; at least two complexing agent(s); agent(s) providing detectable or significant pH modulating activity, wherein, in aspects such a pH modulating agent(s) provide one or more detectable or significant functional activity(ies) which are different from pH modulation; a solvent system comprising solvent compound(s) and, in aspects, acidifying agent(s) wherein, in aspects, the acidifying agent(s) provide(s) one or more detectable or significant functional activity(ies) which are different from solvent acidification; and at least one solubilizing agent.

According to certain aspects, the invention provides ionic liquid-surfactant-solubilizer-complexing system(s), or, e.g., ionic liquid compositions or, e.g., ionic liquid form(s) of API(s), in a form suitable for local oral delivery of the API(s). In aspects, the invention provides such system(s) in the form of an oral dissolve (orally dissolving or orodispersible) ("ODF") film. In aspects, such system(s) are used to treat local oral microbial infections, such as local oral fungal infections, such as, e.g., local oral candidiasis. In aspects, herein, use of "local" means, e.g., at least generally, at least substantially, at least essentially, essentially, or completely provided within a defined area, anatomical region or part, or feature. For example, in aspects, "local oral delivery" refers to delivery (of, e.g., composition(s) or API(s) of composition(s)) to an at least generally contained, at least substantially contained, at least essentially contained, essentially contained, or contained region such as an oral cavity. In aspects, local delivery is used to differentiate from systemic delivery, e.g., delivery via the bloodstream.

In aspects, the invention provides ionic liquid-surfactant-solubilizer complexing system(s) which can be referred to or characterized as ionic liquid compositions or, e.g., ionic liquid form(s) of specific API(s) present in the system (such as, e.g., amphotericin B).

In certain aspects, the invention provides ionic liquid-surfactant-solubilizer complexing system(s) comprising amphotericin B. In aspects, ionic liquid-surfactant-solubilizer complexing system(s) of amphotericin B are referred to or characterized as ionic liquid composition(s) of amphotericin B. In aspects, ionic liquid-surfactant-solubilizer complexing system(s) of amphotericin B are referred to or characterized as ionic liquid(s) of amphotericin B. In aspects, ionic liquid-surfactant-solubilizer complexing system(s) of amphotericin B are referred to or characterized as amphotericin B in ionic liquid form. In aspects, ionic liquid(s) of amphotericin B is/are suitable for use as a component in other composition(s), e.g., in the formulation of, or formation of, an oral dissolve (orally dissolving or orodispersible) ("ODF") film. In aspects, the invention provides effective ODF(s), e.g., ODF composition(s), comprising amphotericin B, e.g., amphotericin B in ionic liquid form. In aspects, ODF(s) provided herein are suitable for use in the treatment of, and are, e.g. effective in the treatment of, oral candidiasis, mucocutaneous candidiasis, and, e.g., refractory mucocutaneous candidiasis. In aspects, ionic liquid form(s) of amphotericin B provided herein provide an increased solubility of the API; a reduced minimum inhibitory concentration of the API against common agents associated with oral fungal infection(s); an increased therapeutic efficacy against one or more infective agent(s) when administered orally, e.g., by ODF; or any combination of any or all thereof. In aspects here and throughout this disclosure, an ODF includes an "oral thin film" or "OTF." In aspects herein, oral delivery is limited to a delivery mechanism such as an ODF which acts locally, e.g., within the oral cavity, and at least generally does not, at least substantially does not, at least essentially does not, essentially does not, or does not act via ingestion (e.g., via passage through the gastrointestinal tract such as that demonstrated by other forms of oral delivery such as, e.g., a tablet or capsule.) In aspects, as described herein, while a detectable amount of API delivered by oral delivery, e.g., ODF(s) described herein, may pass through at least a portion of the gastrointestinal tract, at least generally all, at least substantially all, at least essentially all, or essentially all of the API(s), e.g., amphotericin B, in an oral delivery form described herein, e.g., ODF(s), is delivered locally.

In certain aspects, the invention provides an ionic liquid form of amphotericin B, e.g., amphotericin B in ionic liquid form. In certain aspects, the invention provides antimicrobial ionic liquid composition(s), the composition(s) comprising (1) an antimicrobial component comprising at least one antimicrobial agent (e.g., amphotericin B), (2) a complexing agent component comprising at least a first complexing agent and a second complexing agent, each of the first and the second complexing agents forming a complex with the at least one antimicrobial agent, (3) a solvent component comprising at least one acidified solvent agent, (4) and a solubilizing component comprising at least one solubilizing agent which detectably or significantly increases the solubilization of at least one of the at least one antimicrobial agents. In aspects, constituents of the antimicrobial ionic liquid(s) are present in specific ratios, e.g., are present in carefully selected amounts relative to one another. In aspects, the antimicrobial agent is, e.g., an antifungal agent, such as, e.g., amphotericin B. In aspects, complexing agent(s) comprise ascorbic acid, choline chloride, or both. In aspects, the solvent component comprises dimethyl acetamide. In aspects, a single compound, e.g., ascorbic acid, both acidifies a solvent agent of the solvent component (e.g., dimethyl acetamide) and forms a complex with the antimicrobial agent, e.g., amphotericin B. In aspects, the solubilization component comprises D-a-Tocopheryl polyethylene glycol 1000 succinate (TPGS). In aspects, the invention provides antimicrobial ionic liquid composition(s) of amphotericin B in ionic liquid form, wherein the composition(s) comprise the component(s) of this paragraph.

In some aspects, the invention provides ODF(s) comprising ionic liquid composition(s), e.g., ionic liquid composition(s) such as those described above. In aspects, the ODF(s) comprise an ionic liquid composition of amphotericin B (e.g., comprise amphotericin B in ionic liquid form). In aspects, the ODF(s) comprise ionic liquid composition such as ionic liquid composition(s) described in this summary in addition to a film-inducing component comprising, e.g., a film-forming component, plasticizer component, or both.

According to certain specific aspects, the invention provides ODF(s) comprising (1) an antimicrobial ionic liquid composition, the composition comprising (a) an antimicrobial component comprising at least one antimicrobial agent, (b) a complexing agent component comprising at least a first complexing agent and a second complexing agent, each of the first and the second complexing agents forming a complex with the at least one antimicrobial agent, (c) a solvent component comprising at least one acidified solvent agent, and (d) a solubilizing component comprising at least one solubilizing agent which detectably or significantly increases the solubilization of at least one of the at least one antimicrobial agents; and (2) a film-inducing component wherein the film-forming component comprises (e) a film-forming component comprising one or more film-forming polymer(s) and (f) a plasticizer component comprising one or more plasticizing agent(s). In aspects, constituents of the ODF(s) are present in specific ratios, e.g., are present in carefully selected amounts relative to one another. In aspects, the antimicrobial agent is, e.g., an antifungal agent, such as, e.g., amphotericin B. In aspects, complexing agent(s) comprise ascorbic acid, choline chloride, or both. In aspects, the solvent component comprises dimethyl acetamide. In aspects, a single compound, e.g., ascorbic acid, both acidifies a solvent agent of the solvent component (e.g., dimethyl acetamide) and forms a complex with the antimicrobial agent, e.g., amphotericin B. In aspects, the solubilization component comprises D-a-Tocopheryl polyethylene glycol 1000 succinate (TPGS). In aspects, the film-inducing component comprises polyvinyl alcohol and glycerol. In aspects, ODF(s) comprise an ionic liquid antimicrobial API component, wherein the antimicrobial API component comprises amphotericin B in ionic liquid form.

In certain respects, the invention provides ionic liquid form(s) of amphotericin B provided as ODF(s) which exhibit(s) (e.g., wherein the amphotericin B in ionic liquid form therein exhibit(s)) detectably or significantly increased solubility of amphotericin B in water, saliva, acid pH environments such as those found in the gastrointestinal tract, or any combination of any or all thereof, compared to unmodified amphotericin B. In certain further respects, the invention provides ODF(s) comprising ionic liquid form(s) of amphotericin B which demonstrate(s) (wherein the amphotericin B in ionic liquid form demonstrate(s)) a reduced minimum inhibitory concentration (MIC) against *Candida* spp., specifically, e.g., species of *Candida* which are commonly identified with oral fungal infection(s).

In certain respects, the invention provides amphotericin B in a form suitable for self-administration, e.g., self-administration for the treatment of an oral fungal infection. In aspects, the invention provides amphotericin B in as an ODF wherein a mammal, e.g., a human in need of treatment therefrom, can self-administer ODF(s) without being present at a medical facility (e.g., healthcare provider's office or hospital), without being under the care of an attending medical professional, or both. In aspects, ODF(s) provided herein are suitable for delivering a therapeutically effective dose of an antimicrobial API, such as, e.g., an antifungal API, e.g., amphotericin B for the treatment of oral microbial infection(s), e.g., oral fungal infection(s), e.g., oral candidiasis, mucocutaneous candidiasis, and, e.g., refractory mucocutaneous candidiasis, in environments where receiving extensive or extended medical care at a medical facility is challenging, such as in third world countries or remote areas of the globe.

According to certain aspects, the invention provides amphotericin B in a form suitable for treating a local infection of the oral cavity, such as, e.g., a fungal infection of the oral cavity of a mammal, e.g., a human, wherein the total amount of amphotericin B per dose, the total amount of amphotericin B delivered per day, the total amount of amphotericin B administered over the course of an effective treatment of the local infection is detectably or significantly less than that required to effectively treat at least generally the same, at least substantially the same, at least essentially the same, essentially the same, or the same local infection by amphotericin B administered systemically (e.g., by IV, by passage through the gastrointestinal tract, or, e.g., either or both thereof.)

According to certain aspects, the invention provides amphotericin B in a form suitable for treating a local infection of the oral cavity, such as, e.g., a fungal infection of the oral cavity of a mammal, e.g., a human, wherein the total amount of amphotericin B per dose, the total amount of amphotericin B delivered per day, the total amount of amphotericin B administered over the course of an effective treatment of the local infection is detectably or significantly less than that required to effectively treat at least generally the same, at least substantially the same, at least essentially the same, essentially the same, or the same local infection by one or more other antifungal drugs, such as, e.g., fluconazole.

In aspects, patient compliance with a prescribed treatment of composition(s) described herein, e.g., ODF(s) comprising amphotericin B, to effectively treat a local oral fungal infection is detectably or significantly higher than that demonstrated in the treatment of at least generally the same, at least substantially the same, at least essentially the same, essentially the same, or the same local infection by amphotericin B administered systemically (e.g., by IV, by passage through the gastrointestinal tract, or, e.g., either or both thereof.)

According to certain aspects, the invention provides methods of treating oral microbial infection(s), e.g., oral fungal infection(s), e.g., oral candidiasis, mucocutaneous candidiasis, and, e.g., refractory mucocutaneous candidiasis, the methods comprising administration of therapeutically effective amount(s) of amphotericin B in ionic liquid form, such as, e.g., via ODF(s) comprising amphotericin B in ionic liquid form such as ODF(s) described in this summary. In certain further aspects, the invention provides method(s) of manufacturing ionic liquid(s) of amphotericin B suitable for oral administration and, e.g., ODF(s) comprising such ionic liquid composition(s). According to certain aspects, the invention provides a process for manufacturing ODF(s) comprising preparing an ionic liquid of amphotericin B wherein the ionic liquid comprises the inclusion of at least one solubility enhancing agent; combining the ionic liquid of amphotericin B with at least one film-forming agent and at least one plasticizer agent to form a film; and casting the film such that an administrable form of the ODF may be attained.

According to certain aspects, the invention provides an antifungal ionic liquid composition of amphotericin B comprising (1) amphotericin B; (2) a complexing agent component comprising at least two complexing agents, wherein the at least two complexing agents comprises a first complexing agent and a second complexing agent, each of the first complexing agent and the second complexing agent forming a complex with amphotericin B; (3) a solvent component comprising a solvent compound and a solvent acidifying agent forming an acidified solvent, wherein the solvent acidifying agent further (a) represents one of the first or the second complexing agents forming a complex with amphotericin B, (b) modulates the pH of the composition, or (c) both (a) and (b); and (4) a solubilizing component comprising at least one solubilizing agent which detectably or significantly increases the solubilization of the amphotericin B. In aspects, compositions comprise an ODF comprising the ionic liquid composition described in this paragraph. In aspects, ODFs described in this paragraph are used in the formation of a medicament for the treatment of one or more infectious conditions, such as, e.g., oral candidiasis. In aspects, the ODFs described in this paragraph are used in methods to treat oral candidiasis. In aspects, amphotericin B provided in the ionic liquid composition(s) and ODF(s) described here have a solubility in water of at least about 3 mg/mL, such as, e.g., between about 3 mg/mL and about 5 mg/mL. In aspects, the invention provides ODF film(s) such as those described in this paragraph wherein the oral dissolve film delivers a localized concentration of amphotericin B to the oral cavity of the recipient when the oral dissolve film is dissolved in the oral cavity of the recipient, wherein the localized concentration of amphotericin B available for treating a microbial source of the oral candidiasis is detectably or significantly greater than that provided by an orally delivered, intravenously delivered, or either orally or intravenously delivered treatment comprising amphotericin B.

BRIEF DESCRIPTION OF THE DRAWINGS/FIGURES

The drawings/figures provided here and the associated following brief description of figures are intended to exemplify certain aspects and principles of the invention without limiting its scope.

FIG. 1 provides a DSC thermograph of unmodified amphotericin B and an exemplary amphotericin B ODF.

FIGS. 2A, 2B, and 2C provide black and white photographs of the zone of inhibition results from in vitro antifungal assays testing unmodified amphotericin B and exemplary amphotericin B ODF(s) provided by the invention against *Candida albicans*.

FIGS. 3A, 3B, and 3C provide black and white photographs of the zone of inhibition results from in vitro antifungal assays testing unmodified amphotericin B and amphotericin B ODF(s) provided by the invention against *Candida tropicalis*.

Figure 4:
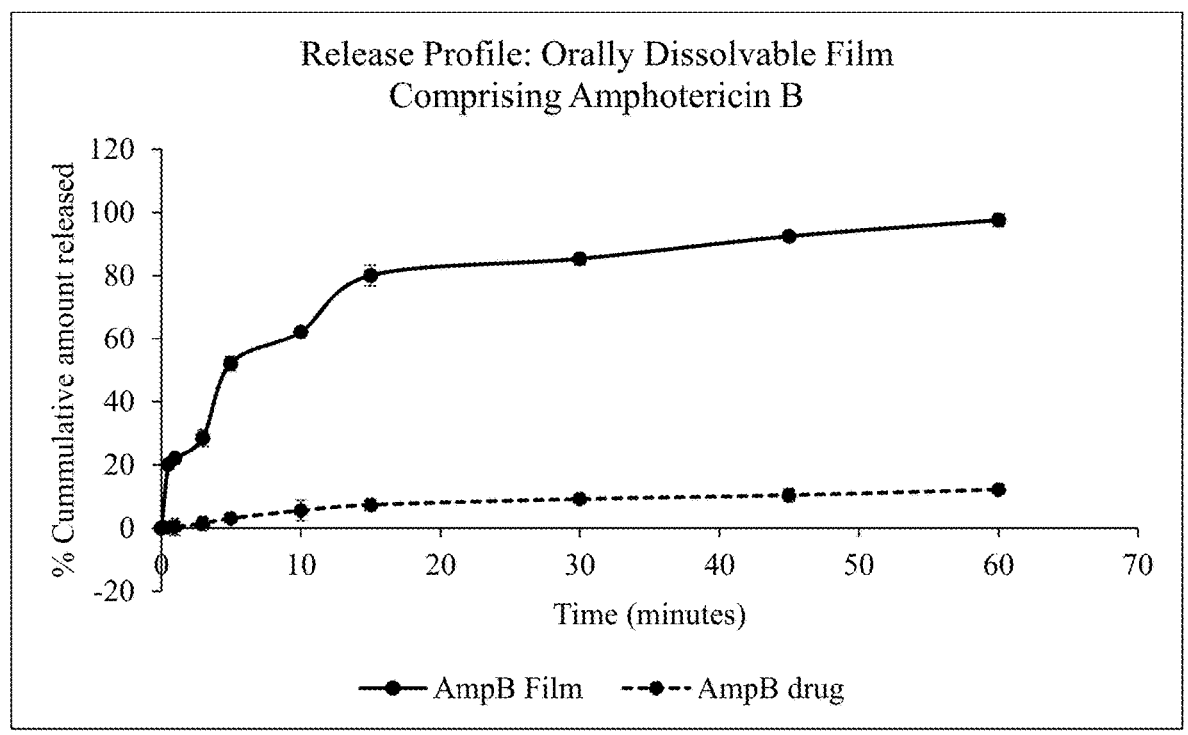

FIG. 4 illustrates a release profile of an ODF comprising amphotericin B provided by the invention compared to unmodified amphotericin B.

Figure 5:
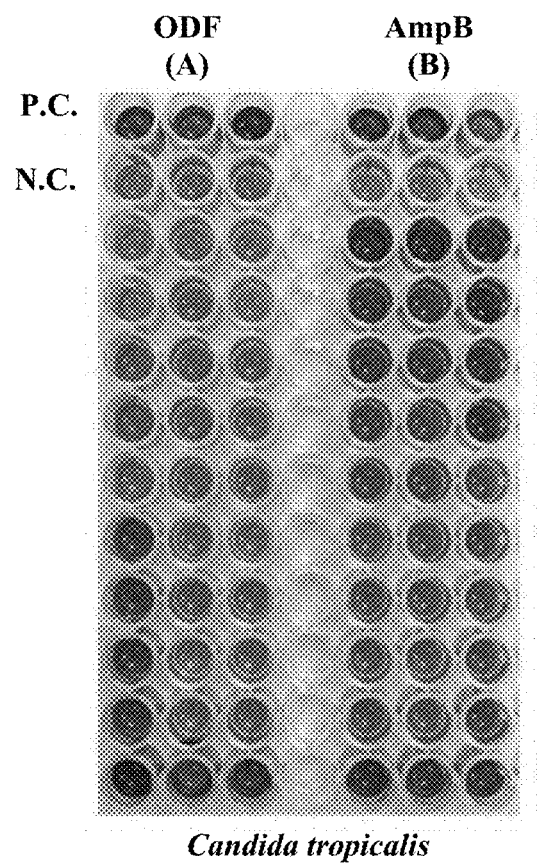
Figure 5:
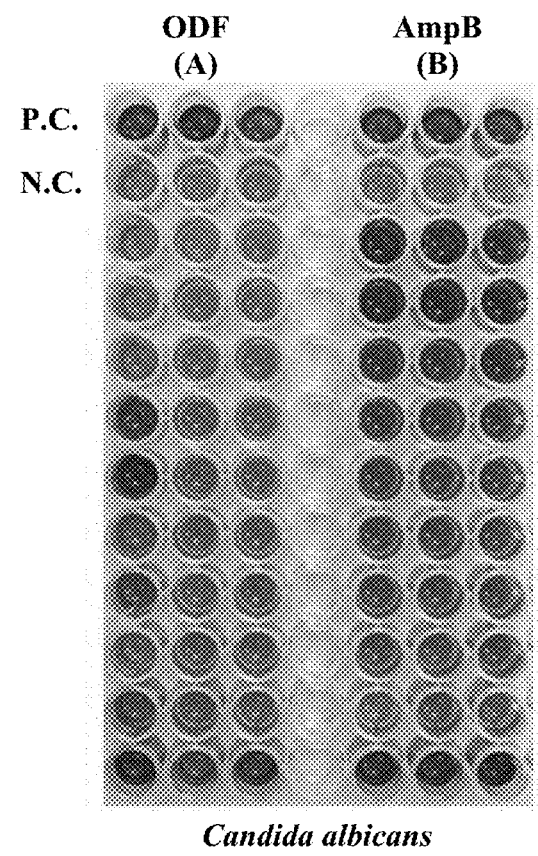

FIG. 5 provides results of a resazurin microtiter assay (REMA) assay performed to compare the minimum inhibitory concentration of ODF(s) provided by the invention to that of unmodified amphotericin B against *Candida tropicalis* and *Candida albicans*.

EXEMPLARY ASPECTS OF THE INVENTION

The following is a non-limiting list of exemplary aspects of the invention, which illustrates embodiments of the invention in a summary form to aid readers in quickly understanding the overall scope of the invention. Similar to patent claims, listed aspects described in the paragraphs of this section may make reference to (depend on/from) one or more other paragraphs. Readers will understand that such references mean that the features/characteristics or steps of such referenced aspects are incorporated into/combined with the referring aspect. E.g., if an aspect in a paragraph (e.g., a paragraph indicated by text at the end of the paragraph as aspect 2) refers to another aspect by one or more aspect numbers (e.g., aspect 1 or "any one or more of aspects 1-3"), it will be understood to include the elements, steps, or characteristics of such referenced aspects (e.g., aspect 1) in addition to those of the aspect in which the reference is made (e.g., if aspect 2 refers to aspect 1, it provides a description of a composition, method, system, device, etc., including the features of aspect 1 and aspect 2).

Lists of aspects describing specific exemplary embodiments of the invention are sometimes employed for aiding the reader in understanding the invention. Such aspects can, within them, reference other exemplary aspects, either individually or as groups of aspects (e.g., via reference to a range within a list of numbered aspects when such aspects are provided as a numbered list). Reference to ranges of aspects should be interpreted as referencing all such aspects individually, each as unique embodiments of the invention, and in combination with one another as unique embodiment(s) of the invention, according to the presentation provided of such aspects unless such an aspect within such a referenced range is either contradictory or non-sensical. If contradicted, reference to the contradictory aspect should be excluded.

In a first aspect, the invention provides an antimicrobial ionic liquid composition, the composition comprising (1) an antimicrobial component comprising at least one antimicrobial agent, (2) a complexing agent component comprising at least a first complexing agent and a second complexing agent, each of the first and the second complexing agents forming a complex with the at least one antimicrobial agent, (3) a solvent component comprising at least one acidified solvent agent, (4) and a solubilizing component comprising at least one solubilizing agent which detectably or significantly increases the solubilization of at least one of the at least one antimicrobial agents. (ASPECT 1.)

In aspects, the invention provides the composition of aspect 1, wherein the antimicrobial component comprises at least one antifungal agent. (ASPECT 2.)

In aspects, the invention provides composition(s) of any or both of aspects 1-2, wherein the antimicrobial component comprises an amphotericin B compound. (ASPECT 3.)

In aspects, the invention provides the composition of any one or more of aspects 1-3, wherein the complexing agent component comprises a first complexing agent and a second complexing agent. (ASPECT 4.)

In aspects, the invention provides the composition of any one or more of aspects 1-4, wherein the first complexing agent is an ionic liquid anion. (ASPECT 5.)

In aspects, the invention provides the composition of any one or more of aspects 1-5, wherein the first complexing agent is ascorbic acid. (ASPECT 6.)

In aspects, the invention provides the composition of any one or more of aspects 1-6, wherein the first complexing agent (1) forms a complex with at least one of the at least one antimicrobial agents and (2) detectably or significantly acidifies the at least one solvent agent of the solvent component. (ASPECT 7.)

In aspects, the invention provides the composition of any one or more of aspects 1-7, wherein the second complexing agent is an ionic liquid cation. (ASPECT 8.)

In aspects, the invention provides the composition of any one or more of aspects 1-8, wherein the second complexing agent is a choline compound. (ASPECT 9.)

In aspects, the invention provides the composition of any one or more of aspects 1-9, wherein the second complexing agent is choline chloride. (ASPECT 10.)

In aspects, the invention provides the composition of any one or more of aspects 1-10, wherein the solvent component comprises a single acidified solvent agent. (ASPECT 11.)

In aspects, the invention provides the composition of any one or more of aspects 1-11, wherein the solvent agent (1) is an organic compound; (2) is an alkyl compound; (3) is a polar compound; (4) is water-miscible; (5) comprises between about 3 carbon atoms and about 10 carbon atoms; (6) comprises between 1 nitrogen atom and about 3 nitrogen atoms; (7) has a boiling point of between about 150° C. (about 329° F.)-about 180° C.; (8) has a molecular weight of between about 70 g/mol and about 100 g/mol; (9) is hygroscopic; or (10) comprises any combination of any two or more of the characteristics described in (1)-(9). (ASPECT 12.)

In aspects, the invention provides the composition of any one or more of aspects 1-12, wherein the solvent agent is dimethyl acetamide. (ASPECT 13.)

In aspects, the invention provides the composition of any one or more of aspects 1-13, wherein the solubilizing component comprises a single solubilizing agent. (ASPECT 14.)

In aspects, the invention provides the composition of any one or more of aspects 1-14, wherein the solubilizing component comprises a surfactant. (ASPECT 15.)

In aspects, the invention provides the composition of any one or more of aspects 1-15, wherein the solubilizing component comprises a non-ionic surfactant. (ASPECT 16.)

In aspects, the invention provides the composition of any one or more of aspects 1-16, wherein the solubilizing component comprises D-a-Tocopheryl polyethylene glycol 1000 succinate (TPGS). (ASPECT 17.)

In aspects, the invention provides the composition of any one or more of aspects 1-17, wherein the composition comprises an antimicrobial component in an amount representing between about 0.5% w/v and about 10% w/v of the composition. (ASPECT 18.)

In aspects, the invention provides the composition of any one or more of aspects 1-18, wherein the composition comprises an antimicrobial component comprising an antifungal agent, and the antifungal agent is present in the composition in an amount representing between about 0.5% w/v and about 10% w/v of the composition. (ASPECT 19.)

In aspects, the invention provides the composition of any one or more of aspects 1-19, where the composition comprises an antimicrobial component comprising an amphotericin B compound, and the amphotericin B compound is present in the composition in an amount representing between about 0.5% w/v and about 10% w/v of the composition. (ASPECT 20.)

In aspects, the invention provides the composition of any one or more of aspects 1-20, wherein the complexing agent component of the composition is present in an amount representing between about 5% w/v and about 50% w/v of the composition. (ASPECT 21.)

In aspects, the invention provides the composition of any one or more of aspects 1-21, where (i.e., wherein) the first complexing agent of the complexing agent component of the composition is present in an amount representing between about 5% w/v and about 30% w/v of the composition. (ASPECT 22.)

In aspects, the invention provides the composition of any one or more of aspects 1-22, wherein the first complexing agent of the complexing agent component of the composition is present in an amount representing between about 20% and about 99% of the complexing agent component. (ASPECT 23.)

In aspects, the invention provides the composition of any one or more of aspects 1-23, wherein the second complexing agent of the complexing agent component of the composition is present in an amount representing between about 0.1% w/v and about 20% w/v of the composition. (ASPECT 24.)

In aspects, the invention provides the composition of any one or more of aspects 1-24, wherein the second complexing agent of the complexing agent component of the composition is present in an amount representing between about 0.3% and about 80% of the complexing agent component. (ASPECT 25.)

In aspects, the invention provides the composition of any one or more of aspects 1-25, wherein the solvent component is present in an amount representing between about 0.5% w/v and about 10% w/v of the composition. (ASPECT 26.)

In aspects, the invention provides the composition of any one or more of aspects 1-26, wherein the solubilizing component is present in an amount representing between about 0.1% w/v and about 20% w/v of the composition. (ASPECT 27.)

In aspects, the invention provides the composition of any one or more of aspects 1-27, wherein the ratio of the concentration (% w/v) of the antimicrobial component to the concentration of the complexing agent component (% w/v) is between about 2:1 and about 1:100. (ASPECT 28.)

In aspects, the invention provides the composition of any one or more of aspects 1-28, wherein the ratio of the concentration (% w/v) of the antimicrobial component to the concentration of the complexing agent component (% w/v) is about 1:10.4. (ASPECT 29).

In aspects, the invention provides the composition of any one or more of aspects 1-29, wherein the antimicrobial component comprises an amphotericin B compound, and the ratio of the concentration (% w/v) of amphotericin B compound to the concentration of the complexing agent component (% w/v) is about 1:10. (ASPECT 30.)

In aspects, the invention provides the composition of any one or more of aspects 1-30, wherein the ratio of the concentration (% w/v) of the antimicrobial component to the concentration (% w/v) of the first complexing agent of the complexing agent component is between about 2:1 and about 1:60. (ASPECT 31.)

In aspects, the invention provides the composition of any one or more of aspects 1-31, wherein the ratio of the concentration (% w/v) of the antimicrobial component to the concentration (% w/v) of the first complexing agent of the complexing agent component is about 1:8.3. (ASPECT 32.)

In aspects, the invention provides the composition of any one or more of aspects 1-32, wherein the antimicrobial component comprises an amphotericin B compound, the first complexing agent of the complexing agent component is ascorbic acid, and the ratio of the concentration (% w/v) of the amphotericin B compound to the concentration (% w/v) of the ascorbic acid is about 1:8.3. (ASPECT 33.)

In aspects, the invention provides the composition of any one or more of aspects 1-33, wherein the ratio of the concentration (% w/v) of the antimicrobial component to the concentration (% w/v) of the second complexing agent of the complexing agent component is between about 100:1 and about 1:40. (ASPECT 34.)

In aspects, the invention provides the composition of any one or more of aspects 1-34, wherein the ratio of the concentration (% w/v) of the antimicrobial component to the concentration (% w/v) of the second complexing agent of the complexing agent component is about 1:2.1. (ASPECT 35.)

In aspects, the invention provides the composition of any one or more of aspects 1-35, wherein the antimicrobial component comprises an amphotericin B compound, the second complexing agent of the complexing agent component is choline chloride, and the ratio of the concentration (% w/v) of the amphotericin B compound to the concentration (% w/v) of the choline chloride acid is about 1:2.1. (ASPECT 36.)

In aspects, the invention provides the composition of any one or more of aspects 1-36, wherein the ratio of the concentration (% w/v) of the antimicrobial component to the concentration (% w/v) of the solubilizing component is between about 100:1 and about 1:40. (ASPECT 37.)

In aspects, the invention provides the composition of any one or more of aspects 1-37, wherein the ratio of the concentration (% w/v) of the antimicrobial component to the concentration (% w/v) of the solubilizing component is about 1:2.1. (ASPECT 38.)

In aspects, the invention provides the composition of any one or more of aspects 1-38, where the antimicrobial component comprises an amphotericin B compound, the solubilizing component comprises TPGS, and the ratio of concentration (% w/v) of the amphotericin B compound to the concentration (% w/v) of TPGS is about 1:2.1. (ASPECT 39.)

In aspects, the invention provides the composition of any one or more of aspects 1-39, wherein the ratio of the concentration (% w/v) of the antimicrobial component to the concentration (% w/v) of the solvent component is between about 20:1 and about 1:20. (ASPECT 40.)

In aspects, the invention provides the composition of any one or more of aspects 1-40, wherein the ratio of the concentration (% w/v) of the antimicrobial component to the concentration (% w/v) of the solvent component is about 1:2.1. (ASPECT 41.)

In aspects, the invention provides the composition of any one or more of aspects 1-41, wherein the antimicrobial component comprises an amphotericin B compound, the solvent component comprises dimethyl acetamide, and the ratio of the concentration (% w/v) of the amphotericin B compound to the concentration (% w/v) of the dimethyl acetamide is about 1:2.1. (ASPECT 42.)

In aspects, the invention provides the composition of any one or more of aspects 1-42, wherein the ratio of the concentration (% w/v) of the first complexing agent of the complexing agent component to the concentration (% w/v) of the second complexing agent of the complexing agent component is between about 300:1 and about 1:4. (ASPECT 43.)

In aspects, the invention provides the composition of any one or more of aspects 1-43, wherein the ratio of the concentration (% w/v) of the first complexing agent of the complexing agent component to the concentration (% w/v) of the second complexing agent of the complexing agent component is about 4:1. (ASPECT 44.)

In aspects, the invention provides the composition of any one or more of aspects 1-41, wherein the first complexing agent of the complexing agent component is ascorbic acid, the second complexing agent of the complexing agent component is choline chloride, and the ratio of the concentration (% w/v) of the ascorbic acid to the concentration (% w/v) of the choline chloride is about 4:1. (ASPECT 45.)

In aspects, the invention provides the composition of any one or more of aspects 1-45, wherein the ratio of the concentration (% w/v) of the first complexing agent of the complexing agent component to the concentration (% w/v) of the solubilization component is between about 300:1 and about 1:4. (ASPECT 46.)

In aspects, the invention provides the composition of any one or more of aspects 1-46, wherein the ratio of the concentration (% w/v) of the first complexing agent of the complexing agent component to the concentration (% w/v) of the solubilization component is about 4:1. (ASPECT 47.)

In aspects, the invention provides the composition of any one or more of aspects 1-47, wherein the first complexing agent of the complexing agent component is ascorbic acid, the solubilization component comprises TPGS, and the ratio of the concentration (% w/v) of the ascorbic acid to the concentration (% w/v) of the TPGS is about 4:1. (ASPECT 48.)

In aspects, the invention provides the composition of any one or more of aspects 1-48, wherein the ratio of the concentration (% w/v) of the first complexing agent of the complexing agent component to the concentration (% w/v) of the solvent component is between about 60:1 and about 1:2. (ASPECT 49.)

In aspects, the invention provides the composition of any one or more of aspects 1-49, wherein the ratio of the concentration (% w/v) of the first complexing agent of the complexing agent component to the concentration (% w/v) of the solvent component is about 4:1. (ASPECT 50.)

In aspects, the invention provides the composition of any one or more of aspects 1-50, where the first complexing agent of the complexing agent component is ascorbic acid, the solvent component comprises dimethyl acetamide, and the ratio of the concentration (% w/v) of the ascorbic acid to the concentration (% w/v) of the dimethyl acetamide is ~4:1. (ASPECT 51.)

In aspects, the invention provides the composition of any one or more of aspects 1-51, wherein the ratio of the concentration (% w/v) of the first complexing agent of the complexing agent component to the concentration (% w/v) of the complexing agent component is between about 6:1 and about 1:10. (ASPECT 52.)

In aspects, the invention provides the composition of any one or more of aspects 1-52, wherein the ratio of the concentration (% w/v) of the first complexing agent of the complexing agent component to the concentration (% w/v) of the complexing agent component is about 1:1.3. (ASPECT 53).

In aspects, the invention provides the composition of any one or more of aspects 1-53, wherein the first complexing agent of the complexing agent component is ascorbic acid and the ratio of the concentration (% w/v) of the ascorbic acid to the concentration (% w/v) of the complexing agent component is about 1:1.3. (ASPECT 54.)

In aspects, the invention provides the composition of any one or more of aspects 1-54, wherein the ratio of the concentration (% w/v) of the second complexing agent of the complexing agent component to the concentration (% w/v) of the solubilization component is between about 200:1 and about 1:200. (ASPECT 55.)

In aspects, the invention provides the composition of any one or more of aspects 1-55, wherein the ratio of the concentration (% w/v) of the second complexing agent of the complexing agent component to the concentration (% w/v) of the solubilization component is about 1:1. (ASPECT 56.)

In aspects, the invention provides the composition of any one or more of aspects 1-56, wherein the second complexing agent of the complexing agent component is choline chloride, the solubilization component comprises TPGS, and the ratio of the concentration (% w/v) of the choline chloride to the concentration (% w/v) of the TPGS is ~1:1. (ASPECT 57.)

In aspects, the invention provides the composition of any one or more of aspects 1-57, wherein the ratio of the concentration (% w/v) of the second complexing agent of the complexing agent component to the concentration (% w/v) of the solvent component is between about 10:1 and about 1:100. (ASPECT 58.)

In aspects, the invention provides the composition of any one or more of aspects 1-58, wherein the ratio of the concentration (% w/v) of the second complexing agent of the complexing agent component to the concentration (% w/v) of the solvent component is about 1:1. (ASPECT 59.)

In aspects, the invention provides the composition of any one or more of aspects 1-59, wherein the second complexing agent of the complexing agent component is choline chloride, the solvent component comprises DMA, and the ratio of the concentration (% w/v) of the choline chloride to the concentration (% w/v) of the DMA is about 1:1. (ASPECT 60.)

In aspects, the invention provides the composition of any one or more of aspects 1-60, wherein the ratio of the concentration (% w/v) of the second complexing agent of the complexing agent component to the concentration (% w/v) of the complexing agent component is between about 4:1 and about 1:500. (ASPECT 61.)

In aspects, the invention provides the composition of any one or more of aspects 1-61, wherein the ratio of the concentration (% w/v) of the second complexing agent of the complexing agent component to the concentration (% w/v) of the complexing agent component is about 1:5. (ASPECT 62.)

In aspects, the invention provides the composition of any one or more of aspects 1-62, wherein the second complexing agent of the complexing agent component is choline chloride and the ratio of the concentration (% w/v) of the choline chloride to the concentration (% w/v) of the complexing agent component is about 1:5. (ASPECT 63.)

In aspects, the invention provides the composition of any one or more of aspects 1-63, wherein the ratio of the concentration (% w/v) of the solubilization component to the concentration (% w/v) of the solvent component is between about 40:1 and about 1:100. (ASPECT 64.)

In aspects, the invention provides the composition of any one or more of aspects 1-64, wherein the ratio of the concentration (% w/v) of the solubilization component to the concentration (% w/v) of the solvent component is about 1:1. (ASPECT 65.)

In aspects, the invention provides the composition of any one or more of aspects 1-65, wherein the solubilization component comprises TPGS, the solvent component comprises dimethyl acetamide, and the ratio of the concentration (% w/v) of the TPGS to the concentration (% w/v) of the dimethyl acetamide is about 1:1. (ASPECT 66.)

In aspects, the invention provides the composition of any one or more of aspects 1-66, wherein the ratio of the concentration (% w/v) of the solubilization component to the concentration (% w/v) of the complexing agent component is between about 4:1 and about 1:500. (ASPECT 67.)

In aspects, the invention provides the composition of any one or more of aspects 1-67, wherein the ratio of the concentration (% w/v) of the solubilization component to the concentration (% w/v) of the complexing agent component is about 1:5. (ASPECT 68.)

In aspects, the invention provides the composition of any one or more of aspects 1-68, wherein the solubilization component comprises TPGS and the ratio of the concentration (% w/v) of the TPGS to the concentration (% w/v) of the complexing agent component is about 1:5. (ASPECT 69.)

In aspects, the invention provides the composition of any one or more of aspects 1-69, wherein the ratio of the concentration (% w/v) of the solvent component to the concentration (% w/v) of the complexing agent component is between about 2:1 and about 1:100. (ASPECT 70.)

In aspects, the invention provides the composition of any one or more of aspects 1-70, wherein the ratio of the concentration (% w/v) of the solvent component to the concentration (% w/v) of the complexing agent component is about 1:5. (ASPECT 71.)

In aspects, the invention provides the composition of any one or more of aspects 1-71, wherein the solvent component comprises DMA and the ratio of the concentration (% w/v) of the DMA to the concentration (% w/v) of the complexing agent component is about 1:5. (ASPECT 72.)

In aspects, the invention provides the composition of any one or more of aspects 1-72, wherein the composition demonstrates a detectably or significantly greater solubility of at least one antimicrobial agent, e.g., at least one antifungal agent, e.g., amphotericin B compound in (1) water at a neutral pH; (2) saliva; (3) an acidic pH environment such as gastric juice(s) of the gastrointestinal tract; or (4) any combination of two or more of (1)-(3) than the same at least one antimicrobial agent, e.g., at least one antifungal agent, e.g., amphotericin B compound, in unmodified form. (ASPECT 73.)

In aspects, the invention provides the composition of aspect 73, wherein the composition demonstrates a detectably or significantly greater solubility of an amphotericin B compound in saliva than amphotericin B provided in unmodified form. (ASPECT 74.)

In aspects, the invention provides the composition of any one or more of aspects 1-74, wherein the composition comprises amphotericin B in a form which, when delivered by a form of administration, such as, e.g., an ODF, is detectably or significantly more bioavailable than amphotericin B in unmodified form delivered by the same form of administration. (ASPECT 75.)

In aspects, the invention provides the composition of any one or more of aspects 1-75, wherein the composition provides a detectably or significantly greater bioavailability of amphotericin B (e.g., provide amphotericin B in detectably or significantly more bioavailable form) when administered to a mammalian recipient than at least generally the same, at least substantially the same, at least essentially the same, essentially the same, or the same composition(s) comprising amphotericin B in unmodified form as determined by an appropriately conducted and controlled trial, e.g., a trial recognized by a recognized regulatory body such as the United States Food and Drug Administration (US FDA). (ASPECT 76.)

In aspects, the invention provides the composition of any one or more of aspects 1-76, wherein the composition provides a detectably or significantly greater absorption of an amphotericin B compound in the gastrointestinal tract of a mammalian recipient when administered thereto than the absorption of amphotericin B provided in unmodified form as determined by an appropriately conducted and controlled trial, e.g., a trial recognized by a recognized regulatory body such as the US FDA (e.g., a well-controlled and adequate clinical study performed in compliance with generally prevailing regulatory authority standards.) (ASPECT 77).

In aspects, the invention provides the composition of any one or more of aspects 1-77, wherein the composition demonstrates a detectably or significantly lower minimum inhibitory concentration (MIC) against one or more species of Candida than that demonstrated against of the same species of Candida by unmodified amphotericin B. (ASPECT 78).

In aspects, the invention provides the composition of any one or more of aspects 1-78, wherein the MIC of the composition against one or more species of Candida is at least about 10% lower than that required for effectively inhibiting growth of the same species of Candida with unmodified amphotericin B. (ASPECT 79.)

In aspects, the invention provides the composition of any one or more of aspects 1-79, wherein the MIC of the composition against one or more species of Candida is at least about 20% lower than that required for effectively inhibiting growth of the same species of Candida with unmodified amphotericin B. (ASPECT 80.)

In aspects, the invention provides the composition of any one or more of aspects 1-80, wherein the MIC of the composition against one or more species of Candida is at least about 30% lower than that required for effectively inhibiting growth of the same species of Candida with unmodified amphotericin B. (ASPECT 81.)

In aspects, the invention provides the composition of any one or more of aspects 1-81, wherein the MIC of the composition against one or more species of Candida is at least about 40% lower than that required for effectively inhibiting growth of the same species of Candida with unmodified amphotericin B. (ASPECT 82.)

In aspects, the invention provides the composition of any one or more of aspects 1-82, wherein the composition is formulated for delivery via an oral dissolve (orally dissolvable or orodispersible) film (ODF), wherein the ODF comprises the ionic liquid composition and further comprises a film-inducing component. (ASPECT 83.)

In aspects, the invention provides an ODF wherein the ODF comprises an antimicrobial ionic liquid composition according to any one or more of aspects 1-83 and a film-inducing component. (ASPECT 84.)

In aspects, the invention provides the ODF of aspect 84, wherein the ODF comprises a film-inducing component comprising a film-forming component, and wherein the film-forming component comprises at least one film-forming polymer. (ASPECT 85.)

In aspects, the invention provides the ODF of any one or more of aspects 83-85, wherein the film-inducing component comprises a film forming component, and the film-forming component comprises a water-soluble synthetic polymer. (ASPECT 86.)

In aspects, the invention provides the ODF of any one or more of aspects 83-86, wherein the film-inducing component comprises a film forming component, and the film-forming component comprises polyvinyl alcohol. (ASPECT 87.)

In aspects, the invention provides the ODF of any one or more of aspects 83-87, wherein the film-inducing component comprises a film forming component, and film-forming component represents between about 40% and about 80% of the total weight of the ODF. (ASPECT 88.)

In aspects, the invention provides the ODF of any one or more of aspects 83-88, wherein the film-inducing component comprises a film forming component, and the film-forming component represents between about 60% and about 65% of the total weight of the ODF. (ASPECT 89.)

In aspects, the invention provides the ODF of any one or more of aspects 83-89, wherein film-inducing component comprises a film-forming component, the film-forming component comprises a water-soluble synthetic polymer, and the water-soluble synthetic polymer is present in the ODF in an amount representing between about 40% and about 80% of the total weight of the ODF. (ASPECT 90.)

In aspects, the invention provides the ODF of any one or more of aspects 83-90, wherein the film-inducing component comprises a film-forming component, the film-forming component comprises a water-soluble synthetic polymer, and the water-soluble synthetic polymer is present in the ODF in an amount representing between about 60% and about 65% of the total weight of the ODF. (ASPECT 91.)

In aspects, the invention provides the ODF of any one or more of aspects 83-91, wherein the film-inducing component comprises a film-forming component comprising polyvinyl alcohol, and the polyvinyl is present in the ODF in an amount representing between about 40% and about 80% of the total weight of the ODF. (ASPECT 92.)

In aspects, the invention provides the ODF of any one or more of aspects 83-92, wherein the film-inducing component comprises a film-forming component comprising polyvinyl alcohol, and the polyvinyl alcohol is present in the ODF in an amount representing between about 60% and about 65% of the total weight of the ODF. (ASPECT 93.)

In aspects, the invention provides the ODF of any one or more of aspects 83-93, wherein the film-inducing component comprises a plasticizer component comprising one or more plasticizing agent(s). (ASPECT 94.)

In aspects, the invention provides the ODF of any one or more of aspects 83-94, wherein the film-inducing component comprises a plasticizer component, and the plasticizer component is present in an amount representing between about 1% and about 10% of the total weight of the ODF. (ASPECT 95.)

In aspects, the invention provides the ODF of any one or more of aspects 83-95, wherein the film-inducing component comprises a plasticizer component present in an amount representing between about 5% and about 7% of the total weight of the ODF. (ASPECT 96.)

In aspects, the invention provides the ODF of any one or more of aspects 83-96, wherein the film-inducing component comprises a plasticizer component comprising glycerol, and the glycerol is present in an amount representing between about 1% and about 10% of the total weight of the ODF. (ASPECT 97.)

In aspects, the invention provides the ODF of any one or more of aspects 83-97, wherein the film-inducing component comprises a plasticizer component comprising glycerol, and the glycerol is present in an amount representing between about 5% and about 7% of the total weight of the ODF. (ASPECT 98.)

In aspects, the invention provides the ODF of any one or more of aspects 83-98, wherein the ODF comprises a ratio of the total weight of ionic liquid component constituents to the total weight of the film-inducing component constituents of between about 2:1 and about 1:7. (ASPECT 99).

In aspects, the invention provides the ODF of any one or more of aspects 83-99, wherein the ODF comprises a ratio of the total weight of ionic liquid component constituents to the total weight of the film-inducing component constituents of about 1:2.2. (ASPECT 100.)

In aspects, the invention provides the ODF of any one or more of aspects 83-100, wherein the film-inducing component of the ODF comprises a film-forming component, and the ratio of the total weight of ionic liquid component constituents to the total weight of the film-forming component is between about 2:1 and about 1:7. (ASPECT 101.)

In aspects, the invention provides the ODF of any one or more of aspects 83-101, wherein the film-inducing component of the ODF comprises a film-forming component, and the ratio of the total weight of ionic liquid component constituents to the total weight of the film-forming component is about 1:2. (ASPECT 102.)

In aspects, the invention provides the ODF of any one or more of aspects 83-102, wherein the film-inducing component of the ODF comprises a film-forming component comprising polyvinyl alcohol, and the ratio of the total weight of ionic liquid component constituents to the total weight of the polyvinyl alcohol is between about 2:1 and about 1:7. (ASPECT 103.)

In aspects, the invention provides the ODF of any one or more of aspects 83-103, wherein the film-inducing component of the ODF comprises a film-forming component comprising polyvinyl alcohol, and the ratio of the total weight of ionic liquid component constituents to the total weight of the polyvinyl alcohol is about 1:2. (ASPECT 104.)

In aspects, the invention provides the ODF of any one or more of aspects 83-105, wherein the film-inducing component of the ODF comprises a plasticizer component, and the ratio of the total weight of ionic liquid component constituents to the total weight of the plasticizer component is between about 60:1 and about 1:1. (ASPECT 105).

In aspects, the invention provides the ODF of any one or more of aspects 83-105, wherein the film-inducing component of the ODF comprises a plasticizer component, and the ratio of the total weight of ionic liquid component constituents to the total weight of the plasticizer component is about 5:1. (ASPECT 106).

In aspects, the invention provides the ODF of any one or more of aspects 83-106, wherein the film-inducing component of the ODF comprises a plasticizer component comprising glycerol, and the ratio of the total weight of ionic liquid component constituents to the total weight of the glycerol is between about 60:1 and about 1:1. (ASPECT 107).

In aspects, the invention provides the ODF of any one or more of aspects 83-107, wherein the film-inducing component of the ODF comprises a plasticizer component comprising glycerol, and the ratio of the total weight of ionic liquid component constituents to the total weight of the glycerol is about 5:1. (ASPECT 108).

In aspects, the invention provides the ODF of any one or more of aspects 83-108, wherein the film-inducing component of the ODF comprises a film-forming component, and the ratio of the total weight of film-forming component constituents to the total weight of the film-inducing component constituents is between about 2:1 and about 1:3. (ASPECT 109.)

In aspects, the invention provides the ODF of any one or more of aspects 83-109, wherein the film-inducing component of the ODF comprises a film-forming component comprising polyvinyl alcohol, and the ratio of the total weight of the polyvinyl alcohol to the total weight of the film-inducing component constituents is between about 2:1 and about 1:3. (ASPECT 110.)

In aspects, the invention provides the ODF of any one or more of aspects 83-110, wherein the film-inducing component of the ODF comprises a film-forming component, and the ratio of the total weight of the film-forming component constituents to the total weight of the film-inducing component constituent is about 1:1.1. (ASPECT 111.)

In aspects, the invention provides the ODF of any one or more of aspects 83-111, wherein the film-inducing component of the ODF comprises a film-forming component comprising polyvinyl alcohol, and the ratio of the total weight of the polyvinyl alcohol to the total weight of the film-inducing component constituents is about 1:1.1. (ASPECT 112.)

In aspects, the invention provides the ODF of any one or more of aspects 83-112, wherein the film-inducing component comprises a film-forming component and a plasticizer component, and the ratio of the total weight of the film-forming component constituents to the total weight of the plasticizer component constituents is between about 80:1 and about 40:1. (ASPECT 113.)

In aspects, the invention provides the ODF of any one or more of aspects 83-113, wherein the film-inducing component comprises a film-forming component comprising polyvinyl alcohol, and a plasticizer component comprising glycerol, and the ratio of the total weight of the polyvinyl alcohol to the total weight of the glycerol is between about 80:1 and about 40:1. (ASPECT 114.)

In aspects, the invention provides the ODF of any one or more of aspects 83-114, where the film-inducing component comprises a film-forming component and a plasticizer component, and the ratio of the total weight of the film-forming component constituents to the total weight of the plasticizer component constituents is ~10:1. (ASPECT 115.)

In aspects, the invention provides the ODF of any one or more of aspects 83-115, wherein the film-inducing component comprises a film-forming component comprising polyvinyl alcohol, and a plasticizer component comprising glycerol, and the ratio of the total weight of the polyvinyl alcohol to the total weight of the glycerol is about 10:1. (ASPECT 116.)

In aspects, the invention provides the ODF of any one or more of aspects 83-116, wherein the film-inducing component comprises a plasticizer component, and the ratio of the total weight of the plasticizer component constituents to the total weight of the film-inducing component constituents is between about 1:4 and about 1:90. (ASPECTS 117.)

In aspects, the invention provides the ODF of any one or more of aspects 83-117, wherein the film-inducing component comprises a plasticizer component comprising glycerol, and the ratio of the total weight of the glycerol to the total weight of the film-inducing component constituents is between about 1:4 and about 1:90. (ASPECTS 118.)

In aspects, the invention provides the ODF of any one or more of aspects 83-118, wherein the film-inducing component comprises a plasticizer component, and the ratio of the total weight of the plasticizer component constituents to the total weight of the film-inducing component constituents is about 1:11. (ASPECT 119.)

In aspects, the invention provides the ODF of any one or more of aspects 83-119, wherein the film-inducing component comprises a plasticizer component comprising glycerol, and the ratio of the total weight of the glycerol to the total weight of the film-inducing component constituents is about 1:11. (ASPECT 120.)

In aspects, the invention provides an oral dissolve (orally dissolvable or orodispersible) film (ODF) comprising (1) an antimicrobial ionic liquid composition, the composition comprising (a) an antimicrobial component comprising at least one antimicrobial agent, (b) a complexing agent component comprising at least a first complexing agent and a second complexing agent, each of the first and the second complexing agents forming a complex with the at least one antimicrobial agent (in this and other similar aspects, uncontradicted, phrases such as forming a complex comprises or means forming a complex under normal conditions of preparation/manufacture or storage exemplified herein (e.g., typically in terms of temperature, pH, or other conditions exemplified here, in aspects also including addition of heat in step(s) in the process of forming the complex or preparation of agents that form the complex, if applicable, or addition other agents/elements described/exemplified herein, or equivalents thereof)), (c) a solvent component comprising at least one acidified solvent agent, and (d) a solubilizing component comprising at least one solubilizing agent which detectably or significantly increases the solubilization of at least one of the at least one antimicrobial agents; and (2) a film-inducing component wherein the film-forming component comprises a film-forming component comprising one or more film-forming polymer(s) and a plasticizer component comprising one or more plasticizing agent(s). (ASPECT 121.)

In aspects, the invention provides the ODF of aspect 121, wherein the antimicrobial component is present in an amount representing between about 1% and about 5% of the total weight of the ODF; the complexing agent component is present in an amount representing between about 10% and about 30% of the total weight of the ODF; the first complexing agent is present in an amount representing between about 10% and about 25% of the total weight of the ODF; the second complexing agent is present in an amount representing between about 1% and about 10% of the total weight of the ODF; the solvent component is present in an amount representing between about 1% and about 10% of the total weight of the ODF; the solubilizing component is present in an amount representing between about 1% and about 10% of the total weight of the ODF; the film-inducing component is present in an amount representing between about 40% and about 80% of the total weight of the ODF; the film-forming component is present in an amount representing between about 50% and about 75% of the total weight of the ODF; and the plasticizer component is present in an amount representing between about 1% and about 10% of the total weight of the ODF. (ASPECT 122.)

In aspects, the invention provides the ODF of any one or both of aspects 121 or 122, wherein the antimicrobial component comprises an amphotericin B compound present in an amount representing between about 1% and about 5% of the total weight of the ODF; the first complexing agent comprises ascorbic acid present in an amount representing between about 10% and about 25% of the total weight of the ODF; the second complexing agent comprises choline chloride present in an amount representing between about 1% and about 10% of the total weight of the ODF; the solvent component comprises dimethyl acetamide present in an amount representing between about 1% and about 10% of the total weight of the ODF; the solubilizing component comprises TPGS present in an amount representing between about 1% and about 10% of the total weight of the ODF; the film-forming component comprises polyvinyl alcohol present in an amount representing between about 50% and about 75% of the total weight of the ODF; and the plasticizer component comprises glycerol present in an amount representing between about 1% and about 10% of the total weight of the ODF. (ASPECT 123.)

In aspects, the invention provides the ODF of any one or more of aspects 83-123, wherein the ODF is provided in individual, dose-sized pieces of film (single dose film(s)) averaging in size of between about 1 cm and 5 cm by between about 1 cm and 5 cm, such as having an average size of about 2 cm by 3 cm each. (ASPECT 124.)

In aspects, the invention provides the ODF of any one or more of aspects 83-124, wherein the ODF is provided in individual, dose-sized pieces of film (single dose film(s)) having an average weight of between about 80 mg and about 100 mg, such as between about 85 mg and about 95 mg. (ASPECT 125.)

In aspects, the invention provides the ODF of any one or more of aspects 83-125, wherein the average solubility of the amphotericin B in water is between about 3 mg/mL and about 4 mg/mL. (ASPECT 126.)

In aspects, the invention provides the ODF of any one or more of aspects 83-126, wherein the ODF demonstrates a detectably or significantly greater solubility in water than that of unmodified amphotericin B, such as, e.g., a solubility in water which is at least about 5 times greater than that of unmodified amphotericin B. (ASPECT 127.)

In aspects, the invention provides the ODF of any one or more of aspects 83-127, wherein at least about 98% of the amount of drug expected to be present in the ODF is detectable upon extraction from the ODF; in aspects the extraction method comprises use of methanol and a bath sonicator wherein the extract is centrifuged and the resulting supernatant analyzed by HPLC. (ASPECT 128.)

In aspects, the invention provides the ODF of any one or more of aspects 83-128, wherein the average amount of amphotericin B present in film(s) across a plurality of films is at least about 98%. (ASPECT 129.)

In aspects, the invention provides the ODF of any one or more of aspects 83-129, wherein the ODF is a flexible film, capable of being folded 1800 at least about 40 times at the same location within the film without breaking when stored at 4C, when stored at 25° C.±2° C. and 60% relative humidity ±5%, or when stored at 40° C.±2° C./75% relative humidity ±5% for a period of at least about 1 month. (ASPECT 130.)

In aspects, the invention provides the ODF of any one or more of aspects 83-130, wherein the ODF is a flexible film, capable of being folded 180° at least about 50 times at the same location within the film without breaking when stored at 4° C., when stored at 25° C.±2° C. and 60% relative humidity ±5%, or when stored at 40° C.±2° C./75% relative humidity ±5% for a period of at least about 1 month. (ASPECT 131.)

In aspects, the invention provides the ODF of any one or more of aspects 83-131, wherein the ODF is a flexible film, capable of being folded 180° at least about 60 times at the same location within the film without breaking when stored at 4C, when stored at 25° C.±2° C. and 60% relative humidity ±5%, or when stored at 40° C.±2° C./75% relative humidity ±5% for a period of at least about 1 month. (ASPECT 132.)

In aspects, the invention provides the ODF of any one or more of aspects 83-132, wherein the ODF is a flexible film, capable of being folded 180° at least about 70 times at the same location within the film without breaking when stored at 4C, when stored at 25° C.±2° C. and 60% relative humidity ±5%, or when stored at 40° C.±2° C./75% relative humidity ±5% for a period of at least about 1 month. (ASPECT 133.)

In aspects, the invention provides the ODF of any one or more of aspects 83-133, wherein the ODF is a flexible film, capable of being folded 180° at least about 75 times at the same location within the film without breaking when stored at 4° C., when stored at 25° C.±2° C. and 60% relative humidity ±5%, or when stored at 40° C.±2° C./75% relative humidity ±5% for a period of at least about 1 month. (ASPECT 134.)

In aspects, the invention provides the ODF of any one or more of aspects 83-134, wherein the ODF is a flexible film, capable of being folded 180° at least about 80 times at the same location within the film without breaking when stored at 4° C., when stored at 25° C.±2° C. and 60% relative humidity ±5%, or when stored at 40° C.±2° C./75% relative humidity ±5% for a period of at least about 1 month. (ASPECT 135.)

In aspects, the invention provides the ODF of any one or more of aspects 83-135, wherein the ODF has a surface pH of between about 5 and about 7. (ASPECT 136.)

In aspects, the invention provides the ODF of any one or more of aspects 83-136, wherein the ODF has a surface pH of about 5.8. (ASPECT 137.)

In aspects, the invention provides the ODF of any one or more of aspects 83-137, wherein the ODF demonstrates no more than a 5% change in weight after storage in a sealed container, such as an amber colored Type I glass vial comprising a stopper, at 40° C. and 75% relative humidity for a period of at least about 1 week. (ASPECT 138.)

In aspects, the invention provides the ODF of any one or more of aspects 83-138, wherein the ODF demonstrates no more than a 4% change in weight after storage in a sealed container, such as an amber colored Type I glass vial comprising a stopper, at 40° C. and 75% relative humidity for a period of at least about 1 week. (ASPECT 139.)

In aspects, the invention provides the ODF of any one or more of aspects 83-139, wherein the ODF demonstrates no more than a 3% change in weight after storage in a sealed container, such as an amber colored Type I glass vial comprising a stopper, at 40° C. and 75% relative humidity for a period of at least about 1 week. (ASPECT 140.)

In aspects, the invention provides the ODF of any one or more of aspects 83-140, wherein the ODF demonstrates no more than a 2% change in weight after storage in a sealed container, such as an amber colored Type I glass vial comprising a stopper, at 40° C. and 75% relative humidity for a period of at least about 1 week. (ASPECT 141.)

In aspects, the invention provides the ODF of any one or more of aspects 83-141, wherein the ODF demonstrates no more than a 1% change in weight after storage in a sealed container, such as an amber colored Type I glass vial comprising a stopper, at 40° C. and 75% relative humidity for a period of at least about 1 week. (ASPECT 142.)

In aspects, the invention provides the ODF of any one or more of aspects 83-142, wherein the average disintegration time of 2 cm by 3 cm pieces of the ODF in water buffered with a phosphate buffer to a pH of 6.4 is between about 30 seconds and about 1 minute. (ASPECT 143.)

In aspects, the invention provides the ODF of any one or more of aspects 83-143, wherein the average disintegration time of 2 cm by 3 cm pieces of the ODF in water buffered with a phosphate buffer to a pH of 6.4 is between about 40 seconds and about 50 seconds. (ASPECT 144.)

In aspects, the invention provides the ODF of any one or more of aspects 83-144, wherein the average disintegration time of 2 cm by 3 cm pieces of the ODF in water buffered with a phosphate buffer to a pH of 6.4 is about 48 seconds. (ASPECT 145.)

In aspects, the invention provides the ODF of any one or more of aspects 83-145, wherein at least about 40% of the antimicrobial component, e.g., an antifungal agent, e.g., amphotericin B, is released from the ODF when the ODF is placed in pH 6.4 phosphate buffer at 37° C.±0.5° C. within about 5 minutes. (ASPECT 146).

In aspects, the invention provides the ODF of any one or more of aspects 83-146, wherein at least about 50% of the antimicrobial component, e.g., an antifungal agent, e.g., amphotericin B, is released from the ODF when the ODF is placed in pH 6.4 phosphate buffer at 37° C.±0.5° C. within about 5 minutes. (ASPECT 147).

In aspects, the invention provides the ODF of any one or more of aspects 83-147, wherein at least about 50% of the antimicrobial component, e.g., an antifungal agent, e.g., amphotericin B, is released from the ODF when the ODF is placed in pH 6.4 phosphate buffer at 37° C.±0.5° C. within about 10 minutes. (ASPECT 148).

In aspects, the invention provides the ODF of any one or more of aspects 83-148, wherein at least about 60% of the antimicrobial component, e.g., an antifungal agent, e.g., amphotericin B, is released from the ODF when the ODF is placed in pH 6.4 phosphate buffer at 37° C.±0.5° C. within about 10 minutes. (ASPECT 149).

In aspects, the invention provides the ODF of any one or more of aspects 83-149, wherein at least about 70% of the antimicrobial component, e.g., an antifungal agent, e.g., amphotericin B, is released from the ODF when the ODF is placed in pH 6.4 phosphate buffer at 37° C.±0.5° C. within about 15 minutes. (ASPECT 150.)

In aspects, the invention provides the ODF of any one or more of aspects 83-150, wherein at least about 80% of the antimicrobial component, e.g., an antifungal agent, e.g., amphotericin B, is released from the ODF when the ODF is placed in pH 6.4 phosphate buffer at 37° C.±0.5° C. within about 15 minutes. (ASPECT 151.)

In aspects, the invention provides the ODF of any one or more of aspects 83-151, wherein the ODF maintains at least about 97% of the initial amount of antimicrobial component, e.g., antifungal agent, e.g., amphotericin B, when stored at 4° C., when stored at 25° C.±2° C. and 60% relative humidity ±5% (e.g., within a stability chamber), or when stored under either such condition for a period of at least about 1 month, such as, e.g., for a period of at least about 1 month, 2 months, 3 months, 6 months, 9 months, or, e.g., at least about 12 months. (ASPECT 152.)

In aspects, the invention provides the ODF of any one or more of aspects 83-152, wherein the ODF maintains at least about 98% of the initial amount of antimicrobial component, e.g., antifungal agent, e.g., amphotericin B, when stored at 4° C., when stored at 25° C.±2° C. and 60% relative humidity ±5% (e.g., within a stability chamber), or when stored under either such condition for a period of at least about 1 month, 2 months, 3 months, 6 months, 9 months, or, e.g., at least about 12 months. (ASPECT 153.)

In aspects, the invention provides the ODF of any one or more of aspects 83-153, wherein the ODF demonstrates a zone of inhibition of *Candida* spp., e.g., *Candida albicans*, *Candida tropicalis*, or both, which is at least about 10% greater than that demonstrated against the same species by unmodified amphotericin B when assessed using standard microbiological culture and testing techniques. (ASPECT 154.)

In aspects, the invention provides the ODF of any one or more of aspects 83-154, wherein the ODF demonstrates a zone of inhibition of *Candida* spp., e.g., *Candida albicans*, *Candida tropicalis*, or both, which is at least about 15% greater than that demonstrated against the same species by unmodified amphotericin B when assessed using standard microbiological culture and testing techniques. (ASPECT 155.)

In aspects, the invention provides the composition of any one or more of aspects 1-83, wherein the composition demonstrates a detectably or significantly lower minimum inhibitory concentration against *Candida* spp., e.g., one or more species of *Candida*, e.g., *Candida albicans*, *Candida tropicalis*, or both, than that of unmodified amphotericin B. (ASPECT 156.)

In aspects, the invention provides the composition of any one or more of aspects 1-83 or aspect 156, wherein the composition demonstrates a minimum inhibitory concentration at 48 hours ($MIC_{48h}$) against *Candida* spp., e.g., one or more species of *Candida*, e.g., *Candida albicans*, *Candida tropicalis*, or both, which is no more than about 35% of that of unmodified amphotericin B. (ASPECT 157.)

In aspects, the invention provides the composition of any one or more of aspects 1-83 or aspects 156-157, wherein the composition demonstrates a minimum inhibitory concentration at 48 hours ($MIC_{48h}$) against *Candida* spp., e.g., one or more species of *Candida*, e.g., *Candida albicans*, *Candida tropicalis*, or both, which is no more than about 30% of that of unmodified amphotericin B. (ASPECT 158.)

In aspects, the invention provides the composition of any one or more of aspects 1-83 or aspects 156-158, wherein the composition demonstrates a minimum inhibitory concentration at 48 hours ($MIC_{48h}$) against *Candida* spp., e.g., one or more species of *Candida*, e.g., *Candida albicans*, *Candida tropicalis*, or both, which is no more than about 25% of that of unmodified amphotericin B. (ASPECT 159.)

In aspects, the invention provides the composition of any one or more of aspects 1-83 or aspects 156-159, wherein the minimum inhibitory concentration at 48 hours ($MIC_{48h}$) against *Candida* spp., e.g., one or more species of *Candida*, e.g., *Candida albicans*, *Candida tropicalis*, or both, is less than 1 µM. (ASPECT 160.)

In aspects, the invention provides the composition of any one or more of aspects 1-83 or aspects 156-160, wherein the minimum inhibitory concentration at 48 hours ($MIC_{48h}$) against *Candida* spp., e.g., one or more species of *Candida*, e.g., *Candida albicans*, *Candida tropicalis*, or both, is less than 0.8 µM. (ASPECT 161.)

In aspects, the invention provides the composition of any one or more of aspects 1-83 or aspects 156-161, wherein the minimum inhibitory concentration at 48 hours ($MIC_{48h}$) against *Candida* spp. e.g., one or more species of *Candida*, e.g., *Candida albicans*, *Candida tropicalis*, or both, is less than 0.6 µM. (ASPECT 162.)

In aspects, the invention provides the composition of any one or more of aspects 1-83 or aspects 156-162, wherein the minimum inhibitory concentration at 48 hours ($MIC_{48h}$) against *Candida* spp., e.g., one or more species of *Candida*, e.g., *Candida albicans*, *Candida tropicalis*, or both, is less than 0.4 µM. (ASPECT 163.)

In aspects, the invention provides the composition of any one or more of aspects 1-83 or aspects 156-163, wherein the minimum inhibitory concentration at 48 hours ($MIC_{48h}$) against *Candida* spp., e.g., one or more species of *Candida*, e.g., *Candida albicans*, *Candida tropicalis*, or both, is less than 0.35 µM. (ASPECT 164.)

In aspects, the invention provides the ODF of any one or more of aspects 84-155, wherein the ODF demonstrates a detectably or significantly lower minimum inhibitory concentration against *Candida* spp., e.g., one or more species of *Candida*, e.g., *Candida albicans*, *Candida tropicalis*, or both, than that of unmodified amphotericin B. (ASPECT 165.)

In aspects, the invention provides the ODF of any one or more of aspects 84-155 or aspect 165, wherein the ODF demonstrates a minimum inhibitory concentration at 48 hours ($MIC_{48h}$) against *Candida* spp., e.g., one or more species of *Candida*, e.g., *Candida albicans*, *Candida tropicalis*, or both, which is no more than about 35% of that of unmodified amphotericin B. (ASPECT 166.)

In aspects, the invention provides the ODF of any one or more of aspects 84-155 or aspects 165-166, wherein the ODF demonstrates a minimum inhibitory concentration at 48 hours ($MIC_{48h}$) against *Candida* spp., e.g., one or more species of *Candida*, e.g., *Candida albicans*, *Candida tropicalis*, or both, which is no more than about 30% of that of unmodified amphotericin B. (ASPECT 167.)

In aspects, the invention provides the ODF of any one or more of aspects 84-155 or aspects 165-167, wherein the ODF demonstrates a minimum inhibitory concentration at 48 hours ($MIC_{48h}$) against *Candida* spp., e.g., one or more species of *Candida*, e.g., *Candida albicans*, *Candida tropicalis*, or both, which is no more than about 25% of that of unmodified amphotericin B. (ASPECT 168.)

In aspects, the invention provides the ODF of any one or more of aspects 84-155 or aspects 165-168, wherein the minimum inhibitory concentration at 48 hours ($MIC_{48h}$) against *Candida* spp., e.g., one or more species of *Candida*, e.g., *Candida albicans*, *Candida tropicalis*, or both, is less than 1 µM. (ASPECT 169.)

In aspects, the invention provides the ODF of any one or more of aspects 84-155 or aspects 165-169, wherein the minimum inhibitory concentration at 48 hours ($MIC_{48h}$) against *Candida* spp., e.g., one or more species of *Candida*, e.g., *Candida albicans*, *Candida tropicalis*, or both, is less than 0.8 µM. (ASPECT 170.)

In aspects, the invention provides the ODF of any one or more of aspects 84-155 or aspects 165-170, wherein the minimum inhibitory concentration at 48 hours ($MIC_{48h}$) against *Candida* spp., e.g., one or more species of *Candida*, e.g., *Candida albicans*, *Candida tropicalis*, or both, is less than 0.6 µM. (ASPECT 171.)

In aspects, the invention provides the ODF of any one or more of aspects 84-155 or aspects 165-171, wherein the minimum inhibitory concentration at 48 hours ($MIC_{48h}$) against *Candida* spp., e.g., one or more species of *Candida*, e.g., *Candida albicans*, *Candida tropicalis*, or both, is less than 0.4 µM. (ASPECT 172.)

In aspects, the invention provides the ODF of any one or more of aspects 84-155 or aspects 165-172, wherein the minimum inhibitory concentration at 48 hours ($MIC_{48h}$) against *Candida* spp., e.g., one or more species of *Candida*, e.g., *Candida albicans*, *Candida tropicalis*, or both, is less than 0.35 µM. (ASPECT 173.)

In aspects, the invention provides a method of manufacturing the composition of any one or more of aspects 1-83 or aspects 156-164, wherein the composition comprises an amphotericin B compound and the method of manufacture comprises (1) acidifying a solvent with an acidification agent which also acts as a first complexing agent with the amphotericin B compound; (2) mixing the solvent with an alcohol; (3) adding the amphotericin B compound to the acidified solvent—alcohol mixture; (4) adding a second complexing agent; and (4) adding a solubilizing agent. (ASPECT 174.)

In aspects, the invention provides the method of aspect 174, wherein the solvent acidifying agent (acidification agent) which also acts as a first complexing agent with the amphotericin B compound is ascorbic acid. (ASPECT 175.)

In aspects, the invention provides the method of any one or both of aspects 174-175, wherein the method comprises heating the acidified solvent prior to the addition of the alcohol. (ASPECT 176.)

In aspects, the invention provides the method of any one or more of aspects 174-176, wherein the method comprises preparing a 1:75 mixture of acidified solvent and alcohol to which the amphotericin B compound is added. (ASPECT 177.)

In aspects, the invention provides the method of any one or more of aspects 174-177, wherein the second complexing agent and the solubilizing agent are added in a 1:1 ratio relative to one another based on their representative percentage w/v of the composition. (ASPECT 178.)

In aspects, the invention provides the method of any one or more of aspects 174-178, wherein (1) the solvent is dimethyl acetamide; (2) the alcohol is methanol; (3) the second complexing agent is choline chloride; (4) the solubilizing agent is TPGS; or (5) any combination of (1)-(4) is true. (ASPECT 179.)

In aspects, the invention provides the method of any one or more of aspects 174-179, wherein the method further comprises utilizing the resulting composition in the preparation of an oral dissolve (orally dissolvable or orodispersible) film (ODF). (ASPECT 180.)

In aspects, the invention provides the method of aspect 180, wherein the method comprises adding one or more film-forming agents and one or more plasticizing agents to the composition resulting from any one or more of aspects 174-179. (ASPECT 181.)

In aspects, the invention provides the method of any one or more of aspects 180-181, wherein the film-forming agent(s) and plasticizing agent(s) are added in a ratio of about 10:1 relative to one another based on their representative percent w/v of the resulting mixture. (ASPECT 182.)

In aspects, the invention provides the method of aspect 182, wherein the resulting mixture is formed into a film. (ASPECT 183.)

In aspects, the invention provides the method of any one or more of aspects 180-183, wherein the film is formed into single dose-sized pieces. (ASPECT 184.)

In aspects, the invention provides the method of any one or more of aspects 180-184, wherein the film is packaged in light protected packaging. (ASPECT 185.)

In aspects, the invention provides the ODF of any one or more of aspects 84-155 or aspects 165-173, wherein the ODF is provided in single dose packaging. (ASPECT 186.)

In aspects, the invention provides the ODF of any one or more of aspects 84-155 or aspects 165-173, wherein the ODF is provided in multi-dose packaging. (ASPECT 187.)

In aspects, the invention provides the ODF of one or both of aspects 186 and 187, wherein the packaging protects ODF(s) maintained therein from an amount of light sufficient to detectably or significantly reduce the stability of the ODF(s) maintained therein compared to packaging comprising at least substantially the same ODF(s) which does not provide protection of ODF(s) maintained therein from detectable or significant light exposure. (ASPECT 188.)

In aspects, the invention provides the ODF of any one or more of aspects 186-188, wherein the packaging is film dispensing packaging designed for use, e.g., for accessing content(s) therein, by medical or non-medical personnel. (ASPECT 189.)

In aspects, the invention provides the ODF of any one or more of aspects 186-189, wherein the packaging is capable of maintaining the chemical stability (e.g., as determined by maintenance of API, lack of impurity(ies), maintenance of pH, or any combination thereof), physical stability (such as, e.g., physical integrity, foldability, color, etc.) or both chemical and physical stability of the ODF(s) maintained therein for a period of at least about 1 month when stored at about 4° C., when stored at about 25° C.±2° C. and about 60%±5% relative humidity, or when stored under either such condition. (ASPECT 190.)

In aspects, the invention provides the ODF of any one or more of aspects 186-190, wherein the packaging is capable of maintaining the chemical stability (e.g., as determined by maintenance of API, lack of impurity(ies), maintenance of pH, or any combination thereof), physical stability (such as, e.g., physical integrity, foldability, color, etc.) or both chemical and physician stability of the ODF(s) maintained therein for a period of at least about 3 months when stored at about 4° C., when stored at about 25° C.±2° C. and about 60%±5% relative humidity, or when stored under either such condition. (ASPECT 191.)

In aspects, the invention provides the ODF of any one or more of aspects 186-191, wherein the packaging is capable of maintaining the chemical stability (e.g., as determined by maintenance of API, lack of impurity(ies), maintenance of pH, or any combination thereof), physical stability (such as, e.g., physical integrity, foldability, color, etc.) or both chemical and physician stability of the ODF(s) maintained therein for a period of at least about 6 months when stored at about 4° C., when stored at about 25° C.±2° C. and about 60%±5% relative humidity, or when stored under either such condition. (ASPECT 192.)

In aspects, the invention provides the ODF of any one or more of aspects 186-192, wherein the packaging is capable of maintaining the chemical stability (e.g., as determined by maintenance of API, lack of impurity(ies), maintenance of pH, or any combination thereof), physical stability (such as, e.g., physical integrity, foldability, color, etc.) or both chemical and physician stability of the ODF(s) maintained therein for a period of at least about 9 months when stored at about 4° C., when stored at about 25° C.±2° C. and about 60%±5% relative humidity, or when stored under either such condition. (ASPECT 193.)

In aspects, the invention provides the ODF of any one or more of aspects 186-193, wherein the packaging is capable of maintaining the chemical stability (e.g., as determined by maintenance of API, lack of impurity(ies), maintenance of pH, or any combination thereof), physical stability (such as, e.g., physical integrity, foldability, color, etc.) or both chemical and physician stability of the ODF(s) maintained therein for a period of at least about 12 months when stored at about 4° C., when stored at about 25° C.±2° C. and about 60%±5% relative humidity, or when stored under either such condition. (ASPECT 194.)

In aspects, the invention provides the ODF of any one or more of aspects 186-194, wherein the packaging is capable of maintaining the chemical stability (e.g., as determined by maintenance of API, lack of impurity(ies), maintenance of pH, or any combination thereof), physical stability (such as, e.g., physical integrity, foldability, color, etc.) or both chemical and physician stability of the ODF(s) maintained therein for a period of at least about 18 months when stored at about 4° C., when stored at about 25° C.±2° C. and about 60%±5% relative humidity, or when stored under either such condition. (ASPECT 195.)

In aspects, the invention provides the ODF of any one or more of aspects 186-195, wherein the packaging is capable of maintaining the chemical stability (e.g., as determined by maintenance of API, lack of impurity(ies), maintenance of pH, or any combination thereof), physical stability (such as, e.g., physical integrity, foldability, color, etc.) or both chemical and physician stability of the ODF(s) maintained therein for a period of at least about 24 months when stored at refrigerated conditions (e.g., about 1° C.-about 8° C. such as about 4° C.), when stored at about 25° C.±2° C. and about 60%±5% relative humidity, or when stored under either such condition. (ASPECT 196.)

In aspects, the invention provides a method of treating one or more microbial infection(s) within the oral cavity of a mammal, such as, e.g., a human, wherein the method comprises administering a therapeutically effective amount of any one or more of the ODFs described in any one or more of aspects 84-155, aspects 165-173, or any other aspect(s) directed to ODF(s) provided in this section. (ASPECT 198.)

In aspects, the invention provides the method of aspect 198, wherein the ODF(s) comprise(s) the composition of any one or more of aspects 1-84. (ASPECT 199.)

In aspects, the invention provides a method of treating oral candidiasis, mucocutaneous candidiasis, refractory mucocutaneous candidiasis, or any combination thereof in a mammal, such as, e.g., a human, wherein the method comprises administering a therapeutically effective amount of any one or more of the ODFs described in any one or more of aspects 85-156, aspects 166-174, or any other aspect(s) directed to ODF(s) provided in this section. (ASPECT 200.)

In aspects, the invention provides the method of aspect 200, wherein the ODF(s) comprise(s) the composition of any one or more of aspects 1-84. (ASPECT 201.)

In aspects, the invention provides the method of any one or more aspects 198-201, wherein the method comprises the recipient mammal self-administering the ODF(s) without the assistance of a trained healthcare provider. (ASPECT 202.)

In aspects, the invention provides the method of any one or more aspects 198-202, wherein the method comprises the administration of the ODF(s) in a private setting, e.g., a setting which is not designated as a medical facility (such as, e.g., a physician's office or hospital). (ASPECT 203.)

In aspects, the invention provides the method of any one or more of aspects 198-203, wherein the method comprises administering between about 1 and about 5 ODF(s) per day to a patient in need of treatment therewith for a period of about 1 day to 14 days. (ASPECT 204.)

In aspects, the invention provides the method of any one or more of aspects 198-204, wherein the method comprises administering between about 1 and about 3 ODF(s) per day to a patient in need of treatment therewith for a period of about 1 day to 10 days. (ASPECT 205.)

In aspects, the invention provides the method of any one or more of aspects 198-205, wherein the method comprises administration of a detectably or significantly lower individual dose, lower total dose per day, lower total dose per treatment period, or any combination of any or all thereof, than treatment with amphotericin B administered systemically. (ASPECT 206.)

In aspects, the invention provides the method of any one or more of aspects 198-206, wherein the method demonstrates a detectable or significant increase in efficacy in the treatment of the one or more microbial infection(s) within the oral cavity of the mammal compared to that of systemically administered amphotericin B (e.g., amphotericin B administered by intravenous injection (IV)), wherein efficacy is determined by one or more well controlled and adequate clinical studies performed in compliance with generally prevailing regulatory authority standards. (ASPECT 207.)

In aspects, the invention provides the method of any one or more of aspects 198-207, wherein patient compliance with the method for a sufficient period of time to detectably or significantly reduce or eliminate the one or more microbial infection(s) within the oral cavity of the mammal is detectably or significantly greater than that demonstrated with the treatment of at least generally the same, at least substantially the same, at least essentially the same, essentially the same, or the same condition by systemic (e.g., orally delivered tablet or capsule or, e.g., IV) administration of amphotericin B. (ASPECT 208.)

DETAILED DESCRIPTION OF THE INVENTION

For convenience, both combinations of elements/steps and individual elements/steps may be described in this section of this disclosure. Despite the inclusion of passages focused on specific elements/steps, any aspect, facet, embodiment, or other description of particular step(s) or element(s) can be applied to any general description of the compositions/methods of the invention, or any other recited element(s)/step(s) thereof, which are provided in any part of this disclosure.

Uncontradicted, the word "exemplary" here means "serving as an example, instance, or illustration." The following detailed description is merely exemplary in nature and is not intended to limit application and uses. Any embodiment described herein as "exemplary" is not necessarily to be construed as preferred or advantageous over other embodiments.

According to certain aspects, the invention herein provides ionic liquid composition(s) of antimicrobial active pharmaceutical ingredient(s) (API(s)), such as, e.g., antifungal API(s), e.g., amphotericin B. In certain aspects, the invention herein provides oral dissolve (or "orally dissolvable" or "orodispersible") film(s) (ODF(s)), e.g., ODF composition(s), comprising antimicrobial API(s), such as, e.g., antifungal API(s), e.g., amphotericin B. In aspects, ODF(s) provided by the invention comprise ionic liquid(s) of antimicrobial API(s), such as ionic liquid(s) of antifungal API(s), e.g., ionic liquid(s) of amphotericin B.

Compositions

In certain aspects, the invention provides ionic liquid-surfactant-solubilizer-complexing system(s). In aspects, the ionic liquid-surfactant-solubilizer-complexing system improves the solubility of one or more active pharmaceutical ingredient(s) (API(s)), such as, e.g., amphotericin B. In aspects, such system(s) are referred to as composition(s) or ionic liquid(s). In aspects, composition(s) herein, can comprise one or more API(s), and one or more additional constituent(s), including, e.g., one or more excipient(s), in amount(s) exemplified and described herein wherein such amount(s) are, in aspects, therapeutically effective, pharmaceutically effective, or, e.g., pharmacologically effective amount(s). In aspects, composition(s) herein, can comprise one or more API(s), and one or more additional constituent(s), including, e.g., one or more excipient(s) in a given amount. In aspects, composition(s) herein, can comprise one or more API(s), and one or more additional constituent(s), including, e.g., one or more excipient(s), in therapeutically effective, pharmaceutically effective, or, e.g., pharmacologically effective amount(s). In aspects, composition(s) comprise one or more constituent(s), e.g., amphotericin B, wherein the amount of such constituent(s), e.g., amphotericin B, present in composition(s), e.g., their concentration(s) within composition(s), when a therapeutically effective amount of composition(s) is administered to a population of subjects having an amphotericin B treatable condition, results in a measurable therapeutic effect in a statistically significant number of such subjects. In aspects, efficacy of composition(s) is derived from specific compositional constituent(s), amount(s) of such compositional constituent(s), or both. In aspects, for example, efficacy of composition(s) (in, e.g., providing an increased solubility of an API) is derived from specific complexing agent(s), amount(s) of such complexing agent(s), or both.

In aspects, composition(s) described herein represent a dynamic complex. In aspects, an ionic liquid composition provided herein is a dynamic composition, wherein one or more agents form a complex with amphotericin B, then disassociate with an API, e.g., amphotericin B, such that at any given time composition(s) can comprise, e.g., in aspects, free amphotericin B molecule(s), amphotericin B molecule(s) in a complex with one complexing agent, amphotericin B molecule(s) in a complex with two or more complexing agents, etc.

According to certain aspects, the invention provides ionic liquid-surfactant-solubilizer complexing system(s) wherein the system(s) comprise an API. According to certain aspects, the invention provides ionic liquid-surfactant-solubilizer complexing system(s) wherein the system(s) comprise at least two complexing agent(s). According to certain aspects, the invention provides ionic liquid-surfactant-solubilizer complexing system(s) wherein the system(s) comprise agent(s) providing detectable or significant pH modulating activity, wherein, in aspects such a pH modulating agent(s) provide one or more detectable or significant functional activity(ies) which are different from pH modulation. According to certain aspects, the invention provides ionic liquid-surfactant-solubilizer complexing system(s) wherein the system(s) comprise a solvent system comprising solvent compound(s) and, in aspects, acidifying agent(s) wherein, in aspects, the acidifying agent(s) provide(s) one or more detectable or significant functional activity(ies) which are different from solvent acidification. According to certain aspects, the invention provides ionic liquid-surfactant-solubilizer complexing system(s) wherein the system(s) comprise at least one solubilizing agent. According to certain aspects, the invention provides ionic liquid-surfactant-solubilizer complexing system(s) wherein the system(s) comprise an API; at least two complexing agent(s); agent(s) providing detectable or significant pH modulating activity, wherein, in aspects such a pH modulating agent(s) provide one or more detectable or significant functional activity(ies) which are different from pH modulation; a solvent system comprising solvent compound(s) and, in aspects, acidifying agent(s) wherein, in aspects, the acidifying agent(s) provide(s) one or more detectable or significant functional activity(ies) which are different from solvent acidification; and at least one solubilizing agent.

In aspects, the invention provides ionic liquid-surfactant-solubilizer complexing system(s) which can be referred to or characterized as ionic liquid compositions or, e.g., ionic liquid form(s) of specific API(s) present in the system (such as, e.g., amphotericin B).

In certain aspects, the invention provides ionic liquid-surfactant-solubilizer complexing system(s) comprising amphotericin B. In aspects, ionic liquid-surfactant-solubilizer complexing system(s) of amphotericin B are referred to or characterized as ionic liquid composition(s) of amphotericin B. In aspects, ionic liquid-surfactant-solubilizer complexing system(s) of amphotericin B are referred to or characterized as ionic liquid(s) of amphotericin B. In aspects, ionic liquid-surfactant-solubilizer complexing system(s) of amphotericin B are referred to or characterized as amphotericin B in ionic liquid form.

Uncontradicted, use of the phrase "ionic liquid-surfactant-solubilizer complexing system(s)" here should be interpreted as simultaneously disclosing "ionic liquid composition(s)", "[API] in ionic liquid form," or both, wherein "[API]" is the active pharmaceutical ingredient(s), specifically identified or left unspecified, as would be understood in context.

According to aspects, the invention provides ionic liquid form(s) of API(s), e.g., antimicrobial API(s), such as, e.g., ionic liquid form(s) of amphotericin B. In aspects, such an ionic liquid form of the compound(s) can be referred to as a composition. In aspects, an ionic liquid form of an API is present in a larger composition, e.g., solubilized in a liquid. In aspects, the invention provides composition(s), such as, e.g., such larger composition(s), for example composition(s) comprising an ionic liquid component (comprising, e.g., API(s) in ionic liquid form, e.g., amphotericin B in ionic liquid form) and one or more other component(s) or constituent(s). In aspects, composition(s) provided herein comprise an ionic liquid component comprising an ionic liquid form of one or more API(s) and, e.g., one or more additional components designed to provide the one or more API(s) in ionic liquid form via specific delivery form, such as, e.g., an oral dissolve (orally dissolvable or orodispersible) film (ODF). In aspects, composition(s) provided by the invention comprise an ionic liquid component and, e.g., a film-inducing component. In aspects, an ionic liquid component of composition(s) herein can comprise, e.g., an API component, a solvent component, a complexing agent component, a solubilizing component, or a combination of any or all thereof.

In aspects, composition(s) provided herein (e.g., ionic liquid form(s) of an API or, e.g., composition(s) comprising an API in ionic liquid form) comprise an API component comprising one or more API compound(s). In aspects, an API component comprises one or more API(s) which provides or demonstrates detectable or significant antimicrobial activity and thus may be referenced as an antimicrobial component. In aspects, composition(s) comprise API(s) in a form providing detectably or significantly greater solubility of the API compared to the API in unmodified form. According to aspects, the invention provides composition(s) comprising an ionic liquid form of antimicrobial API(s). In aspects, the invention provides composition(s) comprising an ionic liquid form of antifungal API(s) and one or more other components, such as, e.g., a film-inducing component. In aspects, such a second component, e.g., film-inducing component, aides in the provision of the API in a specific delivery form, such as, e.g., an oral dissolve (orally dissolvable or orodispersible) film (ODF). In aspects, the invention provides composition(s) comprising an ionic liquid form of amphotericin B. In aspects, composition(s) provided by the invention comprise an ionic liquid form of such API(s) wherein, e.g., a solvent component, a complexing agent component, a solubilizing component, or any combination of any or all thereof are present to aid in the formation of the ionic liquid or to aid in the provision of the ionic liquid to a larger composition (e.g., an ionic liquid form of an API solubilized in solvent(s)). In aspects, the phrase "ionic liquid component" is used herein to describe a composition comprising an API component comprising at least one API, a solvent component comprising at least one solvent, a complexing agent component comprising at least one complexing agent, and a solubilizing component comprising at least one solubilizing agent.

As used herein, the term "ionic liquid" refers to a salt comprising cation(s) and anion(s) which are liquid at or below 100° C. As "ionic liquids" as form(s) of compound(s), generally, are known in the art, a detailed description of ionic liquid(s) as a type or class of compound(s) is not provided here. Aspects of ionic liquids are described in, for example, Lei, et. al., "Introduction: Ionic Liquids," Chem. Rev. 2017, 117, 10, 6633-6635, Published May 24, 2017, which readers may find useful in putting certain aspects of the invention herein to practice, and accordingly this reference is specifically incorporated herein with respect to such liquids and the production, use, or both, thereof.

Ionic Liquid Composition(s)

In aspects, the invention provides ionic liquid composition(s) comprising an API component, e.g., an antimicrobial component, comprising at least one API, e.g., at least one API in ionic liquid form. In aspects, the invention provides ionic liquid composition(s) comprising a solvent component comprising at least one solvent agent. In aspects, the invention provides ionic liquid composition(s) comprising a complexing agent component comprising at least one complexing agent. In aspects, the invention provides ionic liquid composition(s) comprising a solubilizing component comprising at least one solubilizing agent. In aspects, the invention provides ionic liquid composition(s) comprising any combination of such component(s) provided in this paragraph. In aspects, ionic liquid composition(s) provided herein represent one embodiment of the invention.

In aspects, ionic liquid composition(s) provided herein can serve as a one component of a larger composition or formulation, e.g., being present in a composition representing a particular delivery form such as, e.g., an ODF. In aspects, such larger compositions, e.g., a specific delivery form of an ionic liquid, is another embodiment of the invention described herein. In aspects, any component(s) described herein, e.g., a component described as being a component of an ionic liquid composition or ionic liquid component should be interpreted as also disclosed as being a component of a larger composition, such as, e.g., a particular delivery form such as an ODF.

Active Pharmaceutical Ingredient Component/API(s))

In aspects, the invention provides composition(s), e.g., ionic liquid composition(s) (and when, e.g., such ionic liquid composition(s) serve as a component of a larger composition, such as, e.g., an ODF, such ODF composition(s)) comprising an API component comprising one or more API compound(s), often referred to herein simply as "API(s)". In aspects, the invention provides composition(s) comprising an API component comprising one or more API compound(s) (API(s)) wherein each of the provided API(s) is in a form which provides detectably or significantly greater solubility of the API than the API when provided in unmodified form, such as, e.g., detectably or significantly greater solubility in water, saliva, acidic pH environment(s) such as acidic environment(s) of the gastrointestinal tract of a mammal, or any combination of any or all thereof. In certain aspects, the invention provides ionic liquid composition(s) comprising ionic liquid forms of an API compound (API). In aspects, the invention provides ionic liquid composition(s) comprising ionic liquid forms of an API compound (API) wherein the API demonstrates detectable or significant antimicrobial activity. In aspects, the invention provides ionic liquid composition(s) comprising ionic liquid forms of an API demonstrating detectable or significant antifungal activity.

According to aspects, the invention provides compositions comprising one or more API(s) amenable to formation as an ionic liquid, e.g., the API is capable of forming an ionic liquid when exposed to particular environment(s) such as, e.g., when combined with one or more additional component(s)/agent(s)/compound(s), or, e.g., when exposed to such environment(s) under particular condition(s), such as during defined method(s) of manufacture.

In aspects, composition(s) provided by the invention comprise API(s) comprising at least one hydrophobic (non-polar region). In aspects, composition(s) provided by the invention comprise API(s) comprising at least one hydrophilic (polar) region. In aspects, composition(s) provided by the invention comprise API(s) comprising at least one hydrophobic (non-polar) region and at least one hydrophilic (polar) region, such that the API compound(s) is/are characterizable as amphiphilic. In aspects, composition(s) provided by the invention comprise only API(s) characterizable as amphiphilic.

In aspects, composition(s) provided by the invention comprises API(s) capable of reacting as an acid. In aspects, composition(s) provided by the invention comprise API(s) capable of reacting as a base. In aspects, composition(s) provided by the invention comprise API(s) characterizable as amphoteric, e.g., zwitterionic compound(s) capable of reacting as both an acid and a base. In aspects, composition(s) provided by the invention comprises only API(s) characterizable as amphoteric (zwitterionic API(s)).

In aspects, composition(s) provided by the invention comprise API(s) comprising at least one carboxylate functional group. In aspects, composition(s) provided by the invention comprise API(s) comprising at least one amine functional group. In aspects, composition(s) provided by the invention comprise API(s) comprising at least one carboxylate functional group and at least one amine functional group.

According to certain aspects, composition(s) provided herein comprise one or more API(s) wherein the API is characterizable as both amphiphilic and amphoteric.

In aspects, composition(s) provided by the invention comprise one or more antimicrobial API compound(s) (API(s)), such as, e.g., one or more antiparasitic API(s), antimicrobial API(s), antifungal API(s), or one or more such API(s) providing one or more such activity(ies). In aspects wherein API compound(s) demonstrating antimicrobial activity are present, an ionic liquid composition can be referred to as an antimicrobial ionic liquid composition.

In aspects, composition(s) provided herein comprise one or more API compound(s) which are capable of detectably or significantly binding to a microbial organism membrane, such as, e.g., a bacterial cell or fungal cell membrane. In aspects, composition(s) provided herein comprise one or more API compound(s) capable of detectably or significantly binding to one or more microbial membrane components (e.g., microbial membrane compound(s) or one or more specific chemical group(s) within or associated with one or more compound(s) of a microbial membrane), such as, e.g., one or more microbial membrane component(s) that regulate permeability of the microbial membrane, fluidity across/through the membrane, or both. In aspects, composition(s) provided herein comprise one or more API compound(s) that detectably or significantly bind to one or more sterol(s) of a microbial organism membrane. In aspects, composition(s) comprise one or more API compound(s) capable of detectably or significantly binding to one or more oxysterol compounds, such as, e.g., a 5,-diene oxysterol, as in e.g., in a specific example, ergosterol. In aspects, composition(s) comprise one or more API compound(s) capable of detectably or significantly binding to one or more ergostane-based sterol(s). In aspects, composition(s) comprise one or more API compound(s) characterizable as a polyene antimicrobial, e.g., having the characteristic(s) of the class of compounds capable of detectably or significantly binding to ergosterol in a microbial membrane, leading to a detectable or significant increase in membrane permeability, membrane leakage (e.g., of intracellular material(s) such as cation(s)), and, e.g., cell death.

In aspects, composition(s) comprise one or more API(s) which detectably or significantly bind to one or more microbial membrane compound(s), e.g., sterol(s), e.g., ergosterol, wherein the binding is sufficient to form transmembrane channel(s). In aspects, composition(s) provided by the invention demonstrate detectable or significant antimicrobial activity, e.g., antiparasitic activity, antibacterial activity, or, e.g., antifungal activity, wherein such detectable or significant activity is sufficient to demonstrate a detectable or significant therapeutic effect when such compound(s) are provided in therapeutically effective amount(s). In aspects, composition(s) provided herein comprise one or more API compound(s) which, when present in therapeutically effective amounts, demonstrate antimicrobial activity, such as, e.g., antiparasitic, antibacterial, or antifungal effect (or a combination thereof), wherein, in aspects, such activity is achieved via damaging a microbial membrane (barrier) leading to cell death (such as, e.g., by leakage of essential nutrients from the microbe cell.)

Antifungal API(s)-Amphotericin B

In aspects, composition(s) provided by the invention comprise an API component, e.g., an antimicrobial component, comprising API compound(s) demonstrating detectable or significant antifungal activity(ies). In aspects, composition(s) provided by the invention comprise antifungal API compound(s) belonging to classes of antifungal agents such as, e.g., polyenes, imidazoles, triazoles, thiazoles, allylamines, and echinocandins. In aspects, composition(s) comprise an API compound which is a member of the mycoasamine family, such as, e.g., nystatin, candicidin, rimodicin, amphotericin B, etc. In aspects, composition(s) comprise polyene antifungal agent(s) such as, e.g., amphotericin B, candicidin, filipin, hamycin, natamycin, nystatin, rimocidin, etc. In aspects, composition(s) comprise imidazole antifungal agent(s), e.g., bifonazole, butoconazole, clotrimazole, econazole, fenticonazole, isoconazole, ketoconazole, luliconazole, miconazole, omoconazole, oxiconazole, sertaconazole, sulconazole, tioconazole, etc. In aspects, composition(s) comprise an API compound which is a triazole antifungal such as, e.g., albaconazole, efinaconazole, epoxiconazole, fluconazole, isavuconazole, itraconazole, posaconazole, propiconazole, ravuconazole, terconazole, voriconazole, etc. In aspects, composition(s) comprise other antifungal agent(s) such as, e.g., tiazoles, griseofulvin, abafungin, amorolfine, butenafine, naftifine, terbinafine, anidulafingin, caspofungin, micafungin, etc.

According to certain aspects, composition(s) comprise one or more polyene antifungal API compound(s), or, e.g., compound(s) having a heavily hydroxylated ring region.

In aspects, composition(s) provided comprise antimicrobial compounds further characterizable as being amphoteric or amphiphilic/amphipathic compounds. Examples of such compounds can include curcumin (turmeric) compound(s), amphotericin B compound(s), etc.

In aspects, composition(s) provided by the invention comprise zwitterionic, polyene antifungal API compound(s). In aspects, composition(s) provided by the invention comprise an amphotericin B compound, e.g., the invention provides ionic liquid composition(s) of amphotericin B and, e.g., ODF(s) comprising amphotericin B in ionic liquid form.

API (amount)

In aspects, composition(s) provided by the invention comprise an API component, e.g., an antimicrobial component, comprising one or more antimicrobial agent(s), e.g., one or more antifungal agent(s), e.g., a compound of amphotericin B. In aspects, amphotericin B is present as an ionic liquid. In aspects, composition(s) comprise an effective amount of such a component/agent(s), wherein the effective amount is a therapeutically effective amount, e.g., an amount sufficient to provide a detectable or significant amelioration of one or more symptoms(s) associated with target condition(s). In aspects, an effective amount is an amount capable of detectably or significantly reducing one or more marker(s), indicator(s), or symptom(s) in a subject suffering from target condition(s). In aspects, composition(s) comprise between about 0.5% w/v and about 10% w/v of an API component, e.g., antimicrobial component, e.g., one or more antifungal agent(s), e.g., a compound of amphotericin B, such as, e.g., ~0.5% w/v-~9% w/v, ~0.5% w/v-~8% w/v, ~0.5% w/v-~7% w/v, ~0.5% w/v-~6% w/v, ~0.5% w/v-~5% w/v, ~0.5% w/v-~4% w/v, ~0.5% w/v-~3% w/v, or ~0.5% w/v-~2% w/v of an antimicrobial API component, e.g., antifungal agent, e.g., amphotericin B.

In aspects, composition(s) comprise between about 0.6% w/v and about 10% w/v of an API component, e.g., antimicrobial component, e.g., one or more antifungal agent(s), e.g., a compound of amphotericin B, such as, e.g., ~0.8% w/v-~10% w/v, ~1% w/v-~10% w/v, ~1.2% w/v-~10% w/v, ~1.4% w/v-~10% w/v, ~1.6% w/v-~10% w/v, ~1.8% w/v-~10% w/v, or, e.g., ~2% w/v-~10% w/v of an API component, e.g., antimicrobial component, e.g., one or more antifungal agent(s), e.g., a compound of amphotericin B.

In aspects, composition(s) comprise between about 0.6% w/v and about 9% w/v of API component, e.g., antimicrobial component, e.g., one or more antifungal agent(s), e.g., a compound of amphotericin B, such as, e.g., ~0.8% w/v-~8% w/v, ~1% w/v-~7% w/v, ~1.2% w/v-~6% w/v, ~1.4% w/v-~5% w/v, ~1.6% w/v-~4% w/v, or ~1.8% w/v-~3% w/v of an API component, e.g., antimicrobial component, e.g., one or more antifungal agent(s), e.g., a compound of amphotericin B. such as, e.g., ~0.5% w/v-~5% w/v, or, e.g., ~2% w/v of an API component, e.g., antimicrobial component, e.g., one or more antifungal agent(s), e.g., a compound of amphotericin B.

In certain aspects, an API component, e.g., antimicrobial component, e.g., one or more antifungal agent(s), e.g., a compound of amphotericin B, of composition(s) can be present in an amount greater than about 10% w/v, such as, e.g., in an amount representing at least about 11% w/v, ≥~12% w/v, ≥~13% w/v, ≥~14% w/v, ≥~15% w/v, ≥~16% w/v, ≥~17% w/v, ≥~18% w/v, ≥~19% w/v, or, e.g., ≥~20% w/v of composition(s).

In certain aspects, an API component, e.g., antimicrobial component, e.g., one or more antifungal agent(s), e.g., a compound of amphotericin B, of composition(s) can be present in an amount greater than about 20% w/v, such as, e.g., in an amount representing at least about 21% w/v, ≥~22% w/v, ≥~23% w/v, ≥~24% w/v, ≥~25% w/v, ≥~26% w/v, ≥~27% w/v, ≥~28% w/v, ≥~29% w/v, or, e.g., ≥~30% w/v of composition(s).

In aspects, an API component, e.g., antimicrobial component, e.g., one or more antifungal agent(s), e.g., a compound of amphotericin B, of composition(s) is present in an amount representing between about 1% and about 5% of the total weight of composition(s) provided in the form of an ODF, such as, e.g., ~1%-~4%, ~1%-~3%, or ~1%-~2%, such as, e.g., ~2%-~5% or, e.g., ~2% of the total weight of composition(s) provided as an ODF.

In aspects, an API component, e.g., antimicrobial component, e.g., one or more antifungal agent(s), e.g., a compound of amphotericin B, of composition(s) is present in an amount representing no more than about 10% of the total weight of composition(s) provided in the form of an ODF, such as, e.g., in an amount representing ≤~9%, ≤~8%, ≤~7%, ≤~6%, ≤~5%, ≤~4%, ≤~3%, ≤~2.5%, ≤~2.2%, or ≤~2% of the total weight of composition(s) provided in the form of an ODF.

Amount Per Dose

In aspects, each dose of composition provided by the invention, e.g., a single ODF as described herein, provides between about 0.5 mg and about 10 mg of API, e.g., antifungal agent(s), e.g., amphotericin B compound. In aspects, a single ODF provides ~0.5 mg-~10 mg, ~0.5 mg-~9 mg, ~0.5 mg-~8 mg, ~0.5 mg-~7 mg, ~0.5 mg-~6 mg, or ~0.5 mg-~5 mg, such as, e.g., ~1 mg-~10 mg, ~2 mg-~10 mg, ~3 mg-~10 mg, ~4 mg-~10 mg, or, e.g., ~5 mg-~10 mg, as in, e.g., ~2 mg-~9 mg, ~3 mg-~8 mg, ~4 mg-~7 mg, or, e.g., ~5 mg-~6 mg of API.

Amount Per 24-Hour Period

In aspects, the total amount of composition provided by the invention, e.g., a one or more ODF(s) as described herein, administered per 24-hour period during the course of treatment of a target condition described herein typically provides between about 1 mg and about 30 mg of API, e.g., antifungal agent(s), e.g., amphotericin B compound per day (e.g., between about 1 mg-30 mg/24 hours. In aspects, a treatment regimen comprising administration of ODF(s) described herein can provide, e.g., ~1 mg-~25 mg, ~1 mg-~20 mg, ~1 mg-~15 mg, ~1 mg-~10 mg, or, e.g., ~1 mg-~5 mg, such as ~5 mg-~30 mg, ~10 mg-~30 mg, ~15 mg-~30 mg, ~20 mg-~30 mg, or, e.g., ~25 mg-~30 mg, such as, e.g., ~5 mg-~25 mg, or ~10 mg-~20 mg of API (e.g., antifungal agent(s), e.g., amphotericin B compound) per day (e.g., per 24 hour period.) In aspects, ODF(s) provided herein can be administered so as to deliver up to about 2, ~3, ~4, or, e.g., ~5 mg/Kg/day of API(s), e.g., amphotericin B compound.

In aspects, a therapeutically effective amount of API(s), e.g., antifungal agent(s), e.g., amphotericin B compound, administered per dose, per 24-hour period, or both, when provided in composition(s) provided herein, such as, e.g., when provided as an ODF, is detectably or significantly lower than (less than) the amount of amphotericin B required to obtain at least generally the same, at least substantially the same, at least essentially the same, essentially the same, or the same therapeutic effect per dose, per 24-hour period, or both, when administered in an alternative form such as, e.g., via a comparator form as described herein, such as, e.g., when administered systemically such as by intravenous (IV) administration.

Solvent Component (Solvent(s)) & Related Addifying Agent(s)

In aspects, the invention provides composition(s), e.g., ionic liquid composition(s) (and when, e.g., such ionic liquid composition(s) serve as a component of a larger composition, such as, e.g., an ODF, such ODF composition(s)) comprising a solvent component. In aspects, a solvent component of composition(s) comprises one or more solvent agent(s). In aspects, a solvent agent is any pharmaceutically acceptable compound suitable for use in formulating composition(s) for mammalian administration, in which at least some, at least most, at least generally all, at least essentially all, or all API compound(s) of the composition is/are dissolved. In aspects, a solvent is a material which detectably or significantly dissolves solute(s), e.g., API compound(s), to form a solution. In certain aspects, a solvent can be characterized as a cosolvent (as in, e.g., DMA as described herein can be characterized as a cosolvent, aiding in the detectable or significant solubilization of amphotericin B in TPGS.) In aspects, a solvent herein is a solvent providing for a detectably or significantly greater solubility of amphotericin B than that demonstrated by ethanol, PEG 400, propylene glycol, glycerin, or any or all thereof, alone.

In aspects, a solvent component of composition(s) provided herein can comprise any pharmaceutically acceptable solvent(s). In aspects, a solvent compound is an organic compound. In aspects, a solvent compound is an alkyl compound. In aspects, a solvent compound is a polar compound. In aspects, a solvent compound is hygroscopic. In aspects, a solvent compound is water miscible. In aspects, a solvent compound can have any one or more of such characteristics, e.g., be a hygroscopic, polar, or organic alkyl compound which also or alternatively is water miscible.

In certain aspects, suitable solvent compounds comprise between about 3 carbon atoms and about 10 carbon atoms, such as, e.g., ~3-~10 carbon atoms, ~4-~10 carbon atoms, ~3-~9 carbon atoms, ~3-~8 carbon atoms, ~3-~7 carbon atoms, ~3-~6 carbon atoms, ~3-~5 carbon atoms, ~3-~4 carbon atoms, or, e.g., ~4-~9 carbon atoms, ~4-~8 carbon atoms, ~4-~7 carbon atoms, ~4-~6 carbon atoms, ~4-~5 carbon atoms, or, e.g., ~4 carbon atoms.

In certain aspects, suitable solvent compounds comprise between about 1 nitrogen atom and about 3 nitrogen atoms, e.g., ~1-~2 nitrogen atoms, ~2-~3 nitrogen atoms, or, e.g., ~1 nitrogen atom.

In certain aspects, suitable solvent compounds have a boiling point of between about 150° C. and about 180° C. (about 329° F.-about 356° F.), such as, e.g., ~155° C.-~180° C., ~160° C.-~180° C., ~165° C.-~180° C., ~170° C.-~180° C., or ~175° C.-~180° C., such as, e.g., ~150° C.-~175° C., ~150° C.-~170° C., ~150° C.-~165° C., ~150° C.-~160° C., or ~150° C.-~155° C., as in, e.g., ~155° C.-~175° C., or ~160° C.-~170° C., such as, for example ~163° C.-~165° C.

In aspects, suitable solvent compounds have a molecular weight of between about 70 g/mol and about 100 g/mol, such as, e.g., ~70 g/mol-~95 g/mol, ~70 g/mol-~90 g/mol, or ~70 g/mol-~85 g/mol, e.g., ~75 g/mol-~100 g/mol, ~80 g/mol-~100 g/mol, or ~85 g/mol-~100 g/mol, such as ~75 g/mol-~95 g/mol, ~80 g/mol-~90 g/mol, or ~85 g/mol-~90 g/mol, such as, e.g., ~87 g/mol.

In aspects, exemplary suitable solvents include, e.g., N, N-dimethylacetamide, N, N-dimethylformamide, and dimethyl sulfoxide. In aspects, a suitable solvent is a solvent approved for use, e.g., for parenteral administration, by a recognized regulatory body, e.g., a recognized regulatory authority, such as, e.g., the United States Food and Drug Administration (US FDA). According to certain aspects, composition(s) comprise dimethyl acetamide.

In certain aspects, composition(s) provided herein can comprise one or more solvent(s) wherein the solvent is acidified. In aspects, composition(s) provided herein comprise one or more solvent(s) in acidified form. In aspects, acidification of a solvent is conducted as a step of a manufacturing process. In aspects, composition(s) provided herein can comprise any pharmaceutically acceptable acidified solvent (solvent in acidified form), such as, e.g., acidified dimethyl acetamide.

In aspects, any pharmaceutically acceptable acidifying agent/compound can be used to acidify a solvent. In aspects, an acidifying agent is an acid. In aspects, an acidifying agent is a naturally occurring acid. In aspects, an acidifying agent is water soluble. In aspects, an acidifying agent is a vitamin. In aspects, an acidifying agent demonstrates detectable or significant antioxidant activity. In aspects, an acidifying agent provides detectable or significant pH modulating effect. In aspects, an acidifying agent provides detectable or significant saliva stimulating activity.

In aspects, an acidifying agent is a compound comprising between about 2 and about 15 carbon atoms, such as, e.g., ~2-~14 carbons, ~2-~13 carbons, ~2-~12 carbons, ~2-~11 carbons, ~2-~10 carbons, ~2-~9 carbons, ~2-~8 carbons, ~2-~7 carbons, or, e.g., ~2-~6 carbons, e.g., ~3-~15 carbons, ~4-~15 carbons, ~5-~15 carbons, or ~6-~15 carbons, as in, for example, ~3-~12 carbons, ~4-~10 carbons, ~5-~8 carbons, or, e.g., ~6 carbon atoms.

In aspects, an acidifying agent is a compound having a molecular weight of between about 100 g/mol and about 300 g/mol, such as, e.g., ~110 g/mol-~300 g/mol, ~120 g/mol-~300 g/mol, ~130 g/mol-~300 g/mol, ~140 g/mol-~300 g/mol, ~150 g/mol-~300 g/mol, ~160 g/mol-~300 g/mol, or, e.g., ~170 g/mol-~300 g/mol. In aspects, an acidifying agent is a compound having a molecular weight of between about 100 g/mol and about 280 g/mol, such as, e.g., ~100 g/mol-~260 g/mol, ~100 g/mol-~240 g/mol, ~100 g/mol-~220 g/mol, ~100 g/mol-~200 g/mol, or, e.g., ~100 g/mol-~180 g/mol, such as for example ~110 g/mol-~280 g/mol, ~120 g/mol-~260 g/mol, ~130 g/mol-~240 g/mol, ~140 g/mol-~220 g/mol, ~150 g/mol-~200 g/mol, ~160 g/mol-~190 g/mol, ~170 g/mol-~180 g/mol, or, e.g., ~176 g/mol.

In certain aspects, a suitable acidifying agent is ascorbic acid. In aspects, a suitable solvent is acidified dimethyl acetamide. In aspects, suitable solvent is dimethyl acetamide acidified using ascorbic acid.

In certain aspects, composition(s) can comprise a co-solvent. In aspects, a solvent component of composition(s) can comprise one or more co-solvents. In certain aspects, a solvent component can comprise one or more co-solvent alcohol compounds. In aspects, a solvent component can comprise one or more alcohol compounds in addition to one or more solvent(s). In aspects, the one or more alcohol compounds may be at least generally absent from, at least substantially absent from, at least essentially absent from, essentially absent from, or absent from final composition(s) in a form ready for administration, such as, e.g., ODF(s). In aspects, one or more alcohol compound(s) operating as co-solvent(s) are utilized during the manufacture of composition(s) herein but are removed, either actively or passively, such as, e.g., by evaporation, during a manufacturing process such that the one or more alcohol compound(s) are substantively absent from a final composition (e.g., a composition in a form ready for administration, such as, e.g., an ODF). In aspects, composition(s), e.g., an ionic liquid form of amphotericin B, an ODF composition comprising an ionic liquid form of amphotericin B, or both, provided by the invention, comprise one or more alcohol co-solvent compound(s), such as, e.g., methanol, during at least one stage of manufacture. In aspects, such composition(s) comprise an ionic liquid form of amphotericin B and further comprise one or more alcohol co-solvent compound, such as, e.g., methanol, during at least one stage of manufacture, but the one or more alcohol co-solvent(s), e.g., methanol, is present in the final composition in deliverable form (such as, e.g., ODF) in an amount less than about 0.5% by weight, e.g., <~0.4%, <~0.3%, <~0.2%, <~0.1%, <~0.05%, <~0.01%, <~0.005%, <~0.001%, <~0.0005%, or less than about 0.0001% by weight.

In aspects, a co-solvent can be any pharmaceutically acceptable co-solvent. In aspects, a co-solvent can be, e.g., an organic solvent, such as for example ethanol, methanol, dimethyl sulfoxide (DMS), etc.

According to certain aspects, a solvent component of composition(s) provided herein comprise dimethyl acetamide and methanol. In aspects, methanol is only present during manufacture of a finished product, such as, e.g., an ODF comprising an ionic liquid form of and API, e.g., an antifungal agent, e.g., amphotericin B.

In aspects, a solvent component, at least during one stage of the manufacture of a final product, can comprise a first solvent agent and second solvent agent (e.g., co-solvent agent). In aspects, a first solvent agent and a second solvent agent can be present in specific amount(s) relative to one another. In aspects, first and second solvent agents are present in a ratio of between about 1:50 and about 1:100 relative to one another, such as, e.g., in a ratio of ~1:55-~1:100, ~1:60-~1:100, ~1:65-~1:100, ~1:70-~1:100, or ~1:75-~1:100, such as, e.g., ~1:50-~1:95, ~1:50-~1:90, ~1:50-~1:85, ~1:50-~1:80, or, e.g., ~1:50-~1:75, as in, for example, ~1:55-~1:95, ~1:60-~1:90, ~1:65-~1:85, ~1:70-~1:80, or, e.g., in a ratio of ~1:75 relative to one another. In aspects, a first solvent agent is dimethyl acetamide. In aspects, a second solvent agent is methanol. In aspects, acidified dimethyl acetamide (A-DMA) and methanol are present in a 1:75 ratio during at least the manufacturing process of a composition provided herein. In aspects, an ionic form of an API, e.g., an ionic form of an antifungal agent, e.g., an ionic form of amphotericin B, is formed, in part, by its addition to a mixture of A-DMA and methanol wherein the A-DMA and methanol are present in a ratio of 1:75 relative to one another.

In this and any other ingredient aspect of the invention, the invention also can be characterized as comprising a "means" for providing a recited function, here imparting/providing an effective, detectable, or significant solvent effect (e.g., increased dissolution of one or more constituents of the composition, e.g., API, e.g., antifungal agent, e.g., amphotericin B). In such a respect, any known equivalents of such named agents can also be, e.g., are, incorporated into compositions or methods of the invention. As with other sections similarly described herein, any of the components of the invention can be, where suitable, described as means (e.g., the above-described solvent agents/compounds or components can be described as solvent means or means for providing effective, detectable, or significant dissolution activity/characteristics to the composition or one or more constituents of the composition.)

Solvent Component Amount

In aspects, composition(s) provided by the invention comprise a solvent component comprising one or more solvent agent(s). In cases, composition(s) comprise an effective amount of such a component/agent(s), wherein the effective amount is an amount suitable for dissolving at least some, at least generally all, at least substantially all, at least essentially all, essentially all, or all of one or more constituents of an API component, e.g., an antimicrobial component, e.g., antifungal agent(s)/compound(s), e.g., amphotericin B.

In aspects, composition(s) comprise between about 0.5% w/v and about 10% w/v of a solvent component, such as, e.g., ~0.5% w/v-~9% w/v, ~0.5% w/v-~8.5% w/v, ~0.5% w/v-~8% w/v, ~0.5% w/v-~7.5% w/v, ~0.5% w/v-~7% w/v, ~0.5% w/v-~6.5% w/v, ~0.5% w/v-~6% w/v, ~0.5% w/v-~5.5% w/v, ~0.5% w/v-~5% w/v, or ~0.5% w/v-~4.5% w/v of solvent component, such as, e.g., dimethyl acetamide.

In aspects, composition(s) comprise between about 0.6% w/v and about 10% w/v of solvent component, such as, e.g., ~0.8% w/v-~10% w/v, ~1% w/v-~10% w/v, ~1.5% w/v-~10% w/v, ~2% w/v-~10% w/v, ~2.5% w/v-~10% w/v, ~3% w/v-~10% w/v, ~3.5% w/v-~10% w/v, ~4% w/v-~10% w/v, or, e.g., ~4.5% w/v-~10% w/v of a solvent component, such as, e.g., dimethyl acetamide.

In aspects, composition(s) comprise between about 0.6% w/v and about 9% w/v of a solvent such as, e.g., ~0.8% w/v-~8% w/v, ~1% w/v-~7% w/v, ~1.5% w/v-~6% w/v, ~2% w/v-~5% w/v, ~2.5% w/v-~4.5% w/v, or e.g., between about 2.5% w/v and about 7.5% w/v, such as, e.g., about 4.2% w/v of a solvent component, such as, e.g., dimethyl acetamide.

In aspects, a solvent component is present in composition(s) in the form of an ODF in an amount representing between about 1% and ~10% of the total weight of the ODF, such as, e.g., ~1%-~10%, ~2%-~10%, ~3%-~10%, or, e.g., ~4%-~10%, such as, e.g., ~1%-~9%, ~1%-~8%, ~1%-~7%, ~1%-~6%, ~1%-~5%, or, e.g., ~1%-~4%, e.g., ~2%-~8%, ~3%-~6%, ~3%-~5%, or, e.g., about 4% such as about 4.2% of the total weight of an ODF.

In certain aspects, amount(s) of a solvent component described herein represents amount(s) of a solvent absent a co-solvent (e.g., does not include amount(s) of co-solvent(s) which may be present at one or more stage(s) of manufacture of a finished product.)

Complexing Agent Component (Complexing Agent(s))

In aspects, the invention provides composition(s), e.g., ionic liquid composition(s) (and when, e.g., such ionic liquid composition(s) serve as a component of a larger composition, such as, e.g., an ODF, such ODF composition(s)) comprising a complexing agent component. In aspects, a complexing agent component of composition(s) comprises one or more complexing agent(s). In aspects, a complexing agent is any pharmaceutically acceptable compound suitable for use in formulating composition(s) for mammalian administration which forms a complex with at least some, at least most, at least generally all, at least essentially all, or all API compound(s) of the composition. In aspects, complexing agent(s) of composition(s) detectably or significantly stabilize amphotericin B compound(s), increase solubility of amphotericin B compound(s), or both, when complexed with such compound(s). In aspects, complexing agent(s) form a complex with amphotericin B and stabilize, increase solubility of, or both, amphotericin B compound(s) in one or more environments, such as, e.g., in a micellar system. In aspects such a micellar system comprises dimethyl acetamide. In aspects, such a micellar system comprises TPGS. In aspects, such a micellar system comprises dimethyl acetamide and TPGS.

In aspects, a complexing agent is a compound which forms a complex with (complexes with) an API compound, e.g., amphotericin B, at a location of the API compound comprising a carboxylate functional group. In aspects, a complexing agent is a compound which forms a complex with an API compound, e.g., amphotericin B, at a location of the API compound comprising an amine functional group. In aspects, a complexing agent is characterizable as an ionic liquid cation. In aspects, a complexing agent is characterizable as an ionic liquid anion. In aspects, composition(s) comprises both an ionic liquid anion and an ionic liquid cation. In aspects, composition(s) comprise a complexing agent component comprising two or more compound(s)/agent(s), each or all of which capable of forming a complex with one or more API(s), such that, e.g., two or more such compound(s)/agent(s) can simultaneously complex with the same API/API molecule(s).

In aspects, composition(s) provided by the invention comprise a complexing agent component comprising one or more complexing agent(s), e.g., at least two, at least three, or, e.g., at least 4 complexing agents. In aspects, composition(s) herein comprise at least two agents which bind to an API, e.g., amphotericin B, to form a complex. In aspects, both agents can be complexed with an amphotericin B compound simultaneously. In aspects, a complexing agent detectably or significantly increases the solubility of the API compound(s), e.g., antifungal agent(s), e.g., amphotericin B, with which it forms a complex. In aspects, a complexing agent participates in the formation of an ionic liquid form of an API, e.g. antifungal agent, e.g., amphotericin B with which it forms a complex.

In aspects, complexing agent(s) can further provide, e.g., acidification of a composition constituent, e.g., a solvent compound. In aspects, a complexing agent can provide one or more further functional activities, such as, e.g., detectable or significant antioxidant activity, detectable or significant pH modulating effect, or both. In aspects, a complexing agent can provide detectable or significant saliva stimulating effect. In certain aspects, a complexing agent can provide, e.g., a detectable or significant solubilizing effect to an API, e.g., by the participation in the formation of an ionic liquid form of the API, detectable or significant acidification effect of a solvent, detectable or significant antioxidant effect, detectable or significant pH modulating activity, detectable or significant saliva stimulating activity, or, e.g., a combination of any or all thereof.

In aspects, any pharmaceutically acceptable complexing agent can be used. In aspects, a complexing agent is an acid. In aspects, a complexing agent is a naturally occurring acid. In aspects, a complexing agent is water soluble. In aspects, a complexing agent is a vitamin. In aspects, a complexing agent demonstrates detectable or significant antioxidant activity. In aspects, a complexing agent provides detectable or significant pH modulating activity. In aspects, a complexing agent provides detectable or significant saliva stimulating activity.

In aspects, a complexing agent is a compound comprising a single carbon atom. In aspects, a complexing agent is a compound comprising between about 2 and about 15 carbon atoms, such as, e.g., ~2-~14 carbons, ~2-~13 carbons, ~2-~12 carbons, ~2-~11 carbons, ~2-~10 carbons, ~2-~9 carbons, ~2-~8 carbons, ~2-~7 carbons, or, e.g., ~2-~6 carbons, e.g., ~3-~15 carbons, ~4-~15 carbons, ~5-~15 carbons, or ~6-~15 carbons, as in, for example, ~3-~12 carbons, ~4-~10 carbons, ~5-~8 carbons, or, e.g., ~5 carbon atoms or ~6 carbon atoms.

In aspects, a complexing agent is a compound having a molecular weight of between about 100 g/mol and about 300 g/mol, such as, e.g., ~110 g/mol-~300 g/mol, ~120 g/mol-~300 g/mol, ~130 g/mol-~300 g/mol, ~140 g/mol-~300 g/mol, ~150 g/mol-~300 g/mol, ~160 g/mol-~300 g/mol, or, e.g., ~170 g/mol-~300 g/mol. In aspects, a complexing agent is a compound having a molecular weight of between about 100 g/mol and about 280 g/mol, such as, e.g., ~100 g/mol-~260 g/mol, ~100 g/mol-~240 g/mol, ~100 g/mol-~220 g/mol, ~100 g/mol-~200 g/mol, ~100 g/mol-~180 g/mol, ~100 g/mol-~160 g/mol, or, e.g., ~100 g/mol-~140 g/mol, such as for example ~110 g/mol-~280 g/mol, ~120 g/mol-~260 g/mol, ~130 g/mol-~240 g/mol, ~130 g/mol-~220 g/mol, ~130 g/mol-~200 g/mol, ~130 g/mol-~180 g/mol, ~140 g/mol-~220 g/mol, ~150 g/mol-~200 g/mol, ~160 g/mol-~190 g/mol, ~170 g/mol-~180 g/mol, or, such as, e.g., ~140 g/mol or ~176 g/mol.

In aspects, suitable complexing agents include, for example, arginine, meglumine, choline compound(s), e.g., choline chloride, or, e.g., 1-butyl-3-methylimidazolium tetrafluoroborate, 1-butyl-2,3dimethylimidazolium tetrafluoroborate, 1-hexyl-3-methylimidazolium tetrafluoroborate, 1-octyl-3-methylimidazolium tetrafluoroborate, 1-allyl-3-ethylimidazolium tetrafluoroborate, 1-butyl-3-methylimidazolium bromide, 1-methyl-3-tetradecylimidazolium bromide, N-octylimidazolium chloride, 1-dodecyl-3-methylimidazolium chloride, 1-methyl-3-tetradecylimidazolium chloride, 1-hexyl-3-methylimidazolium chloride, 3-methyl-1-octylimidazolium chloride, 1-hexadecyl-3-methylimidazolium chloride, 1-octyl-3-methyl imidazolium chloride, 1-allyl-3-methylimidazolium chloride, 1-ethyl-3-methylimidazolium acetate, 1-ethyl-3-methylimidazolium methylphosphonate, dimethylimidazolium dimethylphosphate, 1-butyl-3-methylimidazolium octylsulfate, dimethylimidazolium dodecanesulfate, 1-ethyl-3-methylimidazolium ethylsulfate, 1-butyl-3-methylimidazolium dicyanamide, N-ethyl-2-hydroxy-N,N-dimethylethanammonium bis (trifluoro methyl sulfonyl)amide), 1-ethyl-3-methylimidazolium bis(trifluoromethanesulfonyl) imide, 1-butyl-3-methylimidazolium bis(trifluoromethylsulfonyl)imide, 1-hexyl-3-methylimidazolium bis(trifluoromethanesulfonyl)imide, 1-decyl-3-methylimidazolium bis (trifluoromethanesulfonyl)imide, 1-ethyl-3-methylimidazolium trifluoromethanesulfonate, 1-butyl-3-methylimidazolium trifluoromethanesulfonate, 1-decyl-3-methylimidazolium trifluoromethanesulfonate, 1-butyl-3-methylimidazolium hexafluorophosphate, 1-hexyl-3-methylimidazolium hexafluorophosphate, 1-octyl-3-methylimidazolium hexafluorophosphate, 1-butyl-3-methylimidazolium thiocyanate, triethyl[2-ethoxy-2-oxoethyl]ammonium bromide, N-butylammonium acetate, N-hexylammonium acetate, N-octylammonium acetate, N-butylammonium oleate, N-hexylammonium oleate, N-octylammonium oleate, 1-methoxyethyl-3-methylimidazolium methanesulfonate, 1-(2-hydroxyethyl)-3-methylimidazolium chloride, didecyldimethylammonium nitrate, N-trimethyl-N-butylammonium bis(trifluoromethanesulfonyl) imide, cholinium alaninate, cholinium isoleucine, cholinium geranate, cholinium L-glutaminate, cholinium glycinate, cholinium leucinate, cholinium phenylalanine, cholinium prolinate, cholinium serinate, cholinium tryptophan, 4,4'-(butane-1,4-diyl)bis(4-dodecyl-morpholin-4-ium)hydroxide, tributyltetradecylphosphonium chloride, trihexyltetradecylphosphonium chloride, trihexyltetradecylphosphonium bis(trifluoromethylsulfonyl)imide, 1-butyl-3-methylpyridinium dichloroiodate, 1-hexyl-3-hexyloxycarbonylpyridinium dicyanamide, 1-hexyl-3-hexyloxycarbonylpyridinium bis (trifluoromethyl sulfonyl) imide, butylmethylpyrrolidinium bis(trifluorosulfonyl)amide, etc.

In aspects, a complexing agent can be, e.g., 1-(hydroxymethyl)1-1methylpyrrolidin-1-ium, 1-(2-hydroxyethyl)-1-methylpyrrolidin-1-ium, 1-ethyl-1-(3-hydroxypropyl)pyrrolidine-1-ium, 1-(3-hydroxypropyl)-1-methylpyrrolidin-1-ium, 1-(4-hydroxybutyl)-1-methylpyrrolidin-1-ium, 1-ethyl-1-(4-hydroxybutyl)pyrrolidine-1-ium, 1-(4-hydroxybutyl)-1-propylpyrrolidin-1-ium, 1-(5-hydroxypentyl)-1-propylpyrrolidin-1-ium, 1-ethyl-1-(5-hydroxypentyl) pyrrolidine-1-ium, 1-(5-hydroxypentyl)-1-methylpyrrolidin-1-ium, 1-(hydroxymethyl)-1-methylpiperidin-1-ium, 1-(2-hydroxyethyl)-1-methylpiperidin-1-ium, 1-ethyl-1-(2-hydroxyethyl)piperidin-1-ium, 1-ethyl-1-(3-hydroxypropyl) piperidin-1-ium, 1-(3-hydroxypropyl)-1-propylpiperidin-1-ium, 1-(3-hydroxypropyl)-1-methylpiperidin-1-ium, 1-(4-hydroxybutyl)-1-methylpiperidin-1-ium, 1-ethyl-1-(4-hydroxybutyl)piperidin-1-ium, 1-(4-hydroxybutyl)-1-propylpiperidin-1-ium, 1-butyl-1-(5-hydroxypentyl) piperidin-1-ium, 1-(5-hydroxypentyl)-1-propylpiperidin-1-ium, 1-ethyl-1-(5-hydroxypentyl)piperidin-1-ium, 1-(5-hydroxypentyl)-1-methylpiperidin-1-ium, 3-ethyl-1-methyl-1H-imidazol-3-ium, 1-methyl-3-propyl-1H-imidazol-3-ium, 3-butyl-1-methyl-1H-imidazol-3-ium, 1-methyl-3-pentyl-1H-imidazol-3-ium, 1,2-dimethyl-3-pentyl-1H-imidazol-3-ium, 3-butyl-1,2-dimethy-1H-imidazol-3-ium, 1,2-dimethyl-3-propyl-1H-imidazol-3-ium, 3-(hydroxymethyl)-1,2-dimethyl-1H-imidazol-3-ium, 3-(2-hydroxyethyl)-1-methyl-1H-imidazole-3-ium, 3-(hydroxymethyl)-1,2,4,5-tetramethyl-1H-imidazol-3-ium, 3-(2-hydroxyethyl)-1,2-dimethyl-1H-imidazole-3-ium, 3-(2-hydroxypropyl)-1,2-dimethyl-1H-imidazole-3-ium, 3-(2-hydroxybutyl)-1,2-dimethyl-1H-imidazole-3-ium, 3-(2-hydroxypentyl)-1,2-dimethyl-1H-imidazole-3-ium, 3-(2-hydroxypentyl)-1-methyl-1H-imidazole-3-ium, 3-(2-hydroxybutyl)-1-methyl-1H-imidazole-3-ium, 3-(2-hydroxypropyl)-1-methyl-1H-imidazole-3-ium, 3-(2-hydroxyethyl)-1,2,4,5-tetramethyl-1H-imidazol-3-ium, 3-(3-hydroxypropyl)-1,2,4,5-tetramethyl-1H-imidazol-3-ium, 3-(4-hydroxybutyl)-1,2,4,5-tetramethyl-1H-imidazol-3-ium, 3-(4-hydroxypentyl)-1,2,4,5-tetramethyl-1H-imidazol-3-ium, 1-(5-hydroxypentyl) pyridine-1-ium, 1-(4-hydroxybutyl)pyridine-1-ium, 1-(3-hydroxypropyl)pyridine-1-ium, 1-(2-hydroxyethyl) pyridine-1-ium, 1-(hydroxymethyl)pyridine-1-ium, 1-hydroxypyridin-1-ium, (hydroymethyl)trimethylphosphonium, triethyl(hydroxymethyl)phosphonium, triethyl(hydroxymeethyl)phosphonium, triethyl(2-hydroxyethyl)phosphonium, (2-hydroxyethyl)tripropylphosphonium. (3-hydroxypropyl)tripropylphosphonium, tributyl(3-hydroxypropyl)phosphonium, (3-hydroxypropyl)tripentylphosphonium, (4-hydroxybutyl)tripentylphosphonium, (5-hydroxypentyl)tripentylphosphonium, etc.

In aspects, e.g., a complexing agent can be acetic acid, EDTA, undecanoic acid or, e.g., ascorbic acid, etc.

In aspects, a complexing component of a composition comprises at least two complexing agents, wherein a first complexing agent which provides, detectable or significant solubilizing effect to an API, e.g., by the participation in the formation of an ionic liquid form of the API; detectable or significant acidification effect of a solvent; detectable or significant antioxidant effect; detectable or significant pH modulating activity; detectable or significant saliva stimulating activity; or, e.g., a combination of any or all thereof. In aspects, such a complexing agent is ascorbic acid.

In aspects, composition(s) comprise a complexing agent component comprising at least one complexing agent constituent, e.g., choline chloride. In aspects, compositions comprise a complexing agent component comprising at least a first and a second complexing agent. In aspects, compositions comprise a complexing agent component comprising at least a 1$^{st}$ complexing agent, e.g., ascorbic acid, and at least a 2nd complexing agent, e.g., choline chloride.

In certain aspects, composition(s) comprise at least one complexing agent forming a complex with an amine group of an API. In certain aspects, such an agent can be, e.g., ascorbic acid. In certain aspects, composition(s) comprise at least one complexing agent forming a complex with a carboxylic acid group of an API. In certain aspects, such an agent can be, e.g., choline chloride.

In this and any other ingredient aspect of the invention, the invention also can be characterized as comprising a "means" for providing a recited function, here imparting/providing an effective, detectable, or significant complexing effect (e.g., leading to the formation of a complex with one or more API(s), contributing to a detectable or significant increase in solubility of API(s) either alone or in combination with other complexing agent(s)). In such a respect, any known equivalents of such named agents can also be, e.g., are, incorporated into compositions or methods of the invention. As with other sections similarly described herein, any of the components of the invention can be, where suitable, described as means (e.g., the above-described complexing agents/compounds or components can be described as complexing means or means for providing for the formation of an effective, detectable, or significant amount of complexed API(s).)

Complexing Agent Component Amount

In aspects, a complexing agent component is present in composition(s) herein in any effective amount. In aspects, a complexing agent component is present in an amount representing between about, e.g., 5% w/v and about 50% w/v of a composition, such as, e.g., ~5% w/v-~45% w/v, ~5% w/v-~40% w/v, ~5% w/v-~35% w/v, ~5% w/v-~30% w/v, ~5% w/v-~25% w/v, ~5% w/v-~20% w/v, ~5% w/v-~15% w/v, or ~5% w/v-~10% w/v, such as, e.g., ~10% w/v-~50% w/v, ~15% w/v-~50% w/v, ~20% w/v-~50% w/v, ~25% w/v-~50% w/v, ~30% w/v-~50% w/v, ~35% w/v-~50% w/v, ~40% w/v-~50% w/v, or ~45% w/v-~50% w/v, as in, for example, ~10% w/v-~45% w/v, ~15% w/v-~40% w/v, ~15% w/v-~35% w/v, ~15% w/v-~30% w/v, or, e.g., ~15% w/v-~25% w/v, such as ~20% w/v-~21% w/v of a composition.

In aspects, complexing agent component is present in composition(s) provided in the form of an ODF in an amount representing between about 10% and about 30% of the total weight of the ODF, such as, e.g., ~10%-~28%, ~10%-~26%, ~10%-~24%, or, e.g., ~10%-~22%, e.g., ~12%-~30%, ~14%-~30%, ~16%-~30%, ~18%-~30%, or, e.g., ~20%-~30%, such as, e.g., ~12%-~28%, ~14%-~26%, ~16%-~24%, ~18%-~22%, or, e.g., ~20% or ~21% of the total weight of the ODF.

First Complexing Agent (e.g.. Ascorbic Acid) Amount

In aspects, a complexing agent component comprises at least one complexing agent. In aspects, a complexing agent component comprises at least two complexing agents, such as, e.g., two complexing agents. In aspects, a complexing agent, or, e.g., a first complexing agent, is present in composition(s) provided herein in an amount representing between about 5% w/v and about 30% w/v of compositions, such as, e.g., ~5% w/v-~28% w/v, ~5% w/v-~26% w/v, ~5% w/v-~24% w/v, ~5% w/v-~22% w/v, ~5% w/v-~20% w/v, or, e.g., ~8% w/v-~30% w/v, ~12% w/v-~30% w/v, ~16% w/v-~30% w/v, or ~20% w/v-~30% w/v, such as, e.g., ~8% w/v-~28% w/v, ~10% w/v-~26% w/v, ~12% w/v-~24% w/v, ~14% w/v-~22% w/v, ~14% w/v-~20% w/v, ~14% w/v-~18% w/v, or, e.g., ~16% w/v or ~17% w/v of a composition. In aspects, such an agent is ascorbic acid.

In aspects, a complexing agent, e.g., a first complexing agent component constituent, is present in composition(s) provided in the form of an ODF in an amount representing between about 10% and about 25% of the total weight of the ODF, such as, e.g., ~10%-~24%, ~10%-~22%, ~10%-~20%, ~10%-~18%, or, e.g., ~10%-~16%, e.g., ~11%-~25%, ~12%-~25%, ~13%-~25%, ~14%-~25%, ~15%-~25%, or, e.g., ~16%-~25%, such as, e.g., ~12%-~24%, ~13%-~22%, ~14%-~20%, ~15%-~18%, or, e.g., ~16% or ~17% of the total weight of the ODF. In aspects, such an agent is ascorbic acid.

Second Complexing Agent Amount

In aspects, a complexing agent component constituent, or, e.g., a second complexing agent component constituent, is present in composition(s) provided herein in an amount representing between about 0.1% w/v and about 20% w/v of compositions, such as, e.g., ~0.1% w/v-~18% w/v, ~0.1% w/v-~16% w/v, ~0.1% w/v-~14% w/v, ~0.1% w/v-~12% w/v, ~0.1% w/v-~10% w/v, ~0.1% w/v-~8% w/v, ~0.1% w/v-~6% w/v, or ~0.1% w/v-~4% w/v, or, e.g., ~0.5% w/v-~20% w/v, ~1% w/v-~20% w/v, ~1.5% w/v-~20% w/v, ~2% w/v-~20% w/v, ~2.5% w/v-~20% w/v, ~3% w/v-~20% w/v, ~3.5% w/v-~20% w/v, or ~4% w/v-~20% w/v, such as, e.g., ~0.5% w/v-~15% w/v, ~1% w/v-~10% w/v, ~1.5% w/v-~8% w/v, ~2% w/v-~6% w/v, ~2.5% w/v-~5.5% w/v, ~3% w/v-~5% w/v, or, e.g., ~2.5% w/v-~10% w/v, e.g., ~4% w/v of a composition. In aspects, such an agent is choline chloride.

In aspects, a second complexing agent is present in composition(s) provided in the form of an ODF in an amount representing between about 1% and about 10% of the total weight of the ODF, such as, e.g., ~1%-~10%, ~2%-~10%, ~3%-~10%, or, e.g., ~4%-~10%, such as, e.g., ~1%-~9%, ~1%-~8%, ~1%-~7%, ~1%-~6%, ~1%-~5%, or, e.g., ~1%-~4%, e.g., ~2%-~8%, ~3%-~6%, ~3%-~5%, or, e.g., about 4% such as about 4.2% of the total weight of the ODF. In aspects, such an agent is choline chloride.

Solubilizing Component (Solubilizing Agent(s))

In aspects, the invention provides composition(s), e.g., ionic liquid composition(s) (and when, e.g., such ionic liquid composition(s) serve as a component of a larger composition, such as, e.g., an ODF, such ODF composition(s)) comprising a solubilizing component. In aspects, a solubilizing component of composition(s) comprises one or more solubilizing agent(s). In aspects, a solubilizing agent is any pharmaceutically acceptable compound suitable for use in formulating composition(s) for mammalian administration, which detectably or significantly increases the solubility of API(s) in a solvent, including, e.g., increasing the solubility of an ionic liquid of API(s) in a solvent. In certain aspects, solubilizing agent(s) can demonstrate one or more additional activity(ies), such as, e.g., providing detectable or significant antioxidant activity.

In aspects, a solubilizing component of composition(s) provided herein can comprise any pharmaceutically acceptable solubilizing agent(s) (solubilizer(s)). In aspects, a solubilizing agent is a surfactant. In aspects, a solubilizing agent is characterizable as a non-ionic surfactant. In aspects, a solubilizing agent is a compound, e.g., a surfactant compound, which does not have a net ionic charge and does not detectably or significantly dissociate in aqueous media. In aspects, exemplary solubilizing agents include, e.g., macrogol esters and ethers and sorbitan derivatives (e.g., ethylene, propylene oxide, sorbitan esters, ethyxylates, and copolymers, etc.) Suitable non-ionic surfactants may be found in references such as, e.g., Remington, The Science and Practice of Pharmacy, 23$^{rd}$ Edition, published Oct. 30, 2020, and other similarly recognized publications such as, e.g., Martindale, The Complete Drug Reference, 40$^{th}$ Edition, published May 2020. In aspects, a suitable solubilizing agent is, e.g., a polyoxyl castor oil compound, polysorbates, a Tween™, block copolymers of ethylene oxide and propylene oxide, glycol and glyceryl esters of fatty acids and their derivatives, polyoxyethylene esters of fatty acids (macrogol esters), polyoxyethylene ethers of fatty acids and their derivatives (macrogol ethers), polyvinyl alcohols, and sorbitan esters, sorbitan monoesters, ethers formed from fatty alcohols and polyethylene glycol, polyoxyethylene-polypropylene glycol, alkyl polyglycoside, Cetomacrogol 1000, cetosteryl alcohol, cetyl alcohol, cocamide DEA, cocamide MEA, decyl glycoside, decyl polyglucose, glycerol monostearate, IGEPAL CA-630, isoceteth-20, lauryl glucoside, maltosides, monolaurin, mycosubtilin, Nonidet P-40, nonxynol-9, non-oxynols, NP-40, octaethylene glycol monodoecyl ether, N-Octyl beta-D-thioglucopyranoside, octyl glucoside, olyl alcohol, PEG-10 sunflower glycerides, pentaethylene glycol monododecyl ether, polidocanol, poloxamer, poloxamer 407, polyethoxylated tallow amine, polyglycerol polyricinoleate, sorbitan, sorbitan monolaurate, sorbitan monostearate, sorbitan tristearate, stearyl alcohol, surfactin, Triton X-100, etc. In aspects, a suitable solubilizing agent is, e.g., sodium lauryl sulfate. In aspects, a suitable solubilizing agent is benzalkonium chloride. In aspects, a suitable solubilizing agent is a polysorbate. In certain aspects, a suitable solubilizing agent is, e.g., polysorbate 80, polysorbate 20, Kolliphor RH 40, Kolliphor EL, etc. In aspects, a suitable solubilizing agent comprises a vitamin component. In aspects, a suitable solubilizing agent comprises a vitamin component conjugated to a polymer. In aspects, a suitable solubilizing agent comprises a component providing detectable or significant antioxidant activity. In aspects, a suitable solubilizing agent comprises a vitamin component providing detectable or significant antioxidant activity conjugated to a polymer. In aspects, a suitable solubilizing agent is D-a-Tocopheryl polyethylene glycol 1000 succinate (TPGS).

In this and any other ingredient aspect of the invention, the invention also can be characterized as comprising a "means" for providing a recited function, here imparting/providing an effective, detectable, or significant solubilizing effect (e.g., detectably or significantly increasing the solubilization of API(s), including ionic liquid form(s) of API(s)). In such a respect, any known equivalents of such named agents can also be, e.g., are, incorporated into compositions or methods of the invention. As with other sections similarly described herein, any of the components of the invention can be, where suitable, described as means (e.g., the above-described solubilizing agents/compounds or components can be described as solubilizing means or means for increasing the solubilization of API(s), including ionic liquid form(s) of API(s).)

Solubilization Component Amount

In aspects, a solubilization component, e.g., a surfactant, e.g., a non-ionic surfactant, e.g., TPGS, is present in composition(s) in any effective amount. In aspects, compositions comprise a solubilization component, e.g., a surfactant, e.g., a non-ionic surfactant, e.g., TPGS, in an amount representing between about 0.1% w/v and about 20% w/v of compositions, such as, e.g., ~0.1% w/v-~18% w/v, ~0.1% w/v-~16% w/v, ~0.1% w/v-~14% w/v, ~0.1% w/v-~12% w/v, ~0.1% w/v-~10% w/v, ~0.1% w/v-~8% w/v, ~0.1% w/v-~6% w/v, or ~0.1% w/v-~4% w/v, or, e.g., ~0.5% w/v-~20% w/v, ~1% w/v-~20% w/v, ~1.5% w/v-~20% w/v, ~2% w/v-~20% w/v, ~2.5% w/v-~20% w/v, ~3% w/v-~20% w/v, ~3.5% w/v-~20% w/v, or ~4% w/v-~20% w/v, such as, e.g., ~0.5% w/v-~15% w/v, ~1% w/v-~10% w/v, ~1.5% w/v-~8% w/v, ~2% w/v-~6% w/v, ~2.5% w/v-~5.5% w/v, ~3% w/v-~5% w/v, or, e.g., ~2.5% w/v-~10% w/v, e.g., ~4% w/v of a composition. In aspects, the solubilization component comprises TPGS.

In aspects, a solubilizing agent, e.g., a surfactant, e.g., a non-ionic surfactant, e.g., TPGS, is present in an amount of at least about 0.001% w/v, ≥~0.005% w/v, ≥~0.01% w/v, ≥~0.05% w/v, ≥~0.1% w/v, ≥~0.5% w/v, ≥~1% w/v, ≥~2% w/v, ≥~3% w/v, or, e.g., ≥~4% w/v of a composition. In aspects, the solubilizing agent is TPGS.

In aspects, a solubilizing component is present in composition(s) provided in the form of an ODF in an amount representing between about 1% and about 10% of the total weight of the ODF, such as, e.g., ~1%-~10%, ~2%-~10%, ~3%-~10%, or, e.g., ~4%-~10%, such as, e.g., ~1%-~9%, ~1%-~8%, ~1%-~7%, ~1%-~6%, ~1%-~5%, or, e.g., ~1%-~4%, e.g., ~2%-~8%, ~3%-~6%, ~3%-~5%, or, e.g., about 4% such as about 4.2% of the total weight of the ODF. In aspects, the solubilizing component comprises TPGS.

Independent Use of Ionic Liquid Composition(s)

According to certain aspects, the invention provides an ionic liquid form of an API, e.g., an antifungal agent, e.g., amphotericin B. In aspects, the invention provides such an ionic liquid form of, e.g., amphotericin B, within a composition such that the ionic liquid of amphotericin B is solubilized. In aspects, the amphotericin B in ionic liquid form or, e.g., a composition comprising an ionic liquid of amphotericin B, e.g., amphotericin B solubilized in one or more solvents can be used as a component in the formulation of one or more delivery forms of the API, such as, e.g., oral delivery forms, topical delivery forms, transdermal delivery forms, transmucosal delivery forms, injectable delivery forms, forms designed for systemic administration, inhaled delivery forms, ophthalmic delivery forms, vaginal delivery forms, etc.

Film Inducing Component

According to certain aspects, the invention provides ionic liquid-surfactant-solubilizer-complexing system(s), or, e.g., ionic liquid composition(s) or, e.g., ionic liquid form(s) of API(s), in a form suitable for local oral delivery of the API(s). In aspects, therefore, composition(s) described herein further comprise one or more component(s) comprising one or more agent(s) which aid in the provision of the composition(s) in such a form. In aspects, for example, the invention provides such system(s) in the form of an oral dissolve (orally dissolving or orodispersible) ("ODF") film. Accordingly, in aspects, for example, the invention provides composition(s) described herein comprising ionic liquid-surfactant-solubilizer-complexing system(s), or, e.g., ionic liquid composition(s) or, e.g., ionic liquid form(s) of API(s) (e.g., an "ionic liquid composition") and, e.g., a film-inducing component.

According to certain aspects, composition(s) provided by the invention comprise an ionic liquid composition as one component (e.g., an ionic liquid component) of the composition(s) and one or more additional components. In aspects, such one or more additional component(s) comprise a film-inducing component. In aspects, a film-inducing component comprises one or more film-inducing component subcomponents which, in aspects, are used to provide the API as a film, e.g., an oral dissolve (orally dissolvable or orodispersible) film (ODF). In aspects, a film-inducing component comprises a film-forming component comprising one or more film-forming agent(s), a plasticizer component comprising one or more plasticizing agent(s), or both a film-forming component and a plasticizer component.

Film-forming Component/Film-forming Polymer(s)

In aspects, composition(s) provided herein are characterizable as ODF(s). In aspects, ODF(s) provided by the invention comprise a film-forming component. In aspects, a film-forming component comprises one or more constituent(s)/agent(s) participating in the provision of one or more API compound(s), e.g., one or more API compound(s) in ionic liquid form, as an ODF.

In aspects, film-forming agent(s) of composition(s) herein can be any pharmaceutically acceptable film-forming agent. In aspects, a suitable film-forming agent of a film-forming component is a polymer. In aspects, a film-forming polymer is a synthetic polymer. In aspects a film-forming component can comprise a single polymer. In alternative aspects, two or more polymers may be used, such as, e.g., two, three, four or more polymers may be present in a film-forming component of composition(s).

In aspects, such a polymer can be any pharmaceutically acceptable polymer. In aspects, a suitable polymer is water-soluble. In aspects, a suitable polymer is a water-soluble synthetic polymer. In aspects, a suitable polymer is non-toxic. In aspects, a suitable polymer is non-irritating, especially, e.g., to mucosal tissue (e.g., tissue of the mouth/oral cavity). In aspects, a suitable polymer is one demonstrating sufficient wetting and spreading properties so as to allow for an operable ODF (e.g., an ODF which dissolves within a target period of time within the oral cavity, releases (API(s) thereof according to a target release profile, etc.) In aspects, a suitable polymer is selected based upon the tensile strength it provides to an ODF. In aspects, a suitable polymer provides for an appropriate and tolerable feeling of an ODF in the mouth/oral cavity. In aspects, a suitable polymer does not provide detectable or significant interference with the functionality of any one or more constituent(s) of composition(s) or, e.g., impede the functionality of the ODF itself. In aspects, a suitable polymer does not detectably or significantly interfere with disintegration time of the ODF or, e.g., cause or contribute to secondary infection(s) within the oral cavity.

In aspects, film-forming agent(s) of composition(s) herein can be any pharmaceutically acceptable film-forming agent or pharmaceutically acceptable combination of agents operating as film former(s), such as, e.g., pullulan, starch (e.g., corn starch), gelatin, pectin, sodium alginate, maltodextrins, dextran, carrageen, chitosan, or, e.g., polymerized resin. In aspects, film-forming agent(s) can include, e.g., synthetic polymers such as, e.g., hydroxy propyl methylcellulose, carboxy methylcellulose, methylcellulose, sodium carboxy methylcellulose, croscarmellose sodium, polyethylene oxide, hydroxypropyl cellulose, polyvinylpyrrolidone, polyvinyl alcohol (e.g., polyvinyl alcohol being produced by the polymerization of vinyl acetate to poly vinyl acetate followed by hydrolysis of poly vinyl acetate to poly vinyl alcohol; commercial grades of PVA having a high degree of hydrolysis are available), such as, e.g., polyvinyl alcohol 4-88, etc. In aspects, film-forming agents include, e.g., Eudragit, microcrystalline cellulose (e.g., Avicel 200), or, e.g., microcrystalline cellulose-carboxymethylcellulose sodium (e.g., Avicel CL-611). In aspects, film-forming agents include, e.g., combinations of any two or more such compound(s)/agent(s) provided herein. In aspects for example, combinations of gelatins, mixtures of high-methoxy pectin and chitosan or low-methoxy pectin, HPMC E-15 and PEG 400, HPMC E-15 and glycerin, HPMC K4M, HPMC E-15 and pullalan, HPMC E-15 and polyvinyl alcohol (PVA), HPMC E-15 and polyvinylpyrrolidone (PVP), HPMC-15 and microcrystalline cellulose, HPMC E-15 with both PVA and microcrystalline cellulose, PVA, PVA with both PVP and glycerin, PVA with both PVP and PEG 400, PVP, pullalan and PVA, gelatin, Eudragite RL-100, and, e.g., pullalan with guar gum, xanthan gum, and carrageenan, etc. may be suitable. In certain aspects, a film-forming component of a composition comprises polyvinyl alcohol (PVA).

In this and any other ingredient aspect of the invention, the invention also can be characterized as comprising a "means" for providing a recited function, here imparting/providing an effective, detectable, or significant film-forming effect (e.g., participating in the formation of a film composition). In such a respect, any known equivalents of such named agents can also be, e.g., are, incorporated into compositions or methods of the invention. As with other sections similarly described herein, any of the components of the invention can be, where suitable, described as means (e.g., the above-described film-forming agents/compounds or components can be described as film-forming means or means for forming film(s))

Film-forming Polymer Amount

In aspects, a film-forming component, comprising one or more film forming agent(s), can be present in composition(s) in any effective amount. In aspects, composition(s) herein comprise a film-forming component present in an amount representing between about 20% w/v and about 99% w/v of composition(s), e.g., ~20% w/v-~95% w/v, ~20% w/v-~90% w/v, ~20% w/v-~85% w/v, ~20% w/v-~80% w/v, ~20% w/v-~75% w/v, ~20% w/v-~70% w/v, ~20% w/v-~65% w/v, or ~20% w/v-~60% w/v, e.g., ~25% w/v-~99% w/v, ~30% w/v-~99% w/v, ~35% w/v-~99% w/v, ~40% w/v-~99% w/v, ~45% w/v-~99% w/v, ~50% w/v-~99% w/v, ~55% w/v-~99% w/v, or ~60% w/v-~99% w/v, such as, e.g., ~30% w/v-~90% w/v, ~40% w/v-~80% w/v, ~50% w/v-~70% w/v, or, e.g., ~60% w/v-~65% w/v, as in, e.g., ~62% w/v or ~63% w/v. In aspects, the film forming component comprises polyvinyl alcohol.

In aspects, the invention provides ODF(s) wherein the film-forming component represents between about 40% and about 80% of the total weight of the ODF, such as, e.g., ~40%-~80%, ~40%-~75%, ~40%-~70%, ~40%-~65%, or, e.g., ~45%-~80%, ~50%-~80%, ~55%-~80%, ~60%-~80% or ~65%-~80%, such as, e.g., ~50%-~70%, ~55%-~65%, or, e.g., ~60%, such as, e.g., ~62% or ~63% of the total weight of the ODF. In aspects, the film-forming component comprises polyvinyl alcohol.

In aspects, a film-forming component is present in composition(s) provided in the form of an ODF in an amount representing between about 50% and about 75% of the total weight of the ODF, such as, e.g., ~50%-~72%, ~50%-~70%, ~50%-~68%, or, e.g., ~50%-~66%, or ~55%-~75%-58%-~75%, ~60%-~75%, ~62%-~75%, or ~64%-~75%, e.g., ~52%-~72%, ~54%-~70%, ~56%-~68%, ~58%-~66%, ~60%-~64%, or, e.g., ~62% or ~63% of the total weight of the ODF. In aspects, the film-forming component comprises polyvinyl alcohol.

Plasticizer Component/Plasticizer(s)

In aspects, composition(s) provided herein are characterizable as ODF(s). In aspects, ODF(s) provided by the invention comprise a plasticizer component. In aspects, a plasticizer component comprises one or more constituent(s)/agent(s) participating in the provision of one or more API compound(s), e.g., one or more API compound(s) in ionic liquid form, as an ODF having a suitable flexibility, e.g., present in an effective amount to reduce brittleness, impart foldability/pliability, or, e.g., enhance durability of ODF(s).

In aspects, plasticizing agent(s) of composition(s) herein can be any pharmaceutically acceptable plasticizing agent. In aspects, plasticizing agent(s) of composition(s) herein can be any pharmaceutically acceptable plasticizing agent which does not interfere with the performance of (e.g., is compatible with), any one or more API(s) of the composition, any one or more solvent(s) of the composition, any one or more film-forming agent(s) of the composition(s), or any one or more other constituent(s) of composition(s). In aspects, a suitable plasticizing agent of a plasticizer component is any pharmaceutically acceptable plasticizing agent. In aspects, a suitable plasticizing agent detectably or significantly increases the flexibility of an ODF, detectably or significantly reduces the friability of the ODF, detectably or significantly lowers the glass transition temperature (Tg), or any combination of any or all thereof. In aspects, a suitable plasticizing agent detectably or significantly increases the tensile strength of a composition, e.g., ODF.

In aspects, plasticizing agent(s) present in composition(s) herein can include, e.g., polyethylene glycol (PEG), e.g., polyethylene glycol 400, glycerol (glycerin), sorbitol, mannitol, glycerin, diethyl phthalate, triethyl citrate, tributyl citrate, macrogol, propylene glycol, citric acid esters, propylene glycol, malic acid, sorbitol, castor oil, triethyl citrate, tributyl citrate, and tracetin, glyceryl oleate, erythritol, glycerin polysorbate, monocaprylate, polyethylene oxide, colloidal silicon dioxide, etc. In aspects, any two or more such plasticizing agent(s) can be used in combination, such as, e.g., polyethylene glycol and glycerol in combination. In aspects, the plasticizing component comprises glycerol.

In this and any other ingredient aspect of the invention, the invention also can be characterized as comprising a "means" for providing a recited function, here imparting/providing an effective, detectable, or significant plasticizing effect (e.g., participating in detectible or significant increase in flexibility, e.g., pliability, or, e.g., tensile strength of composition(s) such as ODF(s)). In such a respect, any known equivalents of such named agents can also be, e.g., are, incorporated into compositions or methods of the invention. As with other sections similarly described herein, any of the components of the invention can be, where suitable, described as means (e.g., the above-described plasticizing agents/compounds or components can be described as plasticizing means or means for improving the flexibility, pliability, friability, tensile strength, etc. of composition(s).)

Plasticizer Amount

In aspects, composition(s) provided by the invention, e.g., ODF(s), comprise a plasticizer component present in any effective amount. In aspects, composition(s) comprise a plasticizer component present in an amount representing between about 0.1% w/v and about 20% w/v of composition(s), such as, e.g., ~0.1% w/v-~18% w/v, ~0.1% w/v-~16% w/v, ~0.1% w/v-~14% w/v, ~0.1% w/v-~12% w/v, ~0.1% w/v-~10% w/v, ~0.1% w/v-~8% w/v, or ~0.1% w/v-~6% w/v, e.g., ~0.5% w/v-~20% w/v, ~1% w/v-~20% w/v, ~1.5% w/v-~20% w/v, ~2% w/v-~20% w/v, ~2.5% w/v-~20% w/v, ~3% w/v-~20% w/v, ~3.5% w/v-~20% w/v, ~4% w/v-~20% w/v, ~4.5% w/v-~20% w/v, ~5% w/v-~20% w/v, ~5.5% w/v-~20% w/v, ~6% w/v-~20% w/v, or ~6.5% w/v-~20% w/v, such as, e.g., ~0.5% w/v-~18% w/v, ~1% w/v-~16% w/v, ~1.5% w/v-~14% w/v, ~2% w/v-~12% w/v, ~2.5% w/v-~10% w/v, ~3% w/v-~8% w/v, ~4% w/v-~7% w/v, ~5% w/v-~7% w/v, or, e.g., ~2.5% w/v-~10% w/v, e.g., about 6% w/v of composition(s). In aspects, the plasticizer component comprises glycerol.

In aspects, the invention provides ODF(s) wherein the plasticizer component is present in an amount representing between about 1% and about 10% of the total weight of the ODF, such as, e.g., ~1%-~9%, ~1%-~8%, ~1%-~7%, or, e.g., ~1%-~6%, such as ~2%-~10%, ~3%-~10%, ~4%-~10%, ~5%-~10% or, e.g., ~6%-~10%, such as, e.g., ~2%-~9%, ~3%-~8%, ~4%-~7%, or, e.g., ~5%-~7%, such as, about 6% or ~6.25% of the total weight of the ODF. In aspects, the plasticizer component comprises glycerol.

In aspects, a film-inducing component is present in composition(s) provided in the form of an ODF in an amount representing between about 40% and about 80% of the total weight of the ODF, such as, e.g., ~50%-~80%, ~60%-~80%, or ~70%-~80%, or, e.g., ~40%-~70%, or ~40%-~60%, such as, e.g., ~45%-~75%, ~50%-~70%, ~55%-~70%, ~60%-~70%, ~65%-~70%, or, e.g., ~68% or ~69% of the total weight of the ODF. In aspects, the plasticizer component comprises glycerol.

According to certain aspects, the invention provides ionic liquid-surfactant-solubilizer-complexing system(s), or, e.g., ionic liquid compositions or, e.g., ionic liquid form(s) of API(s), wherein such system(s) are provided in the form of an oral dissolve (orally dissolving or orodispersible) ("ODF") film. In aspects, the ODF(s) comprise an ionic liquid composition component and a film-inducing component. In aspects, such system(s) are used to treat local oral microbial infections, such as local oral fungal infections, such as, e.g., local oral candidiasis.

Other Excipients

According to aspects, composition(s) provided herein can comprise one or more other excipients. In aspects, such excipient(s) can be any pharmaceutically acceptable excipient(s) present in any effective amount suitable and required to promote a desired effect, achieve a target functionality, or impart a target characteristic upon composition(s).

In aspects, composition(s) can comprise, e.g., binder(s), suspension/suspending agent(s), saliva stimulant(s), disintegrant(s) or superdisintegrant(s) (disintegrants having a superior disintegration effect compared to typical disintegrants), taste masking agent(s)/sweetener(s), flavoring agent(s), coloring agent(s), pH modulating agent(s), etc.

pH Modulating Agent(s)

In aspects, composition(s) provided herein comprise pH modulating agent(s). In aspects, pH modulating agent(s) participate in establishing composition(s) at a target pH, maintaining a target pH of composition(s), or both.

In aspects, composition(s) can comprise any pharmaceutically acceptable pH modulating agent(s) such as, e.g., acidifying agent(s), alkalizing agent(s), buffering agent(s), etc. In aspects, pH modulating agent(s) can comprise, e.g., citric acid monohydrate, anhydrous citric acid, lactic acid, phosphoric acid, sulfuric acid, hydrochloric acid, ascorbic acid, etc. In aspects, pH modulating agent(s) can comprise, e.g., tromethamine, trolamine, sodium hydroxide, potassium hydroxide, etc. In aspects, composition(s) comprise ascorbic acid.

In aspects, composition(s) can comprise pH modulating agent(s) in any effective amount. In aspects, pH modulating agent(s) is/are present in composition(s) provided herein in an amount representing between about 5% w/v and about 30% w/v of compositions, such as, e.g., ~5% w/v-~28% w/v, ~5% w/v-~26% w/v, ~5% w/v-~24% w/v, ~5% w/v-~22% w/v, ~5% w/v-~20% w/v, or, e.g., ~8% w/v-~30% w/v, ~12% w/v-~30% w/v, ~16% w/v-~30% w/v, or ~20% w/v-~30% w/v, such as, e.g., ~8% w/v-~28% w/v, ~10% w/v-~26% w/v, ~12% w/v-~24% w/v, ~14% w/v-~22% w/v, ~14% w/v-~20% w/v, ~14% w/v-~18% w/v, or, e.g., ~10% w/v-~20% w/v, such as ~16% w/v or ~17% w/v of a composition. In aspects, a pH modulating agent is ascorbic acid.

In aspects, a pH modulating agent is present in composition(s) provided in the form of an ODF in an amount representing between about 10% and about 25% of the total weight of the ODF, such as, e.g., ~10%-~24%, ~10%-~22%, ~10%-~20%, ~10%-~18%, or, e.g., ~10%-~16%, e.g., ~11%-~25%, ~12%-~25%, ~13%-~25%, ~14%-~25%, ~15%-~25%, or, e.g., ~16%-~25%, such as, e.g., ~12%-~24%, ~13%-~22%, ~14%-~20%, ~15%-~18%, or, e.g., ~16% or ~17% of the total weight of the ODF. In aspects, such an agent is ascorbic acid or a derivative, analog, or an equivalent thereof.

In this and any other ingredient aspect of the invention, the invention also can be characterized as comprising a "means" for providing a recited function, here imparting/providing an effective, detectable, or significant pH modulating effect (e.g., participating in establishing, maintaining, or both, the pH of composition(s) such as ODF(s)). In such a respect, any known equivalents of such named agents can also be, e.g., are, incorporated into compositions or methods of the invention. As with other sections similarly described herein, any of the components of the invention can be, where suitable, described as means (e.g., the above-described pH modulating agents/compounds or components can be described as pH modulating means or means for establishing or maintaining the pH of composition(s).) Binder/Suspending Agent(s)

In certain aspects, composition(s) provided by the invention comprise one or more binding agent(s) such as, e.g., microcrystalline cellulose (Avicel 200) or microcrystalline cellulose-carboxymethylcellulose sodium (Avicel CL-611). In aspects, a binding agent can, e.g., detectably or significantly enhance the mechanical strength of composition(s), such as, e.g., composition(s) provided as an ODF. In aspects, binder(s)/suspending agent(s) can be present in any suitable amount, such as, e.g., in an amount representing between about 1% w/v and about 25% w/v of compositions, such as, e.g., ~5% w/v-~15% w/v, e.g., ~10% w/v of composition(s). In certain aspects, composition(s) provided herein do not comprise binding agent(s). In aspects, composition(s) provided herein do not comprise suspension agent(s).

In this and any other ingredient aspect of the invention, the invention also can be characterized as comprising a "means" for providing a recited function, here imparting/providing an effective, detectable, or significant binding or strengthening effect (e.g., providing a detectable or significant increase in strength of composition(s) such as ODF(s)). In such a respect, any known equivalents of such named agents can also be, e.g., are, incorporated into compositions or methods of the invention. As with other sections similarly described herein, any of the components of the invention can be, where suitable, described as means (e.g., the above-described binding/suspending agents/compounds or components can be described as binding, suspending, or strengthening means or means for increasing the binding or strength of composition(s).)

Saliva Stimulant(s)

In certain aspects, composition(s) provided by the invention comprise one or more saliva stimulating agent(s). In aspects, a saliva stimulating agent detectably or significantly increases the production rate of saliva in a recipient, e.g., in the mouth of a recipient, when, e.g., composition(s) are provided for oral use, such as, e.g., as an ODF. In aspects, the presence of one or more saliva stimulates detectably or significantly decreases the amount of time it takes for a composition (e.g., an ODF) to break down.

In aspects exemplary saliva stimulants include, e.g., ascorbic acid, malic acid, citric acid, tartaric acid, lactic acid, etc.

In aspects, a saliva stimulant can be present in compositions in any effective amount, such as, e.g., in an amount representing between about 2% w/v and about 6% w/v of composition(s). In certain aspects, composition(s) do not comprise a saliva stimulant. In aspects, compositions provide a single saliva stimulant which provides/performs one or more other function(s), such as, e.g., pH modulation, solvent acidification, serving as a complexing agent, providing detectable or significant antioxidant activity, or any combination of any or all thereof. In aspects, composition(s) comprise ascorbic acid.

In this and any other ingredient aspect of the invention, the invention also can be characterized as comprising a "means" for providing a recited function, here imparting/providing an effective saliva stimulating effect (e.g., participating in increasing saliva production caused by intake of composition(s) such as ODF(s)). In such a respect, any known equivalents of such named agents can also be, e.g., are, incorporated into compositions or methods of the invention. As with other sections similarly described herein, any of the components of the invention can be, where suitable, described as means (e.g., the above-described saliva stimulating agents/compounds or components can be described as saliva stimulating means or means for stimulating saliva production.)

Disintegrant(s)/Superdisintegrant(s)

In aspects, composition(s) can comprise one or more disintegrant(s) or one or more superdisintegrant(s), wherein a superdisintegrant demonstrates a detectable or significant disintegration effect compared to a typical disintegrant (as, e.g., recognized in the art). In aspects, disintegrant agent(s) or super disintegrant agent(s) (disintegrant/superdisintegrant agent(s)) detectably or significantly increase the rate of disintegration of composition(s), such as, e.g., composition(s) provided as an ODF. In aspects, a disintegrant or superdisintegrant detectably increases the water absorption, swelling, or both water absorption and swelling of composition(s), such as, e.g., composition(s) provided as an ODF.

In aspects, exemplary disintegrant(s)/superdisintegrant(s) comprise, e.g., sodium starch glycollate, crosspovidone, and, e.g., polacrilin potassium.

In aspects, disintegrant(s)/superdisintegrant(s) can be present in any effective amount, such as, e.g., between about 0.05% w/v and about 8% w/v. In aspects, compositions do not comprise a compound characterizable as a disintegrant/superdisintegrant.

In this and any other ingredient aspect of the invention, the invention also can be characterized as comprising a "means" for providing a recited function, here, e.g., detectably or significantly increasing the disintegration time of composition(s), detectably or significantly increasing water absorption, or both, of composition(s) such as ODF(s). In such a respect, any known equivalents of such named agents can also be, e.g., are, incorporated into compositions or methods of the invention. As with other sections similarly described herein, any of the components of the invention can be, where suitable, described as means (e.g., the above-described disintegrant/superdisintegrant agents/compounds or components can be described as disintegration means or means for increasing the disintegration rate of composition(s).)

Coloring Agent(s)

In aspects, composition(s) provided by the invention comprise one or more coloring agent(s). In aspects, coloring agent(s) detectably or significantly change the color of composition(s), such as, e.g., composition(s) provided as an ODF. In aspects, a coloring agent detectably changes the visible appearance of composition(s), such as, e.g., ODF, to impart an aesthetically pleasing color, a color to coincide with product branding, or both. In aspects, a coloring agent can be any coloring agent imparting any color, e.g., red, orange, yellow, green, blue, purple, brown, black, white, pink, etc. or tints or hues of any or all thereof.

In aspects, exemplary coloring agent(s) include Food, Drug, and Cosmetic (FD and C) Act approved colorant(s) and European Commission (EU) approved colorant(s), natural coloring agent(s), or other pigment(s). In certain exemplary aspects, a coloring agent can be, e.g., titanium oxide, silicon dioxide, zinc dioxide, etc.

In aspects, coloring agent(s) can be present in any effective amount, such as, e.g., an amount representing between about 0.000001% w/v and about 1% w/v of a composition. In certain aspects, composition(s) do not comprise coloring agent(s).

In this and any other ingredient aspect of the invention, the invention also can be characterized as comprising a "means" for providing a recited function, here imparting/providing an effective, detectable, or significant coloring effect of composition(s) such as ODF(s). In such a respect, any known equivalents of such named agents can also be, e.g., are, incorporated into compositions or methods of the invention. As with other sections similarly described herein, any of the components of the invention can be, where suitable, described as means (e.g., the above-described coloring agents/compounds or components can be described as coloring/coloration means or means for establishing a color of composition(s).)

Taste Masking Agent(s)/Sweetener(s)

In aspects, composition(s) provided by the invention comprise one or more taste masking agent(s) or one or more sweetener(s). In aspects, taste masking agent(s), sweetener(s), or both, detectably or significantly change the taste of composition(s), such as, e.g., composition(s) provided as an ODF. In aspects, taste masking agent(s), sweetener(s), or both, detectably changes the taste composition(s), such as, e.g., ODF, to impart a pleasing or masking flavor to composition(s). In aspects, such agent(s) may detectably or significantly increase compliance with a prescribed treatment regimen of the composition(s). In aspects, such agent(s) may detectable or significantly increase the tolerability of composition(s) described herein, such as, e.g., ODF(s) described herein.

In aspects, exemplary taste masking agent(s), sweetener(s), or both, include, e.g., natural sweeteners such as, e.g., sucrose, mannitol, sorbitol, dextrose, glucose, liquid glucose, fructose, maltose, isomaltose, stevioside, thaumatin, etc., artificial sweeteners such as, e.g., Advantame, aspartame, saccharin (e.g., saccharin-Na), isomalt, sucralose, acesulfame-K, cyclamate, alitam, neotame, etc. In aspects, taste masking agent(s) include polyols such as, e.g., xylitol, maltitol or polyhydric alcohols such as sorbitol, maltitol, etc. In aspects, taste masking agent(s) include erythritol. In aspects, one or more taste masking agent(s)/sweetener(s) can, e.g., impart additional characteristic(s) to composition(s), such as, e.g., leaving a pleasant feeling in the mouth, for example a cold or refreshing feeling in the mouth, such as for example those imparted by some polyhydric alcohol compounds. In certain aspects, exemplary taste modifier(s) include, e.g., gymnemic acid, monoammonium glycyrrhizinate, cyclodextrins, ion exchange resins, citric acid, alkalizers, etc.

In aspects, taste masking agent(s), sweetener(s), or both, can be present in any effective amount, such as, e.g., an amount representing between about 1% w/v and about 6% w/v of a composition, such as, e.g., ~5% of a composition. In aspects, composition(s) herein do not comprise taste masking agent(s) or sweetener(s).

In this and any other ingredient aspect of the invention, the invention also can be characterized as comprising a "means" for providing a recited function, here imparting/providing effective, detectable, or significant taste masking effect in composition(s) such as ODF(s). In such a respect, any known equivalents of such named agents can also be, e.g., are, incorporated into compositions or methods of the invention. As with other sections similarly described herein, any of the components of the invention can be, where suitable, described as means (e.g., the above-described taste masking agents/compounds or components can be described as taste masking means or means for masking taste of composition(s).)

Flavoring Agent(s)

In aspects, composition(s) provided by the invention comprise one or more flavoring agent(s). In aspects, flavoring agent(s) detectably or significantly change the flavor of composition(s), such as, e.g., composition(s) provided as an ODF. In aspects, flavoring agent(s) detectably changes the flavor of composition(s), such as, e.g., ODF, to impart a pleasing or inviting flavor to composition(s). In aspects, such agent(s) may detectably or significantly increase compliance with a prescribed treatment regimen of the composition(s). In aspects, such agent(s) may detectable or significantly increase the tolerability of composition(s) described herein, such as, e.g., ODF(s) described herein.

In aspects, exemplary flavoring agent(s) are selected based upon the API(s) present in the composition(s). In aspects, flavoring agent(s) present in composition(s) is/are detectable by the recipient of the composition(s) within about 5 seconds of receiving the composition(s), such as, e.g., within ~4 seconds, ~3 seconds, ~2 seconds, or, e.g., within ~1 second of receiving the composition(s). In aspects, flavoring agent(s) present in composition(s) is/are detectable by the recipient of composition(s) for a period of time after consumption of the composition is complete, e.g., after an ODF has completely dissolved, such as, e.g., for a period of at least about 1 second, at least about 5 seconds, at least about 15 seconds, at least about 30 seconds, at least about 1 minute, or, e.g., at least about 2, 3, 4, or 5 minutes after, e.g., an ODF is completely dissolved.

In aspects, exemplary flavoring agent(s) include, e.g., salty, bitter, sour, or sweet flavoring agent(s). In aspects, flavoring agent(s) can provide, e.g., mint (e.g., peppermint spearmint, etc.), cinnamon, clove, citrus (e.g., lemon, lime, lemon-lime, grapefruit, orange), fruit (e.g., apricot, raspberry, strawberry, peach, cherry, pineapple, passion fruit, plum, apple, e.g., green apple), butterscotch, maple, vanilla, licorice, chocolate, anise, walnut, or any other appealing or otherwise desirable flavor. In aspects, flavoring agent(s) can comprise, e.g., volatile or aromatic oils, e.g., eugenol (clove oil), etc.

In aspects, flavoring agent(s) can be present in any effective amount, such as, e.g., an amount representing between about 0.00001% w/v and about 5% w/v of a composition. In certain aspects, composition(s) provided herein do not comprise flavoring agent(s).

In this and any other ingredient aspect of the invention, the invention also can be characterized as comprising a "means" for providing a recited function, here imparting/providing a detectable, or significant flavor to composition(s) such as ODF(s). In such a respect, any known equivalents of such named agents can also be, e.g., are, incorporated into compositions or methods of the invention. As with other sections similarly described herein, any of the components of the invention can be, where suitable, described as means (e.g., the above-described flavoring agents/compounds or components can be described as flavoring means or means for providing a flavor to composition(s).)

According to specific aspects, at least four components of composition(s) aid in the provision of amphotericin B in a form which is at least detectably or significantly more soluble than unmodified amphotericin B and, further, wherein removal of any one or more of the at least four components results in a detectably or significantly decreased solubility of the amphotericin B. In aspects, exemplary constituents comprise, e.g., ascorbic acid, choline chloride, dimethyl acetamide, and TPGS.

Additional Means/Steps for Performing Functions

In aspects, compositions provided by the invention comprise one or more means for performing one or more specific functions and methods of the invention include steps for performing functions. In general, any element described herein as a "means" for performing a function can also, wherever suitable, serve as a "step for" performing a function in the context of methods of the invention, and vice versa. E.g., a component described herein as a means for forming a film in a composition also simultaneously and implicitly supports a method of making such a composition comprising a step of forming a film.

In one aspect, compositions provided by the invention comprise means for dissolving one or more composition constituents, in aspects such means for dissolution detectably or significantly dissolving of one or more composition constituents, e.g., one or more active pharmaceutical ingredients, e.g., one or more antifungal agent(s), e.g., amphotericin B, detectably or significantly maintaining the dissolution of one or more composition constituents for a detectably or significantly longer period of time, or both ("solvent means"). Support for solvent means can be found in, e.g., the section entitled "Solvent Component (Solvent(s) & Related Acidifying Agent(s)."

In one aspect, compositions provided by the invention comprise means for forming a complex with an API, e.g., an antifungal agent, e.g., amphotericin B, in aspects such means for forming a complex with an API, e.g., amphotericin B detectably or significantly increasing the solubility of the API(s), e.g., amphotericin B in a solvent ("complexing means"). Support for complexing means can be found in, e.g., the section entitled "Complexing Agent Component (Complexing Agent(s)."

In one aspect, compositions provided by the invention comprise means for solubilizing an API, e.g., an antifungal agent, e.g., amphotericin B, in aspects such means for solubilizing an API, e.g., amphotericin B detectably or significantly increasing the solubility of the API(s), e.g., amphotericin B in a solvent ("solubilizing means"). Support for solubilizing means can be found in, e.g., the section entitled "Solubilizing Component (Solubilizing Agent(s)."

In one aspect, compositions provided by the invention comprise means for inducing the formation of a film, in aspects such means for forming a film participates in the provision of an API, e.g., an antifungal agent, e.g., amphotericin B, via an ODF ("film-forming means"). Support for film-forming means can be found in, e.g., the sections entitled "Film Inducing Component" and "Film-Forming Component/Film-Forming Polymer(s)."

In one aspect, compositions provided by the invention comprise means for inducing the formation of a film, in aspects such means for forming a film participates in the provision of an API, e.g., an antifungal agent, e.g., amphotericin B, via an ODF ("film-forming means"). Support for film-forming means can be found in, e.g., the sections entitled "Film Inducing Component" and "Film-Forming Component/Film-Forming Polymer(s)."

In one aspect, compositions provided by the invention comprise means for imparting/providing an effective, detectable, or significant plasticizing effect (e.g., participating in detectible or significant increase in flexibility, e.g., pliability, or, e.g., tensile strength of composition(s) such as ODF(s)) ("plasticizing means"). Support for plasticizing means can be found in, e.g., the sections entitled "Film Inducing Component" and "Plasticizer Component/Plasticizer(s)."

In one aspect, compositions provided by the invention comprise means for establishing, modulating, or maintaining the pH of composition(s), in aspects such means for pH modulation establishing a surface pH of composition(s) provided as, e.g., ODF(s), of between about 5 and about 6 ("pH modulation means"). Support for pH modulation means can be found in, e.g., the section entitled "pH Modulating Agent(s)."

In one aspect, compositions provided by the invention comprise means for binding, suspending, or otherwise increasing the strength of composition(s), such as, e.g., composition(s) provided in the form of an ODF, in aspects such means for binding/suspending detectably or significantly increasing the mechanical strength of composition(s) such as composition(s) provided as an ODF ("binding, suspending, or strengthening means"). Support for binding, suspending, or strengthening means can be found in, e.g., the section entitled "Binder/Suspending Agent(s)."

In one aspect, compositions provided by the invention comprise means for stimulating saliva production, in aspects such means for stimulating saliva production detectably or significantly decreasing the amount of time it takes for a composition, e.g., a composition provided in the form of an ODF, to break down in the mouth, e.g., oral cavity, of a recipient ("saliva stimulation means"). Support for saliva stimulation means can be found in, e.g., the section entitled "Saliva Stimulant(s)."

In one aspect, compositions provided by the invention comprise means for increasing the rate of disintegration of composition(s), e.g., composition(s) provided as ODF(s), in aspects such means for increasing the rate of disintegration decreasing the amount of time it takes for a composition, e.g., a composition provided in the form of an ODF, to break down in the mouth, e.g., oral cavity, of a recipient ("disintegration means"). Support for disintegration means can be found in, e.g., the section entitled "Disintegrant(s)/Superdisintegrant(s)."

In one aspect, compositions provided by the invention comprise means for providing color to composition(s), e.g., composition(s) provided as ODF(s), in aspects such means for coloring composition(s) detectably changing the visible appearance of composition(s), such as, e.g., an ODF ("coloring means" or "coloration means"). Support for coloring/coloration means can be found in, e.g., the section entitled "Coloring Agent(s)."

In one aspect, compositions provided by the invention comprise means for hiding or masking the taste of composition(s) or component(s) of composition(s), e.g., composition(s) provided as ODF(s), in aspects such means for taste masking detectably improving the taste or tolerability of composition(s), such as, e.g., an ODF ("taste masking means"). Support for taste masking means can be found in, e.g., the section entitled "Taste Masking Agent(s)/Sweetener(s)."

In one aspect, compositions provided by the invention comprise means for flavoring composition(s), e.g., composition(s) provided as ODF(s), in aspects such means for an "ionic liquid composition" or "ionic liquid component," wherein the sums of each such individual component(s) can be added to form values for an ionic liquid component which can be used to form ratio(s) with other component(s)/compound(s) or combination(s) thereof.

To exemplify this disclosure, the following table is provided. Table 1 below, e.g., illustrating a ratio array, demonstrates the types of ratios which the reader should understand to be encompassed by the disclosure herein.

TABLE 1

Exemplary component/constituent ratios.

|  | API | SOV | CPX | SOB | FIC | FFC | PLC | PHM | BSS | SST | DIS | CLR | TMA | FLV |
|---|---|---|---|---|---|---|---|---|---|---|---|---|---|---|
| API | — | SOV:API | CPX:API | SOB:API | FIC:API | FFC:API | PLC:API | PHM:API | BSS:API | SST:API | DIS:API | CLR:API | TMA:API | FLV:API |
| SOV | API:SOV | — | CPX:SOV | SOB:SOV | FIC:SOV | FFC:SOV | PLC:SOV | PHM:SOV | BSS:SOV | SST:SOV | DIS:SOV | CLR:SOV | TMA:SOV | FLV:SOV |
| CPX | API:CPX | SOV:CPX | — | SOB:CPX | FIC:CPX | FFC:CPX | PLC:CPX | PHM:CPX | BSS:CPX | SST:CPX | DIS:CPX | CLR:CPX | TMA:CPX | FLV:CPX |
| SOB | API:SOB | SOV:SOB | CPX:SOB | — | FIC:SOB | FFC:SOB | PLC:SOB | PHM:SOB | BSS:SOB | SST:SOB | DIS:SOB | CLR:SOB | TMA:SOB | FLV:SOB |
| FIC | API:FIC | SOV:FIC | CPX:FIC | SOB:FIC | — | FFC:FIC | PLC:FIC | PHM:FIC | BSS:FIC | SST:FIC | DIS:FIC | CLR:FIC | TMA:FIC | FLV:FIC |
| FFC | API:FFC | SOV:FFC | CPX:FFC | SOB:FFC | FIC:FFC | — | PLC:FFC | PHM:FFC | BSS:FFC | SST:FFC | DIS:FFC | CLR:FFC | TMA:FFC | FLV:FFC |
| PLC | API:PLC | SOV:PLC | CPX:PLC | SOB:PLC | FIC:PLC | FFC:PLC | — | PHM:PLC | BSS:PLC | SST:PLC | DIS:PLC | CLR:PLC | TMA:PLC | FLV:PLC |
| PHM | API:PHM | SOV:PHM | CPX:PHM | SOB:PHM | FIC:PHM | FFC:PHM | PLC:PHM | — | BSS:PHM | SST:PHM | DIS:PHM | CLR:PHM | TMA:PHM | FLV:PHM |
| BSS | API:BSS | SOV:BSS | CPX:BSS | SOB:BSS | FIC:BSS | FFC:BSS | PLC:BSS | PHM:BSS | — | SST:BSS | DIS:BSS | CLR:BSS | TMA:BSS | FLV:BSS |
| SST | API:SST | SOV:SST | CPX:SST | SOB:SST | FIC:SST | FFC:SST | PLC:SST | PHM:SST | BSS:SST | — | DIS:SST | CLR:SST | TMA:SST | FLV:SST |
| DIS | API:DIS | SOV:DIS | CPX:DIS | SOB:DIS | FIC:DIS | FFC:DIS | PLC:DIS | PHM:DIS | BSS:DIS | SST:DIS | — | CLR:DIS | TMA:DIS | FLV:DIS |
| CLR | API:CLR | SOV:CLR | CPX:CLR | SOB:CLR | FIC:CLR | FFC:CLR | PLC:CLR | PHM:CLR | BSS:CLR | SST:CLR | DIS:CLR | — | TMA:CLR | FLV:CLR |
| TMA | API:TMA | SOV:TMA | CPX:TMA | SOB:TMA | FIC:TMA | FFC:TMA | PLC:TMA | PHM:TMA | BSS:TMA | SST:TMA | DIS:TMA | CLR:TMA | — | FLV:TMA |
| FLV | API:FLV | SOV:FLV | CPX:FLV | SOB:FLV | FIC:FLV | FFC:FLV | PLC:FLV | PHM:FLV | BSS:FLV | SST:FLV | DIS:FLV | CLR:FLV | TMA:FLV | — |

Abbreviations: API (active pharmaceutical ingredient component; also referred to as an antimicrobial component if the API is an antimicrobial API); SOV (solvent component); CPX (complexing agent component); SOB (solubilizing component); FIC (film-inducing component); FFC (film-forming component); PLC (plasticizer component); PHM (pH modulating agent(s)); BSS (binder/suspension/strength agent(s)); SST (saliva stimulant(s)); DIS (disintegrant(s)/superdisintegrant(s)); CLR (coloring agent(s)); TMA (taste masking agent(s)); FLV (flavoring agent(s))

flavoring detectably improving the taste or tolerability of composition(s), such as, e.g., an ODF ("flavoring means"). Support for flavoring means can be found in, e.g., the section entitled "Flavoring Agent(s)."

Ratios

According to aspects, any component(s) or compound(s)/agent(s) described herein can be present in composition(s) in therapeutically effective amount(s), compositionally compatible amount(s), or both. In aspects, any single component or compound/agent provided herein can be present in a relationship with, such as, e.g., in a ratio with, any one or more other single component or compound/agent. In aspects, any combination of component(s) or compound(s)/agent(s) provided herein can be present in a ratio with any other combination of component(s) or compound(s)/agent(s). In aspects, ratio(s) between such component(s) or compound(s)/agent(s) or combinations thereof can be established using any provided amounts for each disclosed herein, including, e.g., values within ranges of such amounts disclosed herein. As an example, in aspects, an API component, complexing agent component, solubilizing component, and solvent component, can, e.g., be combined to form Provided in Table 2 are exemplary amounts of exemplary component(s)/ingredient(s), which, in aspects, can be/are present in composition(s) provided by the invention in a ratio with any one or more other component(s)/compound(s) disclosed, wherein such ratios can, in aspects, be in a ratio formed by such disclosed amounts.

TABLE 2

Exemplary Ingredients and Exemplary Amounts from Which Ratio(s) Can be Derived.

| Component/Compound Description* | Exemplary Compound(s) (if component provided) | Exemplary Amount(s) (% w/v) |
|---|---|---|
| Ionic liquid composition (Ionic liquid component) | API component (e.g., amphotericin B) + complexing agent component (e.g., ascorbic acid and choline chloride) + solvent component (e.g., DMA) + solubilizing component (e.g., TPGS) | 6-70 |

TABLE 2-continued

Exemplary Ingredients and Exemplary Amounts from Which Ratio(s) Can be Derived.

| Component/Compound Description* | Exemplary Compound(s) (if component provided) | Exemplary Amount(s) (% w/v) |
|---|---|---|
| API Component (also referred to as an "antimicrobial component" if the API is an antimicrobial agent) | Amphotericin B | 0.5-10 |
| Complexing Agent Component | First complexing agent (e.g., ascorbic acid) + Second complexing agent (e.g., choline chloride) | 5-50 |
| First complexing agent | Ascorbic acid | 5-30 |
| Second complexing agent | Choline chloride | 0-20 |
| Solubilizing component | D-α-Tocopheryl polyethylene glycol 1000 succinate (TPGS) | 0-20 |
| Solvent Component | Dimethyl acetamide (DMA) | 0.5-10 |
| Film-inducing Component | Film forming component (e.g., polyvinyl alcohol) + Plasticizer component (e.g., glycerol) | 20-99 |
| Film-forming component | Polyvinyl alcohol (Parteck® MXP) | 20-99 |
| Plasticizer component | Glycerol | 0-2 |
| pH modulating component | Ascorbic acid | 5-30 |

*Note:
One or more components may be absent from compositions herein or, e.g., one or more component(s)/compound(s) can provide two or more functions (e.g., ascorbic acid may be present in composition(s) and may provide two or more functions, such as, e.g., operating as a first complexing agent as well as a pH modulating component/agent.)

According to certain aspects, compositions(s) provided herein, such as, e.g., ODF composition(s) comprising one or more API(s) in ionic liquid form, e.g., amphotericin B in ionic liquid form, comprise at least one complexing agent present in a 1:1 ratio with solubilizing agent(s). In aspects, composition(s) comprise choline chloride in a 1:1 ratio with TPGS.

In aspects, composition(s) provided herein, such as, e.g., ODF composition(s) comprising one or more API(s) in ionic liquid form, e.g., amphotericin B in ionic liquid form, comprise at least one complexing agent present in a 1:1 ratio with a solvent. In aspects, composition(s) comprise choline chloride in a 1:1 ratio with DMA, such as, e.g., acidified DMA.

In aspects, composition(s) provided herein such as, e.g., ODF composition(s) comprising one or more API(s) in ionic liquid form, e.g., amphotericin B in ionic liquid form, comprise at least one solubilizing agent present in a 1:1 ratio with a solvent. In aspects, composition(s) comprise TPGS in a 1:1 ratio with DMA, such as, e.g., acidified DMA.

In aspects, composition(s) provided herein such as, e.g., ODF composition(s) comprising one or more API(s) in ionic liquid form, e.g., amphotericin B in ionic liquid form, comprise at least one complexing agent, at least one solubilizing agent, and at least one solvent present in a 1:1:1 ratio; that is, composition(s) comprise about equivalent amounts of each such constituent. In aspects, composition(s) comprise choline chloride, TPGS, and DMA, e.g., acidified DMA, each present in the same amount(s).

In aspects, composition(s) are provided wherein the ratio of the concentration (% w/v) of an antimicrobial component to the concentration of a complexing agent component (% w/v) is between about 2:1 and about 1:100, such as, e.g., about ~2:1-~1:50, ~1:1-~1:40, ~1:2-~1:30, ~1:1-~1:20, or, e.g., about 1:10 such as, e.g., ~1:10.4. In aspects, the antimicrobial component is an amphotericin B compound, e.g., amphotericin B in ionic liquid form.

In aspects, the invention provides composition(s) wherein the ratio of the concentration (% w/v) of an antimicrobial component to the concentration (% w/v) of a first complexing agent of a complexing agent component is between about 2:1 and about 1:60, such as, e.g., ~2:1-~1:50, ~2:1-~1:20, ~1:1-~1:20, ~1:2-~1:10, or, e.g., ~1:8 such as, e.g., ~1:8.3. In aspects, the antimicrobial component is an amphotericin B compound, e.g., amphotericin B in ionic liquid form. In aspects, the first complexing agent is ascorbic acid.

In aspects, the invention provides composition(s) wherein the ratio of the concentration (% w/v) of an antimicrobial component to the concentration (% w/v) of a second complexing agent of a complexing agent component is between about 100:1 and about 1:40, such as, e.g., ~50:1-~1:30, ~20:1-~1:20, ~10:1-~1:10, ~1:1-~1:10, or, e.g., ~1:1-~1:5, such as, e.g., ~1:2, e.g., ~1:2.1. In aspects, the antimicrobial component is an amphotericin B compound, e.g., amphotericin B in ionic liquid form. In aspects, a second complexing agent is choline chloride.

In aspects, the invention provides composition(s) wherein the ratio of the concentration (% w/v) of an antimicrobial component to the concentration (% w/v) of a solubilizing component is between about 100:1 and about 1:40 such as, e.g., ~50:1-~1:30, ~20:1-~1:20, ~10:1-~1:10, ~1:1-~1:10, or, e.g., ~1:1-~1:5, such as, e.g., ~1:2, e.g., ~1:2.1. In aspects, the antimicrobial component is an amphotericin B compound, e.g., amphotericin B in ionic liquid form. In aspects, the solubilizing component is TPGS.

In aspects, the invention provides composition(s) wherein the ratio of the concentration (% w/v) of an antimicrobial component to the concentration (% w/v) of a solvent component is between about 20:1 and about 1:20 such as, e.g., ~10:1-~1:20, ~20:1-~1:10, ~10:1-~1:10, ~1:1-~1:10, or, e.g., ~1:1-~1:5, such as, e.g., ~1:2, e.g., ~1:2.1. In aspects, the antimicrobial component is an amphotericin B compound, e.g., amphotericin B in ionic liquid form. In aspects, the solvent component is dimethyl acetamide (DMA), such as, e.g., acidified DMA (A-DMA).

In aspects, the invention provides composition(s) wherein the ratio of the concentration (% w/v) of a first complexing agent of a complexing agent component to the concentration (% w/v) of a second complexing agent of the complexing agent component is between about 300:1 and about 1:4, such as, e.g., ~200:1-~1:4, ~100:1-~1:4, ~50:1-~1:4, ~20:1-~1:4, ~10:1-~1:4, ~5:1-~1:1, or, e.g., ~4:1. In aspects, the first complexing agent is ascorbic acid. In aspects, the second complexing agent is choline chloride.

In aspects, the invention provides composition(s) wherein the ratio of the concentration (% w/v) of a first complexing agent of a complexing agent component to the concentration (% w/v) of a solubilization component is between about 300:1 and about 1:4, such as, e.g., ~200:1-~1:4, ~100:1-~1:4, ~50:1-~1:4, ~20:1-~1:4, ~10:1-~1:4, ~5:1-~1:1, or, e.g., ~4:1. In aspects, the first complexing agent is ascorbic acid. In aspects, the solubilization component is TPGS.

In aspects, the invention provides composition(s) wherein the ratio of the concentration (% w/v) of a first complexing agent of a complexing agent component to the concentration (% w/v) of a solvent component is between about 60:1 and about 1:2, such as, e.g., ~40:1-~1:2, ~20:1-~1:2, ~10:1-~1:2, ~10:1-~1:1, ~5:1-~1:1, or, e.g., ~4:1. In aspects, the first complexing agent is ascorbic acid. In aspects, the solvent component is dimethyl acetamide, e.g., acidified dimethyl acetamide.

In aspects, the invention provides composition(s) wherein the ratio of the concentration (% w/v) of a first complexing agent of a complexing agent component to the concentration (% w/v) of the complexing agent component is between about 6:1 and about 1:10, such as, e.g., ~5:1-~1:8, ~4:1-~1:6, ~3:1-~1:4, ~2:1-~1:2, or, e.g., ~1:1, such as, e.g., ~1:1.3. In aspects, the first complexing agent is ascorbic acid. In aspects, the complexing agent component comprises ascorbic acid and choline chloride.

In aspects, the invention provides composition(s) wherein the ratio of the concentration (% w/v) of a second complexing agent of a complexing agent component to the concentration (% w/v) of a solubilization component is between about 200:1 and about 1:200, such as, e.g., ~150:1-~1:150, ~100:1-~1:50, ~50:1-~1:100, ~20:1-~1:20, ~10:1-~1:5, ~5:1-~1:5, ~2:1-~1:2, or, e.g., ~1:1. In aspects, the second complexing agent is choline chloride. In aspects, the solubilization component is TPGS.

In aspects, the invention provides composition(s) wherein the ratio of the concentration (% w/v) of a second complexing agent of a complexing agent component to the concentration (% w/v) of a solvent component is between about 10:1 and about 1:100, such as, e.g., ~10:1-~1:50, ~10:1-~1:40, ~5:1-~1:20, ~5:1-~1:10, ~5:1-~1:5, ~2:1-~1:2, or, e.g., ~1:1. In aspects, the second complexing agent is choline chloride. In aspects, the solvent component is dimethyl acetamide, e.g. acidified dimethyl acetamide.

In aspects, the invention provides composition(s) wherein the ratio of the concentration (% w/v) of a second complexing agent of a complexing agent component to the concentration (% w/v) of the complexing agent component is between about 4:1 and about 1:500, such as, e.g., ~4:1-~1:200, ~4:1-~1:100, ~4:1-~1:50, ~4:1-~1:20, ~2:1-~1:10, ~1:1-~1:10, ~1:2-~1:8, or, e.g., ~1:5. In aspects, the second complexing agent is choline chloride. In aspects, a complexing agent component comprises ascorbic acid and choline chloride.

In aspects, the invention provides composition(s) wherein the ratio of the concentration (% w/v) of a solubilization component to the concentration (% w/v) of a solvent component is between about 40:1 and about 1:100, such as, e.g., ~40:1-~1:60, ~30:1-~1:50, ~20:1-~1:20, ~10:1-~1:10, ~5:1-~1:5, ~2:1-~1:2, or, e.g., ~1:1. In aspects, the solubilization component is TPGS. In aspects, the solvent component is dimethyl acetamide, e.g., acidified dimethyl acetamide.

In aspects, the invention provides composition(s) wherein the ratio of the concentration (% w/v) of a solubilization component to the concentration (% w/v) of a complexing agent component is between about 4:1 and about 1:500, such as, e.g., ~4:1-~1:200, ~4:1-~1:100, ~4:1-~1:50, ~3:1-~1:30, ~3:1-~1:20, ~2:1-~1:10, ~1:1-~1:10, ~2:1-~1:8, or, e.g., ~1:5. In aspects, the solubilization component is TPGS. In aspects, the complexing agent component comprises acetic acid and choline chloride.

In aspects, the invention provides composition(s) wherein the ratio of the concentration (% w/v) of a solvent component to the concentration (% w/v) of a complexing agent component is between about 2:1 and about 1:100, such as, e.g., ~2:1-~1:50, ~2:1-~1:20, ~1:1-~1:10, ~1:1-~1:8, ~1:2-~1:8, or, e.g., ~1:5. In aspects, the solvent component is dimethyl acetamide, e.g., acidified dimethyl acetamide. In aspects, the complexing agent component comprises acetic acid and choline chloride.

In aspects, the invention provides ODF(s), wherein the ODF(s) comprise a ratio of the total weight of an ionic liquid component (ionic liquid component constituents) to the total weight of a film-inducing component of between about 2:1 and about 1:7, such as, e.g., ~2:1-~1:5, ~2:1-~1:3, ~1:1-~1:4, ~1:1-~1:3, or, e.g., about 1:2, such as, e.g., ~1:2.2. In aspects, an ionic liquid component comprises an API component, a complexing agent component, a solvent component, and, e.g. a solubilizing component. In aspects, a film-inducing component comprises a film-forming component and a plasticizing component.

In aspects, ODF(s) are provided comprising an ionic liquid component and a film-inducing component, and further wherein the film-inducing component of the ODF(s) comprises a film-forming component, wherein the ratio of the total weight of ionic liquid component constituents to the total weight of the film-forming component is between about 2:1 and about 1:7, such as, e.g., ~2:1-~1:5, ~2:1-~1:4, ~1:1-~1:3, or, e.g., ~1:2. In aspects, an ionic liquid component comprises an API component, a complexing agent component, a solvent component, and a solubilizing component. In aspects, a film-forming component comprises PVA.

In aspects, the invention provides ODF(s) comprising a film-inducing component, the film-inducing component comprising a plasticizer component, wherein the ratio of the total weight of ionic liquid component constituents to the total weight of the plasticizer component is between about 60:1 and about 1:1, such as., e.g., ~50:1-~1:1, ~40:1-~1:1, ~30:1-~20:1, ~10:1-~1:1, ~8:1-~2:1, or, e.g., ~5:1. In aspects, an ionic liquid component comprises an API component, a complexing agent component, a solvent component, and a solubilizing component. In aspects, a plasticizer component comprises glycerol.

In aspects, the invention provides ODF(s) comprising a film-inducing component, the film-inducing component comprising a film-forming component, wherein the ratio of the total weight of film-forming component constituents to the total weight of the film-inducing component constituents is between about 2:1 and about 1:3, such as, e.g., ~2:1-~1:2, ~1:1-~1:3, ~1:1-~1:2, or, e.g., ~1:1, such as, e.g., ~1:1.1. In aspects, a film inducing component comprises a film-forming component and a plasticizer component. In aspects, a film-forming component comprises polyvinyl alcohol.

In aspects, the invention provides ODF(s) comprising a film-inducing component, wherein the film-inducing component comprises a film-forming component and a plasticizer component, and the ratio of the total weight of the film-forming component constituents to the total weight of the plasticizer component constituents is between about 80:1 and about 40:1, such as, e.g., ~70:1-~30:1, ~60:1-~20:1, ~40:1-~10:1, ~20:1-~5:1, or, e.g., ~15:1-~1:1, such as, e.g., ~15:1-~5:1 or, e.g., ~10:1. In aspects, the film-forming component comprises polyvinyl alcohol. In aspects, the plasticizer component comprises glycerol.

In aspects, the invention provides ODF(s) comprising a film-inducing component and wherein the film-inducing component comprises a plasticizer component, and the ratio of the total weight of the plasticizer component constituents to the total weight of the film-inducing component constituents is between about 1:4 and about 1:90, e.g., ~1:4-~1:50, ~1:4-~1:20, ~1:2-~1:20, ~1:1-~1:15, ~1:5-~1:15, or, e.g., ~1:11. In aspects, a film-inducing component comprises a film-forming component and a plasticizer component. In aspects, the plasticizer component comprises glycerol.

Compositions Do Not Comprise (Exclusions)

In aspects, composition(s) and or method(s) described herein are characterizable by one or more constituent(s) or step(s) (as applicable) which are not present. Uncontradicted, the "lack" of an ingredient can be characterized on the basis of the lack of any detectable amount, the lack of any amount that imparts a detectable function or characteristic change in the composition known to be associated with the lacking agent/element, or a relative lack as compared to other agents of the composition (e.g., being present in an amount that is 100-fold/100× less than another element of the composition or more, such as 200-fold/200× less, 500-fold/500× less, 1000-fold/1000× less, 5000-fold/5000× less or 10,000-fold/10,000× less) or being present in a very small amount such as less than ~0.0001%, less than ~0.00001%, less than ~0.000001%, less than 0.00000001%, etc., and the disclosure of "not comprising" an agent or element should be interpreted as providing support for any or all of such types of "lacking" or "absence" from the relevant composition.

In certain specific aspects, composition(s) do not comprise a detergent. In some aspects, composition(s) do not comprise sodium deoxycholate. In aspects, composition(s) are not co-administered with deoxycholate.

In aspects, composition(s) provided herein, e.g., ODF(s) comprising an ionic liquid of amphotericin B described herein, do not comprise pullulan, dextran, maltodextrin, carrageen, hypromellose (HPMC), corn starch, pectin, sodium alginate, modified cellulose, pectin, HHPMC, or any two or more thereof. In aspects, composition(s) do not comprise dextrose-derived polymer film formers (e.g., dextran and maltodextrin), or cellulose-derived film formers (e.g., hydroxypropylmethyl/hydroxypropyl cellulose, or, e.g., hydroxypropylmethyl cellulose acetate succinate and hydroxypropyl cellulose.)

In aspects, composition(s) provided herein, e.g., ODF(s) comprising an ionic liquid of amphotericin B described herein, do not comprise glyceryl oleate, macrogol, propylene glycol, macrogol, polyethylene glycol, sorbitol, erythritol, glycerin polysorbate, monocaprylate, polyethylene oxide, colloidal silicon dioxide, or any two or more thereof.

In aspects, composition(s) provided herein, e.g., ODF(s) comprising an ionic liquid of amphotericin B described herein, do not comprise sorbitol.

In aspects, composition(s) provided herein, e.g., ODF(s) comprising an ionic liquid of amphotericin B described herein, do not comprise microcrystalline cellulose or microcrystalline cellulose-carboxymethylcellulose sodium.

In aspects, composition(s) provided herein, e.g., ODF(s) comprising an ionic liquid of amphotericin B described herein, do not comprise polyethylene glycol 400.

In aspects, composition(s) do not comprise dry triethylamine buffer methanolic solution.

In aspects, composition(s), such as, e.g., ODF(s) comprising ionic liquid form(s) of amphotericin B such as those described herein, do not require water for administration; that is, e.g., in aspects, ODF(s) do not require water to consume. In aspects, composition(s) can be taken/consumed or otherwise administered in low water environment(s), such as, e.g., in third world country(ies), in remote areas, while traveling etc.)

In aspects, composition(s) such as, e.g., ODF(s) comprising ionic liquid form(s) of amphotericin B such as those described herein, at least generally, at least substantially, at least essentially, essentially, or completely bypass the gastrointestinal tract. In aspects, API(s) of composition(s) described herein, when administered via one or more composition(s) described herein at least generally, at least substantially, at least essentially, essentially, or completely bypass the gastrointestinal tract. In aspects, composition(s) such as, e.g., ODF(s) comprising ionic liquid form(s) of amphotericin B such as those described herein, at least generally, at least substantially, at least essentially, essentially, or completely avoid the first pass effect. In aspects, API(s) of composition(s) described herein, when administered via one or more composition(s) described herein at least generally, at least substantially, at least essentially, essentially, or completely avoid the first pass effect.

In aspects, composition(s) such as, e.g., ODF(s) comprising ionic liquid form(s) of amphotericin B such as those described herein, do not require medical professional for administration. In aspects, composition(s) provided herein are not administered intravenously (by IV). In aspects, composition(s) can be self-administered. In aspects, composition(s) can be administered in a non-medical environment, such as, e.g., an environment outside of a medical clinic, medical provider office/facility, or other medical care facility such as a hospital. In aspects, composition(s) can be administered, e.g., at the home of a recipient/patient, while a recipient/patient is traveling, etc.

Characteristics of Compositions

Comparator Composition(s)

In aspects, composition(s) provided by the invention are characterizable by comparison to one or more comparator formulation(s)/composition(s). In aspects, a "comparator formulation" or "comparator composition" is any formulation or composition comprising the same API(s), wherein the API(s) (1) is/are present in a form not characterizable as an ionic liquid; (2) is/are characterizable as an ionic liquid form of the API(s) which is detectably or significantly different than that provided herein, such as comprising one or more different complexing agent(s); (3) is/are solubilized in a detectably or significantly different solvent, is/are solubilized using a detectably or significantly different solubilizer, or both; (4) is required to be present in a detectably or significantly higher amount to achieve at least generally the same, at least substantially the same, at least essentially the same, essentially the same, or the same therapeutic effect or clinical result; or (5) any combination of (1)-(4), used to treat an at least generally the same, at least substantially the same, at least essentially the same, essentially the same, or the same condition. In aspects, a "comparator formulation" or "comparator composition" is a composition provided in the same form of administration, such as, e.g., an ODF, as the present composition. In alternative aspects, a "comparator formulation" or "comparator composition" is a composition provided in a different form of administration, such as a form for delivery by ingestion (e.g., tablet/pill, liquid) or, e.g., a form for delivery by injection, e.g., administered by intravenous (IV) administration. In certain aspects, a "comparator formulation" or "comparator composition" is approved by the Australian Government Therapeutic Goods Administration as ARTG Entry 19295. In aspects, a "comparator formulation" or "comparator composition" is a composition approved by the Australian Government Therapeutic Goods Administration as ARTG Entry 19295 as first approved in 1991. In aspects, a "comparator formulation" or "comparator composition" is a composition approved by the Australian Government Therapeutic Goods Administration as ARTG Entry 19295 as first approved in September 1991, or as modified under the same approval identifier since the time of the original approval (e.g., as approved under the same approval identifier as of 01/01/1995, 01/01/2000, 01/01/2005, 01/01/2010, 01/01/2015, 01/01/2020, or, e.g., 01/01/2023. In aspects, a "comparator formulation" or "comparator composition" is a composition approved by the Australian Government Therapeutic Goods Administration and marketed under the trade name, "FUNGILIN". In aspects, a comparator composition is orally dissolvable mg amphotericin B lozenge(s), e.g., lozenges marketed under the tradename "FUNGILIN."

In aspects comparator formulation(s)/composition(s) is/are composition(s) comprising one or more different API(s), e.g., one or more API(s) which is different from the present composition used to treat an at least generally the same, at least substantially the same, at least essentially the same, essentially the same, or the same condition, such as, e.g., infection within or of the same anatomical region of the body (e.g., oral cavity) by the same infective agent, e.g., a *Candida* spp. In aspects comparator formulation(s)/composition(s) is/are composition(s) comprising one or more different API(s), e.g., one or more API(s) which is different from the present composition, but which is delivered by the same form of administration, such as an ODF, and is used to treat an at least generally the same, at least substantially the same, at least essentially the same, essentially the same, or the same condition, such as, e.g., infection within or of the same anatomical region of the body (e.g., oral cavity) by the same infective agent, e.g., a *Candida* spp.

Increased Solubility

In certain aspects, the invention provides amphotericin B in a form, e.g., an ionic liquid form of amphotericin B, having a detectably or significantly increased solubility (in, e.g., a solvent, water, or, e.g., saliva) compared to that of amphotericin B in an alternative form, such as in unmodified form. In certain aspects, the invention provides highly solubilizable amphotericin B, e.g., a highly solubilizable ionic liquid form of amphotericin B. In aspects, the solubility of amphotericin B compound(s) as described herein is at least about 0.1%, 0.5%, 1%, 5%, 10%, 20%, 30%, 50% 100%, 200%, 500% or more greater than that of amphotericin in unmodified form. In aspects, the solubility of amphotericin B as described herein is at least about 0.1%, 0.5%, 1%, 5%, 10%, 20%, 30%, 50% 100%, 200%, 500% or more greater than that of amphotericin in a form such as that found in comparator formulation(s)/composition(s). In aspects, the solubility of amphotericin B in ionic liquid form, e.g., complexed amphotericin B, as described herein, is at least about 0.1%, 0.5%, 1%, 5%, 10%, 20%, 30%, 50% 100%, 200%, 500% or more greater than that of amphotericin in unmodified form. In aspects, the solubility of amphotericin B as described herein is at least about 0.1%, 0.5%, 1%, 5%, 10%, 20%, 30%, 50% 100%, 200%, 500% or more greater than that of amphotericin in a form such as that found in comparator formulation(s)/composition(s). In aspects, the solubility of amphotericin B in ionic liquid form as described herein is at least about 0.1%, 0.5%, 1%, 5%, 10%, 20%, 30%, 50% 100%, 200%, 500% or more greater than that of amphotericin in a form such as that found in comparator formulation(s)/composition(s).

Herein, solubility can refer to amphotericin B compound(s) described herein, e.g., amphotericin B, or, e.g., amphotericin B in ionic liquid form(s) as described herein. Where reference to the solubility of amphotericin B provided by composition(s) described herein is made, such reference should accordingly include reference to the solubility of amphotericin B in ionic liquid form provided by composition(s) described herein. That is, in aspects, solubility as referred to herein of amphotericin B provided by composition(s) of the invention can refer to solubility of amphotericin provided as an ionic liquid, e.g., as a complex such as is described herein.

In aspects, the invention provides amphotericin B in ionic liquid form and, e.g., composition(s) comprising such amphotericin B compound(s). In aspects, the invention provides amphotericin B in ionic liquid form, and, e.g., composition(s) comprising such amphotericin B compound(s), providing for an increased solubility of amphotericin B of at least about 0.1%, 0.5%, 1%, 5%, 10%, 20%, 30%, 50% 100%, 200%, 500% in one or more pharmaceutically or therapeutically relevant environments, under one or more pharmaceutically or therapeutically relevant conditions, or both, compared to that of amphotericin in unmodified form.

In aspects, the invention provides at least one antimicrobial agent, e.g., at least one antifungal agent, e.g., amphotericin B compound, such as amphotericin B in an ionic liquid form which demonstrates a detectably or significantly increased solubility in water at a neutral pH than the same at least one antimicrobial agent, e.g., at least one antifungal agent, e.g., amphotericin B compound, provided in unmodified form. In aspects, composition(s) herein provide an ionic liquid form of amphotericin B which provide for an at least about 1%, ≥~2%, ≥~3%, ≥~4%, ≥~5%, ≥~6%, ≥~7%, ≥~8%, ≥~9%, ≥~10%, ≥~15%, ≥~20%, ≥~25%, ≥~30%, ≥~35%, ≥~40%, ≥~45%, or, e.g., ≥~50%, increase in the solubility of amphotericin B in water at a neutral pH compared to that of amphotericin B provided in unmodified form.

In aspects, the invention provides at least one antimicrobial agent, e.g., at least one antifungal agent, e.g., amphotericin B compound, such as amphotericin B in an ionic liquid form which demonstrates a higher dose strength soluble in about 250 mL or less of aqueous medium having a pH of between about 1 and about 7 and a temperature of about 37° C. (98.6° C.)±about 2° C. (e.g., a temperature equivalent to the average human body temperature) than the same at least one antimicrobial agent, e.g., at least one antifungal agent, e.g., amphotericin B compound, provided in unmodified form. In aspects, composition(s) herein provide an ionic liquid form of amphotericin B which provides for an at least about 1%, ≥~2%, ≥~3%, ≥~4%, ≥~5%, ≥~6%, ≥~7%, ≥~8%, ≥~9%, ~10%, ≥~15%, ≥~20%, ≥~25%, ≥~30%, ≥~35%, ≥~40%, ≥~45%, or, e.g., ≥~50%, increase in the amount of amphotericin B compound soluble under such a condition compared to amphotericin B provided in unmodified form.

In aspects, the invention provides at least one antimicrobial agent, e.g., at least one antifungal agent, e.g., amphotericin B compound, such as amphotericin B in an ionic liquid form which demonstrates a detectably or significantly increased solubility in saliva, artificial saliva (e.g., compositions mimicking saliva as recognized by those skilled in the art, formulated in a laboratory), or both, than the same at least one antimicrobial agent, e.g., at least one antifungal agent, e.g., amphotericin B compound, provided unmodified form. In aspects, composition(s) herein provide an ionic liquid form of amphotericin B which provide for an at least about 1%, ≥~2%, ≥~3%, ≥~4%, ≥~5%, ≥~6%, ≥~7%, ≥~8%, ≥~9%, ≥~10%, ≥~15%, ≥~20%, ≥~25%, ≥~30%, ≥~35%, ≥~40%, ≥~45%, or, e.g., ≥~50%, increase in the solubility of amphotericin B in saliva or artificial saliva compared to that of amphotericin B provided in unmodified form.

In aspects, the invention provides at least one antimicrobial agent, e.g., at least one antifungal agent, e.g., amphotericin B compound, such as amphotericin B in an ionic liquid form which demonstrates a detectably or significantly increased solubility in an acidic pH environment such as gastric juice(s) of the gastrointestinal tract or laboratory/replicated test environments of the same (e.g., compositions formed in a laboratory and recognized by those skilled in the art as mimicking the environment(s) of the gastrointestinal system), or both, than the same at least one antimicrobial agent, e.g., at least one antifungal agent, e.g., amphotericin B compound, provided in unmodified form. In aspects, composition(s) herein provide an ionic liquid form of amphotericin B which provide for an at least about 1%, ≥~2%, ≥~3%, ≥~4%, ≥~5%, ≥~6%, ≥~7%, ≥~8%, ≥~9%, ≥~10%, ≥~15%, ≥~20%, ≥~25%, ≥~30%, ≥~35%, ≥~40%, ≥~45%, or, e.g., ≥~50%, increase in the solubility of amphotericin B in acidic pH environments of the gastrointestinal tract or simulated environments thereof compared to that of amphotericin B provided in unmodified form.

In certain aspects, the invention provides compositions comprising an amount of solubilized amphotericin B which is detectably or significantly greater than the amount of solubilized amphotericin B provided in a comparator composition comprising amphotericin B in an alternative form or, e.g., in unmodified form. In respect to its use herein, reference to "an alternative form" of amphotericin B includes, e.g., amphotericin B typically provided by intravenous injection, forms of amphotericin B described in, e.g., US patent publication numbers US2015/038594, US2019/0388545, US2021/0361573, US2021/085622, Serrano (supra), In aspects, composition(s) of amphotericin B, e.g., ionic liquid(s) of amphotericin B (amphotericin B in ionic liquid form) provided herein, demonstrate a solubility in water of at least about 1 mg/mL, such as, e.g., ≥~1.2 mg/mL, ≥~1.4 mg/mL, ≥~1.6 mg/mL, ≥~1.8 mg/mL, ≥~2 mg/mL, ≥~2.2 mg/mL, ≥~2.4 mg/mL, ≥~2.6 mg/mL, ≥~2.8 mg/mL, ≥~3 mg/mL, ≥~3.2 mg/mL, ≥~3.4 mg/mL, ≥~3.6 mg/mL, ≥~3.8 mg/mL, or, e.g., ≥~4 mg/mL. In aspects, composition(s) of amphotericin B, e.g., ionic liquid(s) of amphotericin B (amphotericin B in ionic liquid form) provided herein, demonstrate a solubility in water of no less than 1 mg/mL, such as no less than 0.8 mg/mL. In aspects, composition(s) of amphotericin B, e.g., ionic liquid(s) of amphotericin B (amphotericin B in ionic liquid form) provided herein demonstrate a solubility in water of between about 2 mg/mL and about 5 mg/mL, such as, e.g., ~2 mg/mL-~4.8 mg/mL, ~2 mg/mL-~4.6 mg/mL, ~2 mg/mL-~4.4 mg/mL, ~2 mg/mL-~4.2 mg/mL, ~2 mg/mL-~4 mg/mL, ~2 mg/mL-~3.8 mg/mL, ~2 mg/mL-~3.6 mg/mL, ~2 mg/mL-~3.4 mg/mL, or, e.g., ~2.2 mg/mL-~5 mg/mL, ~2.4 mg/mL-~5 mg/mL, ~2.6 mg/mL-~5 mg/mL, ~2.8 mg/mL-~5 mg/mL, ~3 mg/mL-~5 mg/mL, ~3.2 mg/mL-~5 mg/mL, or ~3.4 mg/mL-~5 mg/mL, such as, e.g., ~2.2 mg/mL-~4.8 mg/mL, ~2.4 mg/mL-~4.4 mg/mL, ~2.6 mg/mL-~4 mg/mL, ~2.8 mg/mL-~3.6 mg/mL, ~3 mg/mL-~3.5 mg/mL, ~3.2 mg/mL-~3.5 mg/mL, or, e.g., ~3.4 mg/mL.

In aspects, the invention provides orally dissolvable film(s) comprising amphotericin B, e.g., amphotericin B in ionic liquid form such as ionic liquid(s) of amphotericin B described herein, demonstrating an average solubility in water which is at least about five (5) times greater than that of unmodified amphotericin B, such as, e.g., at least about 2× greater, ≥~3×, ≥~4×, ≥~5×, ≥~6×, ≥~7×, ≥~8×, ≥~9×, or ~10× greater, such as for example at least about 5 times greater, e.g., about 5.4 times greater, than that of unmodified amphotericin B.

In aspects, composition(s) of amphotericin B are provided as ODF(s). In aspects, ODF composition(s) herein comprise ionic liquid form(s) of amphotericin B, e.g., ionic liquid form(s) of amphotericin B described herein, wherein the amphotericin B provided by the ODF is detectably or significantly more soluble in saliva (or, e.g., simulated saliva) than amphotericin B in unmodified form, and, in aspects, the ODF delivers a detectably or significantly higher concentration of, a detectably or significantly higher total dose of, or both a detectably or significantly higher concentration and total dose of, amphotericin B to the oral cavity of a recipient of an ODF than amphotericin B provided by systemic administration, or provided by one or more comparator products such as a comparator product described herein.

Methods of Increasing Solubility

In certain aspect(s), the invention provides method(s) of increasing the solubility of amphotericin B. In aspects, the invention provides method(s) of increasing the solubility of amphotericin B, wherein amphotericin B is formed as an ionic liquid. In aspects, an ionic liquid form of amphotericin B is formed using one or more complexing agent(s) such as one or more complexing agents described herein. In aspects, amphotericin B compound(s) are solubilized in one or more solvent(s) described herein. In aspects, the solubility of amphotericin B is further enhanced using one or more solubilizing agents, such as one or more solubilizing agent(s) described herein. In aspects, the invention provides method(s) of increasing the solubility of amphotericin B comprising forming an ionic liquid of amphotericin B, wherein the ionic liquid form of amphotericin B demonstrates an increased solubility of amphotericin B which is 0.1%, 0.5%, 1%, 5%, 10%, 20%, 30%, 50% 100%, 200%, 500% greater than that of amphotericin B provided in unmodified form, e.g., such an increase in solubility in one or more environments such as, e.g., an aqueous environment at neutral pH, saliva or artificial saliva, or, e.g., the acidic environment of the gastrointestinal tract or simulated versions thereof.

Increased Bioavailability/Local Concentration

In aspects herein, oral delivery is limited to a delivery mechanism such as an ODF which acts locally, e.g., within the oral cavity, and at least generally does not, at least substantially does not, at least essentially does not, essentially does not, or does not act via ingestion (e.g., via passage through the gastrointestinal tract such as that demonstrated by other forms of oral delivery such as, e.g., a tablet or capsule.) In aspects, as described herein, while a detectable amount of API delivered by oral delivery, e.g., ODF(s) described herein, may pass through at least a portion of the gastrointestinal tract, at least generally all, at least substantially all, at least essentially all, or essentially all of the API(s), e.g., amphotericin B, in an oral delivery form described herein, e.g., ODF(s), is delivered locally.

In certain aspects, local concentration of API, e.g., local concentration of amphotericin B in the oral cavity when administered as an ODF described herein, is detectably or significantly higher than that achieved via systemic administration of amphotericin B (e.g., administration of amphotericin B via a route resulting in systemic administration such as, e.g., by oral administration as form to be swallowed, e.g., tablet, capsule, etc. or, e.g., by intravenous (IV) administration; noting that when delivered by IV, the concentration of API delivered is determined by the drug concentration in the bloodstream and the blood circulation to the target locale). In certain aspects, concentration of amphotericin B in the bloodstream is lower upon administration of amphotericin B by ODF(s) described herein than that achieved by administration of amphotericin B by, e.g., systemic route(s), e.g., oral tablet or capsule administration or, e.g., by IV. In aspects, ODF(s) provided herein are directed to providing local activity of the API within the oral cavity. In aspects, ODF(s) described herein provide a detectably or significantly greater local bioavailability of API, e.g., amphotericin B, compared to systemically administered amphotericin B (e.g., oral tablet or capsule administration or, e.g., IV administration.) In aspects, ionic liquid(s) of amphotericin B provided herein provide a detectably or significantly greater solubility of amphotericin B compared to other forms of amphotericin B, such as comparator forms of amphotericin B or, e.g., unmodified amphotericin B. In aspects, ionic liquid(s) of amphotericin B provided herein provide a detectably or significantly greater rate of, greater degree of, or both greater rate and degree of microbial cell wall penetration (e.g., fungal cell wall penetration) within a localized area of treatment, e.g., the oral cavity, with local administration of ODF(s) provided herein compared to that achieved by systemically delivered amphotericin B. In aspects, ODF(s) provided herein provide a detectably or significantly greater local fungicidal activity (e.g., fungicidal activity within the oral cavity) than that of antifungal composition(s) delivered by tablet, capsule, or the like, or, e.g., than antifungal composition(s) delivered by IV.

In aspects, the invention provides an API, e.g., amphotericin B, in a form, e.g., in an ionic liquid form described herein, e.g., delivered as an ODF, wherein a detectably or significantly greater local concentration of the API, e.g., amphotericin B, is achieved compared to than that of amphotericin B provided locally in unmodified form, compared to that of amphotericin B provided by systemic administration, e.g., by orally delivered tablet, capsule, or the like, or, e.g., compared to that of amphotericin B provided by systemic administration such as by IV. In aspects, composition(s) herein comprising amphotericin B, e.g., amphotericin B in ionic liquid form, e.g., delivered by ODF, provide a localized concentration (e.g., concentration within the oral cavity) of amphotericin B which is at least about 0.1%, 0.5%, 1%, 5%, 10%, 20%, 30%, 50% 100%, 200%, 500% greater than that of amphotericin B in an alternative form, such as an unmodified form or, e.g., delivered by alternative means, e.g., by swallowing a tablet, capsule, etc. or by receiving IV administration of the API.

In certain aspects, the invention provides ODF(s) comprising amphotericin B, e.g., an ionic liquid of amphotericin B, for local delivery of the amphotericin B within the oral cavity. In aspects, an at least detectable amount of amphotericin B provided by the ODF(s), though delivered locally (e.g., delivered within the oral cavity as the ODF dissolves), is swallowed and thus an at least detectable amount of amphotericin B may pass through the gastrointestinal tract. In aspects, bioavailability of such amphotericin B provided by the ODF can be assessed.

In aspects, the invention provides amphotericin B in a form which, when delivered by a form of administration, such as, e.g., an ODF and when, e.g., a detectable or significant amount of amphotericin B reaches systemic circulation, the amphotericin B, e.g., amphotericin B in ionic liquid form(s) described herein is detectably or significantly more bioavailable than amphotericin B in unmodified form delivered by the same form of administration. In aspects, the invention provides composition(s) comprising an ionic liquid form of amphotericin B described herein, wherein the composition(s) provide a detectably or significantly greater bioavailability of amphotericin B (e.g., provide amphotericin B in detectably or significantly more bioavailable form) when administered to a mammalian recipient than at least generally the same, at least substantially the same, at least essentially the same, essentially the same, or the same composition(s) comprising amphotericin B in unmodified form as determined by an appropriately conducted and controlled trial, e.g., a trial recognized by a recognized regulatory body such as the United States Food and Drug Administration (US FDA).

In certain aspects, the invention provides amphotericin B in ionic liquid form wherein amphotericin B in ionic liquid form is detectably or significantly more bioavailable than amphotericin B provided in a comparator composition wherein the amphotericin B is provided in an alternative form such as, e.g., in unmodified form.

In certain aspects, the invention provides amphotericin B in ionic liquid form, such as, e.g., ionic liquid form(s) of amphotericin B described herein, providing for increased bioavailability of the API, wherein a detectably or significantly decreased total amount of amphotericin B provides an equivalent or significantly enhanced/improved therapeutic effect than that required for a comparator product comprising amphotericin B in an alternative form, such as an unmodified form, when the two forms of amphotericin B are administered via the same form of delivery. In aspects, the amount of amphotericin B provided in an ionic liquid form described herein providing an equivalent or detectably or significantly improved therapeutic effect in treating one or more condition(s) is at least about 2%, ≥4%, ≥6%, ≥8%, ≥10%, ≥12%, ≥14%, ≥16%, ≥18%, ≥20%, or, e.g., ≥25%, ≥30%, ≥35%, ≥40%, ≥45%, or, e.g., ≥50% less than (lower than) the amount of unmodified amphotericin B required to achieve the same therapeutic effect in the treatment of the same one or more condition(s) when administered via the same form of delivery.

In aspects, the invention provides amphotericin B in a form, e.g., in an ionic liquid form described herein, having a detectably or significantly greater bioavailability than that of amphotericin B in unmodified form. In aspects, composition(s) herein comprising amphotericin B, e.g., amphotericin B in ionic liquid form, provide a bioavailability of amphotericin B which is at least about 0.1%, 0.5%, 1%, 5%, 10%, 20%, 30%, 50% 100%, 200%, 500% greater than that of amphotericin B in an alternative form, such as an unmodified form.

In aspects, the invention provides amphotericin B in a form, e.g., in an ionic liquid form described herein, e.g., provided as an ODF, wherein the ODF, when dissolved in the oral cavity of a recipient, delivers an amount of amphotericin B within the oral cavity of the recipient that is available for treating a microbial source of an oral microbial infection which is detectably or significantly greater than that the amount of amphotericin B delivered to the oral cavity of a recipient receiving an orally swallowed administration form of amphotericin B, an intravenous administration of amphotericin B, or both.

Methods of Increasing Bioavailability/Local Concentration

In certain aspect(s), the invention provides method(s) of increasing the bioavailability of amphotericin B. In aspects, the invention provides method(s) of increasing the bioavailability of amphotericin B, wherein amphotericin B is formed as an ionic liquid. In aspects, an ionic liquid form of amphotericin B is formed using one or more complexing agent(s) such as one or more complexing agents described herein. In aspects, amphotericin B compound(s) are solubilized in one or more solvent(s) described herein. In aspects, the solubilization of amphotericin B is further enhanced using one or more solubilizing agents, such as one or more solubilizing agent(s) described herein. In aspects, the invention provides method(s) of increasing the bioavailability of amphotericin B comprising forming an ionic liquid of amphotericin B, wherein the ionic liquid form of amphotericin B demonstrates an increased bioavailability of amphotericin B, e.g., a bioavailability which is 0.1%, 0.5%, 1%, 5%, 10%, 20%, 30%, 50% 100%, 200%, 500% greater than that of amphotericin B provided in unmodified form.

In certain aspect(s), the invention provides method(s) of increasing the local concentration of an API, e.g., an antimicrobial API, e.g., an antifungal API, e.g., amphotericin B. In certain aspect(s), the invention provides method(s) of increasing the local concentration of an API, e.g., an antimicrobial API, e.g., an antifungal API, e.g., amphotericin B, within the oral cavity. In aspects, the invention provides method(s) of increasing the local concentration of an API, e.g., amphotericin B, wherein the API, e.g., amphotericin B is formed as an ionic liquid, e.g., an ionic liquid composition described herein. In aspects, the invention provides method(s) of increasing the local concentration of an API, e.g., amphotericin B, wherein the API, e.g., amphotericin B, in ionic liquid form is provided as an ODF. In aspects, the detectably or significantly increased solubilization of an API, e.g., amphotericin B, as provided by the composition(s) described herein detectably or significantly increases the local bioavailability of the API, e.g., increasing the locally available concentration of API, e.g., amphotericin B. In aspects, method(s) herein demonstrate a detectably or significantly increased rate of penetration, a detectably or significantly increased degree of penetration, or both, of microbial cell walls of microbial population(s) present in the local environment, leading to a detectably or significantly increased local fungicidal activity. In aspects, the invention provides method(s) of increasing the local concentration of an API, e.g., an antimicrobial API, e.g., an antifungal API, e.g., amphotericin B, comprising forming an ionic liquid of the API, e.g., amphotericin B, and delivering the ionic liquid composition as an ODF, wherein the local concentration of the API, e.g., amphotericin B is at least about 0.1%, 0.5%, 1%, 5%, 10%, 20%, 30%, 50% 100%, 200%, 500% greater (or more) than that of unmodified amphotericin B provided by ODF, than that of amphotericin B delivered by systemic administration such as by tablet, capsule, etc. which is swallowed and passes through the GI tract, or, e.g., by IV administration.

Increased GI Absorption

In aspects, the invention provides composition(s) comprising amphotericin B in a form, e.g., in an ionic liquid form described herein, wherein the composition(s) provide for a detectably or significantly increased absorption of amphotericin B in the GI tract compared to composition(s) comprising amphotericin B in alternative form, such as, e.g., in unmodified form. In aspects, ionic liquid(s) of amphotericin B described herein are delivered locally, e.g., local to the oral cavity, and thus primary route of administration is not systemic (e.g., is not via absorption through the gastrointestinal tract.) In aspects, embodiments herein directed to gastrointestinal absorption refer to an amount of amphotericin B which is inadvertently swallowed or which makes its way to the GI tract when administered in a composition having the primary route of administration be local administration. For example, embodiments herein directed to gastrointestinal absorption refer to amphotericin B administered by ODF, but wherein a detectable portion or amount of the amphotericin B in the ODF is swallowed or otherwise makes its way to the gastrointestinal tract, while at least the majority of the amphotericin B is locally delivered.

In aspects, the invention provides amphotericin B in a form, such as, e.g., an ionic liquid form of amphotericin B, which, if present in the gastrointestinal tract, is absorbed in a detectably or significantly greater amount, is absorbed by the gastrointestinal tract at a detectably or significantly greater rate, or both, compared to amphotericin B present in the gastrointestinal tract in unmodified form.

In certain aspects, the invention provides amphotericin B in ionic liquid form wherein the absorption in the gastrointestinal tract of amphotericin B in ionic liquid form is detectably or significantly greater than the form of amphotericin B provided in a comparator composition, e.g., comprising amphotericin B in an alternative form such as in unmodified form.

In certain aspects, the invention provides amphotericin B in ionic liquid form, such as, e.g., ionic liquid form(s) of amphotericin B described herein, providing for an increased absorption of the API in the gastrointestinal tract, wherein a detectably or significantly decreased total amount of amphotericin B is capable of providing an equivalent or significantly enhanced/improved therapeutic effect than that required for a form of amphotericin B provided in a comparator product, e.g., amphotericin B in an alternative form, such as an unmodified form, when the two forms of amphotericin B are administered via the same form of delivery (e.g., ODF). In aspects, the amount of amphotericin B provided in an ionic liquid form described herein providing an equivalent or detectably or significantly improved therapeutic effect in treating one or more condition(s) is at least about 2%, ≥4%, ≥6%, ≥8%, ≥10%, ≥12%, ≥14%, ≥16%, ≥18%, ≥20%, or, e.g., ≥25%, ≥30%, ≥35%, ≥40%, ≥45%, or, e.g., ≥50% less than (lower than) the amount of unmodified amphotericin B required to achieve the same therapeutic effect in the treatment of the same one or more condition(s) when administered via the same form of delivery.

In aspects, the invention provides amphotericin B in a form, e.g., in an ionic liquid form described herein, wherein the amphotericin B is detectably or significantly more absorbed (e.g., absorbed in greater amount(s) or at a higher rate) in the gastrointestinal tract than amphotericin B in unmodified form. In aspects, composition(s) herein comprising amphotericin B, e.g., amphotericin B in ionic liquid form, provide an absorption in the gastrointestinal tract of amphotericin B which is at least about 0.1%, 0.5%, 1%, 5%, 10%, 20%, 30%, 50% 100%, 200%, 500% greater than that of amphotericin B in an alternative form, such as an unmodified form.

In aspects, the invention provides amphotericin B in a form, e.g., in an ionic liquid form described herein, demonstrating an at least about 0.1%, such as, e.g., at least about 0.3%, ≥~0.3%, ≥~0.4%, ≥~0.5%, ≥~0.6%, ≥~0.7%, ≥~0.8%, ≥~0.9%, or ≥~1% absorption in the gastrointestinal tract.

In aspects, the invention provides amphotericin B in a form, e.g., in an ionic liquid form described herein, demonstrating an at least about 1%, such as, e.g., ≥~1.1%, ≥~1.2%, ≥~1.3%, ≥~1.4%, ≥~1.5%, ≥~1.6%, ≥~1.7%, ≥~1.8%, ≥~1.9%, or, e.g., ≥~2% absorption in the gastrointestinal tract.

In aspects, the invention provides amphotericin B in a form, e.g., in an ionic liquid form described herein, demonstrating an at least about 2%, such as, e.g., ≥~2.1%, ≥~2.2%, ≥~2.3%, ≥~2.4%, ≥~2.5%, ≥~2.6%, ≥~2.7%, ≥~2.8%, ≥~2.9%, or, e.g., ≥~3% absorption in the gastrointestinal tract.

In aspects, the invention provides amphotericin B in a form, e.g., in an ionic liquid form described herein, demonstrating an at least about 3%, such as, e.g., ≥~3.1%, ≥~3.2%, ≥~3.3%, ≥~3.4%, ≥~3.5%, ≥~3.6%, ≥~3.7%, ≥~3.8%, ≥~3.9%, or, e.g., ≥~4% absorption in the gastrointestinal tract.

In aspects, the invention provides amphotericin B in a form, e.g., in an ionic liquid form described herein, demonstrating an at least about 4%, such as, e.g., ≥~4.1%, ≥~4.2%, ≥~4.3%, ≥~4.4%, ≥~4.5%, ≥~4.6%, ≥~4.7%, ≥~4.8%, ≥~4.9%, or, e.g., ≥~5% absorption in the gastrointestinal tract.

In aspects, the invention provides amphotericin B in a form, e.g., in an ionic liquid form described herein, demonstrating an at least about 5%, such as, e.g., ≥~5.1%, ≥~5.2%, ≥~5.3%, ≥~5.4%, ≥~5.5%, ≥~5.6%, ≥~5.7%, ≥~5.8%, ≥~5.9%, or, e.g., ≥~6% absorption in the gastrointestinal tract.

In aspects, the invention provides amphotericin B in a form, e.g., in an ionic liquid form described herein, demonstrating an at least about 6%, such as, e.g., ≥~6.1%, ≥~6.2%, ≥~6.3%, ≥~6.4%, ≥~6.5%, ≥~6.6%, ≥~6.7%, ≥~6.8%, ≥~6.9%, or, e.g., ≥~7% absorption in the gastrointestinal tract.

In aspects, the invention provides amphotericin B in a form, e.g., in an ionic liquid form described herein, demonstrating an at least about 7%, such as, e.g., ≥~7.1%, ≥~7.2%, ≥~7.3%, ≥~7.4%, ≥~7.5%, ≥~7.6%, ≥~7.7%, ≥~7.8%, ≥~7.9%, or, e.g., ≥~8% absorption in the gastrointestinal tract.

In aspects, the invention provides amphotericin B in a form, e.g., in an ionic liquid form described herein, demonstrating an at least about 8%, such as, e.g., ≥~8.1%, ≥~8.2%, ≥~8.3%, ≥~8.4%, ≥~8.5%, ≥~8.6%, ≥~8.7%, ≥~8.8%, ≥~8.9%, or, e.g., ≥~9% absorption in the gastrointestinal tract.

In aspects, the invention provides amphotericin B in a form, e.g., in an ionic liquid form described herein, demonstrating an at least about 9%, such as, e.g., ≥~9.1%, ≥~9.2%, ≥~9.3%, ≥~9.4%, ≥~9.5%, ≥~9.6%, ≥~9.7%, ≥~9.8%, ≥~9.9%, or, e.g., ≥~10% absorption in the gastrointestinal tract.

In aspects, the invention provides amphotericin B in a form, e.g., in an ionic liquid form described herein, demonstrating an at least about 10% absorption in the gastrointestinal tract.

Methods of Increasing Gastrointestinal Absorption

In certain aspect(s), the invention provides method(s) of increasing the gastrointestinal absorption of amphotericin B. In aspects, the invention provides method(s) of increasing the gastrointestinal absorption of amphotericin B, wherein the method comprises forming amphotericin B as an ionic liquid, e.g., as an ionic liquid of amphotericin B described herein. In aspects, an ionic liquid form of amphotericin B is formed using one or more complexing agent(s) such as one or more complexing agents described herein. In aspects, amphotericin B compound(s) are solubilized in one or more solvent(s) described herein. In aspects, the solubilization of amphotericin B is further enhanced using one or more solubilizing agents, such as one or more solubilizing agent(s) described herein. In aspects, the invention provides method(s) of increasing the gastrointestinal absorption of amphotericin B comprising forming an ionic liquid of amphotericin B, wherein the ionic liquid form of amphotericin B demonstrates an increased gastrointestinal absorption of amphotericin B which is 0.1%, 0.5%, 1%, 5%, 10%, 20%, 30%, 50% 100%, 200%, 500% greater than that of amphotericin B provided in unmodified form.

MIC

In aspects, the invention provides ionic liquid forms of amphotericin B, e.g., one or more ionic liquid form(s) of amphotericin B described herein, wherein the ionic liquid form of amphotericin B demonstrates a detectably or significantly lower minimum inhibitory concentration (MIC) against one or more species of *Candida* than that demonstrated against the same species of *Candida* by unmodified amphotericin B.

In aspects, the invention provides ionic liquid forms of amphotericin B, e.g., one or more ionic liquid form(s) of amphotericin B described herein, wherein the MIC of the composition(s) against one or more species of *Candida* is at least about 10% lower than that demonstrated against the same species of *Candida* by unmodified amphotericin B, such as, e.g., ≥~10% lower, ≥~15% lower, ≥~20% lower, ≥~25% lower, ≥~30% lower, ≥~35% lower, ≥~40% lower, ≥~45% lower, ≥~50% lower, ≥~55% lower, ≥~60% lower, ≥~65% lower, ≥~70% lower, ≥~75% lower, or ≥~80% lower, than that demonstrated against the same species of *Candida* by unmodified amphotericin B. In aspects, the invention provides ionic liquid forms of amphotericin B, e.g., one or more ionic liquid form(s) of amphotericin B described herein, wherein the MIC of the amphotericin B in ionic liquid form against one or more species of *Candida* is at least about 25% lower, 25% lower, 30% lower, or, e.g., at least about 35% lower than that demonstrated against the same species of *Candida* by unmodified amphotericin B.

In certain aspects, the invention provides ionic liquid forms of amphotericin B, e.g., one or more ionic liquid form(s) of amphotericin B described herein, wherein the $MIC_{48h}$ of the amphotericin B in ionic liquid form demonstrated against one or more species of *Candida*, e.g., *Candida albicans, Candida tropicalis*, or both, is at least about 10% lower than that demonstrated against the same species of *Candida*, e.g., *Candida albicans, Candida tropicalis*, or both, by unmodified amphotericin B, such as, e.g., ≥~10% lower, ≥~15% lower, ≥~20% lower, ≥~25% lower, ≥~30% lower, ≥~35% lower, ≥~40% lower, ≥~45% lower, ≥~50% lower, ≥~55% lower, ≥~60% lower, ≥~65% lower, ≥~70% lower, ≥~75% lower, or ≥~80% lower, than that demonstrated against the same species of *Candida*, e.g., *Candida albicans, Candida tropicalis*, or both, by unmodified amphotericin B.

In certain aspects, the invention provides ionic liquid forms of amphotericin B, e.g., one or more ionic liquid form(s) of amphotericin B described herein, wherein the $MIC_{48h}$ of the amphotericin B in ionic liquid form against or more species of *Candida*, e.g., *Candida albicans, Candida tropicalis*, or both, is no more than about 90% of that of unmodified amphotericin B, such as no more than ~95%, no more than ~90%, no more than ~85%, no more than ~80%, no more than ~75%, no more than ~70%, no more than ~65%, no more than ~60%, no more than ~55%, or no more than ~50% of that of unmodified amphotericin B, such as, e.g., no more than ~45%, ~40%, ~35%, ~30%, or, e.g., ~25% of that of unmodified amphotericin B.

In aspects, the invention provides ionic liquid forms of amphotericin B, e.g., one or more ionic liquid form(s) of amphotericin B described herein, wherein the $MIC_{48h}$ of the amphotericin B in ionic liquid form against one or more species of *Candida*, e.g., *Candida albicans, Candida tropicalis*, or both, is less than about 1.2 µM, such as, e.g., ≤~1.1 µM, ≤~1 µM, ≤~0.9 µM, ≤~0.8 µM, ≤~0.7 µM, ≤~0.6 µM, ≤~0.5 µM, ≤~0.4 µM, ≤~0.3 µM, ≤~0.2 µM, or ≤~0.1 µM. In aspects, the invention provides ionic liquid forms of amphotericin B, e.g., one or more ionic liquid form(s) of amphotericin B described herein, wherein the $MIC_{48h}$ of the ionic liquid form of amphotericin B against one or more species of *Candida*, e.g., *Candida albicans, Candida tropicalis*, or both, is less than about 0.7 µM, e.g., less than about 0.65 µM, less than about 0.60 µM, less than about 0.55 µM, less than about 0.5 µM, less than about 0.45 µM, less than about 0.4 µM, or less than about 0.35 µM.

In aspects, the invention provides ionic liquid forms of amphotericin B, e.g., one or more ionic liquid form(s) of amphotericin B described herein, wherein the $MIC_{48h}$ of the ionic liquid form of amphotericin B against one or more species of *Candida*, e.g., *Candida albicans, Candida tropicalis*, or both, is between about 0.1 µM and about 1 µM, e.g., ~0.15 µM-~1 µM, ~0.2 µM-~1 µM, ~0.25 µM-~1 µM, ~0.3 µM-~1 µM, or, e.g., ~0.35 µM-~1 µM, such as, e.g., ~0.1 µM-~0.9 µM, ~0.1 µM-~0.8 µM, ~0.1 µM-~0.7 µM, ~0.1 µM-~0.6 µM, ~0.1 µM-~0.5 µM, ~0.1 µM-~0.4 µM, or ~0.1 µM-~0.3 µM, such as, e.g., ~0.15 µM-~0.9 µM, ~0.2 µM-~0.8 µM, ~0.25 µM-~0.7 µM, ~0.3 µM-~0.6 µM, ~0.3 µM-~0.5 µM, or, e.g., ~0.3 µM-~0.4 µM, as in, e.g., ~0.6 µM-~0.8 µM.

In aspects, the invention provides ODF composition(s) of amphotericin B in ionic liquid form described herein wherein the ODF composition(s) demonstrate a detectably or significantly lower minimum inhibitory concentration (MIC) against one or more species of *Candida* than that demonstrated against the same species of *Candida* by unmodified amphotericin B.

In aspects, the invention provides ODF composition(s) of amphotericin B in ionic liquid form described herein wherein the MIC of the composition(s) against one or more species of *Candida* is at least about 10% lower than that demonstrated against the same species of *Candida* by unmodified amphotericin B, such as, e.g., ≥~10% lower, ≥~15% lower, ≥~20% lower, ≥~25% lower, ≥~30% lower, ≥~35% lower, ≥~40% lower, ≥~45% lower, ≥~50% lower, ≥~55% lower, ≥~60% lower, ≥~65% lower, ≥~70% lower, ≥~75% lower, or ≥~80% lower, than that demonstrated against the same species of *Candida* by unmodified amphotericin B. In aspects, the invention provides ODF composition(s) of amphotericin B in ionic liquid form described herein wherein the MIC of the composition(s) against one or more species of *Candida* is at least about 25% lower, 30% lower, or, e.g., at least about 35% lower than that demonstrated against the same species of *Candida* by unmodified amphotericin B.

In certain aspects, the invention provides ODF composition(s) of amphotericin B in ionic liquid form described herein wherein the $MIC_{48h}$ of the composition(s) against one or more species of *Candida*, e.g., *Candida albicans, Candida tropicalis*, or both, is at least about 10% lower than that demonstrated against the same species of *Candida*, e.g., *Candida albicans, Candida tropicalis*, or both, by unmodified amphotericin B, such as, e.g., ≥~10% lower, ≥~15% lower, ≥~20% lower, ≥~25% lower, ≥~30% lower, ≥~35% lower, ≥~40% lower, ≥~45% lower, ≥~50% lower, ≥~55% lower, ≥~60% lower, ≥~65% lower, ≥~70% lower, ≥~75% lower, or ≥~80% lower, than that demonstrated against the same *Candida* spp. by unmodified amphotericin B.

In certain aspects, the invention provides ODF composition(s) of amphotericin B in ionic liquid form described herein wherein the $MIC_{48h}$ of the composition(s) against one or more species of *Candida*, e.g., *Candida albicans, Candida tropicalis*, or both, is no more than about 90% of that demonstrated by unmodified amphotericin B, such as no more than ~95%, no more than ~90%, no more than ~85%, no more than ~80%, no more than ~75%, no more than ~70%, no more than ~65%, no more than ~60%, no more than ~55%, or no more than ~50% of that demonstrated by unmodified amphotericin B, such as, e.g., no more than ~45%, ~40%, ~35%, ~30%, or, e.g., ~25% of that demonstrated by unmodified amphotericin B.

In aspects, the invention provides ODF composition(s) of amphotericin B in ionic liquid form described herein wherein the $MIC_{48h}$ of the composition(s) against one or more species of *Candida*, e.g., *Candida albicans, Candida tropicalis*, or both, is less than about 1.2 µM, such as, e.g., ≤~1.1 µM, ≤~1 µM, ≤~0.9 µM, ≤~0.8 µM, ≤~0.7 µM, ≤~0.6 µM, ≤~0.5 µM, ≤~0.4 µM, ≤~0.3 µM, ≤~0.2 µM, or ≤~0.1 µM. In aspects, the invention provides ODF composition(s) of amphotericin B in ionic liquid form described herein wherein the $MIC_{48h}$ of the composition(s) against one or more species of *Candida*, e.g., *Candida albicans*, is less than about 0.7 µM, e.g., less than about 0.65 µM, less than about 0.60 µM, less than about 0.55 µM, less than about 0.5 µM, less than about 0.45 µM, less than about 0.4 µM, or less than about 0.35 µM.

In aspects, the invention provides ODF composition(s) of amphotericin B in ionic liquid form described herein wherein the $MIC_{48h}$ of the ionic liquid form of amphotericin B against one or more species of *Candida*, e.g., *Candida albicans, Candida tropicalis*, or both, is between about 0.1 µM and about 1 µM, e.g., ~0.15 µM-~1 µM, ~0.2 µM-~1 µM, ~0.25 µM-~1 µM, ~0.3 µM-~1 µM, or, e.g., ~0.35 µM-~1 µM, such as, e.g., ~0.1 µM-~0.9 µM, ~0.1 M-~0.8 µM, ~0.1 µM-~0.7 µM, ~0.1 µM-~0.6 µM, ~0.1 µM-~0.5 µM, ~0.1 µM-~0.4 µM, or ~0.1 µM-~0.3 µM, such as, e.g., ~0.15 µM-~0.9 µM, ~0.2 µM-~0.8 µM, ~0.25 µM-~0.7 µM, ~0.3 µM-~0.6 µM, ~0.3 µM-~0.5 µM, or, e.g., ~0.3 µM-~0.4 µM, as in, e.g., ~0.6 µM-~0.8 µM.

Zone of Inhibition

In aspects, amphotericin B compound(s) described herein, e.g., ionic liquid forms of amphotericin B described herein, demonstrate a zone of inhibition of one or more *Candida* spp., e.g., *Candida albicans* and *Candida tropicalis*, which is at least about 5%, ≥~6%, ≥~7%, ≥~8%, ≥~9%, ≥~10%, ≥~11%, ≥~12%, ≥~13%, ≥~14%, ≥~15%, ≥~16%, ≥~17%, ≥~18%, ≥~19%, or, e.g., ≥~20% greater than that demonstrated against the same species by unmodified amphotericin B when assessed using standard microbiological culture and testing techniques.

In aspects, composition(s) described herein, e.g., ODF composition(s) comprising amphotericin B compound(s) described herein, e.g., ionic liquid forms of amphotericin B described herein, demonstrate a zone of inhibition of one or more *Candida* spp., e.g., *Candida albicans* and *Candida tropicalis*, which is at least about 5%, ≥~6%, ≥~7%, ≥~8%, ≥~9%, ≥~10%, ~11%, ≥~12%, ≥~13%, ≥~14%, ≥~15%, ≥~16%, ≥~17%, ≥~18%, ≥~19%, or, e.g., ≥~20% greater than that demonstrated by a comparator product, such as, e.g., that demonstrated by a comparator product comprising unmodified amphotericin B, when assessed using standard microbiological culture and testing techniques.

Rate of Resistance

In aspects, administration of composition(s) provided herein, e.g., ODF compositions comprising ionic liquid form(s) of amphotericin B described herein, results in a lower rate of development of resistance to amphotericin B by one or more species of *Candida*, e.g., *C. albicans, C. glabrata, C. krusei, C. parapsilosis*, or, e.g., *C. tropicalis*, than the rate of resistance which is developed by one or more species of *Candida*, e.g., *C. albicans, C. glabrata, C. krusei, C. parapsilosis*, or, e.g., *C. tropicalis*, to one or more other antifungal APIs (e.g., fluconazole), administered in/by comparator composition(s); to amphotericin B when amphotericin B is administered in unmodified form; or both, as determined by a well-controlled and adequate clinical studies performed in compliance with generally prevailing regulatory authority standards, as determined by an appropriately designed and conducted laboratory study, or as determined by either such study or similarly recognizable appropriately administered analysis.

Therapeutic Efficacy

In aspects, amphotericin B compound(s) described herein, e.g., amphotericin B in ionic liquid form, demonstrate a detectably or significantly greater solubility in one or more environment(s) compared to amphotericin B in unmodified form. In aspects, such an increase in solubility yields a detectable or significant increase in its therapeutic efficacy, as an increase in solubility in aqueous solutions detectably or significantly increase(s) the concentration of the drug available, such as the concentration of the drug available in systemic circulation or at a local treatment site or both.

In aspects, composition(s) provided herein, comprising an amphotericin B compound, e.g., amphotericin B in ionic liquid form described herein, demonstrate a detectably or significantly greater solubility of amphotericin B in one or more environment(s) compared to amphotericin B in unmodified form. In aspects, such an increase in solubility yields a detectable or significant increase in the therapeutic efficacy of the composition(s), as an increase in solubility in aqueous solutions detectably or significantly increase(s) the concentration of the drug available, such as the concentration of the drug available in systemic circulation or at a local treatment site or both. In aspects, such composition(s) are ODF(s).

In aspects, ionic liquid form(s) of amphotericin B and composition(s) thereof, e.g., ODF(s) thereof, provide for an at least about 1%, ≥~2%, ≥~3%, ≥~4%, ≥~5%, ≥~6%, ≥~7%, ≥~8%, ≥~9%, ≥~10%, ≥~15%, ≥~20%, ≥~25%, ≥~30%, ≥~35%, ≥~40%, ≥~45%, or, e.g., ≥~50%, increase in the therapeutic efficacy of amphotericin B in the treatment of one or more conditions, such as, e.g., infection(s) of one or more infectious fungal agents, compared to that of amphotericin B provided in unmodified form, as determined by an appropriately designed and administered study or trial, such as a study/trial recognized by a recognized regulatory authority such as the United States Food and Drug Administration (US FDA) (e.g., as determined by well-controlled and adequate clinical study(ies) performed in compliance with generally prevailing regulatory authority standards.) In aspects, such therapeutic efficacy is determined based on factor(s) related to condition(s), such as, e.g., biological marker(s) of condition(s), physiological/biological indicator(s) of condition(s), length of condition(s), degree or severity of condition(s), expression of one or more symptom(s) of condition(s) (e.g., number of symptom(s), severity of symptom(s), or both), side effect(s) of condition(s), etc.) In aspects, such a condition is an oral infection, e.g., an oral fungal infection, such as, e.g., oral candidiasis, mucocutaneous candidiasis, refractory mucocutaneous candidiasis, etc.

In aspects, ionic liquid form(s) of amphotericin B described herein and composition(s) thereof, e.g., ODF(s) thereof, provide amphotericin B in a form providing for increased solubilization of the API, increased bioavailability of the API, increased absorption of the API, or any combination of any or all thereof, such that composition(s) provided herein comprising an ionic liquid form of amphotericin B comprise a detectably or significantly decreased amount of amphotericin B compared to a comparator product yet provide an equivalent or significantly enhanced/improved therapeutic effect than a comparator product comprising amphotericin B in an alternative form, such as in unmodified form, as may be, e.g., determined by an appropriately designed and conducted/administered clinical study, such as, e.g., a trial approved by a recognized regulatory body such as the United States Food and Drug Administration (US FDA) (e.g., as determined by well-controlled and adequate clinical study(ies) performed in compliance with generally prevailing regulatory authority standards.)

Specific Characteristics of ODF(s)

According to certain embodiments, the invention herein provides composition(s) comprising one or more API(s), e.g., one or more antifungal agent(s), e.g., one or more API(s) capable of being provided in the form of an ionic liquid, such as, e.g., amphotericin B, e.g., amphotericin B in ionic liquid form, wherein the composition(s) are provided in a form capable of being delivered orally, e.g., to the oral cavity of a recipient in benefitting from treatment therewith. In aspects, composition(s) are provided as an oral dissolve (also referred to as an orally dissolvable or orodispersible) film (ODF). In aspects, such ODF(s) facilitate the ease of administration of, e.g., amphotericin B to treat localized infection (e.g., infection(s)) of the oral cavity, such as, e.g., fungal infection(s) of the oral cavity, such as those described herein.) In specific aspects, the invention is directed to orally dissolving film (ODF) composition(s) comprising amphotericin B. In specific aspects, the invention is directed to ODF composition(s) comprising amphotericin B in ionic liquid form.

According to aspects, the invention provides ODF composition(s) delivering one or more API(s), e.g., amphotericin B, e.g., amphotericin B in ionic liquid form, which detectably or significantly penetrate(s) the oral mucosa and demonstrate a detectable or significant local therapeutic effect. In aspects, the therapeutic effect is a detectable or significant inhibition in the growth of one or more microbial population(s), a detectable or significant reduction in a population of one or microbe(s), or both. In certain aspects, such microbe(s)/microbial population(s) are fungi, e.g., yeasts, e.g., *Candida* spp.

In certain aspects, ODF(s) provided herein are mucoadhesive. In aspects, ODF(s) provided herein are non-mucoadhesive.

Herein, the term oral dissolve film (or, e.g., orally dissolving film, or orodispersible film or ODF) includes, e.g., mucosal film(s), sublingual film(s), delayed release mouth dissolving film(s), and other forms of orally-delivered films known in the art. In aspects, ODF(s) provided herein are characterizable as an oral thin film. In aspects, ODF(s) provided herein are characterizable as a flash release (quick release) film. In aspects, ODF(s) provided herein are characterizable as a mucoadhesive melt away wafer (mucoadhesive wafer). In aspects, ODF(s) provided herein are characterizable as a mucoadhesive sustained-release wafer (mucoadhesive extended-release wafer). In aspects, ODF(s) provided herein are characterizable as a buccal film (designed to remain on the cheek mucosa for a long time.) In certain aspects, ODF(s) described herein are not characterizable as a flash release film. In certain aspects, ODF(s) described herein are not characterizable as a mucoadhesive wafer. In certain aspects, ODF(s) described herein are not characterizable as a mucoadhesive extended-release wafer. In aspects, ODF(s) provided herein are not characterizable as a buccal film.

According to aspects, ODF(s) provided herein are characterizable as flexible/non-brittle (such characteristic(s), e.g., being described in further detail elsewhere herein.)

In certain aspects, ODF composition(s) provided herein are differentiated from one or more other ODF composition(s) by one or more features, such as, e.g., size (e.g., area), thickness, structure (e.g., number of layers), API(s), excipient(s), pharmaceutical phase, application area(s), dissolution profile(s), effect of administration (e.g., local vs. systemic), or, e.g., by any one or more other characteristic(s) of composition(s) described herein.

Ready-to-Use

In aspects, composition(s) provided by the invention, e.g., composition(s) comprising amphotericin B in ionic liquid form(s) described herein, are provided in ready-to-use (RTU) form. In aspects, such a form is an ODF. In aspects, a RTU form of composition(s) does not require dilution or further modification prior to administration. In aspects, such composition(s), are ready for immediate use upon removal from storage, e.g., upon removal from packaging. In aspects, such composition(s) may be provided by a healthcare provider but self-administered by a subject such as a human patient outside of a healthcare setting. In certain aspects, composition(s) can be stored in a non-medical setting, such as, e.g., a patient's home, and is ready for immediate administration, e.g., self-administration, to a subject.

ODF Size

In aspects, composition(s) provided herein are ODF(s) comprising amphotericin B in ionic liquid form. In aspects, an ODF is provided in single dose-sized films. In aspects, an individual/single film has an average size of about 1 cm-about 5 cm by about 1 cm-about 5 cm, such as, e.g., ~1 cm×~1 cm, ~1 cm×~2 cm, ~1 cm×~3 cm, ~1 cm×~4 cm, ~1 cm×~5 cm, ~2 cm×~2 cm, ~2 cm×~3 cm, ~2 cm×~4 cm, ~2 cm×~5 cm, ~3 cm×~3 cm, ~3 cm×~4 cm, ~3 cm×~5 cm, ~4 cm×~4 cm, ~4 cm×~5 cm, or, e.g., ~5 cm×~5 cm, such as, e.g., ~2 cm×~3 cm.

ODF Weight

In aspects, composition(s) provided herein are ODF(s) comprising amphotericin B in ionic liquid form. In aspects, a single ODF, e.g., individual dose-sized ODF(s), have an average weight of between about 80 mg and about 100 mg, such as, e.g., ~80 mg-~98 mg, ~80 mg-~96 mg, ~80 mg-~94 mg, ~80 mg-~92 mg, or ~80 mg-~90 mg, such as ~82 mg-~100 mg, ~84 mg-~100 mg, ~86 mg-~100 mg, ~88 mg-~100 mg, or, e.g., ~90 mg-~100 mg, as in, for example, ~82 mg-~98 mg, ~84 mg-~96 mg, ~86 mg-~94 mg, ~88 mg-~92 mg, or, e.g., about 85 mg to about 95 mg, such as, e.g., ~89 mg-~93 mg, as in about of 91 mg ±about 1.8 mg.

In aspects, on average, individual dose-sized ODF(s) vary in weight by no more than about 5% from one another, such as, e.g., vary by no more than about 4%, ≤~3%, ≤~2%, ≤~1%, ≤~0.7%, ≤~0.5%, ≤~0.3%, or ≤~0.1% from one another.

In aspects, composition(s) provided herein are ODF(s) comprising amphotericin B in ionic liquid form. In aspects, on average ODF(s), e.g., individual dose-sized ODF(s), demonstrate no more than an about 5% change in weight after storage at 40° C. and 75% relative humidity for a period of at least about 1 week when stored in a sealed container (sealed packaging), such as, for example, sealed and light-protected packaging, e.g., an amber colored Type I glass vial comprising a stopper. In aspects, on average ODF(s), e.g., individual dose-sized ODF(s), demonstrate no more than an about 4.5%, ≤~4%, ≤~3.5%, ≤~3%, ≤~2.5%, ≤~2%, ≤~1.5%, ≤~1%, ≤~0.5%, or, e.g., ≤~0.1% change in weight after storage in sealed packaging (e.g., a sealed container such as light-protected packaging, e.g., an amber colored Type I glass vial comprising a stopper) at 40° C. and 75% relative humidity for a period of at least about 2 weeks, ≥~4 weeks (1 month), ≥~2 months, ≥~3 months, ≥~6 months, ≥~9 months, ≥~12 months, ≥~18 months, ≥~24 months, or, e.g., ≥~36 months.

In aspects, change in weight reflects moisture absorption. Thus, in aspects, ODF(s) provided herein absorb no amount of moisture, e.g., water, when stored in sealed packaging (e.g., a sealed container such as light-protected packaging, e.g., an amber colored Type I glass vial comprising a stopper) at 40° C. and 75% relative humidity for a period of at least about 2 weeks, ≥~4 weeks (1 month), ≥~2 months, ≥~3 months, ≥~6 months, ≥~9 months, ≥~12 months, ≥~18 months, ≥~24 months, or, e.g., ≥~36 months, which causes the ODF to experience an increase in weight of more than about 5%, such as more than about 4.5%, ~4%, ~3.5%, ~3%, ~2.5%, ~2%, ~1.5%, ~1%, ~0.5%, or more than ~0.1%.

Thickness

In aspects, composition(s) provided herein are ODF(s) comprising amphotericin B in ionic liquid form. In aspects, on average ODF(s), e.g., individual dose-sized ODF(s), comprise a thickness of between about 10 µm and about 2000 µm, e.g., ~20 µm-~2000 µm, ~30 µm-~2000 µm, ~40 µm-~2000 µm, or ~50 µm-~2000 µm, e.g., ~10 µm-~1800 µm, ~10 µm-~1600 µm, ~10 µm-~1400 µm, ~10 µm-~1200 µm, ~10 µm-~1000 µm, or, e.g., ~20 µm-~1800 µm, ~30 µm-~1600 µm, ~40 µm-~1400 µm, or, e.g., ~50 µm-~1000 µm. In certain aspects, ODF(s) have a thickness of between about 200 µm and about 300 µm (about 0.2 mm and about 0.3 mm.)

In aspects, the thickness of ODF(s) provided herein does not change by more than about 5%, such as, e.g., ≤~4.5%, ≤~4%, ≤~3.5%, ≤~3%, ≤~2.5%, ≤~2%, ≤~1.5%, ≤~1%, ≤~0.5%, or ≤~0.1%, when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months.

Drug Content

In aspects, composition(s) provided herein are ODF(s) comprising amphotericin B in ionic liquid form. In aspects, within a single ODF, e.g., individual dose-sized ODF(s), at least about 95%, ~96%, ~97%, ~98%, ~98.5%, ~99%, ~99.5%, or, e.g., ~100% of the originally incorporated amount of amphotericin B expected to be present according to the manufacturing process is detectable or otherwise measurable in the ODF. In aspects, for example, within a single ODF, at least about 99.79%±0.26% of the originally incorporated amount of amphotericin B expected to be present according to the manufacturing process is detectable or otherwise measurable in the ODF.

Content Uniformity

In aspects, composition(s) provided herein are ODF(s) comprising amphotericin B in ionic liquid form. In aspects, a single ODF, e.g., individual dose-sized ODF(s), comprise [[INSERT]]

In aspects, the relative standard deviation (%) in the amount of API, e.g., amphotericin B in ionic liquid form, present across ODF(s) within a manufactured batch of ODF(s) is less than about 10%, such as, e.g., ≤~9%, ≤~8%, ≤~7%, ≤~6%, ≤~5%, ≤~4%, ≤~3%, ≤~2%, or ≤~1%.

In aspects, the average drug content measured in ODF(s) across a plurality of ODF(s), e.g., at least about 2, ≥~3, ≥~4, ≥~5, ≥~6, ≥~7, ≥~8, ≥~9, ≥~10, ≥~20, ≥~50, ≥~100, ≥~500, or, e.g., ≥~1000 ODF(s), is between about 95% and about 100%, such as, e.g., at least about 95%, ≥~96%, ≥~97%, ≥~98%, ≥~99%, or, e.g., is 100% of that which would be expected according to the manufacture/manufacturing process of the ODF(s) (e.g., that which would be expected according to the formulation.) In aspects, a manufactured batch (e.g., single manufacturing "run" of ODF(s)) of ODF(s) demonstrate a variation in drug content between ODF(s), on average, of less than about 5%, less than about 4%, less than about 3%, less than about 2%, or, e.g., less than about 1%.

Foldability/Flexibility

In aspects, composition(s) provided herein are ODF(s) comprising amphotericin B in ionic liquid form. In aspects, the ODF(s) are flexible films. In aspects, ODF(s) are capable of being folded 180° at at least generally the same, at least substantially the same, at least generally the same, at least essentially the same, essentially the same, or at the same location within the film at least about 40 times without breaking when stored at refrigerated conditions (e.g., about 1° C.-about 8° C. such as about 4° C.), when stored at 25° C.±2° C. and 60% relative humidity ±5%, or when stored at 40° C.±2° C./75% relative humidity ±5% for a period of at least about 1 month. In aspects, ODF(s) are capable of being folded at least generally the same, at least substantially the same, at least generally the same, at least essentially the same, essentially the same, or at the same location within the film at least about 42 times, ≥~44 times, ≥~46 times, ≥~48 times, ≥~50 times, ≥~52 times, ≥~54 times, ≥~56 times, ≥~58 times, ≥~60 times, ≥~62 times, ≥~64 times, ≥~66 times, ≥~68 times, ≥~70 times, ≥~72 times, ≥~74 times, ≥~75 times, ≥~76 times, ≥~78 times, ≥~80 times, ≥~82 times, ≥~84 times, ≥~86 times, ≥~88 times, ≥~90 times, ≥~92 times, ≥~94 times, ≥~96 times, ≥~98 times, or ≥~100 times, without breaking when stored at refrigerated conditions (e.g., about 1° C.-about 8° C. such as about 4° C.), when stored at 25° C.±2° C. and 60% relative humidity ±5%, or when stored at 40° C.±2° C./75% relative humidity ±5% for a period of at least about 1 month, such as a period of at least about 2 months, ≥~3 months, ≥~4 months, ≥~5 months, ≥~6 months, ≥~7 months, ≥~8 months, ≥~9 months, ≥~10 months, ≥~11 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

In aspects, ODF(s) are capable of being folded at least generally the same, at least substantially the same, at least generally the same, at least essentially the same, essentially the same, or at the same location within the film at an angle of 180° at least about 100 times, such as, e.g., ≥~120 times, ≥~140 times, ≥~160 times, ≥~180 times, ≥~200 times, ≥~220 times, ≥~240 times, ≥~260 times, ≥~280 times, or ≥~300 times, without breaking when stored at refrigerated conditions (e.g., about 1° C.-about 8° C. such as about 4° C.), when stored at 25° C.±2° C. and 60% relative humidity ±5%, or when stored at 40° C.±2° C./75% relative humidity ±5% for a period of at least about 1 month, such as for a period of ≥~3 months, ≥~6 months, ≥~9 months, ≥~12 months, ≥~18 months, ≥~24 months, or, e.g., ≥~36 months.

In aspects, composition(s) provided herein are ODF(s) comprising amphotericin B in ionic liquid form. In aspects, the ODF(s) comprise a surface pH of between about 4.6 and about 8, such as, e.g., ~4.8-~8, ~5-~8, ~5.2-~8, ~5.4-~8, ~5.6-~8, or ~5.8-~8, e.g., ~5-~7.8, ~5-~7.6, ~5-~7.4, ~5-~7.2, ~5-~7, ~5-~6.8, ~5-~6.6, ~5-~6.4, ~5-~6.2, ~5-~6, or ~5-~5.8, as in, e.g., ~4.8-~7.6, ~5-~7.2, ~5.2-~6.8, ~5.4-~6.4, ~5.6-~6, or, e.g., ~5.8.

Disintegration Time

In aspects, composition(s) provided herein are ODF(s) comprising amphotericin B in ionic liquid form. In aspects, the about 2 cm×3 cm ODF(s) demonstrate an average disintegration time in water buffered with a phosphate buffer to a pH of 6.4 of between about 10 seconds and about 120 seconds (2 minutes), such as, e.g., ~10 seconds-~100 seconds, ~10 seconds-~80 seconds, ~10 seconds-~60 seconds, or ~10 seconds-~40 seconds, e.g., ~20 seconds-~120 seconds, ~30 seconds-~120 seconds, ~40 seconds-~120 seconds, or ~50 seconds-~120 seconds, such as, for example, ~20 seconds-~100 seconds, ~30 seconds-~80 seconds, ~40 seconds-~60 seconds, ~40 seconds-~50 seconds, or, e.g., ~30 seconds-~60 seconds, or ~48 seconds.

Release Kinetics (Drug Release Rate)

In aspects, composition(s) provided herein are ODF(s) comprising an antimicrobial component, e.g., an antifungal agent, e.g., amphotericin B, e.g., amphotericin B in ionic liquid form. In aspects, at least about 10%, ≥~15%, ≥~20%, ≥~25%, ≥~30%, ≥~35%, ≥~40%, ≥~45%, ≥~50%, ≥~55%, or, ≥~60%, of the antimicrobial component, e.g., an antifungal agent, e.g., amphotericin B in ionic liquid form, is released from the ODF(s) when the ODF(s) is/are placed in pH 6.4 phosphate buffer at 37° C.±0.5° C. within about 5 minutes. In aspects, between about 40% and about 60% of the antimicrobial component, e.g., antifungal agent, e.g., amphotericin B in ionic liquid form, is released from ODF(s) disclosed herein within about 5 minutes when the ODF(s) is/are placed in pH 6.4 phosphate buffer at 37° C.±0.5° C.

In aspects, composition(s) provided herein are ODF(s) comprising an antimicrobial component, e.g., an antifungal agent, e.g., amphotericin B, e.g., amphotericin B in ionic liquid form. In aspects, at least about 20%, ≥~25%, ≥~30%, ≥~35%, ≥~40%, ≥~45%, ≥~50%, ≥~55%, ≥~60%, ≥~65%, or, ≥~70%, of the antimicrobial component, e.g., an antifungal agent, e.g., amphotericin B in ionic liquid form, is released from the ODF(s) when the ODF(s) is/are placed in pH 6.4 phosphate buffer at 37° C.±0.5° C. within about 10 minutes. In aspects, between about 50% and about 70% of the antimicrobial component, e.g., antifungal agent, e.g., amphotericin B in ionic liquid form, is released from ODF(s) disclosed herein within about 10 minutes when the ODF(s) is/are placed in pH 6.4 phosphate buffer at 37° C.±0.5° C.

In aspects, composition(s) provided herein are ODF(s) comprising an antimicrobial component, e.g., an antifungal agent, e.g., amphotericin B, e.g., amphotericin B in ionic liquid form. In aspects, at least about 50%, ≥~55%, ≥~60%, ≥~65%, ≥~70%, ≥~75%, ≥~80%, ≥~85%, ≥~90%, ≥~95%, or, ≥~100%, of the antimicrobial component, e.g., an antifungal agent, e.g., amphotericin B in ionic liquid form, is released from the ODF(s) when the ODF(s) is/are placed in pH 6.4 phosphate buffer at 37° C.±0.5° C. within about 15 minutes. In aspects, between about 60% and about 90% of the antimicrobial component, e.g., antifungal agent, e.g., amphotericin B in ionic liquid form, is released from ODF(s) disclosed herein within about 15 minutes when the ODF(s) is/are placed in pH 6.4 phosphate buffer at 37° C.±0.5° C.

Stability

In aspects, composition(s) provided herein are ODF(s) comprising an antimicrobial component, e.g., an antifungal agent, e.g., amphotericin B, e.g., amphotericin B in ionic liquid form. In aspects, composition(s) maintain at least about 97% of the initial amount of antimicrobial component, e.g., antifungal agent, e.g., amphotericin B (e.g., amphotericin B in ionic liquid form, when stored at refrigerated conditions (e.g., about 1° C.-about 8° C. such as about 4° C.), when stored at 25° C.±2° C. and 60% relative humidity ±5% (such as, e.g., within a stability chamber), or when stored under either such condition for a period of at least about 1 month. In aspects, composition(s) provided herein are ODF(s) comprising amphotericin B in ionic liquid form, wherein composition(s) maintain at least about 97.2%, ≥~97.4%, ≥~97.6%, ≥~97.8%, ≥~98%, ≥~98.2%, ≥~98.4%, ≥~98.6%, ≥~98.8%, ≥~99%, ≥~99.2%, ≥~99.4%, ≥~99.6%, ≥~99.8%, or, e.g., ~100%, of the initial amount of antimicrobial component, e.g., antifungal agent, e.g., amphotericin B (e.g., amphotericin B in ionic liquid form, when stored at refrigerated conditions (e.g., about 1° C.-about 8° C. such as about 4° C.), when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months.

In aspects, composition(s) provided herein are ODF(s) comprising amphotericin B in ionic liquid form, wherein composition(s) maintain a level of total impurities below 5% when stored at refrigerated conditions (e.g., about 1° C.-about 8° C. such as about 4° C.), when stored at 25° C.±2° C. and 60% relative humidity ±5% (such as, e.g., within a stability chamber), or when stored under either such condition for a period of at least about 1 month. In aspects, composition(s) provided herein are ODF(s) comprising amphotericin B in ionic liquid form, wherein composition(s) maintain a level of total impurities below ~4.5%, ≤~4%, ≤~3.5%, ≤~3%, ≤~2.5%, ≤~2%, ≤~1.5%, ≤~1%, ≤~0.5%, or, e.g., ≤~0.1%, when stored at refrigerated conditions (e.g., about 1° C.-about 8° C. such as about 4° C.), when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months.

In aspects, ODF(s) provided herein are stable when stored at standard room temperature, e.g., about 25° C. for at least about 1 month. In aspects, ODF(s) provided herein are stable when stored under refrigerated temperatures for at least about 1 year.

In aspects, the invention provides composition(s), such as, e.g., ODF(s) comprising amphotericin B (e.g., amphotericin B in ionic liquid form) as described herein, wherein the composition(s) demonstrate a detectably or significantly greater stability of amphotericin B compared to composition(s) comprising amphotericin B in unmodified form.

In aspects, the invention provides composition(s), such as, e.g., ODF(s) comprising amphotericin B (e.g., amphotericin B in ionic liquid form) as described herein, wherein the composition(s) demonstrate detectably or significantly greater stability of amphotericin B under acidic conditions, e.g., under conditions having a pH of between about 1 and about 6.9, e.g., a pH of 1-~6.5, ~1-~6, ~1-~5.5, ~1-~5, ~1-~4.5, ~1-~4, ~1-~3.5, ~1-~3, ~1-~2.5, ~1-~2, or ~1-~1.5, e.g., ~1.5-~6.9, ~2-~6.9, ~2.5-~6.9, ~3-~6.9, ~3.5-~6.9, ~4-~6.9, ~4.5-~6.9, ~5-~6.9, ~5.5-~6.9, ~6-~6.9, or ~6-~6.9, e.g., ~1.5-~6.5, ~2-~6, or, e.g., ~3-~5, compared to composition(s) comprising amphotericin B in unmodified form.

In aspects, the invention provides amphotericin B in an ionic liquid form which is detectably or significantly more stable than amphotericin B in unmodified form. In aspects, the invention provides amphotericin B in a form which is detectably or significantly more stable than amphotericin B under acidic conditions, e.g., under conditions having a pH of between about 1 and about 6.9, in unmodified form.

Herein, "stability" can refer to physical stability, chemical stability, or both physical and chemical stability. In aspects, stability refers to the API (e.g., amphotericin B, e.g., amphotericin B in ionic liquid form) at least generally, at least substantially, at least essentially, essentially or completely maintaining its strength/potency at the level present immediately upon completion of manufacture of a finished product comprising the API, or, e.g., as specified on the label of the product comprising the API) for the maximum anticipated shelf-life (the time period from the date of manufacture until administration to a recipient) under environmental conditions likely to be encountered or otherwise anticipated to be encountered during normal use. In aspects, stability refers to the API remaining in at least generally the same, at least substantially the same, at least essentially the same, essentially the same, or the same chemical form when exposed to various environmental conditions which may cause it to deteriorate. In aspects, stability refers to maintaining at least generally the same, at least substantially the same, at least essentially the same, essentially the same, or the same pH when exposed to various environmental conditions which may cause it to deteriorate (such as, e.g., one or more storage condition(s)). In aspects, stability can be measured by any suitable stability assessment technique practiced in the art.

In aspects, stability of a finished ODF can be assessed by, e.g., assessing the stability of the API(s) therein and also or alternatively using any suitable technique, such as, e.g., by assessing one or more of the ODF characteristic(s) described herein such as, e.g., size, shape, weight, morphology, drug content, content uniformity, foldability/flexibility, pH, disintegration time, release kinetics, organoleptic property(ies), strength, appearance, etc.)

In aspects, ODF(s) provided herein demonstrate no more than a 5%, such as, e.g., ≤~4.5%, ≤~4%, ≤~3.5%, ≤~3%, ≤~2.5%, ≤~2%, ≤~1.5%, ≤~1%, ≤~0.5%, or ≤~0.1%, change in the amorphous/crystalline character of the API(s) therein, e.g., amphotericin B, e.g., amphotericin B in ionic liquid form, when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months.

According to certain aspects, ODF(s) described herein at least generally maintain, at least substantially maintain, at least essentially maintain, essentially maintain, or maintain their morphology when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months. In aspects, ODF(s) described herein at least generally maintain, at least substantially maintain, at least essentially maintain, essentially maintain, or maintain their surface morphology when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months, wherein such surface morphology is indicated by, e.g., the smoothness or alternatively roughness of the surface of the ODF(s), the average number of pores per square centimeter, presence or absence of crack(s)/cracking, particle distribution, or, e.g., by any other known measure of film morphology recognized in the art. In aspects, such morphology or any other one or more characteristic(s) of ODF(s) may be determined by, e.g., one or more method(s) known in the art such as, e.g., scanning electron microscopy (SEM), X-ray powder diffraction (XRD), Fourier transform infrared spectroscopy (FT-IR), differential scanning calorimetry (DSC), or, e.g., other technique(s) known in the art.

In aspects, ODF composition(s) herein demonstrate a suitable strength, e.g., tensile strength (maximum tensile force applied until the ODF breaks), to provide suitable stability during storage, to provide suitable functionality upon administration, or both. In aspects, tensile strength of ODF(s) provided herein do not change by more than about 10%, such as, e.g., ≤9%, ≤8%, ≤7%, ≤6%, ≤5%, ≤4%, ≤3%, ≤2%, ≤1%, ≤0.5%, or, e.g., ≤0.1% from that present at the time of manufacture when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months.

In aspects, ODF composition(s) herein demonstrate a water content which does not change by more than about 10%, such as, e.g., ≤9%, ≤8%, ≤7%, ≤6%, ≤5%, ≤4%, ≤3%, ≤2%, ≤1%, ≤0.5%, or, e.g., ≤0.1% from that present at the time of manufacture when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months.

In aspects, ODF composition(s) herein demonstrate a dissolution profile which does not change by more than about 20%, such as, e.g., ≤19%, ≤18%, ≤17%, ≤16%, ≤15%, ≤14%, ≤13%, ≤12%, ≤11%, ≤10%, ≤9%, ≤8%, ≤7%, ≤6%, ≤5%, ≤4%, ≤3%, ≤2%, ≤1%, ≤0.5%, or, e.g., ≤0.1% at one or more time point(s) measured during the course of dissolution of the ODF from that present in the ODF(s) immediate upon completion of manufacture, when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months.

In aspects, ODF composition(s) herein demonstrate a level or degree of transparency (e.g., the amount of light of a given wavelength capable of passing through or being absorbed by the ODF(s)) which does not change by more than about 10%, such as, e.g., ≤9%, ≤8%, ≤7%, ≤6%, 55%, ≤4%, ≤3%, ≤2%, ≤1%, ≤0.5%, or, e.g., ≤0.1% from that present at the time of manufacture when stored at 25° C.±2° C. and 60% relative humidity ±5% (such as, e.g., within a stability chamber), or when stored under either such condition for a period of at least about 1 month, e.g., a period of ≥~2 months, ≥~3 months, ≥~4 months, ≥~6 months, ≥~8 months, ≥~10 months, ≥~12 months, ≥~16 months, ≥~20 months, ≥~24 months, ≥~28 months, ≥~32 months, or, e.g., ≥~36 months. In aspects, transparency may be measured using, e.g., an ultraviolet (UV) spectrophotometer.

In aspects, when describing stability characteristics of composition(s) herein, such stability characteristic(s) are present when composition(s) are stored in their final packaging, such as, e.g., in packaging which holds, protects, or otherwise maintains the composition(s) in an environment which is at least generally the same as/similar to, at least substantially the same as/similar to, at least essentially the same as/similar to, essentially the same as/similar to, or is the same as/similar to that which would be provided to an end user/recipient/patient.

Values provided in this section typically reflect numbers from conducting typical stability testing and, accordingly, can reflect averages, means, median values, etc., and can reflect that most, generally all, or substantially all products meet such specified stability characteristics/performance.

Packaging & Storage Conditions

In aspects, ODF composition(s) provided herein, e.g., ODF composition(s) comprising amphotericin B, e.g., amphotericin B in ionic liquid for, are packaged in packaging which at least generally protects, at least substantially protects, at least essentially protects, essentially protects, or protects the ODF(s) maintained therein from exposure to a detectable or significant amount of light. In aspects, packaging of ODF(s) is an opaque packaging. In aspects, packaging of ODF(s) comprises a colored packaging material. In aspects, packaging of ODF(s) detectably or significantly limits at least some, at least most, at least generally all, at least substantially all, at least essentially all, essentially all, or all light from reaching ODF(s) maintained therein during storage of the ODF(s) in the packaging.

In aspects, ODF(s) provided herein are packaged such that the packaging protects ODF(s) maintained therein from an amount of light sufficient to detectably or significantly reduce the stability of the ODF(s) maintained therein compared to packaging comprising at least substantially the same ODF(s) which does not provide protection of ODF(s) maintained therein from detectable or significant light exposure, wherein stability is indicated by one or more measures of stability described herein. In aspects, ODF(s) provided herein are provided in packaging capable of maintaining the chemical stability (e.g., as determined by maintenance of API, lack of impurity(ies), maintenance of pH, or any combination thereof), physical stability (such as, e.g., physical integrity, foldability, color, etc.) or both chemical and physical stability of the ODF(s) maintained therein for a period of at least about 1 month, e.g., ≥~2 months, ≥~3 months, ≥~4 months, ≥~5 months, ≥~6 months, ≥~7 months, ≥~8 months, ≥~9 months, ≥~10 months, ≥~11 months, ≥~12 months, ≥~15 months, ≥~18 months, ≥~24 months, ≥~28 months, ≥~32 months, or, e.g., ≥~36 months, when stored at refrigerated conditions (e.g., about 1° C.-about 8° C. such as about 4° C.), when stored at about 25° C.±2° C. and about 60%±5% relative humidity, or when stored under either such condition.

In aspects, suitable packaging of ODF(s) is packaging which prevents exposure of the ODF(s) stored/maintained therein from detectable or significant amount(s) of moisture. In aspects, ODF(s) are packaged in packaging which at prevents ODF(s) stored therein from a detectable or significant change in weight from that present at the time of initial storage, when stored at about room temperature about 25° C. or when stored at refrigerated conditions (e.g., about 1° C.-about 8° C. such as about 4° C.) for a period of at least about 1 month, e.g., ≥~2 months, ≥~3 months, ≥~4 months, ≥~5 months, ≥~6 months, ≥~7 months, ≥~8 months, ≥~9 months, ≥~10 months, ≥~11 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

According to certain aspects, ODF(s) described herein are provided in single dose packaging. In other aspects, ODF(s) described herein are provided in multi-dose packaging. In aspects, 2 or more individual ODF(s) may be present in a single package, wherein each ODF represents a single dose. In aspects, ODF(s) may be packaged such that a single package comprises, e.g., about 2, ~3, ~4, ~5, ~6, ~7, ~8, ~9, ~10, ~11, ~12, ~13, ~14, ~15, ~16, ~17, ~18, ~19, ~20, ~22, ~24, ~26, ~28, or, e.g., ~30 or more individual ODF(s), e.g., individual doses, are provided in a single package.

In aspects, the invention provides ODF(s) packaged in film dispensing packaging designed for use or access by medical or non-medical personnel. In aspects, packaging of ODF(s) is suitable for access by non-medical personnel, e.g., recipient(s)/patient(s) of the ODF(s) themselves, without a requirement for special tools or devices, such as, e.g., a needle.

Methods of Use

In aspects, the invention provides method(s) of treating one more condition(s), such as, one or more infection(s), e.g., one or more fungal infection(s). In aspects, the invention provides method(s) of treating one or more fungal infection(s), e.g., a fungal infection of the oral cavity of a mammalian subject, e.g., a human. In aspects, the invention provides method(s) of treating one or more microbial infection(s), e.g. fungal infection(s), within the oral cavity of a mammal, such as, e.g., a human, wherein the method comprises administering a therapeutically effective amount of an amphotericin B compound. In aspects, the invention provides method(s) of treating one or more microbial infection(s), e.g. fungal infection(s), within the oral cavity of a mammal, such as, e.g., a human, wherein the method comprises administering a therapeutically effective amount of an amphotericin B compound provided in the form of an ODF. In aspects, the invention provides method(s) of treating one or more microbial infection(s), e.g. fungal infection(s), within the oral cavity of a mammal, such as, e.g., a human, wherein the method comprises administering a therapeutically effective amount of any one or more of the ODF(s) described herein. In aspects, the ODF(s) comprise an amphotericin B compound, e.g., amphotericin B in ionic liquid form.

In certain specific aspects, the invention provides method(s) of treating oral candidiasis, mucocutaneous candidiasis, refractory mucocutaneous candidiasis, or any combination thereof in a mammal, such as, e.g., a human, wherein the method comprises administering a therapeutically effective amount of any one or more of the ODF(s) described herein. In aspects, the ODF(s) comprise an amphotericin B compound. In aspects, the ODF(s) comprise amphotericin B in ionic liquid form, e.g., amphotericin B in ionic liquid form(s) described herein.

In aspects, the invention provides method(s) of using one or more composition(s) described herein in the treatment of one or more microbial infection(s) in a mammal, such as, e.g., a human. In aspect(s), such an infection is, e.g., an oral infection, wherein the microbial agent(s) are present and causing one or more deleterious or otherwise undesirable effect(s) within the oral cavity or mouth of the mammal including, e.g., the oral vestibule (space between lips or cheeks and teeth) and the oral cavity proper, e.g., the region medial to the teeth. In aspects, the invention provides method(s) of treating one or more microbial infection(s) of one or more of the lip(s), lining of the lip(s), cheek(s), lining of the cheek(s), tongue or a portion of the tongue, upper gum(s), lower gum(s), floor of the mouth under the tongue, roof of the mouth, area behind wisdom teeth, or any combination of such anatomical regions/parts of the mouth. In aspects, such method(s) comprise administration of an effective amount of ODF(s) described herein, administration of ODF(s) described herein for a period of time described herein, or a combination thereof.

In specific aspects, the invention provides method(s) of treating one or more microbial infections, such as, e.g., one or more parasitic or fungal infection(s) such as, e.g., leishmaniasis, mycoses, e.g., opportunistic mycoses, such as for example, aspergillosis, candidiasis, cryptococcosis, fusariosis, mucormycosis, hyalohyphomycosis, and phaohyphomycosis, as well as, e.g., endemic mycoses, e.g., histoplasmosis, paracoccidioidomycosis, blastomycosis, coccidioidomycosis, sporotrichosis, talaromycosis (*Talaromyces marneffei*, formally *Penicillium marneffei*), emergomycosis, and other such microbial infection(s) treatable by the composition(s) described herein. In aspects, such method(s) comprise administration of an effective amount of ODF(s) described herein, administration of ODF(s) described herein for a period of time described herein, or a combination thereof.

In aspects, the invention provides method(s) of treating one or more microbial infections, e.g., fungal infections, wherein the fungal agent is an Asperguillus, *Candida*, or, e.g., *Cryptococcus* spp. In aspects, the invention provides method(s) of treating one or more microbial infections, e.g., fungal infections, wherein the fungal agent is an Asperguillus, *Candida*, or, e.g., *Cryptococcus* spp., and wherein the method comprises administration of a therapeutically effective amount of any one or more of the composition(s) described herein, administration of composition(s) for a period of time described herein, or both. In aspects, the invention provides a method of treating a mammal or, e.g., a group of mammal(s), suffering from one or more microbial infection(s) described herein, with therapeutically effective amount(s) of one or more composition(s) described herein. In aspects, method(s) comprise administering ODF(s) for a period of time described herein. In one specific aspect, the invention provides method(s) of treating a mammal or, e.g., a group of mammal(s), such as, e.g., a human or group of human(s), suffering from one or more of leishmaniasis, mycoses, e.g., opportunistic mycoses, such as for example, aspergillosis, candidiasis, cryptococcosis, fusariosis, mucormycosis, hyalohyphomycosis, and phaohyphomycosis, as well as, e.g., endemic mycoses, e.g., histoplasmosis, paracoccidioidomycosis, blastomycosis, coccidioidomycosis, sporotrichosis, talaromycosis (*Talaromyces marneffei*, formally *Penicillium marneffei*), or, e.g., emergomycosis, wherein the method(s) comprise administration of composition(s) described herein, e.g., ODF(s) described herein, in therapeutically effective amount(s). In aspects, such method(s) comprise administration of composition(s) over the course of a treatment period, e.g., a period of treatment described herein.

According to aspects, the invention provides method(s) of treating an oral fungal infection, such as, e.g., oral candidiasis, mucocutaneous candidiasis, refractory mucocutaneous candidiasis, or any combination thereof, wherein the fungal infective agent is known to be or is expected to be sensitive to or otherwise responsive to treatment with amphotericin B, wherein the method comprises administration of a therapeutically effective amount of amphotericin B provided in ionic liquid form, wherein the ionic liquid of amphotericin B is delivered via an oral dissolve (orally dissolvable or orodispersible) film (ODF).

In aspects, the invention provides method(s) of treating an oral fungal infection, such as, e.g., oral candidiasis, mucocutaneous candidiasis, refractory mucocutaneous candidiasis, or any combination thereof in a mammal, such as, e.g., a human, wherein the method comprises administering an effective amount of an ODF composition comprising an ionic liquid of amphotericin B.

In aspects, the invention provides method(s) of orally administering therapeutically effective amount(s) of amphotericin B. In aspects, the invention provides method(s) of treating one or more infections, e.g., fungal infection(s), by orally administering therapeutically and effective, e.g., therapeutically and locally effective, amount(s) of amphotericin B. In aspects, method(s) comprise administering therapeutically effective amount(s) of amphotericin B via ODF(s). In aspects, ODF(s) comprise amphotericin B in ionic liquid form. In aspects, method(s) comprise administering ODF(s) to a recipient in need thereof.

In aspects, the invention provides method(s) of treating an oral fungal infection, such as, e.g., oral candidiasis, mucocutaneous candidiasis, refractory mucocutaneous candidiasis, or any combination thereof in a mammal, such as, e.g., a human, wherein the method(s) comprise administering an effective amount of ODF composition(s) comprising an ionic liquid of amphotericin B, wherein the ionic liquid of amphotericin B is formed by the combination of amphotericin B; a solvent component; a complexing agent component; and a solubilizing component, wherein the complexing agent component comprises at least two compounds which form a complex with amphotericin B. In certain aspects, at least one complexing agent provides at least one other function in the composition(s), such as, e.g., acidifying one or more solvent compounds of a solvent component, detectably modifying, establishing, or maintaining the pH of the composition, providing detectable or significant antioxidant activity, or any combination of any or all thereof. In aspects, the ODF composition(s) can be any ODF composition(s) described herein, such as, e.g., an ODF comprising an ionic liquid composition described herein, such as an ionic liquid of or comprising an ionic liquid form of amphotericin B, and further comprising a film-inducing component. In aspects, such a film-inducing component comprises a film forming component, a plasticizing component, or both.

Administration

In aspects, the invention provides method(s) such as those described in this section, wherein the method(s) comprise the administration of at least one dose of a composition, e.g., an ODF composition of amphotericin B, e.g., an ODF composition comprising amphotericin B in ionic liquid form. In aspects, a single dose of amphotericin B is a single ODF. In aspects, a single dose of amphotericin B can be a plurality of ODF(s). In aspects, a single dose of amphotericin B requiring multiple ODF(s) is administered by sequentially administering ODF(s), e.g., administering one ODF at a time.

In aspects, the invention provides method(s) such as those described in this section, wherein the method(s) comprise administering ODF(s) described herein to a recipient benefiting from receipt thereof, such as, e.g., administering at least about one ODF, ≥~2 ODF(s), ≥~3 ODF(s), ≥~4 ODF(s), ≥~5 ODF(s), ≥~6 ODF(s), ≥~7 ODF(s), ≥~8 ODF(s), ≥~9 ODF(s), ≥~10 ODF(s), ≥~11 ODF(s), ≥~12 ODF(s), ≥~13 ODF(s), ≥~14 ODF(s), ≥~15 ODF(s), ≥~16 ODF(s), ≥~17 ODF(s), ≥~18 ODF(s), ≥~19 ODF(s), or, ≥~20 ODF(s) to a recipient benefiting from receipt thereof, over a course of treatment. In aspects, one ODF is administered at a time.

In aspects, a course of treatment is any suitable course of treatment required to successfully treat the target condition. In aspects, a suitable course of treatment is about 1 day to about 30 days, such as, e.g., ~1 day-~25 days, ~1 day-~20 days, ~1 day-~15 days, ~1 day-~10 days, or ~1 day-~5 days, e.g., ~5 days-~30 days, ~10 days-~30 days, ~15 days-~30 days, ~20 days-~25 days, or, e.g., ~25 days-~30 days, such as, e.g., ~1 day-~3 days, ~3 days-~5 days, ~1 day-~7 days, ~3 days-~14 days, or, e.g., ~1 day-~10 days or ~1 day-~14 days.

In aspects, ~1, about 2, ~3, or about 4 ODF(s) are administered per 24-hour period, such as, e.g., ~1-~5, ~1-~4, ~1-~3, ~1-~2, ~2-~5, ~3-~5, ~4-~5, or, e.g., ~2-~4 ODF(s) per 24-hour period. In aspects, an administration schedule, including administration frequency and total amount(s) of API(s) administered per 24 hour period, over the total course of administration, or both, is established according to factors such as, e.g., age of the recipient/patient being treated, weight of the recipient/patient being treated, gender of the recipient/patient being treated, general health, organ function(s), or medical condition(s) present in the recipient/patient being treated, the condition (e.g., infection) being treated in the recipient/patient, severity of the condition, e.g., infection present in the recipient/patient being treated, or, e.g., any combination of such factor(s) or other factor(s) known in the art to influence administration schedule(s) of pharmaceutical actives.

According to certain aspects, dosing can be optimized according to pharmacokinetic modeling system(s), e.g., pharmacodynamic modeling system(s). In aspects, an appropriate model can be selected based upon the desired expected pharmacokinetic/pharmacodynamic response in a recipient or recipient population.

In aspects, method(s) disclosed in this section comprise placing ODF(s), e.g., a single ODF, within the oral cavity of the recipient, and allowing the ODF to dissolve in the saliva of the receiving oral cavity. In aspects, the invention provides method(s) described in this section, e.g., method(s) of treatment described in this section, wherein the method(s) comprise administration of ODF(s), wherein the recipient of the ODF(s) is/are instructed to move or "swish" the ODF around in the oral cavity (e.g., in their mouth) while the ODF is allowed to dissolve. In aspects, method(s) comprise exposing at least some, at least most, at least generally all, at least essentially, all, essentially all, or all parts/areas of the oral cavity with saliva containing at least some, at least most, at least generally all, at least essentially all, essentially all, or all of the administered and dissolved ODF. In certain aspects, method(s) disclosed in this section comprise repeating the placement of ODF(s), e.g., single ODF, within the oral cavity of the recipient; allowing the ODF to dissolve in the saliva of the oral cavity; moving or swishing the saliva comprising the dissolved ODF, the ODF itself, or a combination thereof around the oral cavity so as to expose at least some, at least most, at least generally all, at least essentially all, essentially all, or all of the oral cavity to the content(s) of the ODF, or any one or more thereof, at least once over the course of a treatment period, such as e.g., as many number of times as is required to complete all prescribed dose(s) over the course of a treatment period.

According to certain aspects, the invention provides methods of treating local infection(s) of the oral cavity, such as, e.g., a fungal infection of the oral cavity of a mammal, e.g., a human, comprising administration of an effective amount of amphotericin B via ODF(s) described herein, wherein the total amount of amphotericin B per dose, the total amount of amphotericin B delivered per day, the total amount of amphotericin B administered over the course of an effective treatment period of the local infection, or any combination thereof is detectably or significantly less than that required to effectively treat at least generally the same, at least substantially the same, at least essentially the same, essentially the same, or the same local infection by amphotericin B administered systemically (e.g., by IV, by passage through the gastrointestinal tract, or, e.g., either or both thereof.) In aspects, the total amount of amphotericin B per dose, delivered per day, or administered over a course of treatment is at least about 5% less, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, or, e.g., ≥~100% (such as, e.g., ≥~200%, ≥~300%, or ≥~500%) less than that required to effectively treat at least generally the same, at least substantially the same, at least essentially the same, essentially the same, or the same local infection by amphotericin B administered by oral consumption such as by tablet, capsule, etc. or, e.g., by IV administration.

According to certain aspects, the invention provides methods of treating local infection(s) of the oral cavity, such as, e.g., a fungal infection of the oral cavity of a mammal, e.g., a human, comprising administration of an effective amount of amphotericin B via ODF(s) described herein, wherein the total amount of amphotericin B per dose, the total amount of amphotericin B delivered per day, the total amount of amphotericin B administered over the course of an effective treatment period of the local infection, or any combination thereof is detectably or significantly less than that required to effectively treat at least generally the same, at least substantially the same, at least essentially the same, essentially the same, or the same local infection by one or more antifungal drugs, such as, e.g., fluconazole. In aspects, the total amount of amphotericin B per dose, delivered per day, or administered over a course of treatment is at least about 5% less, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, ≥~95%, or, e.g., ≥~100% (such as, e.g., ≥~200%, ≥~300%, or ≥~500%) less than that required to effectively treat at least generally the same, at least substantially the same, at least essentially the same, essentially the same, or the same local infection by one or more other antifungal drugs, such as, e.g., fluconazole.

According to certain aspects, the invention provides methods of treating local infection(s) of the oral cavity, such as, e.g., a fungal infection of the oral cavity of a mammal, e.g., a human, comprising administration of an effective amount of amphotericin B via ODF(s) described herein, wherein the efficacy in treating the local infection with an amount of amphotericin B (per dose, per day, or, e.g., per treatment period) is detectably or significantly greater than the efficacy in treating the infection with at least at least generally the same, at least substantially the same, at least essentially the same, essentially the same, or the same amount of amphotericin B, (per dose, per day, or, e.g., per treatment period, respectively) administered by oral consumption such as by tablet, capsule, etc. or, e.g., by IV administration. According to certain aspects, the invention provides methods of treating local infection(s) of the oral cavity, such as, e.g., a fungal infection of the oral cavity of a mammal, e.g., a human, comprising administration of an effective amount of amphotericin B via ODF(s) described herein, wherein the efficacy in treating the local infection with an amount of amphotericin B (per dose, per day, or, e.g., per treatment period) is detectably or significantly greater than the efficacy in treating the infection with at least at least generally the same, at least substantially the same, at least essentially the same, essentially the same, or the same amount of another antifungal drug, (per dose, per day, or, e.g., per treatment period, respectively) such as, e.g., fuconazole. In aspects such efficacy is measured in the degree or duration of infection, one or more patient symptoms related to the infection, etc. In aspects, efficacy is determined by one or more well controlled and adequate clinical studies performed in compliance with generally prevailing regulatory authority standards.

In aspects, application of method(s) provided herein result in detectably or significantly greater patient compliance with the method for a sufficient period of time to detectably or significantly reduce or eliminate one or more microbial infection(s) within the oral cavity of a mammal to which method(s) are applied to treat than that demonstrated in treating at least generally the same, at least substantially the same, at least essentially the same, essentially the same, or the same condition by systemic administration of amphotericin B, e.g., by administration of an orally delivered (swallowed) tablet or capsule, or, e.g., IV administration. In aspects, application of method(s) provided herein result in detectably or significantly greater patient compliance with the method for a sufficient period of time to detectably or significantly reduce or eliminate one or more microbial infection(s) within the oral cavity of a mammal to which method(s) are applied to treat than that demonstrated in treating at least generally the same, at least substantially the same, at least essentially the same, essentially the same, or the same condition by administration of one or more other antifungal drugs, such as, e.g., fluconazole.

In aspects, method(s) described herein comprise the placement of an ODF in the oral cavity of a recipient, wherein the ODF is allowed to dissolved within the oral cavity of the recipient, and further wherein at least some, at least most, at least generally all, at least substantially all, at least essentially all, essentially all, or all of the API, e.g., amphotericin B, e.g., is absorbed through mucosal surface(s) of the oral cavity before being, e.g., swallowed by the recipient and passing into the gastrointestinal tract.

In certain aspects, method(s) herein provide an amount of an amphotericin B compound, e.g., amphotericin B in ionic liquid form, wherein the majority of the amphotericin B compound is delivered locally but wherein at least a detectable amount of the amphotericin B compound enters the gastrointestinal tract. In aspects, amphotericin B in ionic liquid form(s) described herein entering the gastrointestinal tract demonstrates an increased solubility in the acidic environment of the gastrointestinal tract, an increased bioavailability, or both, than that demonstrated by orally administered (swallowed) amphotericin B in unmodified form.

In aspects, method(s) described herein comprise the administration of an ODF comprising amphotericin B, e.g., amphotericin B in ionic liquid form, wherein the ODF dissolves, e.g., disintegrates, in the receiving oral cavity, within, e.g., at least about 1 minute, such as within ~58 seconds, ~56 seconds, ~54 seconds, ~52 seconds, ~50 seconds, ~48 seconds, ~46 seconds, ~44 seconds, ~42 seconds, ~40 seconds, ~38 seconds, ~36 seconds, ~34 seconds, ~32 seconds, or within ~30 seconds, such as within about 25 seconds, ~20 seconds, ~15 seconds, ~10 seconds, or even faster, within the receiving oral cavity, e.g., in the saliva of the receiving oral cavity.

According to aspects, the invention provides method(s) of treatment described in this section, wherein the method does not require supplemental solid(s) or liquid(s) for administering or receiving the ODF composition(s). In aspect(s), method(s) of treatment described in this section can be performed outside of a medical care/medical treatment facility (e.g., outside of a healthcare professional's office, clinic, hospital, and the like). In aspects, methods of treatment described herein comprise a patient administering to oneself an ODF comprising amphotericin B, e.g., amphotericin B in ionic liquid form. In aspects, the invention provides method(s) herein wherein the method comprises the recipient, e.g., recipient mammal, e.g., human, self-administering the ODF(s) without the assistance of a trained healthcare provider and outside of any regulated healthcare facility, such as, e.g., in a private setting, e.g., a patient's home or while a patient is traveling.

Reduced Toxicity, Side Effect(s), Adverse Event(s)

In aspects, the invention provides method(s) described in this section, wherein the application of the method(s) results in a detectable or significant reduction in one or more negative side effects or adverse events associated with the administration of the same active pharmaceutical ingredient(s) administered systemically, such as, e.g., by oral administration (e.g., swallowing a pill, capsule, etc.) or, e.g., by IV administration. In aspects, the invention provides method(s) described in this section, wherein the composition(s) utilized in the method(s) comprise amphotericin B, e.g., amphotericin B in ionic liquid form, and the application of the method(s) results in a detectable or significant reduction in one or more negative side effects or adverse events associated with the administration of amphotericin B administered systemically.

In aspects, the invention provides method(s) described in this section, wherein composition(s) used in the method(s) are ODF(s) comprising amphotericin B, and the application of the method(s) results in a detectable or significant reduction in the frequency or severity of one or more negative side effects or adverse events associated with the administration of amphotericin B administered intravenously (administered by IV), or, e.g., associated with the administration of one or more antimicrobial API(s), e.g., antifungal API(s), e.g., fluconazole, administered systemically (such as by oral administration as a tablet) as determined by an appropriately conducted and administered clinical study, such as a clinical trial approved by a recognize regulatory authority such as the United States Food and Drug Administration (US FDA), e.g., as determined by well-controlled and adequate clinical study(ies) performed in compliance with generally prevailing regulatory authority standards. In aspects, the invention provides method(s) described in this section, composition(s) used in method(s) are ODF(s) comprising amphotericin B in ionic liquid form, and the application of the method(s) results in a detectable or significant reduction in the frequency or severity of one or more negative side effects or adverse events associated with the administration of amphotericin B administered intravenously (administered by IV), or, e.g., associated with the administration of one or more antimicrobial API(s), e.g., antifungal API(s), e.g., fluconazole, administered systemically (such as by oral administration as a tablet) as determined by an appropriately conducted and administered clinical study, such as a clinical trial approved by a recognize regulatory authority such as the United States Food and Drug Administration (US FDA), e.g., as determined by well-controlled and adequate clinical study(ies) performed in compliance with generally prevailing regulatory authority standards.

In aspects, the invention provides the method(s) described herein, wherein the method(s) comprise administration of ODF(s) comprising amphotericin B, e.g., ionic liquid form(s) of amphotericin B, and the application of the method(s) to/in a group of recipient patients treated for a condition benefitting therefrom results in a detectable or significant reduction in the frequency or severity of one or more negative side effects or adverse events associated with the administration of amphotericin B by IV, or, e.g., associated with the administration of one or more antimicrobial API(s), e.g., antifungal API(s), e.g., fluconazole, administered systemically (such as by oral administration as a tablet), to a similar group of recipients treated for the same condition, and wherein the detectable or significant reduction in the frequency or severity of one or more negative side effects or adverse events results in the population patients subjected to the method(s) being able to sustain treatment for a detectably or significantly longer period of time; in the recipient patient population being able to sustain a detectably or significantly higher total amount of API received over the course of a single treatment event, total treatment period, or both; as determined by an appropriately conducted and administered clinical study such as a trial approved by a recognized regulatory authority such as the United States Food and Drug Administration (US FDA), e.g., as determined by well-controlled and adequate clinical study(ies) performed in compliance with generally prevailing regulatory authority standards.

In aspects, the invention provides the method(s) described herein, wherein the method(s) comprise administration of ODF(s) comprising amphotericin B, e.g., ionic liquid form(s) of amphotericin B, to treat a condition, and the application of the method(s) to/in a group of recipient patients results in a detectably or significantly reduced toxicity, e.g., reduced nephrotoxicity, compared to the treatment of the at least generally the same, at least substantially the same, at least essentially the same, essentially the same, or the same condition in an at least generally similar, at least substantially similar, at least essentially similar, at least similar, or the same group of patients treated with composition(s) of amphotericin B deoxycholate, Fungizone®, AmbiZone®, comparator product (e.g., comparator product described herein), amphotericin B administered by intravenous infusion, e.g., amphotericin B administered as amphotericin B deoxycholate by IV, or any combination of any or all thereof. In aspects, the invention provides the method(s) described herein, wherein the method(s) comprise administration of ODF(s) comprising amphotericin B, e.g., ionic liquid form(s) of amphotericin B, to treat a condition, and the application of the method(s) to/in a group of recipient patients results in a detectably or significantly reduced toxicity, e.g., reduced nephrotoxicity, compared to the treatment of the at least generally the same, at least substantially the same, at least essentially the same, essentially the same, or the same condition in an at least generally similar, at least substantially similar, at least essentially similar, at least similar, or the same group of patients treated with one or more antimicrobial API(s), e.g., antifungal API(s), e.g., fluconazole, administered systemically (such as by oral administration as a tablet).

In aspects, the invention provides the method(s) described herein, wherein the method(s) comprise administration of ODF(s) comprising amphotericin B, e.g., ionic liquid form(s) of amphotericin B, to treat a condition, and the application of the method(s) to/in a group of recipient patients results in a detectable or significant reduction in the frequency, severity, or both, of one or more side effects, adverse events, or combination thereof, compared to that experienced in treating the at least generally the same, at least substantially the same, at least essentially the same, essentially the same, or the same condition in an at least generally similar, at least substantially similar, at least essentially similar, at least similar, or the same group of patients treated with composition(s) of amphotericin B deoxycholate, Fungizone®, AmbiZone®, comparator product (e.g., comparator product described herein), amphotericin B administered by intravenous infusion, e.g., amphotericin B administered as amphotericin B deoxycholate by IV, or any combination of any or all thereof. In aspects, the invention provides the method(s) described herein, wherein the method(s) comprise administration of ODF(s) comprising amphotericin B, e.g., ionic liquid form(s) of amphotericin B, to treat a condition, and the application of the method(s) to/in a group of recipient patients results in a detectably or significantly reduced toxicity, e.g., reduced nephrotoxicity, compared to the treatment of the at least generally the same, at least substantially the same, at least essentially the same, essentially the same, or the same condition in an at least generally similar, at least substantially similar, at least essentially similar, at least similar, or the same group of patients treated with one or more antimicrobial API(s), e.g., antifungal API(s), e.g., fluconazole, administered systemically (such as by oral administration as a tablet).

In aspects, the invention provides the method(s) described herein, wherein the method(s) comprise administration of ODF(s) comprising amphotericin B, e.g., ionic liquid form(s) of amphotericin B, wherein the application of the method(s) result(s) in a detectably or significantly reduced amount of amphotericin B required to provide one or more clinical effect(s) than that required for a comparator product to achieve the same the same clinical effect(s). In aspects, the invention provides the method(s) described herein, wherein the method(s) comprise administration of ODF(s) comprising amphotericin B, e.g., ionic liquid form(s) of amphotericin B, wherein the application of the method(s) result(s) in a detectably or significantly reduced amount of amphotericin B required to provide one or more clinical effect(s) than that required for one or more antimicrobial API(s), e.g., antifungal API(s), e.g., fluconazole, administered systemically (such as by oral administration as a tablet).

In aspects, such a reduction in an administered amount contributes to or otherwise results in a detectable or significant reduction in toxicity, a detectable or significant reduction in one or more side effect(s), a detectable or significant reduction in adverse reaction(s), or any combination of any or all thereof, compared to that demonstrated by or experienced by patient(s) receiving a comparator product. In aspects, such a reduction in an administered amount contributes to or otherwise results in a detectable or significant reduction in toxicity, a detectable or significant reduction in one or more side effect(s), a detectable or significant reduction in adverse reaction(s), or any combination of any or all thereof, compared to that demonstrated by or experienced by patient(s) receiving one or more antimicrobial API(s), e.g., antifungal API(s), e.g., fluconazole, administered systemically (such as by oral administration as a tablet).

In aspects, such side effect(s) or adverse event(s) described above/herein can comprise, e.g., abdominal pain, allergic reaction(s), anemia, asthenia, back pain, increased alkaline phosphatase, increased ALT (SGPT), anorexia, anxiety, asthenia, increased AST (SGOT), bilirubinemia, increased BUN, chest pain, chills (or chills/rigors), confusion, constipation, increased cough, increased creatinine, diarrhea, dizziness, dyspnea, edema, epistaxis, fever, gastrointestinal hemorrhage, headache, hematuria hyperglycemia, hyperglycemia, hypernatremia, hypertension, hyperventilation, hypervolemia, hypocalcemia, hypokalemia, hypomagnesemia, hypotension, hypoxia, infection, insomnia, leukopenia, abnormal liver function test(s), lung disorder(s), malaise, nausea, pain, peripheral edema, phlebitis, pleural effusion, pruritus, rash, renal complication(s) or failure, rhinitis, sepsis, sweating, tachycardia, tachypnea, thrombocytopenia, thrombophlebitis, transfusion reaction, vasodilation, vomiting, weight loss, or, e.g., any one or more other general (body as a whole), allergic, cardiopulmonary, dermatologic, gastrointestinal, hematologic, local, neurologic, renal, laboratory finding(s), or, e.g., any combinations of any or all thereof.

In aspects, the invention provides the method(s) described herein, wherein the method(s) comprise administration of ODF(s) comprising amphotericin B, e.g., ionic liquid form(s) of amphotericin B, wherein the application of the method(s) result(s) in a detectably or significantly reduced time of administration, e.g., length of a course of administration, required to achieve the same clinical effect(s) compared to treatment with a comparator composition, such as, e.g., a comparator composition described herein. In aspects, a course of administration can be, e.g., e.g., at least about 10% shorter, ≥~20% shorter, ≥~30% shorter, ≥~40% shorter, ≥~50% shorter, ≥~60% shorter, ≥~70% shorter, ≥~80% shorter, ≥~90% shorter, or even more, than that required by a comparator composition, including, e.g., one or more antimicrobial API(s), e.g., antifungal API(s), e.g., fluconazole, administered systemically (such as by oral administration as a tablet) to achieve the same clinical effect(s).

In aspects, the invention provides method(s) described herein, where the method(s) comprise administration of ODF(s) comprising amphotericin B, e.g., ionic liquid form(s) of amphotericin B, where the application of the method(s) result(s) in a detectably or significantly reduced frequency in the development of resistance to amphotericin B by microbial organism(s) than that which occurs when treating at least mostly the same, at least generally the same, at least substantially the same, at least essentially the same, essentially the same, or the same population of recipients suffering from at least mostly the same, at least generally the same, at least substantially the same, at least essentially the same, essentially the same, or the same condition(s) with a comparator composition, such as, e.g., a comparator composition described herein. In aspects, the frequency of amphotericin B resistance can be, e.g., at least about 10% less frequent, ≥~20% less frequent, ≥~30% less frequent, ≥~40% less frequent, ≥~50% less frequent, ≥~60% less frequent, ≥~70% less frequent, ≥~80% less frequent, ≥~90% less frequent, or even more (less frequent), than that experienced in the administration of comparator composition(s) for period(s) of time sufficient to achieve the at least generally the same, at least substantially the same, at least essentially the same, essentially same, or same clinical effect(s).

In aspects, the invention provides the method(s) described here, where the method(s) comprise administration of ODF(s) comprising amphotericin B, e.g., ionic liquid form(s) of amphotericin B, wherein such ODF(s) and treatment therewith demonstrate(s) a detectably or significantly broader therapeutic index than demonstrated by comparator composition(s)/treatment(s) therewith, such as, e.g., comparator composition(s) described here.

Methods of Manufacturing

In aspects, the invention provides method(s) of manufacturing one or more composition(s) provided herein.

In aspects, method(s) of manufacturing described herein include, e.g., method(s) of forming an ionic liquid of amphotericin B, such as, e.g., at least in part, method(s) of forming amphotericin complexed with one or more complexing agent(s). In aspects, described herein is at least one method of forming or at least one technology capable of forming such ionic liquid(s). In aspects, described herein is at least one method of forming or at least one technology capable of forming such complex(es) of amphotericin B. One of skill in the art will recognize that there may be alternative method(s), or, e.g., alternative technology(ies) which can be applied at one or more stages of manufacture or stages of ionic liquid formation which will provide an at least substantially similar result. In aspects, such method(s) could comprise, e.g., application of different condition(s), e.g., different temperature conditions, different pH conditions, different energy conditions or application of different technologies (e.g., different heating conditions, application of sonication, etc.)

In aspects, the invention provides method(s) of manufacturing an ionic liquid form of an API, e.g., an antifungal API, e.g., amphotericin B.

In aspects, the invention provides method(s) of manufacturing composition(s) comprising an ionic liquid form of an API, e.g., an antifungal API, e.g., amphotericin B.

In aspects, the invention provides method(s) of manufacturing oral dissolve (orally dissolvable or orodispersible) film(s) (ODF(s)) comprising an ionic liquid form of an API, e.g., an antifungal API, e.g., amphotericin B.

In aspects, method(s) of manufacture/method(s) of manufacturing an end product can be referred to as, e.g., processes of making (a process of making) or processes for making (a process for making) such an end product, e.g., an ionic liquid (or, e.g., a process of or for making a composition comprising such an ionic liquid, e.g., an ODF comprising such an ionic liquid).

In aspects, ionic liquid(s) of API(s) or, e.g., composition(s) thereof, provided by the invention are prepared by using any suitable technique, many of which are known to those skilled in the art, the steps of which can be combined in any order. In describing methods of manufacturing provided by the invention, references to order of operations/steps may be present. It should be understood that steps of described manufacturing process(es) can be performed in any suitable order, provided that the end product is at least substantially, at least generally, or essentially the same. In aspects, method(s) of manufacturing (method(s) of production, the process(es) for forming elements) described herein are inventive and result in detectably or significantly different product(s), detectably or significantly advantageous product(s), or both. In aspects, the method(s) of manufacture, order of operation(s)/step(s) therein, or both is/are relevant to the resulting product(s) and is/are element(s) of the invention provided herein.

Ionic Liquid API

According to certain aspects, the invention provides method(s) of manufacturing an ionic liquid form of an API, e.g., an antifungal API, e.g., an ionic liquid of amphotericin B.

In aspects, method(s) of manufacturing an ionic liquid of, e.g., amphotericin B comprises use of a solvent component. In aspects, the solvent component comprises one or more solvent compound(s)/agent(s). In aspects, method(s) comprise acidifying an amount of solvent(s). In aspects, a single solvent is acidified. In aspects, the solvent is a solvent described herein, such as, e.g., dimethyl acetamide. In aspects, the solvent(s) is/are acidified using acidifying agent(s). In aspects, an amount of acidifying agent(s) is/are added to acidify the solvent(s), e.g., dimethyl acetamide. In aspects, a single acidifying agent is used. In aspects, the acidifying agent is characterizable as a complexing agent, such that, e.g., it is characterizable as a constituent of a complexing agent component as described herein. In aspects, the acidifying agent is an acidifying agent described herein, such as, e.g., ascorbic acid.

According to certain aspects, method(s) of manufacturing an ionic liquid of, e.g., amphotericin B comprise use of an acidified solvent, such as, e.g., acidified dimethyl acetamide (A-DMA). In aspects, an acidified solvent is prepared by dissolving an excess quantity of an acidifying agent, e.g., ascorbic acid, in a solvent, e.g., dimethyl acetamide. In aspects, such a mixture of solvent (e.g., dimethyl acetamide) and acidifying agent (e.g., ascorbic acid) is heated to ensure saturation. In aspects, a mixture can be heated to between about 60° C. and about 100° C., such as, e.g., to ~65° C.-~100° C., ~70° C.-~100° C., ~75° C.-~100° C., ~80° C.-~100° C., ~85° C.-~100° C., ~90° C.-~100° C., or, e.g., ~95° C.-~100° C., such as ~60° C.-~95° C., ~60° C.-~90° C., ~60° C.-~85° C., ~60° C.-~80° C., ~60° C.-~75° C., ~60° C.-~70° C., ~60° C.-~65° C., as in, for example, ~65° C.-~95° C., ~70° C.-~90° C., ~75° C.-~85° C., or, e.g., ~80° C. for a period of about 1 to about 5 minutes, e.g., ~1 minute-~4 minutes, ~1 minute-~3 minutes, or ~1 minute-~2 minutes, e.g., ~2 minutes-~5 minutes, ~3 minutes-~5 minutes, or, e.g., ~4 minutes-~5 minutes, such as, e.g., ~2 minutes-~4 minutes or ~2 minutes to about 3 minutes.

In certain aspects, an acidifying agent which detectably or significantly acidifies a solvent also provides one or more additional detectable or significant activity(ies), such as, e.g., detectably or significantly binding to at least one API, e.g., acting as a complexing agent (e.g., a first of multiple complexing agent(s) representing a complexing agent component of composition(s) described herein) with an API, detectably or significantly establishing, modifying, or, e.g., maintaining a target pH (of composition(s)) (such that it is characterizable as a pH modulating agent), providing detectable or significant antioxidant activity, or any combination of any or all thereof.

In aspects, method(s) of manufacturing an ionic liquid of, e.g., amphotericin B comprises the addition of an amount of one or more co-solvent(s). In aspects, method(s) comprise mixing an amount of acidified solvent, e.g., an acidified solvent such as that described above, e.g., acidified dimethyl acetamide, e.g., dimethyl acetamide acidified with ascorbic acid, described above, with an amount of co-solvent. In aspects, a single co-solvent is used. In aspects, the co-solvent can be any one or more co-solvent(s) described herein, such as, e.g., an alcohol. In aspects, the cosolvent is methanol. In aspects, method(s) comprise mixing a solvent, e.g., dimethyl acetamide, and co-solvent, e.g., methanol, in a particular ratio. In aspects, such a ratio is any suitable ratio resulting in composition(s) demonstrating effect(s) described herein. In aspects, such a ratio is, e.g., a ratio of solvent:co-solvent (e.g., dimethyl acetamide:alcohol, e.g., dimethyl acetamide:methanol) of between about 1:50-about 1:100, such as, e.g., ~1:55-~1:100, ~1:60-~1:100, ~1:65-~1:100, ~1:70-~1:100, ~1:75-~1:100, ~1:80-~1:100, ~1:85-~1:100, ~1:90-~1:100, or ~1:55-~1:100, such as, e.g., ~1:50-~1:95, ~1:50-~1:90, ~1:50-~1:85, ~1:50-~1:80, ~1:50-~1:75, ~1:50-~1:70, ~1:50-~1:65, ~1:50-~1:60, or ~1:50-~1:

55, as in, e.g., ~1:55-~1:95, ~1:60-~1:90, ~1:55-~1:85, ~1:70-~1:80, or, e.g., ~1:75 based on their representative percentage w/v of the composition.

In aspects, method(s) of manufacturing an ionic liquid of, e.g., amphotericin B comprises adding an API component, e.g., adding an amount of at least one API, to one or more other constituent(s). In aspects, the API can be any API described herein, such as, e.g., amphotericin B. In aspects, method(s) comprise adding at least one API, e.g., amphotericin B to the mixture of acidified solvent and co-solvent described above, such as, e.g., dimethyl acetamide acidified with ascorbic acid and mixed with methanol.

In aspects, method(s) of manufacturing an ionic liquid of, e.g., amphotericin B comprises adding complexing agent(s), e.g., one or more constituent(s) of a complexing agent component, to one or more other constituent(s). In aspects, a first complexing agent also serves as an acidifying agent, e.g., acidifying a solvent. In aspects, such a first complexing agent is ascorbic acid. In aspects, method(s) comprise the addition of an amount of a separate complexing agent, e.g., a second complexing agent, to one or more other constituent(s). In aspects, complexing agent(s) can be any complexing agent(s) described herein, such as, e.g., choline chloride. In aspects, method(s) comprise adding a complexing agent, e.g., a second complexing agent, such as, e.g., choline chloride, to a mixture comprising the API in solvent/co-solvent, e.g., such as that described above, e.g., amphotericin B mixed with dimethyl acetamide acidified with ascorbic acid further mixed with methanol.

In aspects, method(s) of manufacturing an ionic liquid of, e.g., amphotericin B comprise use of a solubilizing component. In aspects, method(s) of manufacturing an ionic liquid of, e.g., amphotericin B, comprise adding a solubilizing component, e.g., an amount of one or more solubilizing agent(s), to one or more other constituent(s). In aspects, method(s) comprise adding a single solubilizing agent. In aspects, solubilizing agent(s) can be any solubilizing agent(s) described herein, such as, e.g., TPGS. In aspects, method(s) comprise adding a solubilizing agent, e.g., TPGS, to a mixture of acidifying agent(s), e.g., ascorbic acid; solvent(s); e.g., dimethyl acetamide; co-solvent(s), e.g., methanol; API(s), e.g., amphotericin B; and complexing agent(s), e.g., ascorbic acid, choline chloride, or both; such as, e.g., described above.

In aspects, method(s) comprise mixing an amount of a complexing agent, e.g., a second complexing agent, e.g., choline chloride, and, e.g., an amount of a solubilizing agent, e.g., TPGS, in a particular ratio. In aspects, such a ratio is any suitable ratio resulting in composition(s) demonstrating effect(s) described herein. In aspects, such a ratio is, e.g., a ratio of complexing agent, e.g., second complexing agent, e.g., choline chloride to solubilizing agent, e.g., TPGS, of between about 10:1 and about 1:10, e.g., ~10:1-~1:9, ~10:1-~1:8, ~10:1-~1:7, ~10:1-~1:6, ~10:1-~1:5, ~10:1-~1:4, ~10:1-~1:3, ~10:1-~1:2, or ~10:1-~1:1, such as, e.g., ~9:1-~10:1, ~8:1-~10:1, ~7:1-~10:1, ~6:1-~10:1, ~5:1-~10:1, ~4:1-~10:1, ~3:1-~10:1, ~2:1-~10:1, or ~1:1-~10:1, as in, for example, ~9:1-~1:9, ~8:1-~1:8, ~7:1-~1:7, ~6:1-~1:6, ~5:1-~1:5, ~4:1-~1:4, ~3:1-~1:3, ~2:1-~1:2, or, e.g., ~1:1, based on their representative percentage w/v of the composition.

In aspects, method(s) of manufacturing an ionic liquid of amphotericin B comprise (1) acidifying an amount of solvent with an amount of acidification agent, wherein, in aspects, the acidification agent also acts as a first complexing agent with amphotericin B; (2) mixing the solvent with an amount of a co-solvent, e.g., an amount of an alcohol; (3) adding an amount of amphotericin B to the acidified solvent—alcohol mixture; (4) adding an amount of a second complexing agent; and (4) adding an amount of a solubilizing agent.

In aspects, method(s) of manufacturing an ionic liquid of amphotericin B comprise (1) acidifying an amount of dimethyl acetamide with an amount of an acidification agent, wherein, in aspects, the acidification agent also acts as a first complexing agent with amphotericin B; (2) mixing the acidified dimethyl acetamide with an amount of a co-solvent, e.g., an amount of an alcohol; (3) adding an amount of amphotericin B to the acidified solvent-alcohol mixture; (4) adding an amount of a second complexing agent; and (4) adding an amount of a solubilizing agent.

In aspects, method(s) of manufacturing an ionic liquid of amphotericin B comprise (1) acidifying an amount of dimethyl acetamide with an amount of ascorbic acid, wherein, in aspects, the ascorbic acid also detectably or significantly forms a complex with amphotericin B; (2) mixing the acidified dimethyl acetamide with an amount of a co-solvent, e.g., an alcohol; (3) adding an amount of amphotericin B to the acidified dimethyl acetamide-alcohol mixture; (4) adding an amount of a second complexing agent; and (4) adding an amount of a solubilizing agent.

In aspects, method(s) of manufacturing an ionic liquid of amphotericin B comprise (1) acidifying an amount of dimethyl acetamide with an amount of ascorbic acid, wherein, in aspects, the ascorbic acid also detectably or significantly forms a complex with amphotericin B; (2) mixing the acidified dimethyl acetamide with an amount of methanol; (3) adding amphotericin B to the acidified dimethyl acetamide-methanol mixture; (4) adding an amount of a second complexing agent; and (4) adding an amount of a solubilizing agent.

In aspects, method(s) of manufacturing an ionic liquid of amphotericin B comprise (1) acidifying an amount of dimethyl acetamide with an amount of ascorbic acid, wherein, in aspects, the ascorbic acid also detectably or significantly forms a complex with amphotericin B; (2) mixing the acidified dimethyl acetamide with an amount of methanol; (3) adding an amount of amphotericin B to the acidified dimethyl acetamide-methanol mixture; (4) adding an amount of choline chloride; and (4) adding an amount of a solubilizing agent.

In aspects, method(s) of manufacturing an ionic liquid of amphotericin B comprise (1) acidifying an amount of dimethyl acetamide with an amount of ascorbic acid, wherein, in aspects, the ascorbic acid also detectably or significantly forms a complex with amphotericin B; (2) mixing the acidified dimethyl acetamide with an amount of methanol; (3) adding an amount of amphotericin B to the acidified dimethyl acetamide-methanol mixture; (4) adding an amount of choline chloride; and (4) adding an amount of TPGS.

According to certain aspects, method(s) of manufacturing ionic liquid(s) of API(s), e.g., amphotericin B, provided herein comprise heating the acidified solvent, e.g., dimethyl acetamide acidified with ascorbic acid, prior to the addition of a co-solvent, e.g., alcohol, e.g., methanol.

ODF

In aspects, the invention provides method(s) of manufacturing ODF(s) comprising an ionic liquid form of an API, e.g., an antifungal API, e.g., amphotericin B, wherein one or more property(ies) of the API, e.g., one or more physiochemical properties of the API, dictate the selection of one or more constituent(s) of the ODF, e.g., the solvent, utilized in the method(s). In aspects, one or more property(ies) of the API, e.g., one or more physiochemical property(ies) of the API, include, e.g., one or more of the API's compatibility with one or more film-forming excipient(s) used in the method(s); the API's compatibility with one or more solvent(s) used in the method(s); the polymorphic nature of the API selected; the sensitivity to temperature of the API; or, e.g., a combination of any two or more such properties.

In aspects, the invention provides method(s) of manufacturing ODF(s) comprising an ionic liquid form of an API, e.g., an antifungal API, e.g., amphotericin B. In aspects, method(s) of manufacturing ODF(s) comprising an ionic liquid form of an API, e.g., an antifungal API, e.g., amphotericin B, can incorporate any film-forming technique known in the art, such as, e.g., a solvent casting method, semisolid casting method, hot-melt extrusion (HME) method, solid-dispersion extrusion method, rolling method, or, e.g., a combination of any two or more such method(s). In aspects, manufacturing method(s) of ODF(s) described herein comprise use of solvent casting.

In aspects, method(s) of manufacturing ODF(s) herein comprise use of a solvent casting method, wherein the solvent casting method comprises the dissolution of water-soluble ingredient(s) to form a clear, aqueous solution. In aspects, other film-forming method(s) can be used as, e.g., described elsewhere herein. In aspects, the solution formed prior to air removal is a viscous solution. In aspects, entrapped air is removed by vacuum. In aspects, removal of entrapped air participates in the creation of a final film having a desired target uniformity and thickness. In aspects, the resulting final, deaerated solution is cast as a film. In aspects, the solution is allowed to dry to film-form. In aspects, the film is cut into target-sized pieces.

In aspects, the invention provides method(s) of manufacturing ODF(s) comprising an ionic liquid form of an API, e.g., an antifungal API, e.g., amphotericin B, wherein, in aspects, such method(s) comprise the method(s) of manufacturing an ionic liquid form of an API described herein, e.g., in this "Methods of Manufacturing" section. In aspects, the invention provides method(s) of manufacturing a composition comprising an ionic liquid form of an API, e.g., an antifungal API, e.g., amphotericin B. In aspects, such composition(s) are ODF(s).

In aspects, the invention provides method(s) of manufacturing ODF(s) comprising an ionic liquid form of an API, e.g., an antifungal API, e.g., amphotericin B, wherein, the method(s) comprise the method(s) of manufacturing an ionic liquid form of an API described herein, e.g., in this "Methods of Manufacturing" section, and wherein the method(s) further comprise the addition of a film-inducing component. In aspects, the film-inducing component comprises a film-forming component comprising one or more film-forming agents; a plasticizing component comprising one or more plasticizing agents; or both a film-forming component and a plasticizing component.

In aspects, the invention provides method(s) of manufacturing ODF(s) comprising an ionic liquid form of an API, e.g., an antifungal API, e.g., amphotericin B, wherein, the method(s) comprise the method(s) of manufacturing an ionic liquid form of an API described herein, e.g., in this "Methods of Manufacturing" section and wherein the method(s) further comprise the addition of a film-inducing component comprising a film-forming component. In aspects, the film-forming component comprises one or more film-forming agent(s). In aspects, the film-film forming agent(s) can be any film forming agent(s) described herein, such as, e.g., polyvinyl alcohol.

In aspects, the invention provides method(s) of manufacturing ODF(s) comprising an ionic liquid form of an API, e.g., an antifungal API, e.g., amphotericin B, wherein the method(s) comprise the method(s) of manufacturing an ionic liquid form of an API described herein, e.g., in this "Methods of Manufacturing" section and wherein the method(s) further comprise the addition of a film-inducing component comprising a plasticizing component. In aspects, the plasticizing component comprises one or more plasticizing agent(s). In aspects, the plasticizing agent(s) can be any plasticizing agent(s) described herein, such as, e.g., glycerol.

In aspects, the invention provides method(s) of manufacturing ODF(s) comprising an ionic liquid form of an API, e.g., an antifungal API, e.g., amphotericin B, wherein, the method(s) comprise the method(s) of manufacturing an ionic liquid form of an API described herein, e.g., described in this "Methods of Manufacturing" section and wherein method(s) further comprise the addition of a film-inducing component comprising a film forming component and a plasticizing component. In aspects, the film forming component comprises polyvinyl alcohol and the plasticizing component comprises glycerol.

In aspects, method(s) comprise mixing an amount of a film-forming component, comprising at least one film-forming agent, and, e.g., an amount of a plasticizing component, comprising at least one plasticizing agent, in a particular ratio. In aspects, such a ratio is any suitable ratio resulting in composition(s) demonstrating effect(s) described herein. In aspects, such a ratio is, e.g., a ratio of film-forming component (film-forming agent), e.g., polyvinyl alcohol, to plasticizing agent, e.g., glycerol, of between about 20:1 and about 1:1, e.g., ~19:1-~1:1, ~18:1-~1:1, ~17:1-~1:1, ~16:1-~1:1, ~15:1-~1:1, ~14:1-~1:1, ~13:1-~1:1, ~12:1-~1:1, ~11:1-~1:1, or ~10:1-~1:1, e.g., ~20:1-~1:2, ~20:1-~1:2, ~20:1-~1:4, ~20:1-~1:5, ~20:1-~1:6, ~20:1-~1:7, ~20:1-~1:8, ~20:1-~1:9, or, e.g., ~20:1-~1:10, such as, e.g., ~19:1-~2:1, ~18:1-~3:1, ~17:1-~4:1, v~16:1-~5:1, ~15:1-~6:1, ~14:1-~7:1, ~13:1-~9:1, ~12:1-~9:1, ~11:1-~9:1, or, e.g., ~10:1, based on their representative percentage w/v of the composition.

In aspects, method(s) of manufacturing ODF(s) provided herein comprise limiting exposure of film(s) to moisture, such as, e.g., limiting exposure of film(s) to an amount of moisture which detectably or significantly reduces the chemical or physical stability, including e.g., mechanical strength, of the film(s) or component(s)/agent(s) therein.

In aspects, method(s) of manufacturing ODF(s) provided herein comprise limiting exposure of film(s) to a temperature which detectably or significantly reduces the chemical or physical stability of the film(s) or component(s)/agent(s) therein (e.g., the API therein) or detectably or significantly impacts the viscosity of the composition(s) at one or more stage(s) of the manufacturing process which negatively impacts the production of the ODF(s) or characteristic(s) of finished ODF(s).

In aspects, method(s) of manufacturing an ODF comprising an ionic liquid of amphotericin B comprise (1) acidifying an amount of a solvent with an amount of acidification agent, wherein the acidification agent, in aspects, also acts as a first complexing agent with amphotericin B; (2) mixing the solvent with an amount of a co-solvent, e.g., an amount of an alcohol; (3) adding an amount of amphotericin B to the acidified solvent—alcohol mixture; (4) adding an amount of a second complexing agent; and (4) adding an amount of a solubilizing agent, thereby establishing an ionic liquid form of amphotericin B, and further (5) forming a film-inducing component comprising a film-forming component and a plasticizing component, (6) adding the ionic liquid component to the film-inducing component, and (7) forming the resulting mixture as a film.

According to certain aspects, method(s) of manufacturing an ODF comprising an ionic liquid of amphotericin B comprise use of a solvent casting method. In aspects, method(s) comprise weighing an amount of amphotericin B. In aspects, method(s) comprise adding an amount of amphotericin B to a solvent component, the solvent component comprising one or more solvent(s) and one or more co-solvent(s), wherein, in aspects, one or more solvent(s) is an acidified solvent; a complexing agent component comprising one or more complexing agent(s); and, e.g., a solubilizing component comprising one or more solubilizing agent(s). In aspects, one or more solvent(s) is dimethyl acetamide and one or more co-solvents is methanol. In aspects, one or more solvent(s) is acidified with ascorbic acid. In aspects, one or more complexing agent(s) is choline chloride. In aspects, the resulting mixture results in an ionic liquid of amphotericin B. In aspects, the ionic liquid of amphotericin B is added to a film-inducing component. In aspects, the film-inducing component comprises a film-forming component, comprising one or more film-forming agent(s), such as, e.g. polyvinyl alcohol. In aspects, the film-inducing component comprises a plasticizing component comprising one or more plasticizing agent(s) such as, e.g., glycerol. In aspects, the resulting mixture is cast into a film.

In one exemplary aspect, the invention provides method(s) of manufacturing, e.g., preparing, a composition in the form of an ODF comprising amphotericin B, wherein the method(s) comprise preparing an ionic liquid of amphotericin B wherein the preparation of an ionic liquid of amphotericin B comprises use of a solubilization component comprising one or more solubility-enhancing agent(s). In aspects, method(s) comprise adding a suitable amount of a film-inducing component to form a film, the film-inducing component comprising a film-forming component and a plasticizing component, wherein the film-forming component comprises at least one film-forming agent and the plasticizing component comprises at least one plasticizing agent. In aspects, the method(s) comprise casting the film into an administrable form or, e.g., casting the film such that it can form into a film which can be adapted (e.g., cut, sized, or otherwise shaped) into an administrable form.

In certain specific aspects, method(s) of manufacturing ODF film(s) of amphotericin B comprise, e.g., weighing an amount of amphotericin B. In aspects, method(s) further comprise adding amphotericin B to a methanolic solution comprising choline chloride, dimethyl acetamide, ascorbic acid and TPGS. In aspects, method(s) comprise adding the resulting composition to an aqueous solution of polyvinyl alcohol and glycerol. In aspects, method(s) comprise adding the methanolic solution comprising the API slowly, e.g., dropwise, added to the aqueous solution of polyvinyl alcohol and glycerol. In aspects, the resulting composition is cast into a suitable container to form as a film, while, e.g., methanol, water, or both are allowed to evaporate at room temperature.

In aspects, method(s) of manufacturing ODF film(s) of amphotericin B comprise, e.g., the addition of or, e.g., addition of one or more composition constituent(s) to, a film-forming component, a plasticizer component, or both, e.g., film-inducing component comprising a mixture of a film-forming component and a plasticizer component. In aspects, upon the inclusion of a film-forming component, plasticizing component, or both, the resulting composition can be centrifuged to remove any free API if any is present. In aspects, composition(s) can be centrifuged at between about 1500 rpm and about 2500 rpm, such as, e.g., ~1700 rpm-~2500 rpm, ~1900 rpm-~2500 rpm, ~2100 rpm-~2500 rpm, or, ~2300 rpm-~2500 rpm, e.g., ~1500 rpm-~2300 rpm, ~1500 rpm-~2100 rpm, ~1500 rpm-~1900 rpm, or, e.g., ~1500 rpm-~1700 rpm, e.g., ~1700 rpm-~2300 rpm, ~1900 rpm-~2100 rpm, or, e.g., ~2000 rpm for a period of about 1 minute to about 10 minutes, e.g., ~2 minutes-~10 minutes, ~4 minutes-~10 minutes, ~6 minutes-~10 minutes, or ~2 minutes-~12 minutes, such as ~1 minute-~8 minutes, ~1 minute-~6 minutes, ~1 minute-~4 minutes, or ~1 minute-~2 minutes, as in, e.g., ~2 minutes-~8 minutes, ~3 minutes-~7 minutes, ~4 minutes-~6 minutes, or, e.g., for a period of about 5 minutes.

In aspects, method(s) of manufacturing described herein comprise forming the mixture as a film, or, e.g., casting composition(s) as a film, wherein such casting comprises sufficient evaporation of composition(s) e.g., evaporation of a co-solvent and, e.g., any water-containing component(s).) In aspects, a film is formed after casting within about 48 hours, e.g., within about 44 hours, about 40 hours, ~36 hours, ~32 hours, or ~28 hours. In aspects, a film is formed after casting within about 24 hours, such as, e.g., within about 22 hours, within about 20 hours, within about 18 hours, within about 16 hours, within about 14 hours, within about 12 hours, within about 10 hours, within about 8 hours, within about 6 hours, within about 4 hours, or, e.g., within about 2 hours. In aspects, a film is formed after casting within a period of time of less than about 2 hours, e.g., within about 90 minutes, withing about 60 minutes, or, e.g., within about 30 minutes. In aspects, composition(s) are maintained at room temperature during film casting, film formation, or both. In aspects, composition(s) are exposed to heat to facilitate the formation of a film within a period of time shorter than, or, e.g., less than, that which would be required for the film to form at room temperature, such as, e.g., a temperature of between about 30° C. and about 60° C., e.g., ~30° C.-~55° C., ~30° C.-~50° C., ~30° C.-~45° C., ~30° C.-~40° C., or ~30° C.-~35° C., e.g., ~35° C.-~60° C., ~40° C.-~60° C., ~45° C.-~60° C., ~50° C.-~60° C., or ~55° C.-~60° C., as in, e.g., ~35° C.-~55° C., or, e.g., ~40° C.-~50° C. In aspects, such a heated environment is provided by an oven.

In aspects, method(s) of manufacturing ODF(s) comprise use of solvent casting, hot-melt extrusion, semisolid casting, solid-dispersion extrusion, and rolling.

In aspects, method(s) of manufacturing ODF(s) comprise cutting, sizing, or otherwise forming a film resulting from other step(s) of a manufacturing process film into smaller-sized pieces, such as, e.g., single dose-sized pieces.

In aspects, method(s) of manufacturing ODF(s) comprise packaging one or more film(s) in final packaging. In aspects, such packaging is packaging protecting contents therein from detectable or significant amount(s) of light. In aspects, such packaging can be any packaging described herein. In aspects, such light-protective packaging prevents detectable or significant degradation, e.g., decrease of chemical or physical stability of contents therein, e.g., ODF(s) there. In aspects, ODF(s) are packaged in film dispensing container(s). In aspects, film dispensing container(s) are made of light-protective material.

According to certain aspects, method(s) of manufacturing ODF(s) provided herein result in an administrable form of amphotericin B having a cost of manufacture which is beneficially, e.g., significantly, less than the cost of manufacturing other administrable form(s) of amphotericin B, such as, e.g., lipid formulation(s) of amphotericin B.

In aspects, the invention provides method(s) of manufacturing composition(s) suitable for the treatment of one or more microbial infection(s) wherein the method(s) comprise any one or more of the method(s) of manufacturing described herein, e.g., in this "Methods of Manufacturing" section. In aspects, the invention provides method(s) of manufacturing antimicrobial composition(s) (e.g., antiparasitic composition(s), antifungal composition(s), or, e.g., composition(s) demonstrating both detectable or significant antiparasitic and antifungal activity), such composition(s) demonstrating equivalent or superior therapeutic efficacy to one or more comparator composition(s) when administered to treat at least generally the same, at least substantially the same, at least effectively the same, effectively the same, or the same condition in at least generally the same, at least substantially the same, at least effectively the same, effectively the same, or the same population of target recipients, as determined by an appropriately administered, powered, and conducted study or as determined by a study or clinical trial suitable for approval by or approved by a reputable regulatory authority, such as, e.g., the United States Food and Drug Administration (US FDA), wherein the cost of manufacturing an amount of composition(s) is detectably or significantly less than the cost to manufacture an amount of a comparator composition capable of achieving the same therapeutic effect in at least generally the same, at least substantially the same, at least effectively the same, effectively the same, or the same population of recipients. In aspects, the cost to manufacture composition(s) provided herein is an advantage of such composition(s). In aspects, the cost to manufacture composition(s) herein detectably or significantly increases the population of people capable of accessing such composition(s). In aspects, the cost to manufacture composition(s) herein detectably or significantly increases access to such compositions for those in developing and emerging countries, remote populations, or those living areas of the world to which access is challenging, and thus is an element of the novelty and benefit of composition(s) and method(s) described herein.

Product-by-Process Aspects

In aspects, the invention provides a product, e.g., an API in ionic liquid form, e.g., an ionic liquid form of amphotericin B, composition(s) thereof (e.g., ODF(s)), or both, wherein such product(s) are made by any one or more method(s) of manufacturing described herein, including, e.g., any combination of any two or more manufacturing process steps described herein. In aspects, such a "product-by-process" has any one or more of the characteristic(s) of such product(s) described herein, can be used in any one or more method(s) of use described herein, demonstrate(s) any one or more of the outcome(s) of method(s) of use described herein, or any combination of any or all thereof. In aspects, the invention provides ODF(s) made by one or more method(s) of manufacturing described herein, wherein the method comprises solvent casting, hot-melt extrusion, semi-solid casting, solid-dispersion extrusion, and rolling.

REPRESENTATIVE EXPERIMENTS/EMBODIMENTS ("EXAMPLES")

The following detailed exemplary expository descriptions or experiments involving embodiments, applications, or related principles, of or otherwise related to the invention ("Examples") are provided to assist readers in further understanding aspects of the invention or principles related to the invention or practice of aspects of the invention.

Any particular materials, methods, steps, and conditions employed/described in the following Examples, and any results thereof, are merely intended to further illustrate aspects of the invention. These Examples reflect exemplary embodiments of the invention, and the specific methods, findings, principles of such Examples, and the general implications thereof, can be combined with any other part of this disclosure. However, readers should understand that the invention is not limited by these Examples or any part thereof.

Example 1

An ionic liquid of amphotericin B was made according to the formulation in Table 3.

TABLE 3

| Exemplary Ionic Liquid of Amphotericin B. | |
|---|---|
| Ingredient | Percentage (% w/v) |
| Amphotericin B | 0.5-10 |
| Ascorbic acid | 5-30 |
| Choline chloride | 0.1-20 |
| D-α-Tocopheryl polyethylene glycol 1000 succinate (TPGS) | 0.1-20 |
| Dimethyl acetamide | 0.5-10 |

The following manufacturing process was used to make the composition of Table 3.

Acidified dimethylacetamide (A-DMA) was prepared by dissolving an excess quantity of ascorbic acid in DMA, thus forming A-DMA.

The A-DMA mixture was heated at 80° C. for 2-3 minutes to ensure saturation was achieved.

A 1:75 mixture of A-DMA and methanol was prepared.

The required amount of amphotericin B, e.g., about 10 mg of amphotericin B, was dissolved in the 1:75 A-DMA: methanol preparation.

An amount of choline chloride and an amount of D-α-Tocopheryl polyethylene glycol 1000 succinate were added, wherein the amount(s) of each compound were added in a 1:1 ratio with one another (equal amounts of each).

The addition of choline chloride and D-α-Tocopheryl polyethylene glycol 1000 succinate resulted in the formation of an ionic liquid and detectably increased the solubility of amphotericin B.

This Example demonstrates a method of successfully formulating an ionic liquid of amphotericin B.

The resulting amphotericin B ionic liquid was used to formulate an orally dissolving film composition described in Example 2.

Example 2

An orally dissolving film composition comprising the amphotericin B ionic liquid described in Example 1 was made according to the formulation in Table 4.

TABLE 4

Exemplary orally dissolving amphotericin B film composition.

| Ingredient | Percentage (% w/v) |
|---|---|
| Amphotericin B ionic liquid according to Example 1 | |
| Polyvinyl alcohol (Parteck ® MXP) | 20-100 |
| Glycerol | 0.1-20 |

The following manufacturing process was used to make the orally dissolvable amphotericin B film composition of Table 4.

Post-solubilization of amphotericin B in/as (an) ionic liquid, a 20% w/v solution of Parteck® MXP, a polyvinyl alcohol, a film former, and 2% v/v glycerol, a plasticizer, were added to the amphotericin composition.

The resulting composition was centrifuged at 2000 revolutions per minute (rpm) for 5 minutes (mins) to remove any remaining free amphotericin B (amphotericin B not in ionic liquid form).

The resulting supernatant was cast into a film.

This Example demonstrates that the ionic liquid(s) of amphotericin B described herein and as exemplified in Example 1 can be successfully formulated as an orally dissolvable film.

Example 3

This Example describes the formulation and characterization of exemplary orally dissolvable film(s) comprising amphotericin B.

Preparation of an orally dissolvable film comprising amphotericin B was completed. Acidified dimethylacetamide (DMA) (A-DMA) was prepared by dissolving an excess quantity of ascorbic acid in DMA. A saturated system of A-DMA was obtained by heating the mixture at 80° C. for 2-3 minutes. Amphotericin B was dissolved in a mixture of A-DMA and methanol wherein the ratio of A-DMA:methanol in the mixture was 1:75. Solubility of the amphotericin B was further increased by the addition of choline chloride and TPGS to the dispersion, wherein the ratio of the amounts of choline chloride to TPGS added was 1:1. The resulting composition was sonicated for 10 minutes in a bath sonicator. Post-solubilization of amphotericin B, polyvinyl alcohol 4-88 and glycerol were added to the composition. The resulting composition was centrifuged at 2000 rpm for 5 minutes to remove any remaining free (undissolved) amphotericin B, if present. The resulting supernatant was cast into a film using 9 cm petri dishes (9 cm petri plates). Table 5 (below) provides the final composition of the resulting orally dissolvable film comprising amphotericin B.

TABLE 5

Composition of orally dissolvable film comprising amphotericin B.

| Components | Percentage (%) | Per 9 cm petri plate |
|---|---|---|
| Amphotericin B | 2 | 0.020 g |
| Ascorbic acid | 16.67 | 0.166 g |
| Choline chloride | 4.2 | 0.042 g |
| D-α-Tocopheryl polyethylene glycol 1000 succinate (TPGS) | 4.2 | 0.042 g |
| Dimethyl acetamide | 4.2 | 0.042 g |
| Polyvinyl alcohol 4-88 | 62.5 | 3.12 ml |
| Glycerol | 6.25 | 0.062 g |

Films resulting from the manufacturing process above were characterized according to weight variation, solubility, drug (API) content, content uniformity, folding endurance, surface pH, moisture absorption, disintegration time, in vitro dissolution, and stability. Table 6 below summarizes these results.

TABLE 6

Characterization of orally dissolvable film(s) comprising amphotericin B.

| Characterization | Result |
|---|---|
| Weight Variation | |
| Ten films, 2 cm × 3 cm each, were randomly selected and individual weights of the films recorded. An average weight of the films was calculated. | Uniform, transparent films weighed an average of 91 mg ± 1.78 mg. |
| Solubility | |
| An equivalent amount of unmodified amphotericin B and orally dissolvable film comprising amphotericin B were added to 0.5 mL of MiliQ water. The resulting dispersion was shaken on a shaker incubator at room temperature for 6 hours. After 6 hours, the compositions were centrifuged at 5000 rpm for 15 minutes. The resulting supernatant was suitably diluted with water and the concentration of amphotericin B was quantified by HPLC. | Amphotericin B film demonstrated an average concentration of 3.4 mg/mL. Unmodified amphotericin B demonstrated an average concentration of 0.63 mg/mL. |
| Drug Content | |
| Amphotericin B from 2 cm × 3 cm orally dissolvable film(s) comprising amphotericin B was extracted in methanol using a bath sonicator. The extract was centrifuged at 5000 rpm for 10 minutes and the resulting | The average drug content of each film was 99.79 ± 0.26% of the amount expected. |

TABLE 6-continued

Characterization of orally dissolvable film(s) comprising amphotericin B.

| Characterization | Result |
|---|---|
| supernatant was analyzed for drug content at 408 nm using HPLC. The analysis was performed in triplicate. | |
| Content Uniformity | |
| 2 cm × 3 cm film(s) were weighed and disintegrated in 3 mL of MiliQ water. Compositions were then diluted with methanol to ensure full drug solubilization. Samples were centrifuged to precipitate undissolved excipients at 5000 rpm for 10 minutes. Amphotericin B dissolved in the supernatant was quantified by HPLC. The analysis was performed in triplicate. | The average drug content across films was 98.35% ± 0.76%. |
| Folding Endurance | |
| Folding endurance was manually assessed by counting the number of times a film could be folded 180° at the same location within the film without breaking. Folding endurance of film(s) was assessed when films were stored under multiple storage conditions for a period of 1 month (see also stability data): refrigerated temperature of 4° C.; 25° C. ± 2 ° C. and 60% RH ± 5% (stability chamber), and 40° C. ± 2° C./75% RH ± 5% (stability chamber). | The film was found to be flexible and on average each film could be folded (bent) up to 75 times without breaking. Folding endurance results specific to storage conditions are provided in table 7 below, alongside stability data. |
| Surface pH | |
| Film(s) were placed in a petri dish and moistened with 0.5 mL of distilled water and maintained for a period of 30 seconds. The surface pH was measured by means of pH paper placed on the surface of the film(s). | The surface pH of the film was 5.8 ± 0.14. |
| Moisture absorption | |
| Moisture uptake by film(s) was assessed by placing film(s) in amber colored Type I glass vial(s), each with a stopper, and maintained at 40° C. and 75% relative humidity (RH) for 1 week. Moisture uptake was measured as a percent increase in weight of the film(s). The analysis was performed in triplicate. | Film(s) showed less than a 2% change in weight after storage at 40° C. and 75% relative humidity (RH) for 1 week. |
| Disintegration time | |
| Disintegration of 2 cm × 3 cm film(s) was measured in 3 mL of MiliQ water and phosphate buffer (pH 6.4) in petri plate(s). A single film was placed on the surface of the media and the time required for complete dissolution of the film was measured. The analysis was performed in triplicate. | The average disintegration time of the film(s) was 48 seconds ± 0.42 seconds. |
| In vitro dissolution | |
| 2 cm × 3 cm film(s) were placed in 20 mL of phosphate buffer, pH of 6.4, at 37° C. + 0.5° C. under slow magnetic stirring (50 rpm). 1 mL samples were withdrawn at 1, 2, 4, 6, 8, 10, 15, and 30 minutes. Media was replaced with fresh buffer solution after each withdrawal. Aliquots were centrifuged at 10,000 rpm in a microcentrifuge for 10 min. and the supernatant was tested for the amount of amphotericin B by HPLC. | Film(s) demonstrated a fast-dissolving behavior, with 80% release within 15 minutes. This data is presented in FIG. 4. |
| Stability | |
| Film(s) were placed in Type I amber glass vial(s) and maintained at 3 different when for a period of one much under each temperatures: refrigerated temperature of 4° C.; 25° C. ± 2° C. and 60% RH ± 5% | Amphotericin B provided as an orally dissolvable film demonstrated stability |

TABLE 6-continued

Characterization of orally dissolvable film(s) comprising amphotericin B.

| Characterization | Result |
|---|---|
| of three tested conditions. Stability data is presented in Table 7 below. | (stability chamber), and 40° C. ± 2° C./75% RH ± 5% (stability chamber). Stability was measured after 1 month of storage at each condition. |

TABLE 7

Stability of amphotericin B orally dissolvable film(s).

STORAGE CONDITION: 4° C.

| AmpB Film* | Duration | Weight | Folding endurance | Assay |
|---|---|---|---|---|
| | Initial | 92.13 mg | >75 folds | 98.47 ± 0.76% |
| | 1 month | 91.47 mg | >75 folds | 98.51 ± 0.83% |
| | 2 months | 90.43 mg | >75 folds | 98.07 ± 0.49% |

STORAGE CONDITION: 25° C. ± 2° C./60% RH ± 5%

| AmpB Film | Duration | Weight | Folding endurance | Assay |
|---|---|---|---|---|
| | Initial | 92.13 mg | >75 folds | 98.47 ± 0.76% |
| | 1 month | 93.06 mg | >75 folds | 97.32 ± 0.17% |
| | 2 months | 97.19 mg | >75 folds | 94.17 ± 0.36% |

STORAGE CONDITION: 40° C. ± 2° C./75% RH ± 5%

| AmpB Film | Duration | Weight | Folding endurance | Assay |
|---|---|---|---|---|
| | Initial | 92.13 mg | >75 folds | 98.47 ± 0.76% |
| | 1 month | 105.9 mg | Moist film | 62.59 ± 1.76% |

*AmpB Film = orally dissolvable film comprising amphotericin B.

Example 3 demonstrates the ability to successfully manufacture ionic liquid(s) of amphotericin B which can be further formulated as orally dissolvable films.

In aspects, the invention provides, as shown in this Example, orally dissolvable film(s) comprising amphotericin B having a size of about 2 cm×about 3 cm and an average weight of about 89 mg-about 93 mg, such as an average weight demonstrated in this Example of 91 mg±1.78 mg.

In aspects, the invention provides, as shown in this Example, orally dissolvable film(s) comprising amphotericin B demonstrating an average solubility of amphotericin B in water of between about 3 mg/mL and about 4 mg/mL, such as an average solubility in water demonstrated in this Example of 3.4 mg/mL.

In aspects, the invention provides, as shown in this Example, orally dissolvable film(s) comprising amphotericin B with an average drug content of each film of between about 96% and about 100%, such as an average drug content demonstrated in this Example of 99.79±0.26%.

In aspects, the invention provides, as shown in the Example, ODF(s) comprising amphotericin B demonstrating an average drug content uniformity across multiple ODF(s) of between about 95% and about 100%, such as, e.g., an average content uniformity demonstrated in this Example of 98.35%±0.76%.

In aspects, the invention provides, as shown in this Example, orally dissolvable film(s) comprising amphotericin B which demonstrate flexibility, e.g., the ability to withstand repeated folding after extended storage without breaking. In aspects, film(s) are capable of withstanding folding more than 75 times after storage for a period of at least about 1 month at a refrigerated temperature of 4° C.; 25° C.±2° C. and 60% RH±5%; or 40° C.±2° C. n5% RH±5%.

In aspects, the invention provides, as shown in this Example, orally dissolvable film(s) comprising amphotericin B having a surface pH of between about 5 and about 6, such as a surface pH demonstrated in this Example of 5.8±0.14.

In aspects, the invention provides, as shown in this Example, orally dissolvable film(s) comprising amphotericin B wherein films demonstrate a change in average weight after storage at 40° C. and 75% relative humidity (RH) for a period of 1 week.

In aspects, the invention provides, as shown in this Example, orally dissolvable film(s) comprising amphotericin B having an average size of about 2 cm×3 cm demonstrating an average disintegration time of between about 47 and about 49 seconds in a simulated oral environment (water buffered with phosphate buffer at pH 6.4), such as an average disintegration time demonstrated in this Example of 48 seconds ±0.42 seconds in such conditions.

FIG. 4 provides the release profile of ODF(s) comprising amphotericin B (solid line) compared to the release profile of unmodified amphotericin B drug alone (dashed line). In aspects, the invention provides, as shown in this Example, orally dissolvable film(s) comprising amphotericin B are characterizable as fast-dissolving films. As illustrated in FIG. 4, in aspects, orally dissolvable film(s) comprising amphotericin B provided by the invention demonstrate a release rate of API (amphotericin B) of at least 80% within a period of 15 minutes of administration.

In aspects, the invention provides, as shown in this Example, stable, orally dissolvable film(s) comprising amphotericin B. In aspects, orally dissolvable film(s) of amphotericin B maintain at least about 97% of the amphotericin B originally present in the film when stored at 4° C., when stored at 25° C.±2° C. and 60% RH±5%, or when stored under either condition for a period of at least about 1 month. In aspects, film(s) stored under such conditions further demonstrate the ability to withstand folding at least 75 times after storage under such condition(s) for a period of at least about 2 months.

Example 4

This Example describes the characterization of the active pharmaceutical ingredient amphotericin B in the orally dissolvable films disclosed herein compared to that of unmodified amphotericin B. Orally dissolvable amphotericin B-containing film(s) utilized in this Example comprised amphotericin B as an ionic liquid such as that described in Example 2.

Differential scanning calorimetry (DSC) was used to identify the difference in the amount of heat required to increase the temperature of an orally dissolvable film preparation of amphotericin B compared to that of unmodified amphotericin B.

Samples were prepared according to the preparation method described in Example 3.

DSC thermographs of unmodified amphotericin B and amphotericin B-containing orally dissolvable films were recorded in 40 µL aluminum pans.

Samples were thermally scanned over a range of 30° C. to 200° C., with heat adjusted at a rate of 10° C. per minute, with a Mettler DSC 1 differential scanning calorimeter (Mettler Toledo, US). Thermograms obtained were evaluated using OriginPro data analysis software.

The DSC thermograms of unmodified amphotericin B (indicated by a circle) and orally dissolvable amphotericin B-containing film (indicated by a square) are shown in FIG. 1 ("DSC Thermograms. Amphotericin B vs. Amphotericin B Film.")

As shown in FIG. 2, the thermogram of pure, unmodified amphotericin B (indicated by a circle) shows an endothermic event (melting endothermic event) at a temperature of 118.45° C. A second endothermic event occurred at 208.63° C. Meanwhile, the thermogram of amphotericin B-containing orally dissolvable film demonstrated no melting endotherm for amphotericin B. See arrows provided in FIG. 1 indicating these events.

Accordingly, Example 4 demonstrates that the amphotericin B in the amphotericin B-containing orally dissolvable film is in amorphic form, providing for an improved dissolution of amphotericin B compared to amphotericin B in crystallized form.

Example 5

This Example provides a description of the antifungal activity of the active pharmaceutical ingredient amphotericin B in the orally dissolvable films disclosed herein compared to that of unmodified amphotericin B. Test organisms utilized in this experiment were *Candida albicans* and *Candida tropicalis*. Orally dissolvable amphotericin B-containing film(s) utilized in this Example were made according to the process described in Example 3.

Two different species of infectious fungal genus *Candida* were cultured. A first mixture of sabouraud dextrose agar and broth was inoculated with *Candida albicans* and allowed to sit at room temperature for a period of two days under aerobic conditions. A second mixture of sabouraud dextrose agar and broth was inoculated with *Candida tropicalis* and allowed to sit at room temperature for 2 days under aerobic conditions. This established two cultures (one each) of the test organisms.

To standardize the respective cultures, the optical density of each culture was adjusted using a 0.5 McFarland (turbidity) standard, approximating cultures to be approximately 106 colony forming units per milliliter (cfu/mL).

Each respective suspension was mixed until homogeneous to provide a final culture density of about 1×104 cfu/mL.

Agar cup diffusion was used for testing antifungal activity of the test compositions. 0.1 mL of each respective sample of amphotericin B or amphotericin B-containing film was provided in a cylinder. Film concentration was 1.8 mg amphotericin B per film. Each test plate contained two samples (two cylinders). Tests were performed in triplicate (3 plates per test composition). Plates were incubated at room temperature for a period of 2 days as amphotericin B test compositions were allowed to diffuse into the agar layer containing test organism(s).

Amphotericin B and amphotericin B-containing films were then evaluated for in vitro antifungal activity by measuring the zone of inhibition and microbial inhibition concentration (MIC) of each sample. Results are shown in FIGS. 2A, 2B, and 2C for the test organism *Candida albicans* and FIGS. 3A, 3B, and 3C for the test organism *Candida tropicalis*. Therein, amphotericin B samples are indicated as "A" and amphotericin B-containing films are indicated as "B".

The zone of inhibition (in mm) for the unmodified amphotericin B and amphotericin B-containing film is shown below in Table 8.

TABLE 8

Zone of Inhibition: Amphotericin B (AmpB) and Amphotericin B-Comprising Film (AmpB Film.

| | | Zone of Inhibition (mm) | | | | | | | |
|---|---|---|---|---|---|---|---|---|---|
| | | AmpB Film | | | | AmpB | | | |
| Sr. No. | Sample | Set 1 | Set 2 | Set 3 | Effective Zone of Inhibition | Set 1 | Set 2 | Set 3 | Effective Zone of Inhibition |
| 1. | *Candida albicans* | 22 | 22 | 23 | 22.23 ± 0.57 | 19 | 19 | 20 | 19.33 ± 0.57 |
| 2. | *Candida tropicalis* | 24 | 25 | 24 | 24.33 ± 0.57 | 20 | 22 | 22 | 21.33 ± 1.15 |

The results of Example 5 demonstrate a statistically significant difference in the effective zone of inhibition between the amphotericin B-containing film and unmodified amphotericin B. The amphotericin B-comprising film demonstrated an approximate 15% increase in the zone of inhibition compared to unmodified amphotericin B in the testing against *Candida albicans*. The amphotericin B-comprising film demonstrated an approximate 14% increase in the zone of inhibition compared to unmodified amphotericin B in the testing against *Candida tropicalis*.

Example 5 illustrates that the composition(s) of the present invention, e.g., composition(s) provided in the form of an orally dissolvable amphotericin B-comprising film, provide a remarkable improvement in efficacy in treating fungal infections caused by multiple species of *Candida*, e.g., *Candida albicans* and *Candida tropicalis* compared to treatment with unmodified amphotericin B.

Example 6

Tis Example provides a description of antifungal efficacy testing wherein minimum inhibitor concentration (MIC) of the active pharmaceutical ingredient amphotericin B in the orally dissolvable films disclosed herein compared to that of unmodified amphotericin B. The test organism utilized in this experiment was *Candida albicans*.

Three to five colonies of a single *Candida albicans* strain were selected from stock YPD agar (agar comprising yeast extract, peptone, and dextrose; also referred to as YEPD agar) plates and suspended in Roswell Park Memorial Institute (RPMI) 1640 medium. The process was repeated to form a number of suspensions of *Candida albicans*. The *Candida albicans* suspensions were then each diluted to achieve an initial inoculum with an $Abs_{600}$ of 0.010.

Test compositions of unmodified amphotericin B in DMSO and orally dissolvable films of amphotericin B in aqueous media were added, followed by serial dilution of the RPMI media.

A growth inhibition assay was performed in triplicate and results determined using a resazurin colorimetric assay. All plated compositions were incubated at 30° C. for 48±2 hours. Minimum inhibitory concentration (MIC) values were recorded at 48 hours ($MIC_{48h}$). After incubation, 20 µL of resazurin dye (0.02% w/v) was added to each well and observed for a change in dye color to determine cell viability.

Results of this experiment demonstrated dose-dependent anti-fungal activity. The average $MIC_{48h}$ for unmodified amphotericin B in DMSO was 1.25 µM. The average $MIC_{48h}$ for the orally dissolvable film of amphotericin B was 0.3125 µM.

This experiment illustrates that amphotericin B-containing orally dissolvable films provided by the present invention are capable of demonstrating a $MIC_{48h}$ against *Candida albicans* which is 25% of that of unmodified amphotericin B.

Example 7

This Example provides a description of antifungal efficacy testing wherein minimum inhibitor concentration (MIC) of the active pharmaceutical ingredient amphotericin B in the orally dissolvable films disclosed herein compared to that of unmodified amphotericin B. The test organisms utilized in this experiment were *Candida tropicalis* and *Candida albicans*.

A resazurin microtiter assay (REMA) assay was performed using orally dissolvable films prepared according to the process described in Example 3 and unmodified amphotericin B. Samples were run in triplicate as Sets 1-3 for each test material against each pathogen. Results are provided in Table 9 below.

TABLE 9

Minimum Inhibitory Concentration (MIC) of Amphotericin B and Orally Dissolvable Films Comprising Amphotericin B (AmpB Film).

| | | Minimum Inhibitory Concentration (mg/mL) | | | | | | | |
|---|---|---|---|---|---|---|---|---|---|
| | | AmpB Film | | | | AmpB | | | |
| Sr. No. | Sample | Set 1 | Set 2 | Set 3 | Avg. | Set 1 | Set 2 | Set 3 | Avg. |
| 1. | *Candida albicans* | 0.0007 | 0.0007 | 0.0007 | 0.0007 | 0.0011 | 0.0011 | 0.0011 | 0.0011 |
| 2. | *Candida tropicalis* | 0.0007 | 0.0007 | 0.0007 | 0.0007 | 0.0011 | 0.0011 | 0.0011 | 0.0011 |

Results demonstrate that the average MIC for orally dissolvable films comprising amphotericin B against *Candida albicans* was 0.0007 mg/mL (0.7 µg/mL). The average MIC for orally dissolvable films comprising amphotericin B against *Candida tropicalis* was also 0.0007 mg/mL (0.7 µg/mL). Thus the average MIC for orally dissolvable films comprising amphotericin B against *Candida* spp. tested is demonstrated to be about 0.0007 mg/mL (0.7 µg/mL).

Images of the microtiter plates used to conduct this experiment are shown in FIG. 5, illustrating the results of MIC assay. FIG. 5 shows 96-well microtiter plates containing test sample(s), test organism(s), and dye. Results of the orally dissolvable film ("ODF (A)") and unmodified amphotericin B ("AmpB (B)") against *Candida tropicalis* and *Candida albicans* are shown in the microtiter plates on the left and right, respectively. The first row of each microtiter plate (top) contains a positive control ("P.C."). The second row of each microtiter plate contains a negative control ("N.C.").

The average MIC for unmodified amphotericin B against *Candida albicans* in this example was demonstrated to be 0.0011 mg/mL (1.1 µg/mL). The average MIC for unmodified amphotericin B against *Candida tropicalis* was also 0.0011 mg/mL (1.1 µg/mL). Thus the average MIC for unmodified amphotericin B against *Candida* spp. tested is demonstrated to be about 0.0011 mg/mL (1.1 µg/mL).

The data from Example 7 demonstrates an MIC of orally dissolvable films comprising amphotericin B, e.g., amphotericin B in ionic liquid form as provided herein, against *Candida* spp. which is about 36% less than that of unmodified amphotericin B.

What is claimed is:

1. An antifungal ionic liquid composition of amphotericin B comprising (1) amphotericin B; (2) a complexing agent component comprising a first complexing agent and a second complexing agent, wherein the first complexing agent and the second complexing agent form a single ionic complex with the amphotericin B; (3) a solvent component comprising an amount of at least one solvent compound and at least one solvent acidifying agent that when combined with the solvent compound forms an acidified solvent, wherein the at least one solvent acidifying agent further (a) represents one of the first or the second complexing agents forming the ionic complex with the amphotericin B and (b) detectably modulates the pH of the composition; and (4) a solubilizing component comprising an amount of at least one solubilizing agent which detectably or significantly increases the solubilization of the amphotericin B, wherein each of the solvent acidifying agent and the solvent compound are present in the composition in an amount representing between about 0.5% w/v and about 5% w/v of the composition.

2. The antifungal ionic liquid composition of claim 1, wherein the amphotericin B is present in the composition in an amount representing between about 0.5% w/v and about 10% w/v of the composition.

3. The antifungal ionic liquid composition of claim 1, wherein at least one of the first or second complexing agents is choline chloride.

4. The antifungal ionic liquid composition of claim 3, wherein the choline chloride is present in the composition as the second complexing agent, and the ratio of the first complexing agent to the choline chloride in the composition is between about 5:1 and about 1:1 based on the percent weight/volume of each constituent in the composition.

5. The antifungal ionic liquid composition of claim 4, wherein the ratio of the first complexing agent to the choline chloride is about 4:1 based on the percent weight/volume of each constituent in the composition.

6. The antifungal ionic liquid composition of claim 1, wherein the at least one solubilizing agent is present in the composition in an amount of between about 2.5% w/v and about 10% w/v of the composition.

7. The antifungal ionic liquid composition of claim 1, wherein the solubility in water of the amphotericin B provided by the composition is at least about 3 mg/mL.

8. The antifungal ionic liquid composition of claim 1, wherein (1) the at least one solvent compound is dimethyl acetamide; (2) the at least one acidifying agent is ascorbic acid; (3) the at least one solubilizing agent is D-α-tocopheryl polyethylene glycol 1000 succinate (TPGS); or (4) the composition exhibits any combination of (1)-(3).

9. A pharmaceutically acceptable composition in the form of an oral dissolve film comprising the antifungal ionic liquid composition of claim 1.

10. A pharmaceutically acceptable composition in the form of an oral dissolve film comprising the antifungal ionic liquid composition of claim 8.

11. An antifungal ionic liquid composition of amphotericin B comprising (1) amphotericin B; (2) a complexing agent component comprising a first complexing agent and a second complexing agent, wherein the first complexing agent and the second complexing agent form a single ionic complex with the amphotericin B; (3) a solvent component comprising an amount of at least one solvent compound and at least one solvent acidifying agent that when combined with the solvent compound forms an acidified solvent, wherein the at least one solvent acidifying agent further (a) represents one of the first or the second complexing agents forming the ionic complex with the amphotericin B and (b) detectably modulates the pH of the composition; and (4) a solubilizing component comprising an amount of at least one solubilizing agent which detectably or significantly increases the solubilization of the amphotericin B, wherein (a) at least one of the first complexing agent and the second complexing agent, (b) the one or more solvent compounds, and (c) the at least one solubilizing agent, are present in the composition in an about 1:1:1 ratio with one another based on the percent weight/volume of each in the composition.

12. The antifungal ionic liquid composition of claim 11, wherein the amphotericin B is present in the composition in an amount representing between about 0.5% w/v and about 10% w/v of the composition.

13. The antifungal ionic liquid composition of claim 11, wherein at least one of the first or second complexing agents is choline chloride.

14. The antifungal ionic liquid composition of claim 13, wherein the ratio of the first complexing agent to the choline chloride is between about 5:1 and about 1:1 based on the percent weight/volume of each constituent in the composition.

15. The antifungal ionic liquid composition of claim 11, wherein the at least one solubilizing agent is present in the composition in an amount of between about 2.5% w/v and about 10% w/v of the composition.

16. The antifungal ionic liquid composition of claim 11, wherein the solubility in water of amphotericin B provided by the composition is at least about 3 mg/mL.

17. The antifungal ionic liquid composition of claim 11, wherein (1) the at least one solvent compound is dimethyl acetamide; (2) the at least one acidifying agent is ascorbic acid; (3) the at least one solubilizing agent is D-α-tocopheryl polyethylene glycol 1000 succinate (TPGS); or (4) the composition exhibits any combination of (1)-(3).

18. A pharmaceutically acceptable composition in the form of an oral dissolve film comprising the antifungal ionic liquid composition of claim 11.

19. A pharmaceutically acceptable composition in the form of an oral dissolve film comprising the antifungal ionic liquid composition of claim 14.

20. A pharmaceutically acceptable composition in the form of an oral dissolve film comprising the antifungal ionic liquid composition of claim 17.

* * * * *